US011802155B2

(12) United States Patent
Duey et al.

(10) Patent No.: US 11,802,155 B2
(45) Date of Patent: Oct. 31, 2023

(54) ILT-BINDING AGENTS AND METHODS OF USE THEREOF

(71) Applicant: NGM Biopharmaceuticals, Inc., South San Francisco, CA (US)

(72) Inventors: Dana Yen Mei Duey, San Francisco, CA (US); Allen James Ebens, Jr., San Carlos, CA (US); Daniel David Kaplan, San Mateo, CA (US); Chia-Ying Kao Lam, South San Francisco, CA (US); Kalyani Mondal, San Mateo, CA (US); Geoffrey William Stone, San Francisco, CA (US); Yan Wang, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 96 days.

(21) Appl. No.: 17/244,169

(22) Filed: Apr. 29, 2021

(65) Prior Publication Data
US 2021/0355211 A1    Nov. 18, 2021

Related U.S. Application Data

(60) Provisional application No. 63/122,848, filed on Dec. 8, 2020, provisional application No. 63/019,068, filed on May 1, 2020.

(51) Int. Cl.
| C07K 16/28 | (2006.01) |
| A61K 39/395 | (2006.01) |
| A61K 45/06 | (2006.01) |

(52) U.S. Cl.
CPC ...... C07K 16/2803 (2013.01); A61K 39/3955 (2013.01); A61K 45/06 (2013.01); *C07K 2317/24* (2013.01); *C07K 2317/33* (2013.01); *C07K 2317/76* (2013.01); *C07K 2317/92* (2013.01)

(58) Field of Classification Search
CPC ............ C07K 16/2803; C07K 2317/23; C07K 2317/33; C07K 2317/92; C07K 2317/70; A61K 39/3955; A61K 45/06; A61P 35/00
See application file for complete search history.

(56) References Cited

U.S. PATENT DOCUMENTS

| 7,014,853 | B2 | 3/2006 | Cosman |
| 7,834,157 | B2 | 11/2010 | Cosman |
| 7,943,329 | B2 | 5/2011 | Atwal et al. |
| 8,609,089 | B2 | 12/2013 | Langermann et al. |
| 8,952,136 | B2 | 2/2015 | Carven et al. |
| 9,580,504 | B1 | 2/2017 | Rotem-Yehudar et al. |
| 9,856,320 | B2 | 1/2018 | Cogswell et al. |
| 10,316,089 | B2 | 6/2019 | Baruah et al. |
| 2004/0138126 | A1 | 7/2004 | Cosman |
| 2004/0241167 | A1 | 12/2004 | Suciu-Foca et al. |
| 2004/0253674 | A1 | 12/2004 | Cosman |
| 2005/0238643 | A1 | 10/2005 | Arm et al. |
| 2006/0078564 | A1 | 4/2006 | Cosman |
| 2009/0098109 | A1 | 4/2009 | Shatz et al. |
| 2009/0169542 | A1 | 7/2009 | Atwal et al. |
| 2009/0226457 | A1 | 9/2009 | Cosman |
| 2009/0232794 | A1 | 9/2009 | Tessier-Lavigne et al. |
| 2009/0280109 | A1 | 11/2009 | Suciu-Foca et al. |
| 2009/0285803 | A1 | 11/2009 | Atwal et al. |
| 2015/0174203 | A1 | 6/2015 | Chen et al. |
| 2016/0009782 | A1 | 1/2016 | Shatz et al. |
| 2016/0200815 | A1 | 7/2016 | Feldman et al. |
| 2017/0260508 | A1 | 9/2017 | Bernstein et al. |
| 2017/0274003 | A1 | 9/2017 | Shatz et al. |
| 2018/0086829 | A1 | 3/2018 | Zhang et al. |
| 2018/0177847 | A1 | 6/2018 | Chen et al. |
| 2018/0201676 | A1 | 7/2018 | Blaser et al. |
| 2018/0298096 | A1 | 10/2018 | Joyce-Shaikh et al. |
| 2018/0348227 | A1 | 12/2018 | Sadelain et al. |
| 2019/0194327 | A1 | 6/2019 | Cohen et al. |

FOREIGN PATENT DOCUMENTS

| EP | 1453540 | 9/2004 |
| EP | 0948623 | 1/2010 |
| EP | 1981522 | 9/2012 |
| EP | 2503341 | 9/2012 |
| EP | 2102661 | 9/2013 |
| EP | 2970373 | 1/2016 |
| EP | 3265113 | 1/2018 |
| WO | WO 1998/024906 | 6/1998 |
| WO | WO 1998/048017 | 10/1998 |
| WO | WO 2000/068383 | 11/2000 |
| WO | WO 2003/000199 | 1/2003 |
| WO | WO 2003/041650 | 5/2003 |

(Continued)

OTHER PUBLICATIONS

Almagro JC, Fransson J. Humanization of antibodies. Front Biosci. Jan. 1, 2008;13:1619-33. (Year: 2008).*
Wu et al. Humanization of a murine monoclonal antibody by simultaneous optimization of framework and CDR residues. J Mol Biol. Nov. 19, 1999;294(1):151-62. (Year: 1999).*
Chen et al. Enhancement and destruction of antibody function by somatic mutation: unequal occurrence is controlled by V gene combinatorial associations.EMBO J.Jun. 15, 1995; 14(12): 2784-94. (Year: 1995).*
Rudikoff S et al. Single amino acid substitution altering antigen-binding specificity. Proc Natl Acad Sci U S A. Mar. 1982;79(6):1979-83. (Year: 1982).*

(Continued)

*Primary Examiner* — Aurora M Fontainhas
*Assistant Examiner* — Jennifer A Benavides
(74) *Attorney, Agent, or Firm* — JONES DAY

(57) ABSTRACT

The present disclosure provides binding agents, such as antibodies, that specifically bind ILT2, ILT4, or both ILT2 and ILT4, as well as compositions comprising the binding agents, and methods of their use. The disclosure also provides related polynucleotides and vectors encoding the binding agents and cells comprising the binding agents.

34 Claims, 25 Drawing Sheets

Specification includes a Sequence Listing.

(56) References Cited

FOREIGN PATENT DOCUMENTS

| WO | WO 2005/100998 | 10/2005 |
|---|---|---|
| WO | WO 2007/092165 | 8/2007 |
| WO | WO 2008/061019 | 5/2008 |
| WO | WO 2009/076359 | 6/2009 |
| WO | WO 2009/140361 | 11/2009 |
| WO | WO 2013/181438 | 12/2013 |
| WO | WO 2014/055897 | 4/2014 |
| WO | WO 2014/116846 | 7/2014 |
| WO | WO 2014/164519 | 10/2014 |
| WO | WO 2014/179664 | 11/2014 |
| WO | WO 2015/179633 | 11/2015 |
| WO | WO 2016/044022 | 3/2016 |
| WO | WO 2016/111947 | 7/2016 |
| WO | WO 2016/127247 | 8/2016 |
| WO | WO 2016/144728 | 9/2016 |
| WO | WO 2017/042816 | 3/2017 |
| WO | WO 2017/168348 | 10/2017 |
| WO | WO 2018/027197 | 2/2018 |
| WO | WO 2018/187518 | 10/2018 |
| WO | WO 2019/107387 | 6/2019 |
| WO | WO 2019/126514 | 6/2019 |
| WO | WO 2019/144052 | 7/2019 |

OTHER PUBLICATIONS

Kussie et al. A single engineered amino acid substitution changes antibody fine specificity.J Immunol. Jan. 1, 1994;152(1):146-52. (Year: 1994).*

U.S. Appl. No. 10/138,286, filed Nov. 27, 2018, Shatz et al.

U.S. Appl. No. 10/370,643, filed Aug. 6, 2019, Bernstein et al.

U.S. Appl. No. 10/501,538, filed Dec. 10, 2019, Zhang et al.

International Search Report and Written Opinion in International Appln. No. PCT/US2021/029866, dated Sep. 22, 2021, 20 pages.

Invitation to Pay Additional Fees in International Appln. No. PCT/US2021/029866, dated Jul. 28, 2021, 14 pages.

Borges et al., "A family of human lymphoid and myeloid Ig-like receptors, some of which bind to MHC class I molecules," J Immunol., Dec. 1, 1997, 159(11):5192-5196.

Colonna et al., "A Common Inhibitory Receptor for Major Histocompatibility Complex Class I Molecules on Human Lymphoid and Myelomonocytic Cells," J Exp Med., Dec. 1, 1997, 186(11):1809-1818.

Colonna et al., "Cutting Edge: Human Myelomonocytic Cells Express an Inhibitory Receptor for Classical and Nonclassical MHC Class I Molecules," J Immunol, Apr. 1, 1998, 160(7):3096-3100.

Deng et al., "A motif in LILRB2 critical for Angptl2 binding and activation," Blood, Aug. 7, 2014, 124(6):924-935.

Guerriero et al., "DNA Alkylating Therapy Induces Tumor Regression through an HMGB1-Mediated Activation of Innate Immunity," J Immunol., Mar. 15, 2011, 186(6):3517-3526.

Kang et al., "Inhibitory leukocyte immunoglobulin-like receptors: Immune checkpoint proteins and tumor sustaining factors," Cell Cycle, Jan. 15, 2016, 15(1):25-40.

Lopez-Verges et al., "Expansion of a unique CD57+NKG2Chi natural killer cell subset during acute human cytomegalovirus infection," Proc. Natl. Acad Sci., Sep. 6, 2011, 108(36):14725-14732.

Portal.ct.gov, [online], "Connecticut's Official State Website," 2021, retrieved on Aug. 4, 2021, retrieved from URL<https://portal.ct.gov/>, 4 pages.

* cited by examiner

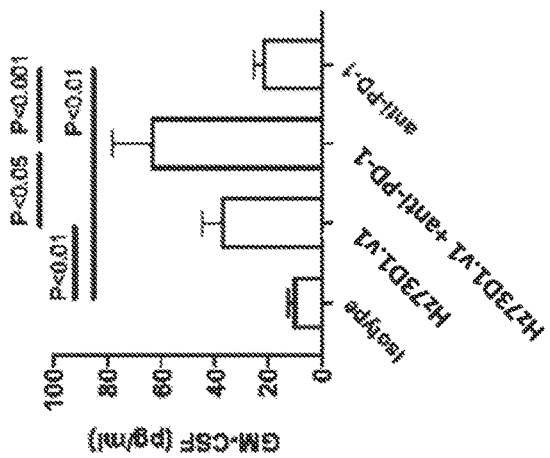
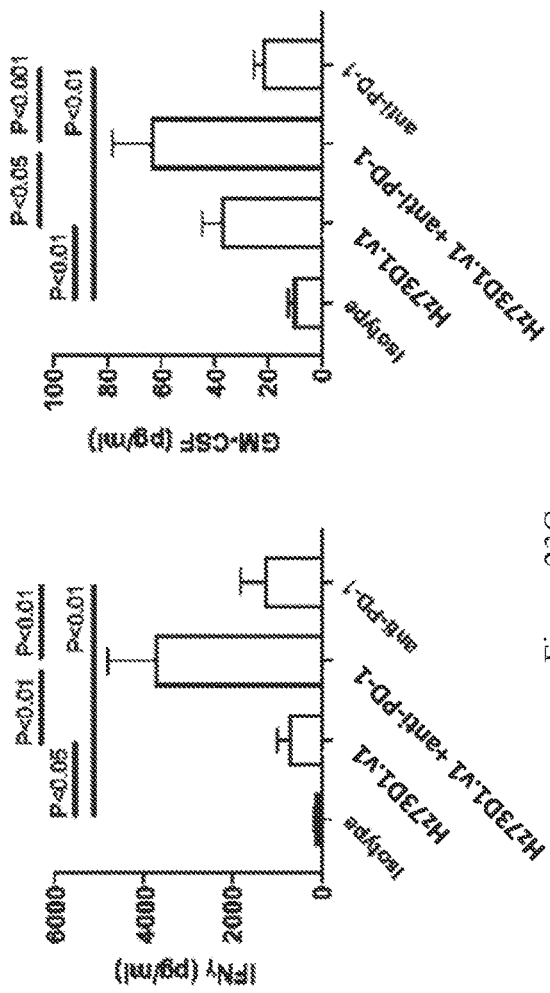
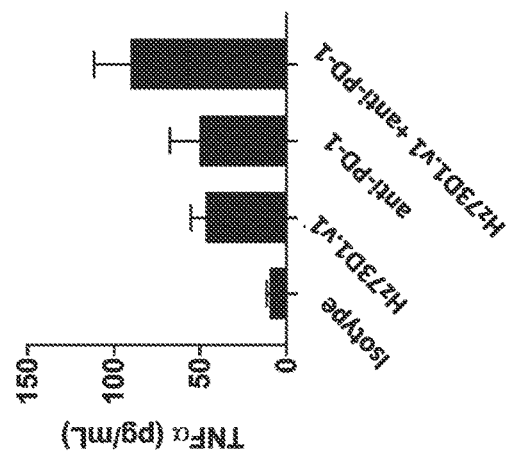

SEQUENCE LISTING

<160> NUMBER OF SEQ ID NOS: 173

<210> SEQ ID NO 1
<211> LENGTH: 650
<212> TYPE: PRT
<213> ORGANISM: Homo sapiens

<400> SEQUENCE: 1

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
```

```
                    290                 295                 300
Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650

<210> SEQ ID NO 2
<211> LENGTH: 627
<212> TYPE: PRT
<213> ORGANISM: Homo sapiens

<400> SEQUENCE: 2

Gly His Leu Pro Lys Pro Thr Leu Trp Ala Glu Pro Gly Ser Val Ile
1               5                   10                  15
```

```
Thr Gln Gly Ser Pro Val Thr Leu Arg Cys Gln Gly Gly Gln Glu Thr
             20                  25                  30
Gln Glu Tyr Arg Leu Tyr Arg Glu Lys Lys Thr Ala Leu Trp Ile Thr
             35                  40                  45
Arg Ile Pro Gln Glu Leu Val Lys Lys Gly Gln Phe Pro Ile Pro Ser
 50                  55                  60
Ile Thr Trp Glu His Ala Gly Arg Tyr Arg Cys Tyr Tyr Gly Ser Asp
 65                  70                  75                  80
Thr Ala Gly Arg Ser Glu Ser Ser Asp Pro Leu Glu Leu Val Val Thr
                 85                  90                  95
Gly Ala Tyr Ile Lys Pro Thr Leu Ser Ala Gln Pro Ser Pro Val Val
                100                 105                 110
Asn Ser Gly Gly Asn Val Ile Leu Gln Cys Asp Ser Gln Val Ala Phe
            115                 120                 125
Asp Gly Phe Ser Leu Cys Lys Glu Gly Glu Asp Glu His Pro Gln Cys
            130                 135                 140
Leu Asn Ser Gln Pro His Ala Arg Gly Ser Ser Arg Ala Ile Phe Ser
145                 150                 155                 160
Val Gly Pro Val Ser Pro Ser Arg Arg Trp Trp Tyr Arg Cys Tyr Ala
                165                 170                 175
Tyr Asp Ser Asn Ser Pro Tyr Glu Trp Ser Leu Pro Ser Asp Leu Leu
                180                 185                 190
Glu Leu Leu Val Leu Gly Val Ser Lys Lys Pro Ser Leu Ser Val Gln
            195                 200                 205
Pro Gly Pro Ile Val Ala Pro Glu Glu Thr Leu Thr Leu Gln Cys Gly
    210                 215                 220
Ser Asp Ala Gly Tyr Asn Arg Phe Val Leu Tyr Lys Asp Gly Glu Arg
225                 230                 235                 240
Asp Phe Leu Gln Leu Ala Gly Ala Gln Pro Gln Ala Gly Leu Ser Gln
                245                 250                 255
Ala Asn Phe Thr Leu Gly Pro Val Ser Arg Ser Tyr Gly Gly Gln Tyr
                260                 265                 270
Arg Cys Tyr Gly Ala His Asn Leu Ser Ser Glu Trp Ser Ala Pro Ser
            275                 280                 285
Asp Pro Leu Asp Ile Leu Ile Ala Gly Gln Phe Tyr Asp Arg Val Ser
    290                 295                 300
Leu Ser Val Gln Pro Gly Pro Thr Val Ala Ser Gly Glu Asn Val Thr
305                 310                 315                 320
Leu Leu Cys Gln Ser Gln Gly Trp Met Gln Thr Phe Leu Leu Thr Lys
                325                 330                 335
Glu Gly Ala Ala Asp Asp Pro Trp Arg Leu Arg Ser Thr Tyr Gln Ser
            340                 345                 350
Gln Lys Tyr Gln Ala Glu Phe Pro Met Gly Pro Val Thr Ser Ala His
            355                 360                 365
Ala Gly Thr Tyr Arg Cys Tyr Gly Ser Gln Ser Ser Lys Pro Tyr Leu
    370                 375                 380
Leu Thr His Pro Ser Asp Pro Leu Glu Leu Val Val Ser Gly Pro Ser
385                 390                 395                 400
Gly Gly Pro Ser Ser Pro Thr Thr Gly Pro Thr Ser Thr Ser Gly Pro
                405                 410                 415
Glu Asp Gln Pro Leu Thr Pro Thr Gly Ser Asp Pro Gln Ser Gly Leu
            420                 425                 430
Gly Arg His Leu Gly Val Val Ile Gly Ile Leu Val Ala Val Ile Leu
```

-continued

```
                435                 440                 445
Leu Leu Leu Leu Leu Leu Leu Leu Phe Leu Ile Leu Arg His Arg Arg
450                 455                 460
Gln Gly Lys His Trp Thr Ser Thr Gln Arg Lys Ala Asp Phe Gln His
465                 470                 475                 480
Pro Ala Gly Ala Val Gly Pro Glu Pro Thr Asp Arg Gly Leu Gln Trp
                485                 490                 495
Arg Ser Ser Pro Ala Ala Asp Ala Gln Glu Glu Asn Leu Tyr Ala Ala
                500                 505                 510
Val Lys His Thr Gln Pro Glu Asp Gly Val Glu Met Asp Thr Arg Ser
                515                 520                 525
Pro His Asp Glu Asp Pro Gln Ala Val Thr Tyr Ala Glu Val Lys His
530                 535                 540
Ser Arg Pro Arg Arg Glu Met Ala Ser Pro Pro Ser Pro Leu Ser Gly
545                 550                 555                 560
Glu Phe Leu Asp Thr Lys Asp Arg Gln Ala Glu Glu Asp Arg Gln Met
                565                 570                 575
Asp Thr Glu Ala Ala Ala Ser Glu Ala Pro Gln Asp Val Thr Tyr Ala
                580                 585                 590
Gln Leu His Ser Leu Thr Leu Arg Arg Glu Ala Thr Glu Pro Pro Pro
                595                 600                 605
Ser Gln Glu Gly Pro Ser Pro Ala Val Pro Ser Ile Tyr Ala Thr Leu
610                 615                 620
Ala Ile His
625

<210> SEQ ID NO 3
<211> LENGTH: 438
<212> TYPE: PRT
<213> ORGANISM: Homo sapiens

<400> SEQUENCE: 3

Gly His Leu Pro Lys Pro Thr Leu Trp Ala Glu Pro Gly Ser Val Ile
1               5                   10                  15
Thr Gln Gly Ser Pro Val Thr Leu Arg Cys Gln Gly Gly Gln Glu Thr
                20                  25                  30
Gln Glu Tyr Arg Leu Tyr Arg Glu Lys Lys Thr Ala Leu Trp Ile Thr
            35                  40                  45
Arg Ile Pro Gln Glu Leu Val Lys Lys Gly Gln Phe Pro Ile Pro Ser
        50                  55                  60
Ile Thr Trp Glu His Ala Gly Arg Tyr Arg Cys Tyr Tyr Gly Ser Asp
65                  70                  75                  80
Thr Ala Gly Arg Ser Glu Ser Ser Asp Pro Leu Glu Leu Val Val Thr
                85                  90                  95
Gly Ala Tyr Ile Lys Pro Thr Leu Ser Ala Gln Pro Ser Pro Val Val
                100                 105                 110
Asn Ser Gly Gly Asn Val Ile Leu Gln Cys Asp Ser Gln Val Ala Phe
            115                 120                 125
Asp Gly Phe Ser Leu Cys Lys Glu Gly Glu Asp Glu His Pro Gln Cys
        130                 135                 140
Leu Asn Ser Gln Pro His Ala Arg Gly Ser Ser Arg Ala Ile Phe Ser
145                 150                 155                 160
Val Gly Pro Val Ser Pro Ser Arg Arg Trp Trp Tyr Arg Cys Tyr Ala
                165                 170                 175
```

-continued

Tyr Asp Ser Asn Ser Pro Tyr Glu Trp Ser Leu Pro Ser Asp Leu Leu
            180                 185                 190

Glu Leu Leu Val Leu Gly Val Ser Lys Lys Pro Ser Leu Ser Val Gln
        195                 200                 205

Pro Gly Pro Ile Val Ala Pro Glu Glu Thr Leu Thr Leu Gln Cys Gly
    210                 215                 220

Ser Asp Ala Gly Tyr Asn Arg Phe Val Leu Tyr Lys Asp Gly Glu Arg
225                 230                 235                 240

Asp Phe Leu Gln Leu Ala Gly Ala Gln Pro Gln Ala Gly Leu Ser Gln
                245                 250                 255

Ala Asn Phe Thr Leu Gly Pro Val Ser Arg Ser Tyr Gly Gly Gln Tyr
            260                 265                 270

Arg Cys Tyr Gly Ala His Asn Leu Ser Ser Glu Trp Ser Ala Pro Ser
        275                 280                 285

Asp Pro Leu Asp Ile Leu Ile Ala Gly Gln Phe Tyr Asp Arg Val Ser
    290                 295                 300

Leu Ser Val Gln Pro Gly Pro Thr Val Ala Ser Gly Glu Asn Val Thr
305                 310                 315                 320

Leu Leu Cys Gln Ser Gln Gly Trp Met Gln Thr Phe Leu Leu Thr Lys
                325                 330                 335

Glu Gly Ala Ala Asp Asp Pro Trp Arg Leu Arg Ser Thr Tyr Gln Ser
            340                 345                 350

Gln Lys Tyr Gln Ala Glu Phe Pro Met Gly Pro Val Thr Ser Ala His
        355                 360                 365

Ala Gly Thr Tyr Arg Cys Tyr Gly Ser Gln Ser Ser Lys Pro Tyr Leu
    370                 375                 380

Leu Thr His Pro Ser Asp Pro Leu Glu Leu Val Val Ser Gly Pro Ser
385                 390                 395                 400

Gly Gly Pro Ser Ser Pro Thr Thr Gly Pro Thr Ser Thr Ser Gly Pro
                405                 410                 415

Glu Asp Gln Pro Leu Thr Pro Thr Gly Ser Asp Pro Gln Ser Gly Leu
            420                 425                 430

Gly Arg His Leu Gly Val
        435

<210> SEQ ID NO 4
<211> LENGTH: 89
<212> TYPE: PRT
<213> ORGANISM: Homo sapiens

<400> SEQUENCE: 4

Pro Lys Pro Thr Leu Trp Ala Glu Pro Gly Ser Val Ile Thr Gln Gly
1               5                   10                  15

Ser Pro Val Thr Leu Arg Cys Gln Gly Gly Gln Glu Thr Gln Glu Tyr
            20                  25                  30

Arg Leu Tyr Arg Glu Lys Lys Thr Ala Leu Trp Ile Thr Arg Ile Pro
        35                  40                  45

Gln Glu Leu Val Lys Lys Gly Gln Phe Pro Ile Pro Ser Ile Thr Trp
    50                  55                  60

Glu His Ala Gly Arg Tyr Arg Cys Tyr Tyr Gly Ser Asp Thr Ala Gly
65                  70                  75                  80

Arg Ser Glu Ser Ser Asp Pro Leu Glu
                85

<210> SEQ ID NO 5

```
<211> LENGTH: 106
<212> TYPE: PRT
<213> ORGANISM: Homo sapiens

<400> SEQUENCE: 5

Leu Val Val Thr Gly Ala Tyr Ile Lys Pro Thr Leu Ser Ala Gln Pro
1               5                   10                  15

Ser Pro Val Val Asn Ser Gly Gly Asn Val Ile Leu Gln Cys Asp Ser
            20                  25                  30

Gln Val Ala Phe Asp Gly Phe Ser Leu Cys Lys Glu Gly Glu Asp Glu
        35                  40                  45

His Pro Gln Cys Leu Asn Ser Gln Pro His Ala Arg Gly Ser Ser Arg
    50                  55                  60

Ala Ile Phe Ser Val Gly Pro Val Ser Pro Ser Arg Arg Trp Trp Tyr
65                  70                  75                  80

Arg Cys Tyr Ala Tyr Asp Ser Asn Ser Pro Tyr Glu Trp Ser Leu Pro
                85                  90                  95

Ser Asp Leu Leu Glu Leu Leu Val Leu Gly
            100                 105

<210> SEQ ID NO 6
<211> LENGTH: 91
<212> TYPE: PRT
<213> ORGANISM: Homo sapiens

<400> SEQUENCE: 6

Val Ser Lys Lys Pro Ser Leu Ser Val Gln Pro Gly Pro Ile Val Ala
1               5                   10                  15

Pro Glu Glu Thr Leu Thr Leu Gln Cys Gly Ser Asp Ala Gly Tyr Asn
            20                  25                  30

Arg Phe Val Leu Tyr Lys Asp Gly Glu Arg Asp Phe Leu Gln Leu Ala
        35                  40                  45

Gly Ala Gln Pro Gln Ala Gly Leu Ser Gln Ala Asn Phe Thr Leu Gly
    50                  55                  60

Pro Val Ser Arg Ser Tyr Gly Gly Gln Tyr Arg Cys Tyr Gly Ala His
65                  70                  75                  80

Asn Leu Ser Ser Glu Trp Ser Ala Pro Ser Asp
                85                  90

<210> SEQ ID NO 7
<211> LENGTH: 97
<212> TYPE: PRT
<213> ORGANISM: Homo sapiens

<400> SEQUENCE: 7

Pro Leu Asp Ile Leu Ile Ala Gly Gln Phe Tyr Asp Arg Val Ser Leu
1               5                   10                  15

Ser Val Gln Pro Gly Pro Thr Val Ala Ser Gly Glu Asn Val Thr Leu
            20                  25                  30

Leu Cys Gln Ser Gln Gly Trp Met Gln Thr Phe Leu Leu Thr Lys Glu
        35                  40                  45

Gly Ala Ala Asp Asp Pro Trp Arg Leu Arg Ser Thr Tyr Gln Ser Gln
    50                  55                  60

Lys Tyr Gln Ala Glu Phe Pro Met Gly Pro Val Thr Ser Ala His Ala
65                  70                  75                  80

Gly Thr Tyr Arg Cys Tyr Gly Ser Gln Ser Ser Lys Pro Tyr Leu Leu
                85                  90                  95
```

Thr

<210> SEQ ID NO 8
<211> LENGTH: 598
<212> TYPE: PRT
<213> ORGANISM: Homo sapiens

<400> SEQUENCE: 8

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

```
Arg Ser Ile His Glu Tyr Pro Lys Tyr Gln Ala Glu Phe Pro Met Ser
        370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
                420                 425                 430

Ile Ser Thr Pro Ala Gly Pro Glu Asp Gln Pro Leu Thr Pro Thr Gly
            435                 440                 445

Ser Asp Pro Gln Ser Gly Leu Gly Arg His Leu Gly Val Val Ile Gly
450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys Asp Thr Gln Pro Glu Asp Gly
530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
                580                 585                 590

Ala Thr Leu Ala Ile His
            595

<210> SEQ ID NO 9
<211> LENGTH: 577
<212> TYPE: PRT
<213> ORGANISM: Homo sapiens

<400> SEQUENCE: 9

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
                20                  25                  30

Glu Ala Gln Glu Tyr Arg Leu Tyr Arg Glu Lys Lys Ser Ala Ser Trp
            35                  40                  45

Ile Thr Arg Ile Arg Pro Glu Leu Val Lys Asn Gly Gln Phe His Ile
        50                  55                  60

Pro Ser Ile Thr Trp Glu His Thr Gly Arg Tyr Gly Cys Gln Tyr Tyr
65                  70                  75                  80

Ser Arg Ala Arg Trp Ser Glu Leu Ser Asp Pro Leu Val Leu Val Met
                85                  90                  95

Thr Gly Ala Tyr Pro Lys Pro Thr Leu Ser Ala Gln Pro Ser Pro Val
                100                 105                 110

Val Thr Ser Gly Gly Arg Val Thr Leu Gln Cys Glu Ser Gln Val Ala
            115                 120                 125

Phe Gly Gly Phe Ile Leu Cys Lys Glu Gly Glu Glu Glu His Pro Gln
        130                 135                 140
```

```
Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
        195                 200                 205

Gln Pro Gly Pro Val Val Ala Pro Gly Glu Ser Leu Thr Leu Gln Cys
    210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Cys Ser Ala Pro
        275                 280                 285

Ser Asp Pro Leu Asp Ile Leu Ile Thr Gly Gln Ile Arg Gly Thr Pro
290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val Val Ile Gly Ile Leu Val Ala Val
        435                 440                 445

Val Leu Leu Leu Leu Leu Leu Leu Leu Phe Leu Ile Leu Arg His
450                 455                 460

Arg Arg Gln Gly Lys His Trp Thr Ser Thr Gln Arg Lys Ala Asp Phe
465                 470                 475                 480

Gln His Pro Ala Gly Ala Val Gly Pro Glu Pro Thr Asp Arg Gly Leu
                485                 490                 495

Gln Trp Arg Ser Ser Pro Ala Ala Asp Ala Gln Glu Glu Asn Leu Tyr
            500                 505                 510

Ala Ala Val Lys Asp Thr Gln Pro Glu Asp Gly Val Glu Met Asp Thr
        515                 520                 525

Arg Ala Ala Ala Ser Glu Ala Pro Gln Asp Val Thr Tyr Ala Gln Leu
    530                 535                 540

His Ser Leu Thr Leu Arg Arg Lys Ala Thr Glu Pro Pro Pro Ser Gln
545                 550                 555                 560
```

```
Glu Arg Glu Pro Pro Ala Glu Pro Ser Ile Tyr Ala Thr Leu Ala Ile
                565                 570                 575
His

<210> SEQ ID NO 10
<211> LENGTH: 440
<212> TYPE: PRT
<213> ORGANISM: Homo sapiens

<400> SEQUENCE: 10

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile
    50                  55                  60

Pro Ser Ile Thr Trp Glu His Thr Gly Arg Tyr Gly Cys Gln Tyr Tyr
65              70                  75                  80

Ser Arg Ala Arg Trp Ser Glu Leu Ser Asp Pro Leu Val Leu Val Met
            85                  90                  95

Thr Gly Ala Tyr Pro Lys Pro Thr Leu Ser Ala Gln Pro Ser Pro Val
        100                 105                 110

Val Thr Ser Gly Gly Arg Val Thr Leu Gln Cys Glu Ser Gln Val Ala
    115                 120                 125

Phe Gly Gly Phe Ile Leu Cys Lys Glu Gly Glu Glu His Pro Gln
        130                 135                 140

Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
            165                 170                 175

Gly Tyr Asp Leu Asn Ser Pro Tyr Val Trp Ser Ser Pro Ser Asp Leu
        180                 185                 190

Leu Glu Leu Leu Val Pro Gly Val Ser Lys Lys Pro Ser Leu Ser Val
    195                 200                 205

Gln Pro Gly Pro Val Val Ala Pro Gly Glu Ser Leu Thr Leu Gln Cys
210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
            245                 250                 255

Gln Ala Asn Phe Thr Leu Gly Pro Val Ser Arg Ser Tyr Gly Gly Gln
        260                 265                 270

Tyr Arg Cys Tyr Gly Ala His Asn Leu Ser Ser Glu Cys Ser Ala Pro
    275                 280                 285

Ser Asp Pro Leu Asp Ile Leu Ile Thr Gly Gln Ile Arg Gly Thr Pro
290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
            325                 330                 335

Lys Ala Gly Ala Ala Asp Ala Pro Leu Arg Leu Arg Ser Ile His Glu
        340                 345                 350
```

```
Tyr Pro Lys Tyr Gln Ala Glu Phe Pro Met Ser Pro Val Thr Ser Ala
            355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val
            435                 440

<210> SEQ ID NO 11
<211> LENGTH: 84
<212> TYPE: PRT
<213> ORGANISM: Homo sapiens

<400> SEQUENCE: 11

Pro Lys Pro Thr Leu Trp Ala Glu Pro Asp Ser Val Ile Thr Gln Gly
1               5                   10                  15

Ser Pro Val Thr Leu Ser Cys Gln Gly Ser Leu Glu Ala Gln Glu Tyr
                20                  25                  30

Arg Leu Tyr Arg Glu Lys Lys Ser Ala Ser Trp Ile Thr Arg Ile Arg
            35                  40                  45

Pro Glu Leu Val Lys Asn Gly Gln Phe His Ile Pro Ser Ile Thr Trp
    50                  55                  60

Glu His Thr Gly Arg Tyr Gly Cys Gln Tyr Tyr Ser Arg Ala Arg Trp
65                  70                  75                  80

Ser Glu Leu Ser

<210> SEQ ID NO 12
<211> LENGTH: 119
<212> TYPE: PRT
<213> ORGANISM: Homo sapiens

<400> SEQUENCE: 12

Asp Pro Leu Val Leu Val Met Thr Gly Ala Tyr Pro Lys Pro Thr Leu
1               5                   10                  15

Ser Ala Gln Pro Ser Pro Val Val Thr Ser Gly Gly Arg Val Thr Leu
                20                  25                  30

Gln Cys Glu Ser Gln Val Ala Phe Gly Gly Phe Ile Leu Cys Lys Glu
            35                  40                  45

Gly Glu Glu Glu His Pro Gln Cys Leu Asn Ser Gln Pro His Ala Arg
    50                  55                  60

Gly Ser Ser Arg Ala Ile Phe Ser Val Gly Pro Val Ser Pro Asn Arg
65                  70                  75                  80

Arg Trp Ser His Arg Cys Tyr Gly Tyr Asp Leu Asn Ser Pro Tyr Val
                85                  90                  95

Trp Ser Ser Pro Ser Asp Leu Leu Glu Leu Leu Val Pro Gly Val Ser
                100                 105                 110

Lys Lys Pro Ser Leu Ser Val
            115

<210> SEQ ID NO 13
<211> LENGTH: 89
<212> TYPE: PRT
```

<213> ORGANISM: Homo sapiens

<400> SEQUENCE: 13

Gln Pro Gly Pro Val Ala Pro Gly Glu Ser Leu Thr Leu Gln Cys
1               5                   10                  15

Val Ser Asp Val Gly Tyr Asp Arg Phe Val Leu Tyr Lys Glu Gly Glu
            20                  25                  30

Arg Asp Leu Arg Gln Leu Pro Gly Arg Gln Pro Gln Ala Gly Leu Ser
        35                  40                  45

Gln Ala Asn Phe Thr Leu Gly Pro Val Ser Arg Ser Tyr Gly Gly Gln
    50                  55                  60

Tyr Arg Cys Tyr Gly Ala His Asn Leu Ser Ser Glu Cys Ser Ala Pro
65                  70                  75                  80

Ser Asp Pro Leu Asp Ile Leu Ile Thr
                85

<210> SEQ ID NO 14
<211> LENGTH: 90
<212> TYPE: PRT
<213> ORGANISM: Homo sapiens

<400> SEQUENCE: 14

Gln Pro Gly Pro Thr Val Ala Ser Gly Glu Asn Val Thr Leu Leu Cys
1               5                   10                  15

Gln Ser Trp Arg Gln Phe His Thr Phe Leu Leu Thr Lys Ala Gly Ala
            20                  25                  30

Ala Asp Ala Pro Leu Arg Leu Arg Ser Ile His Glu Tyr Pro Lys Tyr
        35                  40                  45

Gln Ala Glu Phe Pro Met Ser Pro Val Thr Ser Ala His Ala Gly Thr
    50                  55                  60

Tyr Arg Cys Tyr Gly Ser Leu Asn Ser Asp Pro Tyr Leu Leu Ser His
65                  70                  75                  80

Pro Ser Glu Pro Leu Glu Leu Val Val Ser
                85                  90

<210> SEQ ID NO 15
<211> LENGTH: 639
<212> TYPE: PRT
<213> ORGANISM: Macaca mulatta
<220> FEATURE:
<221> NAME/KEY: MOD_RES
<222> LOCATION: (150)..(150)
<223> OTHER INFORMATION: Any amino acid

<400> SEQUENCE: 15

Met Thr Pro Ile Leu Met Val Leu Ile Cys Leu Gly Leu Ser Leu Gly
1               5                   10                  15

Ser Arg Thr Arg Val Gln Ala Gly Thr Phe Pro Lys Pro Thr Leu Trp
            20                  25                  30

Ala Glu Pro Gly Ser Met Ile Ser Lys Gly Ser Pro Val Thr Leu Arg
        35                  40                  45

Cys Gln Gly Ser Leu Pro Val Gln Asp Tyr Arg Leu Gln Arg Glu Lys
    50                  55                  60

Lys Thr Ala Ser Trp Val Arg Arg Ile Gln Gln Glu Leu Val Lys Lys
65                  70                  75                  80

Gly Tyr Phe Pro Ile Ala Ser Ile Thr Ser Glu His Ala Gly Gln Tyr
                85                  90                  95

Arg Cys Gln Tyr Tyr Ser His Ser Trp Trp Ser Glu Pro Ser Asp Pro

```
                100             105             110
Leu Glu Leu Val Val Thr Gly Ala Tyr Ser Lys Pro Thr Leu Ser Ala
            115                 120                 125
Leu Pro Ser Pro Val Val Ala Ser Gly Gly Asn Val Thr Leu Gln Cys
            130                 135                 140
Asp Ser Gln Val Ala Xaa Gly Gly Phe Val Leu Cys Lys Glu Gly Glu
145                 150                 155                 160
Asp Glu His Pro Gln Cys Leu Asn Ser Gln Pro His Thr Arg Gly Ser
            165                 170                 175
Ser Arg Ala Val Phe Ser Val Gly Pro Val Ser Pro Ser Arg Arg Trp
            180                 185                 190
Ser Tyr Arg Cys Tyr Gly Tyr Asp Ser Arg Ser Pro Tyr Val Trp Ser
            195                 200                 205
Leu Pro Ser Asp Leu Leu Glu Leu Leu Val Pro Gly Val Ser Lys Lys
            210                 215                 220
Pro Ser Leu Ser Val Gln Pro Gly Pro Val Val Ala Pro Gly Asp Lys
225                 230                 235                 240
Leu Thr Leu Gln Cys Gly Ser Asp Ala Gly Tyr Asn Arg Phe Ala Leu
            245                 250                 255
Tyr Lys Glu Gly Glu Arg Asp Phe Leu Gln Arg Pro Gly Arg Gln Pro
            260                 265                 270
Gln Ala Gly Leu Ser Gln Ala Asn Phe Leu Leu Asp Pro Val Arg Arg
            275                 280                 285
Ser His Gly Gly Gln Tyr Arg Cys Ser Gly Ala His Asn Leu Ser Ser
            290                 295                 300
Glu Trp Ser Ala Pro Ser Asp Pro Leu Asp Ile Leu Ile Ala Gly Gln
305                 310                 315                 320
Ile Arg Gly Arg Pro Ser Leu Leu Val Gln Pro Gly Pro Thr Val Val
            325                 330                 335
Ser Gly Glu Asn Val Thr Leu Leu Cys Gln Ser Ser Trp Gln Phe His
            340                 345                 350
Val Phe Leu Leu Thr Gln Ala Gly Ala Ala Asp Ala His Leu His Leu
            355                 360                 365
Arg Ser Met Tyr Lys Tyr Pro Lys Tyr Gln Ala Glu Phe Pro Met Ser
            370                 375                 380
Pro Val Thr Ser Ala His Ala Gly Thr Tyr Arg Cys Tyr Gly Ser His
385                 390                 395                 400
Ser Ser Asp Ser Tyr Leu Leu Ser Ile Pro Ser Asp Pro Leu Glu Leu
            405                 410                 415
Val Val Ser Gly Pro Ser Gly Gly Pro Ser Ser Pro Thr Thr Gly Pro
            420                 425                 430
Thr Ser Thr Cys Gly Pro Glu Asp Gln Pro Leu Thr Pro Thr Gly Ser
            435                 440                 445
Asp Pro Gln Ser Gly Leu Gly Arg His Leu Gly Val Val Thr Gly Val
450                 455                 460
Leu Val Ala Phe Val Leu Leu Phe Leu Leu Leu Leu Phe Leu
465                 470                 475                 480
Val Leu Arg His Arg Arg Gln Gly Lys Arg Trp Thr Ser Ala Gln Arg
            485                 490                 495
Lys Ala Asp Phe Gln His Pro Ala Gly Ala Val Glu Pro Glu Pro Arg
            500                 505                 510
Asp Arg Gly Leu Gln Arg Arg Ser Ser Pro Ala Ala Asn Thr Gln Glu
            515                 520                 525
```

-continued

```
Glu Asn Leu Tyr Ala Ala Val Lys Asp Thr Gln Pro Glu Asp Gly Val
            530                 535                 540

Glu Leu Asp Ser Arg Ser Pro His Asp Glu Asp Pro Gln Ala Val Thr
545                 550                 555                 560

Tyr Ala Arg Val Lys His Ser Arg Pro Arg Glu Met Ala Ser Pro
                565                 570                 575

Pro Ser Pro Leu Ser Glu Glu Phe Leu Asp Thr Lys Asp Thr Gln Ala
            580                 585                 590

Ala Ala Ser Glu Asp Pro Gln Asp Val Thr Tyr Ala Gln Leu Gln Ser
            595                 600                 605

Leu Thr Leu Arg Arg Glu Thr Thr Glu Pro Pro Pro Ser Gln Glu Arg
            610                 615                 620

Glu Pro Pro Val Glu Ser Ser Ile Tyr Ala Thr Leu Thr Ile His
625                 630                 635
```

<210> SEQ ID NO 16
<211> LENGTH: 616
<212> TYPE: PRT
<213> ORGANISM: Macaca mulatta
<220> FEATURE:
<221> NAME/KEY: MOD_RES
<222> LOCATION: (127)..(127)
<223> OTHER INFORMATION: Any amino acid

<400> SEQUENCE: 16

```
Gly Thr Phe Pro Lys Pro Thr Leu Trp Ala Glu Pro Gly Ser Met Ile
1               5                   10                  15

Ser Lys Gly Ser Pro Val Thr Leu Arg Cys Gln Gly Ser Leu Pro Val
            20                  25                  30

Gln Asp Tyr Arg Leu Gln Arg Glu Lys Lys Thr Ala Ser Trp Val Arg
        35                  40                  45

Arg Ile Gln Gln Glu Leu Val Lys Lys Gly Tyr Phe Pro Ile Ala Ser
    50                  55                  60

Ile Thr Ser Glu His Ala Gly Gln Tyr Arg Cys Gln Tyr Tyr Ser His
65                  70                  75                  80

Ser Trp Trp Ser Glu Pro Ser Asp Pro Leu Glu Leu Val Val Thr Gly
                85                  90                  95

Ala Tyr Ser Lys Pro Thr Leu Ser Ala Leu Pro Ser Pro Val Val Ala
            100                 105                 110

Ser Gly Gly Asn Val Thr Leu Gln Cys Asp Ser Gln Val Ala Xaa Gly
        115                 120                 125

Gly Phe Val Leu Cys Lys Glu Gly Glu Asp Glu His Pro Gln Cys Leu
    130                 135                 140

Asn Ser Gln Pro His Thr Arg Gly Ser Ser Arg Ala Val Phe Ser Val
145                 150                 155                 160

Gly Pro Val Ser Pro Ser Arg Arg Trp Ser Tyr Arg Cys Tyr Gly Tyr
                165                 170                 175

Asp Ser Arg Ser Pro Tyr Val Trp Ser Leu Pro Ser Asp Leu Leu Glu
            180                 185                 190

Leu Leu Val Pro Gly Val Ser Lys Lys Pro Ser Leu Ser Val Gln Pro
        195                 200                 205

Gly Pro Val Val Ala Pro Gly Asp Lys Leu Thr Leu Gln Cys Gly Ser
    210                 215                 220

Asp Ala Gly Tyr Asn Arg Phe Ala Leu Tyr Lys Glu Gly Glu Arg Asp
225                 230                 235                 240
```

Phe Leu Gln Arg Pro Gly Arg Gln Pro Gln Ala Gly Leu Ser Gln Ala
              245                 250                 255

Asn Phe Leu Leu Asp Pro Val Arg Arg Ser His Gly Gly Gln Tyr Arg
          260                 265                 270

Cys Ser Gly Ala His Asn Leu Ser Ser Glu Trp Ser Ala Pro Ser Asp
      275                 280                 285

Pro Leu Asp Ile Leu Ile Ala Gly Gln Ile Arg Gly Arg Pro Ser Leu
  290                 295                 300

Leu Val Gln Pro Gly Pro Thr Val Val Ser Gly Glu Asn Val Thr Leu
305                 310                 315                 320

Leu Cys Gln Ser Ser Trp Gln Phe His Val Phe Leu Leu Thr Gln Ala
              325                 330                 335

Gly Ala Ala Asp Ala His Leu His Leu Arg Ser Met Tyr Lys Tyr Pro
          340                 345                 350

Lys Tyr Gln Ala Glu Phe Pro Met Ser Pro Val Thr Ser Ala His Ala
      355                 360                 365

Gly Thr Tyr Arg Cys Tyr Gly Ser His Ser Ser Asp Ser Tyr Leu Leu
  370                 375                 380

Ser Ile Pro Ser Asp Pro Leu Glu Leu Val Val Ser Gly Pro Ser Gly
385                 390                 395                 400

Gly Pro Ser Ser Pro Thr Thr Gly Pro Thr Ser Thr Cys Gly Pro Glu
              405                 410                 415

Asp Gln Pro Leu Thr Pro Thr Gly Ser Asp Pro Gln Ser Gly Leu Gly
          420                 425                 430

Arg His Leu Gly Val Val Thr Gly Val Leu Val Ala Phe Val Leu Leu
      435                 440                 445

Leu Phe Leu Leu Leu Leu Leu Phe Leu Val Leu Arg His Arg Arg Gln
  450                 455                 460

Gly Lys Arg Trp Thr Ser Ala Gln Arg Lys Ala Asp Phe Gln His Pro
465                 470                 475                 480

Ala Gly Ala Val Glu Pro Glu Pro Arg Asp Arg Gly Leu Gln Arg Arg
              485                 490                 495

Ser Ser Pro Ala Ala Asn Thr Gln Glu Glu Asn Leu Tyr Ala Ala Val
          500                 505                 510

Lys Asp Thr Gln Pro Glu Asp Gly Val Glu Leu Asp Ser Arg Ser Pro
      515                 520                 525

His Asp Glu Asp Pro Gln Ala Val Thr Tyr Ala Arg Val Lys His Ser
  530                 535                 540

Arg Pro Arg Arg Glu Met Ala Ser Pro Pro Ser Pro Leu Ser Glu Glu
545                 550                 555                 560

Phe Leu Asp Thr Lys Asp Thr Gln Ala Ala Ala Ser Glu Asp Pro Gln
              565                 570                 575

Asp Val Thr Tyr Ala Gln Leu Gln Ser Leu Thr Leu Arg Arg Glu Thr
          580                 585                 590

Thr Glu Pro Pro Pro Ser Gln Glu Arg Glu Pro Pro Val Glu Ser Ser
      595                 600                 605

Ile Tyr Ala Thr Leu Thr Ile His
  610                 615

<210> SEQ ID NO 17
<211> LENGTH: 437
<212> TYPE: PRT
<213> ORGANISM: Macaca mulatta
<220> FEATURE:
<221> NAME/KEY: MOD_RES

```
<222> LOCATION: (127)..(127)
<223> OTHER INFORMATION: Any amino acid

<400> SEQUENCE: 17
```

| | | | | | | | | | | | | | | |
|---|---|---|---|---|---|---|---|---|---|---|---|---|---|---|
| Gly | Thr | Phe | Pro | Lys | Pro | Thr | Leu | Trp | Ala | Glu | Pro | Gly | Ser | Met | Ile |
| 1 | | | | 5 | | | | | 10 | | | | | 15 | |
| Ser | Lys | Gly | Ser | Pro | Val | Thr | Leu | Arg | Cys | Gln | Gly | Ser | Leu | Pro | Val |
| | | | 20 | | | | | 25 | | | | | 30 | | |
| Gln | Asp | Tyr | Arg | Leu | Gln | Arg | Glu | Lys | Lys | Thr | Ala | Ser | Trp | Val | Arg |
| | | | 35 | | | | | 40 | | | | | 45 | | |
| Arg | Ile | Gln | Gln | Glu | Leu | Val | Lys | Lys | Gly | Tyr | Phe | Pro | Ile | Ala | Ser |
| | 50 | | | | | 55 | | | | | 60 | | | | |
| Ile | Thr | Ser | Glu | His | Ala | Gly | Gln | Tyr | Arg | Cys | Gln | Tyr | Tyr | Ser | His |
| 65 | | | | | 70 | | | | | 75 | | | | | 80 |
| Ser | Trp | Trp | Ser | Glu | Pro | Ser | Asp | Pro | Leu | Glu | Leu | Val | Val | Thr | Gly |
| | | | | 85 | | | | | 90 | | | | | 95 | |
| Ala | Tyr | Ser | Lys | Pro | Thr | Leu | Ser | Ala | Leu | Pro | Ser | Pro | Val | Val | Ala |
| | | | 100 | | | | | 105 | | | | | 110 | | |
| Ser | Gly | Gly | Asn | Val | Thr | Leu | Gln | Cys | Asp | Ser | Gln | Val | Ala | Xaa | Gly |
| | | | 115 | | | | | 120 | | | | | 125 | | |
| Gly | Phe | Val | Leu | Cys | Lys | Glu | Gly | Glu | Asp | Glu | His | Pro | Gln | Cys | Leu |
| | | | 130 | | | | | 135 | | | | | 140 | | |
| Asn | Ser | Gln | Pro | His | Thr | Arg | Gly | Ser | Ser | Arg | Ala | Val | Phe | Ser | Val |
| 145 | | | | | 150 | | | | | 155 | | | | | 160 |
| Gly | Pro | Val | Ser | Pro | Ser | Arg | Arg | Trp | Ser | Tyr | Arg | Cys | Tyr | Gly | Tyr |
| | | | | 165 | | | | | 170 | | | | | 175 | |
| Asp | Ser | Arg | Ser | Pro | Tyr | Val | Trp | Ser | Leu | Pro | Ser | Asp | Leu | Leu | Glu |
| | | | 180 | | | | | 185 | | | | | 190 | | |
| Leu | Leu | Val | Pro | Gly | Val | Ser | Lys | Lys | Pro | Ser | Leu | Ser | Val | Gln | Pro |
| | | | | 195 | | | | | 200 | | | | | 205 | |
| Gly | Pro | Val | Val | Ala | Pro | Gly | Asp | Lys | Leu | Thr | Leu | Gln | Cys | Gly | Ser |
| | | | 210 | | | | | 215 | | | | | 220 | | |
| Asp | Ala | Gly | Tyr | Asn | Arg | Phe | Ala | Leu | Tyr | Lys | Glu | Gly | Glu | Arg | Asp |
| 225 | | | | | 230 | | | | | 235 | | | | | 240 |
| Phe | Leu | Gln | Arg | Pro | Gly | Arg | Gln | Pro | Gln | Ala | Gly | Leu | Ser | Gln | Ala |
| | | | | 245 | | | | | 250 | | | | | 255 | |
| Asn | Phe | Leu | Leu | Asp | Pro | Val | Arg | Arg | Ser | His | Gly | Gly | Gln | Tyr | Arg |
| | | | 260 | | | | | 265 | | | | | 270 | | |
| Cys | Ser | Gly | Ala | His | Asn | Leu | Ser | Ser | Glu | Trp | Ser | Ala | Pro | Ser | Asp |
| | | | 275 | | | | | 280 | | | | | 285 | | |
| Pro | Leu | Asp | Ile | Leu | Ile | Ala | Gly | Gln | Ile | Arg | Gly | Arg | Pro | Ser | Leu |
| | 290 | | | | | 295 | | | | | 300 | | | | |
| Leu | Val | Gln | Pro | Gly | Pro | Thr | Val | Val | Ser | Gly | Glu | Asn | Val | Thr | Leu |
| 305 | | | | | 310 | | | | | 315 | | | | | 320 |
| Leu | Cys | Gln | Ser | Ser | Trp | Gln | Phe | His | Val | Phe | Leu | Leu | Thr | Gln | Ala |
| | | | | 325 | | | | | 330 | | | | | 335 | |
| Gly | Ala | Ala | Asp | Ala | His | Leu | His | Leu | Arg | Ser | Met | Tyr | Lys | Tyr | Pro |
| | | | 340 | | | | | 345 | | | | | 350 | | |
| Lys | Tyr | Gln | Ala | Glu | Phe | Pro | Met | Ser | Pro | Val | Thr | Ser | Ala | His | Ala |
| | | | | 355 | | | | | 360 | | | | | 365 | |
| Gly | Thr | Tyr | Arg | Cys | Tyr | Gly | Ser | His | Ser | Ser | Asp | Ser | Tyr | Leu | Leu |
| | | | 370 | | | | | 375 | | | | | 380 | | |
| Ser | Ile | Pro | Ser | Asp | Pro | Leu | Glu | Leu | Val | Val | Ser | Gly | Pro | Ser | Gly |
| 385 | | | | | 390 | | | | | 395 | | | | | 400 |

```
Gly Pro Ser Ser Pro Thr Thr Gly Pro Thr Ser Thr Cys Gly Pro Glu
            405                 410                 415

Asp Gln Pro Leu Thr Pro Thr Gly Ser Asp Pro Gln Ser Gly Leu Gly
            420                 425                 430

Arg His Leu Gly Val
            435

<210> SEQ ID NO 18
<211> LENGTH: 88
<212> TYPE: PRT
<213> ORGANISM: Macaca mulatta

<400> SEQUENCE: 18

Pro Lys Pro Thr Leu Trp Ala Glu Pro Gly Ser Met Ile Ser Lys Gly
1               5                   10                  15

Ser Pro Val Thr Leu Arg Cys Gln Gly Ser Leu Pro Val Gln Asp Tyr
            20                  25                  30

Arg Leu Gln Arg Glu Lys Lys Thr Ala Ser Trp Val Arg Arg Ile Gln
        35                  40                  45

Gln Glu Leu Val Lys Lys Gly Tyr Phe Pro Ile Ala Ser Ile Thr Ser
    50                  55                  60

Glu His Ala Gly Gln Tyr Arg Cys Gln Tyr Tyr Ser His Ser Trp Trp
65                  70                  75                  80

Ser Glu Pro Ser Asp Pro Leu Glu
                85

<210> SEQ ID NO 19
<211> LENGTH: 106
<212> TYPE: PRT
<213> ORGANISM: Macaca mulatta
<220> FEATURE:
<221> NAME/KEY: MOD_RES
<222> LOCATION: (36)..(36)
<223> OTHER INFORMATION: Any amino acid

<400> SEQUENCE: 19

Leu Val Val Thr Gly Ala Tyr Ser Lys Pro Thr Leu Ser Ala Leu Pro
1               5                   10                  15

Ser Pro Val Val Ala Ser Gly Gly Asn Val Thr Leu Gln Cys Asp Ser
            20                  25                  30

Gln Val Ala Xaa Gly Gly Phe Val Leu Cys Lys Glu Gly Glu Asp Glu
        35                  40                  45

His Pro Gln Cys Leu Asn Ser Gln Pro His Thr Arg Gly Ser Ser Arg
    50                  55                  60

Ala Val Phe Ser Val Gly Pro Val Ser Pro Ser Arg Arg Trp Ser Tyr
65                  70                  75                  80

Arg Cys Tyr Gly Tyr Asp Ser Arg Ser Pro Tyr Val Trp Ser Leu Pro
                85                  90                  95

Ser Asp Leu Leu Glu Leu Leu Val Pro Gly
            100                 105

<210> SEQ ID NO 20
<211> LENGTH: 91
<212> TYPE: PRT
<213> ORGANISM: Macaca mulatta

<400> SEQUENCE: 20

Val Ser Lys Lys Pro Ser Leu Ser Val Gln Pro Gly Pro Val Val Ala
1               5                   10                  15
```

```
Pro Gly Asp Lys Leu Thr Leu Gln Cys Gly Ser Asp Ala Gly Tyr Asn
            20                  25                  30

Arg Phe Ala Leu Tyr Lys Glu Gly Glu Arg Asp Phe Leu Gln Arg Pro
        35                  40                  45

Gly Arg Gln Pro Gln Ala Gly Leu Ser Gln Ala Asn Phe Leu Leu Asp
50                  55                  60

Pro Val Arg Arg Ser His Gly Gly Gln Tyr Arg Cys Ser Gly Ala His
65                  70                  75                  80

Asn Leu Ser Ser Glu Trp Ser Ala Pro Ser Asp
                85                  90

<210> SEQ ID NO 21
<211> LENGTH: 97
<212> TYPE: PRT
<213> ORGANISM: Macaca mulatta

<400> SEQUENCE: 21

Pro Leu Asp Ile Leu Ile Ala Gly Gln Ile Arg Gly Arg Pro Ser Leu
1               5                   10                  15

Leu Val Gln Pro Gly Pro Thr Val Val Ser Gly Glu Asn Val Thr Leu
            20                  25                  30

Leu Cys Gln Ser Ser Trp Gln Phe His Val Phe Leu Leu Thr Gln Ala
        35                  40                  45

Gly Ala Ala Asp Ala His Leu His Leu Arg Ser Met Tyr Lys Tyr Pro
50                  55                  60

Lys Tyr Gln Ala Glu Phe Pro Met Ser Pro Val Thr Ser Ala His Ala
65                  70                  75                  80

Gly Thr Tyr Arg Cys Tyr Gly Ser His Ser Ser Asp Ser Tyr Leu Leu
                85                  90                  95

Ser

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Phe Ser Leu Thr Asn Tyr Gly Val Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Ile Trp Gly Asp Gly Ser Thr Asn Tyr His Ser Ala Leu Ile Ser
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 24

Pro Asn Trp Asp Thr Tyr Ala Met Asp Phe
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Asp Ile Ser Asn Phe Leu Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Thr Ser Lys Leu His Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Gly Asn Thr Leu Pro Pro Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Phe Ser Leu Thr Asn Tyr
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Gly Asp Gly Ser
1               5

<210> SEQ ID NO 30
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Trp Gly Asp Gly Ser Thr Asn
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Tyr Gly Val Ser
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asn Tyr Gly Val Ser
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Leu Gly Ile Ile Trp Gly Asp Gly Ser Thr Asn
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Lys Pro Asn Trp Asp Thr Tyr Ala Met Asp
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35
```

```
Ser Asn Phe Leu Asn Trp Tyr
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Leu Ile Tyr Cys Thr Ser Lys Leu His
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Gly Asn Thr Leu Pro Pro
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Ser Phe Thr Gly Tyr Tyr Met His
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Val Tyr Pro Asn Asn Gly Asp Thr Ser Tyr Asn Gln Lys Phe Lys
1               5                   10                  15

Val

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Thr Val Val Glu Ser Leu Phe Ala Tyr
1               5                   10

<210> SEQ ID NO 41
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 41

Arg Ala Ser Glu Ser Val Asp Asn Tyr Gly Asn Asn Phe Leu His
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Thr Ser Asn Leu Glu Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Ser Asn Glu Asp Pro Tyr Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Ser Phe Thr Gly Tyr
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Pro Asn Asn Gly Asp
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Val Tyr Pro Asn Asn Gly Asp Thr Ser
1               5                   10
```

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Tyr Tyr Met His
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Gly Tyr Tyr Met His
1               5

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Ile Gly Arg Val Tyr Pro Asn Asn Gly Asp Thr Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Arg Gly Ala Thr Val Val Glu Ser Leu Phe Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asn Tyr Gly Asn Asn Phe Leu His Trp Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Leu Ile Tyr Arg Thr Ser Asn Leu Glu
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Ser Asn Glu Asp Pro Tyr
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Tyr Thr Phe Thr Asn Tyr Gly Met Asn
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Ile Asn Thr Tyr Ile Gly Glu Pro Ile Tyr Ala Asp Asp Phe Lys
1               5                   10                  15

Gly

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp Tyr Asp Gly Tyr Ala Met Asp Tyr
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Ser Ser Gln Ser Leu Leu Tyr Ser Gly Asn Gln Lys Asn Tyr Leu
1               5                   10                  15

Ala

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ala Ser Thr Arg Glu Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln His Asp Ser Tyr Pro Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Tyr Thr Phe Thr Asn Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Thr Tyr Ile Gly Glu
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ile Asn Thr Tyr Ile Gly Glu Pro Ile
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Tyr Gly Met Asn
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Asn Tyr Gly Met Asn
1               5

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Met Gly Trp Ile Asn Thr Tyr Ile Gly Glu Pro Ile
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Arg Arg Ser Asp Tyr Asp Gly Tyr Ala Met Asp
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Tyr Ser Gly Asn Gln Lys Asn Tyr Leu Ala Trp Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Leu Ile Tyr Trp Ala Ser Thr Arg Glu
1               5                   10

<210> SEQ ID NO 69
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln His Asp Ser Tyr Pro
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Tyr Thr Phe Thr Asp Tyr Tyr Met Asn
1               5                   10

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Phe Asn Pro Asn Asn Gly Gly Thr Thr Tyr Asn Gln Lys Phe Glu
1               5                   10                  15

Gly

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Arg Phe Tyr Tyr Gly Ser Leu Tyr Ser Phe Asp Tyr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ala Ser Gly Asn Ile His Asn Tyr Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Asn Ala Lys Thr Leu Ala Asp
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln His Phe Trp Thr Ser Ile Thr
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Thr Phe Thr Asp Tyr
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Pro Asn Asn Gly Gly
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Phe Asn Pro Asn Asn Gly Gly Thr Thr
1               5                   10

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Tyr Tyr Met Asn
1               5

<210> SEQ ID NO 80
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 80

Thr Asp Tyr Tyr Met Asn
1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Ile Gly Asp Phe Asn Pro Asn Asn Gly Gly Thr Thr
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Arg Gly Arg Phe Tyr Tyr Gly Ser Leu Tyr Ser Phe Asp
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Asn Tyr Leu Ala Trp Tyr
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Leu Val Tyr Asn Ala Lys Thr Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln His Phe Trp Thr Ser Ile
1               5
```

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Phe Thr Phe Asn Thr Tyr Ala Met His
1               5                   10

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ile Arg Ser Lys Ser Ser Asn Tyr Ala Thr Tyr Tyr Ala Asp Ser
1               5                   10                  15

Val Lys Asp

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Gly Ile Tyr Tyr Tyr Gly Thr Met Tyr Tyr Tyr Ala Met Asp Tyr
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ala Ser Glu Ser Val Asp Tyr Tyr Gly Asn Ser Phe Met Tyr
1               5                   10                  15

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Ala Ser Asn Leu Glu Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 91

Gln Gln Asn Asn Glu Asp Pro Trp Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Phe Thr Phe Asn Thr Tyr
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ser Lys Ser Ser Asn Tyr Ala
1               5

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ile Arg Ser Lys Ser Ser Asn Tyr Ala Thr Tyr
1               5                   10

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Tyr Ala Met His
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Thr Tyr Ala Met His
1               5

<210> SEQ ID NO 97
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Val Ala Arg Ile Arg Ser Lys Ser Ser Asn Tyr Ala Thr Tyr
1               5                   10                  15

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Arg Asp Gly Ile Tyr Tyr Tyr Gly Thr Met Tyr Tyr Tyr Ala Met
1               5                   10                  15

Asp

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Tyr Tyr Gly Asn Ser Phe Met Tyr Trp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Leu Ile Tyr Phe Ala Ser Asn Leu Glu
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Asn Asn Glu Asp Pro Trp
1               5

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 102

Asp Gly Ile Tyr Tyr Tyr Asp Thr Met Tyr Tyr Ala Met Asp Tyr
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Glu Ser Val Asp Tyr Tyr Gly Asn Ser Phe Ile Tyr
1               5                   10                  15

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Arg Asp Gly Ile Tyr Tyr Tyr Asp Thr Met Tyr Tyr Ala Met
1               5                   10                  15

Asp

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Tyr Tyr Gly Asn Ser Phe Ile Tyr Trp Tyr
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Val Asn Pro Asn Asn Gly Gly Thr Ser Tyr Asn Gln Lys Phe Lys
1               5                   10                  15

Gly

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Glu Ile Tyr Phe Tyr Gly Thr Ile Tyr Tyr Ala Met Asp Tyr
1               5                   10                  15
```

```
<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Val Asn Pro Asn Asn Gly Gly Thr Ser
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Ile Gly Asn Val Asn Pro Asn Asn Gly Gly Thr Ser
1               5                   10

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Arg Arg Glu Ile Tyr Phe Tyr Gly Thr Ile Tyr Tyr Tyr Ala Met
1               5                   10                  15

Asp

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Tyr Thr Phe Thr Asp Tyr Tyr Ile Asn
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asn Val Asn Pro Asn Asp Gly Gly Thr Thr Tyr Asn Gln Lys Phe Lys
1               5                   10                  15

Gly

<210> SEQ ID NO 113
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 113

Asn Pro Asn Asp Gly Gly
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Val Asn Pro Asn Asp Gly Gly Thr Thr
1               5                   10

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Tyr Tyr Ile Asn
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Asp Tyr Tyr Ile Asn
1               5

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Ile Gly Asn Val Asn Pro Asn Asp Gly Gly Thr Thr
1               5                   10

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Phe Asn Pro Asn Asn Ala Gly Thr Thr Tyr Asn Gln Lys Phe Glu
1               5                   10                  15
```

Gly

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asn Pro Asn Asn Ala Gly
1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Phe Asn Pro Asn Asn Ala Gly Thr Thr
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Ile Gly Asp Phe Asn Pro Asn Asn Ala Gly Thr Thr
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Leu Ile Tyr Asn Ala Lys Thr Leu Ala
1               5                   10

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Arg Asp Gly Ile Tyr Tyr Tyr Asp Thr Met Tyr Tyr Ala Met
1               5                   10                  15

Asp

<210> SEQ ID NO 124
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 124

Trp Met Gly Asn Val Asn Pro Asn Asp Gly Gly Thr Thr
1               5                   10

<210> SEQ ID NO 125
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Ser Trp Val Arg Gln Pro Pro Gly Lys Gly Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Ala Asp Asp Thr Ala Thr Tyr Tyr Cys Ala
                85                  90                  95

Lys Pro Asn Trp Asp Thr Tyr Ala Met Asp Phe Trp Gly Gln Gly Thr
            100                 105                 110

Ser Val Thr Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Cys Thr Ser Lys Leu His Ser Gly Val Pro Ser Arg Phe Ser Gly
    50                  55                  60

Ser Gly Ser Glu Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Ile
            100                 105

<210> SEQ ID NO 127
<211> LENGTH: 120
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Val Tyr Pro Asn Asn Gly Asp Thr Ser Tyr Asn Gln Lys Phe
    50                  55                  60

Lys Val Lys Ala Ile Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Thr Val Val Glu Ser Leu Phe Ala Tyr Trp Gly Gln
            100                 105                 110

Gly Thr Leu Val Thr Val Ser Ala
        115                 120

<210> SEQ ID NO 128
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Asn Phe Leu His Trp Tyr Gln Gln Lys Pro Gly Gln Pro Pro
        35                  40                  45

Lys Leu Leu Ile Tyr Arg Thr Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Thr Lys Leu Glu Ile Lys
            100                 105                 110

<210> SEQ ID NO 129
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr

```
                    20                  25                  30
Gly Met Asn Trp Val Lys Gln Ala Pro Gly Lys Gly Leu Lys Trp Met
                35                  40                  45

Gly Trp Ile Asn Thr Tyr Ile Gly Glu Pro Ile Tyr Ala Asp Asp Phe
            50                  55                  60

Lys Gly Arg Phe Ala Phe Ser Leu Glu Thr Ser Ala Ser Thr Ala Tyr
 65                 70                  75                  80

Leu Gln Ile Asn Asn Leu Lys Asn Glu Asp Met Ala Thr Tyr Phe Cys
                85                  90                  95

Ala Arg Arg Ser Asp Tyr Asp Gly Tyr Ala Met Asp Tyr Trp Gly Gln
            100                 105                 110

Gly Thr Ser Val Thr Val Ser Ser
            115                 120

<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Ser Gln Ser Pro Ser Ser Leu Ala Val Ser Val Gly
 1               5                  10                  15

Glu Arg Val Thr Met Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                 55                  60

Pro Asp Arg Phe Thr Gly Ser Gly Ser Gly Thr Asp Phe Thr Leu Thr
 65                 70                  75                  80

Ile Ser Ser Val Lys Ala Glu Asp Leu Ala Val Tyr Tyr Cys Gln Gln
                85                  90                  95

His Asp Ser Tyr Pro Thr Phe Gly Gly Gly Ser Arg Leu Glu Ile Lys
            100                 105                 110

<210> SEQ ID NO 131
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Phe Asn Pro Asn Gly Gly Thr Thr Tyr Asn Gln Lys Phe
 50                 55                  60

Glu Gly Lys Ala Thr Leu Thr Val Asp Lys Ser Ser Asn Thr Ala Tyr
 65                 70                  75                  80

Met Asp Leu Arg Ser Leu Thr Ser Glu Asp Ser Ala Val Tyr Tyr Cys
```

```
                    85                  90                  95

Ala Arg Gly Arg Phe Tyr Tyr Gly Ser Leu Tyr Ser Phe Asp Tyr Trp
                100                 105                 110

Gly Gln Gly Thr Thr Leu Thr Val Ser Ser
            115                 120

<210> SEQ ID NO 132
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro His Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Asn Leu Gln Pro
65                  70                  75                  80

Glu Asp Phe Gly Ser Tyr Tyr Cys Gln His Phe Trp Thr Ser Ile Thr
                85                  90                  95

Phe Gly Ala Gly Thr Lys Leu Asp Leu Lys
            100                 105

<210> SEQ ID NO 133
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Arg Leu Glu Trp Ile
            35                  40                  45

Gly Asp Phe Asn Pro Asn Asn Ala Gly Thr Thr Tyr Asn Gln Lys Phe
        50                  55                  60

Glu Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Phe Tyr Tyr Gly Ser Leu Tyr Ser Phe Asp Tyr Trp
                100                 105                 110

Gly Gln Gly Thr Leu Val Thr Val Ser Ser
            115                 120

<210> SEQ ID NO 134
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Thr Ser Ile Thr
                85                  90                  95

Phe Gly Pro Gly Thr Lys Val Asp Ile Lys
            100                 105

<210> SEQ ID NO 135
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Gly Ile Tyr Tyr Tyr Gly Thr Met Tyr Tyr Tyr
            100                 105                 110

Ala Met Asp Tyr Trp Gly Gln Gly Thr Ser Val Thr Val Ser Ser
        115                 120                 125

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Asn Ser Phe Met Tyr Trp Tyr Gln Gln Lys Pro Gly Gln Pro Pro
            35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Ala Asp Ala Ala Ser Tyr Tyr Cys Gln Gln Asn Asn
                85                  90                  95

Glu Asp Pro Trp Thr Phe Gly Gly Gly Thr Lys Leu Glu Ile Lys
            100                 105                 110

<210> SEQ ID NO 137
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Gly Ile Tyr Tyr Tyr Asp Thr Met Tyr Tyr Tyr
            100                 105                 110

Ala Met Asp Tyr Trp Gly Gln Gly Thr Ser Val Thr Val Ser Ser
        115                 120                 125

<210> SEQ ID NO 138
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Asn Ser Phe Ile Tyr Trp Tyr Gln Gln Lys Pro Gly Gln Pro Pro
        35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Ala Asp Ala Ala Ser Tyr Tyr Cys Gln Gln Asn Asn
                85                  90                  95

Glu Asp Pro Trp Thr Phe Gly Gly Gly Thr Lys Leu Glu Ile Lys
                100                 105                 110

<210> SEQ ID NO 139
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
    50                  55                  60

Ser Val Lys Asp Arg Phe Thr Ile Ser Arg Asp Asp Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Ile Tyr Tyr Tyr Asp Thr Met Tyr Tyr Tyr
            100                 105                 110

Ala Met Asp Tyr Trp Gly Gln Gly Thr Leu Val Thr Val Ser Ser
        115                 120                 125

<210> SEQ ID NO 140
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asn Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Tyr
            20                  25                  30

Gly Asn Ser Phe Ile Tyr Trp Tyr Gln Gln Lys Pro Gly Gln Pro Pro
        35                  40                  45

Lys Leu Leu Ile Tyr Phe Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Trp Thr Phe Gly Gly Gly Thr Lys Val Glu Ile Lys
            100                 105                 110

<210> SEQ ID NO 141
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asn Val Asn Pro Asn Asn Gly Gly Thr Ser Tyr Asn Gln Lys Phe
50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Arg Arg Glu Ile Tyr Phe Tyr Gly Thr Ile Tyr Tyr Tyr Ala Met
            100                 105                 110

Asp Tyr Trp Gly Gln Gly Thr Ser Val Thr Val Ser Ser
            115                 120                 125

<210> SEQ ID NO 142
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Tyr
            20                  25                  30

Gly Asn Ser Phe Met Tyr Trp Tyr Gln Gln Lys Pro Gly Arg Pro Pro
        35                  40                  45

Asn Leu Leu Ile Tyr Phe Ala Ser Asn Leu Glu Ser Gly Val Pro Ala
50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
            85                  90                  95

Glu Asp Pro Trp Thr Phe Gly Gly Gly Thr Lys Leu Glu Ile Lys
            100                 105                 110

<210> SEQ ID NO 143
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ser His Gly Lys Ser Leu Gln Trp Ile
        35                  40                  45

Gly Asn Val Asn Pro Asn Asp Gly Gly Thr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Glu Ile Tyr Phe Tyr Gly Thr Ile Tyr Tyr Tyr Ala Met
                100                 105                 110

Asp Tyr Trp Gly Gln Gly Thr Ser Val Thr Val Ser Ser
            115                 120                 125

<210> SEQ ID NO 144
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Asn Trp Val Arg Gln Ala Pro Gly Gln Gly Leu Glu Trp Met
            35                  40                  45

Gly Asn Val Asn Pro Asn Asp Gly Gly Thr Thr Tyr Asn Gln Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Glu Ile Tyr Phe Tyr Gly Thr Ile Tyr Tyr Tyr Ala Met
                100                 105                 110

Asp Tyr Trp Gly Gln Gly Thr Leu Val Thr Val Ser Ser
            115                 120                 125

<210> SEQ ID NO 145
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Asp Tyr Tyr
                20                  25                  30

Gly Asn Ser Phe Met Tyr Trp Tyr Gln Gln Lys Pro Gly Lys Ala Pro
            35                  40                  45

Lys Leu Leu Ile Tyr Phe Ala Ser Asn Leu Glu Ser Gly Val Pro Ser
50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

```
Glu Asp Pro Trp Thr Phe Gly Gly Gly Thr Lys Val Glu Ile Lys
            100                 105                 110
```

<210> SEQ ID NO 146
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Met Asp Met Arg Val Pro Ala Gln Leu Leu Gly Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Asp Tyr Tyr Met Asn Trp Val Arg Gln Ala Pro Gly
50                  55                  60

Gln Arg Leu Glu Trp Ile Gly Asp Phe Asn Pro Asn Asn Ala Gly Thr
65                  70                  75                  80

Thr Tyr Asn Gln Lys Phe Glu Gly Arg Val Thr Ile Thr Val Asp Lys
                85                  90                  95

Ser Ala Ser Thr Ala Tyr Met Glu Leu Ser Ser Leu Arg Ser Glu Asp
            100                 105                 110

Thr Ala Val Tyr Tyr Cys Ala Arg Gly Arg Phe Tyr Tyr Gly Ser Leu
            115                 120                 125

Tyr Ser Phe Asp Tyr Trp Gly Gln Gly Thr Leu Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Gly Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350
```

```
Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470
```

<210> SEQ ID NO 147
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Met Asp Met Arg Val Pro Ala Gln Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gly Asn Ile His Asn Tyr Leu Ala Trp Tyr Gln Lys Pro Gly Lys
    50                  55                  60

Ala Pro Lys Leu Leu Ile Tyr Asn Ala Lys Thr Leu Ala Asp Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln His
            100                 105                 110

Phe Trp Thr Ser Ile Thr Phe Gly Pro Gly Thr Lys Val Asp Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
                225                 230                 235
```

```
                    225                 230                 235
```

<210> SEQ ID NO 148
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Ile
        35                  40                  45

Gly Asp Phe Asn Pro Asn Asn Ala Gly Thr Thr Tyr Asn Gln Lys Phe
    50                  55                  60

Glu Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Phe Tyr Tyr Gly Ser Leu Tyr Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 149
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Thr Ser Ile Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 150
<211> LENGTH: 479
<212> TYPE: PRT
<213> ORGANISM: Artificial Sequence
```

<220> FEATURE:
<223> OTHER INFORMATION: Description of Artificial Sequence: Synthetic
       polypeptide

<400> SEQUENCE: 150

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asn Thr Tyr Ala Met His Trp Val Arg Gln Ala Pro Gly
    50                  55                  60

Lys Gly Leu Glu Trp Val Ala Arg Ile Arg Ser Lys Ser Ser Asn Tyr
65                  70                  75                  80

Ala Thr Tyr Tyr Ala Asp Ser Val Lys Asp Arg Phe Thr Ile Ser Arg
                85                  90                  95

Asp Asp Ala Lys Asn Ser Leu Tyr Leu Gln Met Asn Ser Leu Arg Ala
            100                 105                 110

Glu Asp Thr Ala Val Tyr Tyr Cys Ala Arg Asp Gly Ile Tyr Tyr Tyr
        115                 120                 125

Asp Thr Met Tyr Tyr Ala Met Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Gly Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
```

```
                385                 390                 395                 400
Val Lys Gly Phe Tyr Pro Ser Asp Ile Ala Val Glu Trp Glu Ser Asn
                    405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys
465                 470                 475

<210> SEQ ID NO 151
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Asp Met Arg Val Pro Ala Gln Leu Leu Gly Leu Leu Leu Leu Trp
1               5                   10                  15

Leu Arg Gly Ala Arg Cys Asn Ile Val Leu Thr Gln Ser Pro Asp Ser
            20                  25                  30

Leu Ala Val Ser Leu Gly Glu Arg Ala Thr Ile Asn Cys Arg Ala Ser
        35                  40                  45

Glu Ser Val Asp Tyr Tyr Gly Asn Ser Phe Ile Tyr Trp Tyr Gln Gln
    50                  55                  60

Lys Pro Gly Gln Pro Pro Lys Leu Leu Ile Tyr Phe Ala Ser Asn Leu
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Asn Asn Glu Asp Pro Trp Thr Phe Gly Gly Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 152
<211> LENGTH: 457
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 152

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
    50                  55                  60

Ser Val Lys Asp Arg Phe Thr Ile Ser Arg Asp Asp Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Gly Ile Tyr Tyr Tyr Asp Thr Met Tyr Tyr Tyr
            100                 105                 110

Ala Met Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Gly Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400
```

```
Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 153
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asn Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Tyr
            20                  25                  30

Gly Asn Ser Phe Ile Tyr Trp Tyr Gln Gln Lys Pro Gly Gln Pro Pro
        35                  40                  45

Lys Leu Leu Ile Tyr Phe Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 154
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Asp Met Arg Val Pro Ala Gln Leu Leu Gly Leu Leu Leu Leu Trp
1               5                   10                  15
```

```
Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Asp Tyr Tyr Ile Asn Trp Val Arg Gln Ala Pro Gly
    50                  55                  60

Gln Gly Leu Glu Trp Met Gly Asn Val Asn Pro Asn Asp Gly Gly Thr
65                  70                  75                  80

Thr Tyr Asn Gln Lys Phe Lys Gly Arg Val Thr Met Thr Thr Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Arg Arg Glu Ile Tyr Phe Tyr Gly Thr
        115                 120                 125

Ile Tyr Tyr Tyr Ala Met Asp Tyr Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Gly Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430
```

```
Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys
465                 470                 475

<210> SEQ ID NO 155
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Asp Met Arg Val Pro Ala Gln Leu Leu Gly Leu Leu Leu Leu Trp
1               5                   10                  15

Leu Arg Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Glu Ser Val Asp Tyr Tyr Gly Asn Ser Phe Met Tyr Trp Tyr Gln Gln
    50                  55                  60

Lys Pro Gly Lys Ala Pro Lys Leu Leu Ile Tyr Phe Ala Ser Asn Leu
65                  70                  75                  80

Glu Ser Gly Val Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

Tyr Cys Gln Gln Asn Asn Glu Asp Pro Trp Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 156
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
         35                  40                  45

Gly Asn Val Asn Pro Asn Asp Gly Thr Thr Tyr Asn Gln Lys Phe
     50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                 85                  90                  95

Ala Arg Arg Glu Ile Tyr Phe Tyr Gly Thr Ile Tyr Tyr Tyr Ala Met
             100                 105                 110

Asp Tyr Trp Gly Gln Gly Thr Leu Val Thr Val Ser Ser Ala Ser Thr
         115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
             165                 170                 175

Thr Phe Pro Ala Val Leu Gln Ser Ser Gly Leu Tyr Ser Leu Ser Ser
         180                 185                 190

Val Val Thr Val Pro Ser Ser Ser Leu Gly Thr Gln Thr Tyr Ile Cys
         195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
             245                 250                 255

Asp Thr Leu Met Ile Ser Arg Thr Pro Glu Val Thr Cys Val Val Val
         260                 265                 270

Asp Val Ser His Glu Asp Pro Glu Val Lys Phe Asn Trp Tyr Val Asp
         275                 280                 285

Gly Val Glu Val His Asn Ala Lys Thr Lys Pro Arg Glu Glu Gln Tyr
290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
             325                 330                 335

Pro Ala Pro Ile Glu Lys Thr Ile Ser Lys Ala Lys Gly Gln Pro Arg
         340                 345                 350

Glu Pro Gln Val Tyr Thr Leu Pro Pro Ser Arg Glu Glu Met Thr Lys
         355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
             405                 410                 415

Lys Leu Thr Val Asp Lys Ser Arg Trp Gln Gln Gly Asn Val Phe Ser
         420                 425                 430

Cys Ser Val Met His Glu Ala Leu His Asn His Tyr Thr Gln Lys Ser

```
                435                 440                 445
Leu Ser Leu Ser Pro Gly Lys
    450                 455

<210> SEQ ID NO 157
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Ser Val Asp Tyr Tyr
            20                  25                  30

Gly Asn Ser Phe Met Tyr Trp Tyr Gln Gln Lys Pro Gly Lys Ala Pro
        35                  40                  45

Lys Leu Leu Ile Tyr Phe Ala Ser Asn Leu Glu Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 158
<211> LENGTH: 330
<212> TYPE: PRT
<213> ORGANISM: Homo sapiens

<400> SEQUENCE: 158

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 159
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 160
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 161
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 162
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Gly Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 163
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

Ala Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 165
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 166
<211> LENGTH: 651
<212> TYPE: PRT
<213> ORGANISM: Macaca fascicularis

<400> SEQUENCE: 166

Met Thr Pro Ile Leu Met Val Leu Ile Cys Leu Gly Leu Ser Leu Gly
  1               5                  10                  15

Pro Arg Thr His Val Gln Ala Gly Ile Leu Pro Lys Pro Thr Leu Trp
                 20                  25                  30

Ala Glu Pro Gly Ser Met Ile Ser Glu Gly Ser Pro Val Thr Leu Arg
             35                  40                  45

Cys Gln Gly Ser Leu Gln Val Gln Glu Tyr Arg Leu Tyr Arg Glu Lys
         50                  55                  60

Lys Pro Ala Ser Trp Val Arg Arg Ile Gln Gln Glu Leu Val Lys Lys
 65                  70                  75                  80

Gly Tyr Phe Ala Ile Gly Phe Ile Thr Trp Glu His Thr Gly Gln Tyr
                 85                  90                  95

Arg Cys Gln Tyr Tyr Ser His Ser Trp Trp Ser Glu Pro Ser Asp Pro
                100                 105                 110

Leu Glu Leu Val Val Thr Gly Ala Tyr Ser Lys Pro Thr Leu Ser Ala
            115                 120                 125

Leu Pro Ser Pro Val Val Ala Ser Gly Gly Asn Val Thr Leu Gln Cys
130                 135                 140

Asp Ser Gln Val Ala Phe Asp Ser Phe Thr Leu Cys Lys Glu Gly Glu
145                 150                 155                 160

Asp Glu His Pro Gln Arg Leu Asn Cys Gln Ser His Ala Arg Gly Trp
                165                 170                 175

Ser Trp Ala Val Phe Ser Val Gly Pro Val Ser Pro Ser Arg Arg Trp
            180                 185                 190

Ser Tyr Arg Cys Tyr Gly Tyr Ile Ser Ser Ala Pro Asn Val Trp Ser
                195                 200                 205

Leu Pro Ser Asp Leu Leu Glu Leu Leu Val Pro Gly Val Ser Lys Lys
            210                 215                 220

Pro Ser Leu Ser Val Gln Pro Gly Pro Val Val Ala Pro Gly Asp Lys
225                 230                 235                 240

Leu Thr Leu Gln Cys Gly Ser Asp Ala Gly Tyr Asp Arg Phe Ala Leu
                245                 250                 255

Tyr Lys Glu Gly Glu Gly Asp Phe Leu Gln Arg Pro Val Arg Gln Pro
                260                 265                 270

Gln Ala Gly Leu Ser Gln Ala Asn Phe Leu Leu Gly Pro Val Ser Arg
            275                 280                 285

Ser His Gly Gly Gln Tyr Arg Cys Ser Gly Ala His Asn Leu Ser Ser
            290                 295                 300

Glu Trp Ser Ala Pro Ser Asp Pro Leu Asp Ile Leu Ile Ala Gly Gln
305                 310                 315                 320

Ile Arg Gly Arg Pro Phe Leu Ser Val Gln Pro Gly Pro Lys Val Val
```

```
            325                 330                 335
Ser Gly Glu Asn Val Thr Leu Leu Cys Gln Ser Ser Trp Gln Phe His
            340                 345                 350

Ala Phe Leu Leu Thr Gln Ala Gly Ala Ala Asp Ala His Leu His Leu
            355                 360                 365

Arg Ser Met Tyr Lys Tyr Pro Lys Tyr Gln Ala Glu Phe Pro Met Ser
            370                 375                 380

Pro Val Thr Ser Ala His Ala Gly Thr Tyr Arg Cys Tyr Gly Ser Arg
385                 390                 395                 400

Ser Ser Asn Pro Tyr Leu Leu Ser Val Pro Ser Asp Pro Leu Glu Leu
            405                 410                 415

Val Val Ser Gly Pro Ser Gly Gly Pro Ser Ser Pro Thr Thr Gly Pro
            420                 425                 430

Thr Ser Thr Cys Ala Gly Pro Glu Asp Gln Pro Leu Thr Pro Thr Gly
            435                 440                 445

Ser Asp Pro Gln Ser Gly Leu Gly Arg His Leu Gly Val Val Thr Gly
            450                 455                 460

Ile Leu Val Ala Phe Val Leu Leu Phe Leu Leu Leu Leu Leu Leu Phe
465                 470                 475                 480

Leu Val Leu Arg His Gln Arg Gln Gly Lys His Trp Thr Ser Ala Gln
            485                 490                 495

Arg Lys Ala Asp Phe Gln His Pro Ala Gly Ala Val Glu Pro Glu Pro
            500                 505                 510

Arg Asp Arg Gly Leu Gln Arg Arg Ser Ser Pro Ala Ala Asp Thr Gln
            515                 520                 525

Glu Glu Asn Leu Tyr Ala Ala Val Lys Asp Thr Gln Pro Glu Asp Gly
            530                 535                 540

Val Glu Leu Asp Ser Arg Gln Arg Pro His Asp Glu Asp Pro Gln Ala
545                 550                 555                 560

Val Thr Tyr Ala Arg Val Lys His Ser Arg Pro Arg Arg Glu Met Ala
            565                 570                 575

Ser Pro Pro Ser Pro Leu Ser Glu Glu Phe Leu Asp Thr Lys Asp Thr
            580                 585                 590

Gln Ala Glu Glu Asp Arg Gln Met Asp Thr Glu Ala Ala Ala Ser Glu
            595                 600                 605

Asp Pro Gln Asp Val Thr Tyr Ala Gln Leu Gln Ser Leu Thr Leu Arg
            610                 615                 620

Arg Glu Thr Thr Glu Pro Pro Ser Gln Glu Arg Ala Pro Pro Val
625                 630                 635                 640

Glu Ser Ser Ile Tyr Ala Thr Leu Thr Ile His
            645                 650

<210> SEQ ID NO 167
<211> LENGTH: 628
<212> TYPE: PRT
<213> ORGANISM: Macaca fascicularis

<400> SEQUENCE: 167

Gly Ile Leu Pro Lys Pro Thr Leu Trp Ala Glu Pro Gly Ser Met Ile
1               5                   10                  15

Ser Glu Gly Ser Pro Val Thr Leu Arg Cys Gln Gly Ser Leu Gln Val
            20                  25                  30

Gln Glu Tyr Arg Leu Tyr Arg Glu Lys Lys Pro Ala Ser Trp Val Arg
            35                  40                  45
```

```
Arg Ile Gln Gln Glu Leu Val Lys Lys Gly Tyr Phe Ala Ile Gly Phe
 50                  55                  60

Ile Thr Trp Glu His Thr Gly Gln Tyr Arg Cys Gln Tyr Tyr Ser His
 65                  70                  75                  80

Ser Trp Trp Ser Glu Pro Ser Asp Pro Leu Glu Leu Val Val Thr Gly
                     85                  90                  95

Ala Tyr Ser Lys Pro Thr Leu Ser Ala Leu Pro Ser Pro Val Val Ala
                100                 105                 110

Ser Gly Gly Asn Val Thr Leu Gln Cys Asp Ser Gln Val Ala Phe Asp
                115                 120                 125

Ser Phe Thr Leu Cys Lys Glu Gly Glu Asp Glu His Pro Gln Arg Leu
130                 135                 140

Asn Cys Gln Ser His Ala Arg Gly Trp Ser Trp Ala Val Phe Ser Val
145                 150                 155                 160

Gly Pro Val Ser Pro Ser Arg Arg Trp Ser Tyr Arg Cys Tyr Gly Tyr
                165                 170                 175

Ile Ser Ser Ala Pro Asn Val Trp Ser Leu Pro Ser Asp Leu Leu Glu
                180                 185                 190

Leu Leu Val Pro Gly Val Ser Lys Lys Pro Ser Leu Ser Val Gln Pro
                195                 200                 205

Gly Pro Val Val Ala Pro Gly Asp Lys Leu Thr Leu Gln Cys Gly Ser
210                 215                 220

Asp Ala Gly Tyr Asp Arg Phe Ala Leu Tyr Lys Glu Gly Glu Gly Asp
225                 230                 235                 240

Phe Leu Gln Arg Pro Val Arg Gln Pro Gln Ala Gly Leu Ser Gln Ala
                245                 250                 255

Asn Phe Leu Leu Gly Pro Val Ser Arg Ser His Gly Gly Gln Tyr Arg
                260                 265                 270

Cys Ser Gly Ala His Asn Leu Ser Ser Glu Trp Ser Ala Pro Ser Asp
                275                 280                 285

Pro Leu Asp Ile Leu Ile Ala Gly Gln Ile Arg Gly Arg Pro Phe Leu
                290                 295                 300

Ser Val Gln Pro Gly Pro Lys Val Val Ser Gly Glu Asn Val Thr Leu
305                 310                 315                 320

Leu Cys Gln Ser Ser Trp Gln Phe His Ala Phe Leu Leu Thr Gln Ala
                325                 330                 335

Gly Ala Ala Asp Ala His Leu His Leu Arg Ser Met Tyr Lys Tyr Pro
                340                 345                 350

Lys Tyr Gln Ala Glu Phe Pro Met Ser Pro Val Thr Ser Ala His Ala
                355                 360                 365

Gly Thr Tyr Arg Cys Tyr Gly Ser Arg Ser Ser Asn Pro Tyr Leu Leu
                370                 375                 380

Ser Val Pro Ser Asp Pro Leu Glu Leu Val Val Ser Gly Pro Ser Gly
385                 390                 395                 400

Gly Pro Ser Ser Pro Thr Thr Gly Pro Thr Ser Thr Cys Ala Gly Pro
                405                 410                 415

Glu Asp Gln Pro Leu Thr Pro Thr Gly Ser Asp Pro Gln Ser Gly Leu
                420                 425                 430

Gly Arg His Leu Gly Val Val Thr Gly Ile Leu Val Ala Phe Val Leu
                435                 440                 445

Leu Leu Phe Leu Leu Leu Leu Phe Leu Val Leu Arg His Gln Arg
450                 455                 460

Gln Gly Lys His Trp Thr Ser Ala Gln Arg Lys Ala Asp Phe Gln His
```

```
                465                 470                 475                 480
        Pro Ala Gly Ala Val Glu Pro Glu Pro Arg Asp Arg Gly Leu Gln Arg
                        485                 490                 495

Arg Ser Ser Pro Ala Ala Asp Thr Gln Glu Glu Asn Leu Tyr Ala Ala
                        500                 505                 510

Val Lys Asp Thr Gln Pro Glu Asp Gly Val Glu Leu Asp Ser Arg Gln
                        515                 520                 525

Arg Pro His Asp Glu Asp Pro Gln Ala Val Thr Tyr Ala Arg Val Lys
                        530                 535                 540

His Ser Arg Pro Arg Arg Glu Met Ala Ser Pro Pro Ser Pro Leu Ser
        545                 550                 555                 560

Glu Glu Phe Leu Asp Thr Lys Asp Thr Gln Ala Glu Asp Arg Gln
                        565                 570                 575

Met Asp Thr Glu Ala Ala Ala Ser Glu Asp Pro Gln Asp Val Thr Tyr
                        580                 585                 590

Ala Gln Leu Gln Ser Leu Thr Leu Arg Arg Glu Thr Thr Glu Pro Pro
                        595                 600                 605

Pro Ser Gln Glu Arg Ala Pro Pro Val Glu Ser Ser Ile Tyr Ala Thr
                        610                 615                 620

Leu Thr Ile His
        625

<210> SEQ ID NO 168
<211> LENGTH: 438
<212> TYPE: PRT
<213> ORGANISM: Macaca fascicularis

<400> SEQUENCE: 168

Gly Ile Leu Pro Lys Pro Thr Leu Trp Ala Glu Pro Gly Ser Met Ile
        1               5                   10                  15

Ser Glu Gly Ser Pro Val Thr Leu Arg Cys Gln Gly Ser Leu Gln Val
                        20                  25                  30

Gln Glu Tyr Arg Leu Tyr Arg Glu Lys Lys Pro Ala Ser Trp Val Arg
                        35                  40                  45

Arg Ile Gln Gln Glu Leu Val Lys Lys Gly Tyr Phe Ala Ile Gly Phe
                50                  55                  60

Ile Thr Trp Glu His Thr Gly Gln Tyr Arg Cys Gln Tyr Tyr Ser His
        65                  70                  75                  80

Ser Trp Trp Ser Glu Pro Ser Asp Pro Leu Glu Leu Val Val Thr Gly
                        85                  90                  95

Ala Tyr Ser Lys Pro Thr Leu Ser Ala Leu Pro Ser Pro Val Val Ala
                        100                 105                 110

Ser Gly Gly Asn Val Thr Leu Gln Cys Asp Ser Gln Val Ala Phe Asp
                        115                 120                 125

Ser Phe Thr Leu Cys Lys Glu Gly Glu Asp Glu His Pro Gln Arg Leu
                        130                 135                 140

Asn Cys Gln Ser His Ala Arg Gly Trp Ser Trp Ala Val Phe Ser Val
        145                 150                 155                 160

Gly Pro Val Ser Pro Ser Arg Arg Trp Ser Tyr Arg Cys Tyr Gly Tyr
                        165                 170                 175

Ile Ser Ser Ala Pro Asn Val Trp Ser Leu Pro Ser Asp Leu Leu Glu
                        180                 185                 190

Leu Leu Val Pro Gly Val Ser Lys Lys Pro Ser Leu Ser Val Gln Pro
                        195                 200                 205
```

Gly Pro Val Val Ala Pro Gly Asp Lys Leu Thr Leu Gln Cys Gly Ser
210                 215                 220

Asp Ala Gly Tyr Asp Arg Phe Ala Leu Tyr Lys Glu Gly Glu Gly Asp
225                 230                 235                 240

Phe Leu Gln Arg Pro Val Arg Gln Pro Gln Ala Gly Leu Ser Gln Ala
            245                 250                 255

Asn Phe Leu Leu Gly Pro Val Ser Arg Ser His Gly Gly Gln Tyr Arg
        260                 265                 270

Cys Ser Gly Ala His Asn Leu Ser Ser Glu Trp Ser Ala Pro Ser Asp
    275                 280                 285

Pro Leu Asp Ile Leu Ile Ala Gly Gln Ile Arg Gly Arg Pro Phe Leu
290                 295                 300

Ser Val Gln Pro Gly Pro Lys Val Val Ser Gly Glu Asn Val Thr Leu
305                 310                 315                 320

Leu Cys Gln Ser Ser Trp Gln Phe His Ala Phe Leu Leu Thr Gln Ala
            325                 330                 335

Gly Ala Ala Asp Ala His Leu His Leu Arg Ser Met Tyr Lys Tyr Pro
        340                 345                 350

Lys Tyr Gln Ala Glu Phe Pro Met Ser Pro Val Thr Ser Ala His Ala
    355                 360                 365

Gly Thr Tyr Arg Cys Tyr Gly Ser Arg Ser Ser Asn Pro Tyr Leu Leu
370                 375                 380

Ser Val Pro Ser Asp Pro Leu Glu Leu Val Val Ser Gly Pro Ser Gly
385                 390                 395                 400

Gly Pro Ser Ser Pro Thr Thr Gly Pro Thr Ser Thr Cys Ala Gly Pro
            405                 410                 415

Glu Asp Gln Pro Leu Thr Pro Thr Gly Ser Asp Pro Gln Ser Gly Leu
        420                 425                 430

Gly Arg His Leu Gly Val
        435

<210> SEQ ID NO 169
<211> LENGTH: 88
<212> TYPE: PRT
<213> ORGANISM: Macaca fascicularis

<400> SEQUENCE: 169

Pro Lys Pro Thr Leu Trp Ala Glu Pro Gly Ser Met Ile Ser Glu Gly
1               5                   10                  15

Ser Pro Val Thr Leu Arg Cys Gln Gly Ser Leu Gln Val Gln Glu Tyr
            20                  25                  30

Arg Leu Tyr Arg Glu Lys Lys Pro Ala Ser Trp Val Arg Arg Ile Gln
        35                  40                  45

Gln Glu Leu Val Lys Lys Gly Tyr Phe Ala Ile Gly Phe Ile Thr Trp
    50                  55                  60

Glu His Thr Gly Gln Tyr Arg Cys Gln Tyr Tyr Ser His Ser Trp Trp
65                  70                  75                  80

Ser Glu Pro Ser Asp Pro Leu Glu
                85

<210> SEQ ID NO 170
<211> LENGTH: 106
<212> TYPE: PRT
<213> ORGANISM: Macaca fascicularis

<400> SEQUENCE: 170

```
Leu Val Val Thr Gly Ala Tyr Ser Lys Pro Thr Leu Ser Ala Leu Pro
1               5                   10                  15

Ser Pro Val Ala Ser Gly Gly Asn Val Thr Leu Gln Cys Asp Ser
            20                  25                  30

Gln Val Ala Phe Asp Ser Phe Thr Leu Cys Lys Glu Gly Glu Asp Glu
                35                  40                  45

His Pro Gln Arg Leu Asn Cys Gln Ser His Ala Arg Gly Trp Ser Trp
    50                  55                  60

Ala Val Phe Ser Val Gly Pro Val Ser Pro Arg Arg Trp Ser Tyr
65                  70                  75                  80

Arg Cys Tyr Gly Tyr Ile Ser Ser Ala Pro Asn Val Trp Ser Leu Pro
                85                  90                  95

Ser Asp Leu Leu Glu Leu Leu Val Pro Gly
            100                 105
```

<210> SEQ ID NO 171
<211> LENGTH: 91
<212> TYPE: PRT
<213> ORGANISM: Macaca fascicularis

<400> SEQUENCE: 171

```
Val Ser Lys Lys Pro Ser Leu Ser Val Gln Pro Gly Pro Val Val Ala
1               5                   10                  15

Pro Gly Asp Lys Leu Thr Leu Gln Cys Gly Ser Asp Ala Gly Tyr Asp
            20                  25                  30

Arg Phe Ala Leu Tyr Lys Glu Gly Glu Gly Asp Phe Leu Gln Arg Pro
                35                  40                  45

Val Arg Gln Pro Gln Ala Gly Leu Ser Gln Ala Asn Phe Leu Leu Gly
    50                  55                  60

Pro Val Ser Arg Ser His Gly Gly Gln Tyr Arg Cys Ser Gly Ala His
65                  70                  75                  80

Asn Leu Ser Ser Glu Trp Ser Ala Pro Ser Asp
                85                  90
```

<210> SEQ ID NO 172
<211> LENGTH: 97
<212> TYPE: PRT
<213> ORGANISM: Macaca fascicularis

<400> SEQUENCE: 172

```
Pro Leu Asp Ile Leu Ile Ala Gly Gln Ile Arg Gly Arg Pro Phe Leu
1               5                   10                  15

Ser Val Gln Pro Gly Pro Lys Val Val Ser Gly Glu Asn Val Thr Leu
            20                  25                  30

Leu Cys Gln Ser Ser Trp Gln Phe His Ala Phe Leu Leu Thr Gln Ala
            35                  40                  45

Gly Ala Ala Asp Ala His Leu His Leu Arg Ser Met Tyr Lys Tyr Pro
50                  55                  60

Lys Tyr Gln Ala Glu Phe Pro Met Ser Pro Val Thr Ser Ala His Ala
65                  70                  75                  80

Gly Thr Tyr Arg Cys Tyr Gly Ser Arg Ser Ser Asn Pro Tyr Leu Leu
                85                  90                  95

Ser
```

<210> SEQ ID NO 173
<211> LENGTH: 6
<212> TYPE: PRT

```
<213> ORGANISM: Artificial Sequence
<220> FEATURE:
<223> OTHER INFORMATION: Description of Artificial Sequence: Synthetic
      6xHis tag

<400> SEQUENCE: 173

His His His His His His
1               5
```

ILT-BINDING AGENTS AND METHODS OF USE THEREOF

CROSS-REFERENCE TO RELATED APPLICATIONS

This application claims the benefit of priority of U.S. Provisional Appl. No. 63/019,068, filed May 1, 2020; and U.S. Provisional Appl. No. 63/122,848, filed Dec. 8, 2020; the contents of both of which are incorporated herein by reference in their entirety.

SEQUENCE LISTING

The present specification is being filed with a computer readable form (CRF) copy of the Sequence Listing. The CRF entitled 47702-0094001_SL.txt, which was created on Apr. 26, 2021 and is 178,820 bytes in size, is incorporated herein by reference in its entirety.

FIELD OF THE DISCLOSURE

The present disclosure generally relates to agents that bind immunoglobulin-like transcript (ILT) proteins, particularly antibodies that bind to human ILT2, human ILT4, and both human ILT2 and human ILT4, as well as compositions comprising the ILT-binding agents and methods of using the binding agents and compositions.

BACKGROUND

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include methods to induce or enhance specific immune responses or to inhibit or reduce specific immune responses.

The immune system is a highly complex system made up of a great number of cell types, including but not limited to, T-cells, T-cell subsets, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases or a cytokine storm).

Some of the inhibitory mechanisms of the immune system use proteins from the leukocyte Ig-like receptor (LILR) family. The leukocyte Ig-like receptor subfamily B (LILRB) is a group of type I transmembrane glycoproteins with extracellular Ig-like domains and cytoplasmic immunoreceptor tyrosine-based inhibitory motifs (ITIMs). This group of ITIM-containing receptors includes 5 members: LILRB1 (also known as CD85J, LIR1, ILT2), LILRB2 (also known as CD85D, LIR2, ILT4), LILRB3 (also known as CD85A, LIR3, ILT5), LILRB4 (also known as CD85K, LIR5, ILT3), and LILRB5 (also known as CD85C, LIR8). The biological functions and clinical significance of many of these LILRBs (ILTs) are still being investigated. There is also a LILR subfamily A (LILRA) that is a group of type I transmembrane glycoproteins with extracellular Ig-like domains and cytoplasmic immunoreceptor tyrosine-based activating motifs (ITAMs). This group of ITAM-containing receptors includes 6 members: LILRA1 (also known as CD85I, LIRE), LILRA2 (also known as CD85H, LIR7, ILT1), LILRA3 (also known as CD85E, LIR4, ILT6, monocyte inhibitory receptor HM43/31), LILRA4 (also known as CD85G, ILT7), LILRA5 (also known as CD85F, LIR9, ILT11), and LILRA6 (also known as ILT8). The inhibitory and activating proteins of the LILR family appear to work in concert to modulate immune homeostasis.

The concept of cancer immunosurveillance is based on the theory that the immune system can recognize tumor cells, mount an immune response, and suppress the development and/or growth of a tumor. However, it is clear that many cancerous/tumor cells have developed mechanisms and/or hijacked normal inhibitory mechanisms to evade the immune system which can allow for uninhibited growth of tumor cells. Cancer/tumor immunotherapy (immuno-oncology) focuses on the development of new and novel agents that can activate and/or boost the immune system to achieve a more effective attack against cancer/tumor cells resulting in increased killing of cancer/tumor cells and/or inhibition of cancer/tumor growth.

BRIEF SUMMARY

The present disclosure provides agents that bind immunoglobulin-like transcript 2 (ILT2) and/or immunoglobulin-like transcript 4 (ILT4). Although the LILRB family members are referred to by many names in publications, the terms "ILT2" (LILRB1) and "ILT4" (LILRB2) will be used herein. The agents include, but are not limited to, polypeptides such as antibodies that specifically bind ILT2, ILT4, or both ILT2 and ILT4. Generally, the agents referred to herein as "ILT-binding agents" encompass ILT2-binding agents, ILT4-binding agents, and agents binding to both ILT2 and ILT4 (referred to as "ILT2/ILT4-binding agents"). In some embodiments, an ILT-binding agent inhibits ILT2 and/or ILT4 activity. In some embodiments, an ILT-binding agent enhances an immune response. In some embodiments, an ILT-binding agent reverses suppression of an immune cell activity. The disclosure provides methods of using an ILT-binding agent, for example, in treating cancer (e.g., an advanced solid tumor). In some embodiments, an ILT-binding agent is used in combination therapy in, for example, treating cancer. In some embodiments, an ILT-binding agent is used in combination with at least one additional therapeutic agent in, for example, treating cancer.

In some instances, the ILT-binding agents described herein have one or more (e.g., 1, 2, 3, 4, 5, 6, 7, 8, 9, 10, 11 or more) of the following properties in any combination or permutation:

(1) binds human ILT2;
(2) binds human ILT4;
(3) binds rhesus ILT2;
(4) binds cyno ILT2;
(5) does not bind ILT3, ILT5, and LILRB5;
(6) does not bind LILRA2, LILRA4, LILRA5, and LILRA6;
(7) is an ILT2 antagonist;
(8) is an ILT4 antagonist,
(9) inhibits ILT2 activity;
(10) inhibits ILT4 activity;
(11) inhibits ILT2 signaling in cells that express ILT2;
(12) inhibits ILT4 signaling in cells that express ILT4;
(13) inhibits binding of ILT2 to MHC I molecules;

(14) inhibits binding of ILT4 to MHC I molecules;
(15) inhibits ILT2-induced suppression of myeloid cells;
(16) inhibits ILT4-induced suppression of myeloid cells;
(17) inhibits ILT2-induced suppression of myeloid cell activity;
(18) inhibits ILT4-induced suppression of myeloid cell activity;
(19) restores FcR activation in myeloid cells;
(20) enhances NK cell activity;
(21) enhances cytotoxic T lymphocyte (CTL) activity;
(22) enhances macrophage phagocytosis; and
(23) inhibits MDSC mediated suppression of immune cells.

The disclosure also provides compositions comprising the ILT-binding agents described herein. In some embodiments, the disclosure provides pharmaceutical compositions comprising the ILT-binding agents and a pharmaceutically acceptable carrier. Polynucleotides and/or vectors encoding the ILT-binding agents are provided. Cells comprising the polynucleotides and/or the vectors described herein are also provided. Cells comprising or producing the ILT-binding agents described herein are provided. Methods of making the ILT-binding agents described herein are also provided.

In one aspect, the present disclosure provides ILT-binding agents that bind ILT2. In some embodiments, ILT-binding agents bind human ILT2. In some embodiments, the ILT-binding agents bind rhesus monkey ("rhesus") ILT2. In some embodiments, the ILT-binding agents cynomolgus monkey ("cyno") ILT2. In some embodiments, the ILT-binding agents bind human ILT2 and rhesus ILT2. In some embodiments, the ILT-binding agents bind human ILT2 and cyno ILT2. In some embodiments, the ILT-binding agents bind human ILT2, rhesus ILT2, and cyno ILT2. In some embodiments, the ILT-binding agents bind SEQ ID NO:1, SEQ ID NO:2, SEQ ID NO:3, SEQ ID NO:4, SEQ ID NO:5, SEQ ID NO:6, and/or SEQ ID NO:7. In some embodiments, the ILT-binding agents bind SEQ ID NO:15, SEQ ID NO:16, SEQ ID NO:17, SEQ ID NO:18, SEQ ID NO:19, SEQ ID NO:20, and/or SEQ ID NO:21. In some embodiments, the ILT-binding agents bind SEQ ID NO:166, SEQ ID NO:167, SEQ ID NO:168, SEQ ID NO:169, SEQ ID NO:170, SEQ ID NO:171, and/or SEQ ID NO:172. In some embodiments, the ILT-binding agents are antibodies. In some embodiments, the ILT-binding agents are antibody fragments.

In some embodiments, the ILT-binding agents bind within the extracellular domain of ILT2. In some embodiments, the ILT-binding agents bind SEQ ID NO:3. In some embodiments, the ILT-binding agents bind within amino acids 24-461 of SEQ ID NO:1. In some embodiments, the ILT-binding agents bind within amino acids 27-115 of SEQ ID NO:1. In some embodiments, the ILT-binding agents bind within amino acids 116-221 of SEQ ID NO:1. In some embodiments, the ILT-binding agents bind within amino acids 222-312 of SEQ ID NO:1. In some embodiments, the ILT-binding agents bind within amino acids 313-409 of SEQ ID NO:1. In some embodiments, the ILT-binding agents bind within amino acids 27-221 of SEQ ID NO:1. In some embodiments, the ILT-binding agents bind within amino acids 116-312 of SEQ ID NO:1. In some embodiments, the ILT-binding agents bind within amino acids 222-409 of SEQ ID NO:1. In some embodiments, the ILT-binding agents bind a conformational epitope within the extracellular domain of ILT2. In some embodiments, the ILT-binding agents bind a conformational epitope within one of the Ig-like C2-type domains of ILT2 (e.g., D1, D2, D3, or D4). In some embodiments, the ILT-binding agents bind a conformational epitope within two or more of the Ig-like C2-type domains of ILT2 (D1, D2, D3, and/or D4). In some embodiments, the ILT-binding agents bind a conformational epitope within the D4-stem region of ILT2.

In another aspect, the present disclosure provides ILT-binding agents that bind ILT4. In some embodiments, the ILT-binding agents bind human ILT4. In some embodiments, the ILT-binding agents bind SEQ ID NO:8, SEQ ID NO:9, SEQ ID NO:10, SEQ ID NO:11, SEQ ID NO:12, SEQ ID NO:13, and/or SEQ ID NO:14. In some embodiments, the ILT-binding agents are antibodies. In some embodiments, the ILT-binding agents are antibody fragments.

In some embodiments, the ILT-binding agents bind within the extracellular domain of ILT4. In some embodiments, an agent binds SEQ ID NO:10. In some embodiments, ILT-binding agents bind within amino acids 22-461 of SEQ ID NO:8. In some embodiments, ILT-binding agents bind within amino acids 27-110 of SEQ ID NO:8. In some embodiments, ILT-binding agents bind within amino acids 111-229 of SEQ ID NO:8. In some embodiments, ILT-binding agents bind within amino acids 230-318 of SEQ ID NO:8. In some embodiments, ILT-binding agents bind within amino acids 330-419 of SEQ ID NO:8. In some embodiments, ILT-binding agents bind within amino acids 27-229 of SEQ ID NO:8. In some embodiments, ILT-binding agents bind within amino acids 111-318 of SEQ ID NO:8. In some embodiments, ILT-binding agents bind within amino acids 230-419 of SEQ ID NO:8. In some embodiments, ILT-binding agents bind a conformational epitope within the extracellular domain of ILT4. In some embodiments, ILT-binding agents bind a conformational epitope within one of the Ig-like C2-type domains of ILT4 (e.g., D1, D2, D3, or D4). In some embodiments, ILT-binding agents bind a conformational epitope within two or more of the Ig-like C2-type domains of ILT4 (D1, D2, D3, and/or D4). In some embodiments, ILT-binding agents bind a conformational epitope within the D4-stem region of ILT4.

In one aspect, the present disclosure provides ILT-binding agents that bind human ILT2, human ILT4, or both human ILT2 and ILT4 and have at least one or more (e.g., 1, 2, 3, 4, 5, 6, 7, 8, 9, 10, 11, 12, 13, 14, 15, 16, 17, 18, or 19) of the following properties: (1) binds rhesus ILT2; (2) binds cyno ILT2; (3) does not bind ILT3, ILT5, and LILRB5; (4) does not bind LILRA2, LILRA4, LILRA5, and LILRA6; (5) is an ILT2 antagonist; (6) is an ILT4 antagonist, (7) inhibits ILT2 activity; (8) inhibits ILT4 activity; (9) inhibits ILT2 signaling in cells that express ILT2; (10) inhibits ILT4 signaling in cells that express ILT4; (11) inhibits binding of ILT2 to one or more MHC I molecules; (12) inhibits binding of ILT4 to one or more MHC I molecules; (13) inhibits ILT2-induced suppression of myeloid cells; (14) inhibits ILT4-induced suppression of myeloid cells; (15) inhibits ILT2-induced suppression of myeloid cell activity; (16) inhibits ILT4-induced suppression of myeloid cell activity; (17) restores FcR activation in myeloid cells; (18) enhances NK cell activity; and/or (19) enhances CTL activity. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are antigen-presenting cells (APCs). In some embodiments, the MHC I molecule is HLA-A, HLA-B, HLA-C, HLA-E, and/or HLA-G.

In one aspect, the present disclosure provides agents that specifically bind human ILT2. In some embodiments, the present disclosure provides an ILT2-binding agent, wherein the binding agent comprises: (a) a heavy chain variable region comprising a heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24), and/or (b) a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27). The present disclosure also provides an ILT2-binding agent that comprises the six CDRs of any of the CDR definitions provided in Table 1.

In some embodiments, an ILT2-binding agent comprises: (a) a heavy chain variable region having at least 80% sequence identity to SEQ ID NO:125; and/or (b) a light chain variable region having at least 80% sequence identity to SEQ ID NO:126. In some embodiments, an ILT2-binding agent comprises a heavy chain variable region having at least 80%, at least 85%, at least 90%, at least 95%, at least 96%, at least 97%, at least 98%, or at least 99% sequence identity to SEQ ID NO:125 and/or a light chain variable region having at least 80%, at least 85%, at least 90%, at least 95%, at least 96%, at least 97%, at least 98%, or at least 99% sequence identity to SEQ ID NO:126. In some embodiments, an ILT2-binding agent comprises a heavy chain variable region of SEQ ID NO:125 and/or a light chain variable region of SEQ ID NO:126. In some embodiments, the ILT2-binding agent comprises a heavy chain variable region of SEQ ID NO:125 and a light chain variable region of SEQ ID NO:126.

In some embodiments, an ILT2-binding agent comprises a heavy chain variable region CDR1, CDR2, and CDR3 from the amino acid sequence of SEQ ID NO:125 and a light chain variable region CDR1, CDR2, and CDR3 from the amino acid sequence of SEQ ID NO:126. In some embodiments, an ILT2-binding agent comprises a heavy chain variable region comprising a heavy chain variable region CDR1, CDR2, and CDR3 from the amino acid sequence of SEQ ID NO:125 and a light chain variable region comprising a light chain variable region CDR1, CDR2, and CDR3 from the amino acid sequence of SEQ ID NO:126.

In some embodiments, an ILT4-binding agent comprises (a) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40), and/or (b) a light chain variable region comprising a light chain variable region CDR1 comprising the amino acid sequence RASESVDNYGNNFLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43). The present disclosure also provides an ILT2-binding agent that comprises the six CDRs of any of the CDR definitions provided in Table 2.

In some embodiments, an ILT4-binding agent comprises: (a) a heavy chain variable region having at least 80% identity to SEQ ID NO:127 and/or (b) a light chain variable region having at least 80% identity to SEQ ID NO:128. In some embodiments, an ILT4-binding agent comprises a heavy chain variable region having at least 80%, at least 85%, at least 90%, at least 95%, at least 96%, at least 97%, at least 98%, or at least 99% sequence identity to SEQ ID NO:127 and/or a light chain variable region having at least 80%, at least 85%, at least 90%, at least 95%, at least 96%, at least 97%, at least 98%, or at least 99% sequence identity to SEQ ID NO:128. In some embodiments, an ILT4-binding agent comprises a heavy chain variable region of SEQ ID NO:127 and/or a light chain variable region of SEQ ID NO:128. In some embodiments, the ILT4-binding agent comprises a heavy chain variable region of SEQ ID NO:127 and a light chain variable region of SEQ ID NO:128.

In some embodiments, an ILT4-binding agent comprises a heavy chain variable region CDR1, CDR2, and CDR3 from the amino acid sequence of SEQ ID NO:127 and/or a light chain variable region CDR1, CDR2, and CDR3 from the amino acid sequence of SEQ ID NO:128. In some embodiments, an ILT4-binding agent comprises a heavy chain variable region comprising a heavy chain variable region CDR1, CDR2, and CDR3 from the amino acid sequence of SEQ ID NO:127 and/or a light chain variable region comprising a light chain variable region CDR1, CDR2, and CDR3 from the amino acid sequence of SEQ ID NO:128.

In some embodiments, an ILT4-binding agent comprises (a) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and/or (b) a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59). The present disclosure also provides an ILT2-binding agent that comprises the six CDRs of any of the CDR definitions provided in Table 3.

In some embodiments, an ILT4-binding agent comprises: (a) a heavy chain variable region having at least 80% identity to SEQ ID NO:129 and/or (b) a light chain variable region having at least 80% identity to SEQ ID NO:130. In some embodiments, an ILT4-binding agent comprises a heavy chain variable region having at least 80%, at least 85%, at least 90%, at least 95%, at least 96%, at least 97%, at least 98%, or at least 99% sequence identity to SEQ ID NO:129 and/or a light chain variable region having at least 80%, at least 85%, at least 90%, at least 95%, at least 96%, at least 97%, at least 98%, or at least 99% sequence identity to SEQ ID NO:130. In some embodiments, an ILT4-binding agent comprises a heavy chain variable region of SEQ ID NO:129 and/or a light chain variable region of SEQ ID NO:130. In some embodiments, the ILT4-binding agent comprises a heavy chain variable region of SEQ ID NO:129 and a light chain variable region of SEQ ID NO:130.

In some embodiments, an ILT4-binding agent comprises a heavy chain variable region CDR1, CDR2, and CDR3 from the amino acid sequence of SEQ ID NO:129 and/or a light chain variable region CDR1, CDR2, and CDR3 from the amino acid sequence of SEQ ID NO:130. In some embodiments, an ILT4-binding agent comprises a heavy chain variable region comprising a heavy chain variable region CDR1, CDR2, and CDR3 from the amino acid sequence of SEQ ID NO:129 and/or a light chain variable region comprising a light chain variable region CDR1, CDR2, and CDR3 from the amino acid sequence of SEQ ID NO:130.

In some embodiments, an ILT2/ILT4-binding agent comprises (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPN-NAGTTYNQKFEG (SEQ ID NO:118), and a heavy chain variable region CDR3 comprising the amino acid sequence GRFYYGSLYSFDY (SEQ ID NO:72), and/or (b) a light chain variable region comprising a light chain variable region CDR1 comprising the amino acid sequence RASGNIHNYLA (SEQ ID NO:73), a light chain variable region CDR2 comprising the amino acid sequence NAKT-LAD (SEQ ID NO:74), and a light chain variable region CDR3 comprising the amino acid sequence QHFWTSIT (SEQ ID NO:75). The present disclosure also provides an ILT2/ILT4 binding agent that comprises the six CDRs of any of the CDR definitions provided in Tables 4A and 4B.

In some embodiments, an ILT2/ILT4-binding agent comprises: (a) a heavy chain variable region having at least 80% identity to SEQ ID NO:131 and/or (b) a light chain variable region having at least 80% identity to SEQ ID NO:132. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:131 and/or a light chain variable region having at least 80%, at least 85%, at least 90%, at least 95%, at least 96%, at least 97%, at least 98%, or at least 99% sequence identity to SEQ ID NO:132. In some embodiments, an ILT2/ILT4-binding agent comprises a heavy chain variable region of SEQ ID NO:131 and/or a light chain variable region of SEQ ID NO:132. In some embodiments, the ILT2/ILT4-binding agent comprises a heavy chain variable region of SEQ ID NO:131 and a light chain variable region of SEQ ID NO:132.

In some embodiments, an ILT2/ILT4-binding agent comprises: (a) a heavy chain variable region having at least 80% identity to SEQ ID NO:133 and/or (b) a light chain variable region having at least 80% identity to SEQ ID NO:134. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:133 and/or a light chain variable region having at least 80%, at least 85%, at least 90%, at least 95%, at least 96%, at least 97%, at least 98%, or at least 99% sequence identity to SEQ ID NO:134. In some embodiments, an ILT2/ILT4-binding agent comprises a heavy chain variable region of SEQ ID NO:133 and/or a light chain variable region of SEQ ID NO:134. In some embodiments, the ILT2/ILT4-binding agent comprises a heavy chain variable region of SEQ ID NO:133 and a light chain variable region of SEQ ID NO:134.

In some embodiments, an ILT2/ILT4-binding agent comprises a heavy chain variable region CDR1, CDR2, and CDR3 from the amino acid sequence of SEQ ID NO:131 and/or a light chain variable region CDR1, CDR2, and CDR3 from the amino acid sequence of SEQ ID NO:132. In some embodiments, an ILT2/ILT4-binding agent comprises a heavy chain variable region comprising a heavy chain variable region CDR1, CDR2, and CDR3 from the amino acid sequence of SEQ ID NO:131 and/or a light chain variable region comprising a light chain variable region CDR1, CDR2, and CDR3 from the amino acid sequence of SEQ ID NO:132. In some embodiments, an ILT2/ILT4-binding agent comprises a heavy chain variable region CDR1, CDR2, and CDR3 from the amino acid sequence of SEQ ID NO:133 and/or a light chain variable region CDR1, CDR2, and CDR3 from the amino acid sequence of SEQ ID NO:134. In some embodiments, an ILT2/ILT4-binding agent comprises a heavy chain variable region comprising a heavy chain variable region CDR1, CDR2, and CDR3 from the amino acid sequence of SEQ ID NO:133 and/or a light chain variable region comprising a light chain variable region CDR1, CDR2, and CDR3 from the amino acid sequence of SEQ ID NO:134.

In some embodiments, an ILT2/ILT4-binding agent comprises (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). The present disclosure also provides an ILT2/ILT4 binding agent that comprises the six CDRs of any of the CDR definitions provided in Table 5.

In some embodiments, an ILT2/ILT4-binding agent comprises: (a) a heavy chain variable region having at least 80% identity to SEQ ID NO:135 and/or (b) a light chain variable region having at least 80% identity to SEQ ID NO:136. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:135 and/or a light chain variable region having at least 80%, at least 85%, at least 90%, at least 95%, at least 96%, at least 97%, at least 98%, or at least 99% sequence identity to SEQ ID NO:136. In some embodiments, an ILT2/ILT4-binding agent comprises a heavy chain variable region of SEQ ID NO:135 and/or a light chain variable region of SEQ ID NO:136. In some embodiments, the ILT2/ILT4-binding agent comprises a heavy chain variable region of SEQ ID NO:135 and a light chain variable region of SEQ ID NO:136.

In some embodiments, an ILT2/ILT4-binding agent comprises a heavy chain variable region CDR1, CDR2, and CDR3 from the amino acid sequence of SEQ ID NO:135 and/or a light chain variable region CDR1, CDR2, and CDR3 from the amino acid sequence of SEQ ID NO:136. In some embodiments, an ILT2/ILT4-binding agent comprises a heavy chain variable region comprising a heavy chain variable region CDR1, CDR2, and CDR3 from the amino acid sequence of SEQ ID NO:135 and/or a light chain variable region comprising a light chain variable region CDR1, CDR2, and CDR3 from the amino acid sequence of SEQ ID NO:136.

In some embodiments, an ILT2/ILT4-binding agent comprises (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and/or (b) a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). The present disclosure also provides an ILT2/ILT4 binding agent that comprises the six CDRs of any of the CDR definitions provided in Tables 6A and 6B.

In some embodiments, an ILT2/ILT4-binding agent comprises: (a) a heavy chain variable region having at least 80% identity to SEQ ID NO:137 and/or (b) a light chain variable region having at least 80% identity to SEQ ID NO:138. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:137 and/or a light chain variable region having at least 80%, at least 85%, at least 90%, at least 95%, at least 96%, at least 97%, at least 98%, or at least 99% sequence identity to SEQ ID NO:138. In some embodiments, an ILT2/ILT4-binding agent comprises a heavy chain variable region of SEQ ID NO:137 and/or a light chain variable region of SEQ ID NO:138. In some embodiments, the ILT2/ILT4-binding agent comprises a heavy chain variable region of SEQ ID NO:137 and a light chain variable region of SEQ ID NO:138.

In some embodiments, an ILT2/ILT4-binding agent comprises: (a) a heavy chain variable region having at least 80% identity to SEQ ID NO:139 and/or (b) a light chain variable region having at least 80% identity to SEQ ID NO:140. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:139 and/or a light chain variable region having at least 80%, at least 85%, at least 90%, at least 95%, at least 96%, at least 97%, at least 98%, or at least 99% sequence identity to SEQ ID NO:140. In some embodiments, an ILT2/ILT4-binding agent comprises a heavy chain variable region of SEQ ID NO:139 and/or a light chain variable region of SEQ ID NO:140. In some embodiments, the ILT2/ILT4-binding agent comprises a heavy chain variable region of SEQ ID NO:139 and a light chain variable region of SEQ ID NO:140.

In some embodiments, an ILT2/ILT4-binding agent comprises a heavy chain variable region CDR1, CDR2, and CDR3 from the amino acid sequence of SEQ ID NO:137 and/or a light chain variable region CDR1, CDR2, and CDR3 from the amino acid sequence of SEQ ID NO:138. In some embodiments, an ILT2/ILT4-binding agent comprises a heavy chain variable region comprising a heavy chain variable region CDR1, CDR2, and CDR3 from the amino acid sequence of SEQ ID NO:137 and/or a light chain variable region comprising a light chain variable region CDR1, CDR2, and CDR3 from the amino acid sequence of SEQ ID NO:138. In some embodiments, an ILT2/ILT4-binding agent comprises a heavy chain variable region CDR1, CDR2, and CDR3 from the amino acid sequence of SEQ ID NO:139 and/or a light chain variable region CDR1, CDR2, and CDR3 from the amino acid sequence of SEQ ID NO:140. In some embodiments, an ILT2/ILT4-binding agent comprises a heavy chain variable region comprising a heavy chain variable region CDR1, CDR2, and CDR3 from the amino acid sequence of SEQ ID NO:139 and/or a light chain variable region comprising a light chain variable region CDR1, CDR2, and CDR3 from the amino acid sequence of SEQ ID NO:140.

In some embodiments, an ILT2/ILT4-binding agent comprises (a) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). The present disclosure also provides an ILT2/ILT4 binding agent that comprises the six CDRs of any of the CDR definitions provided in Table 7.

In some embodiments, an ILT2/ILT4-binding agent comprises: (a) a heavy chain variable region having at least 80% identity to SEQ ID NO:141 and/or (b) a light chain variable region having at least 80% identity to SEQ ID NO:142. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:141 and/or a light chain variable region having at least 80%, at least 85%, at least 90%, at least 95%, at least 96%, at least 97%, at least 98%, or at least 99% sequence identity to SEQ ID NO:142. In some embodiments, an ILT2/ILT4-binding agent comprises a heavy chain variable region of SEQ ID NO:141 and/or a light chain variable region of SEQ ID NO:142. In some embodiments, the ILT2/ILT4-binding agent comprises a heavy chain variable region of SEQ ID NO:141 and a light chain variable region of SEQ ID NO:142.

In some embodiments, an ILT2/ILT4-binding agent comprises a heavy chain variable region CDR1, CDR2, and CDR3 from the amino acid sequence of SEQ ID NO:141 and/or a light chain variable region CDR1, CDR2, and CDR3 from the amino acid sequence of SEQ ID NO:142. In some embodiments, an ILT2/ILT4-binding agent comprises a heavy chain variable region comprising a heavy chain variable region CDR1, CDR2, and CDR3 from the amino acid sequence of SEQ ID NO:141 and/or a light chain variable region comprising a light chain variable region CDR1, CDR2, and CDR3 from the amino acid sequence of SEQ ID NO:142.

In some embodiments, an ILT2/ILT4-binding agent comprises (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). The present disclosure also provides an ILT2/ILT4 binding agent that comprises the six CDRs of any of the CDR definitions provided in Tables 8A and 8B.

In some embodiments, an ILT2/ILT4-binding agent comprises: (a) a heavy chain variable region having at least 80% identity to SEQ ID NO:143 and/or (b) a light chain variable region having at least 80% identity to SEQ ID NO:142. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:143 and/or a light chain variable region having at least 80%, at least 85%, at least 90%, at least 95%, at least 96%, at least 97%, at least 98%, or at least 99% sequence identity to SEQ ID NO:142. In some embodiments, an ILT2/ILT4-binding agent comprises a heavy chain variable region of SEQ ID NO:143 and/or a light chain variable region of SEQ ID NO:142. In some embodiments, the ILT2/ILT4-binding agent comprises a heavy chain variable region of SEQ ID NO:143 and a light chain variable region of SEQ ID NO:142.

In some embodiments, an ILT2/ILT4-binding agent comprises: (a) a heavy chain variable region having at least 80% identity to SEQ ID NO:144 and/or (b) a light chain variable region having at least 80% identity to SEQ ID NO:145. In some embodiments, an ILT2/ILT4-binding agent comprises a heavy chain variable region having at least 80%, at least 85%, at least 90%, at least 95%, at least 96%, at least 97%, at least 98%, or at least 99% sequence identity to SEQ ID NO:144 and/or a light chain variable region having at least 80%, at least 85%, at least 90%, at least 95%, at least 96%, at least 97%, at least 98%, or at least 99% sequence identity to SEQ ID NO:145. In some embodiments, an ILT2/ILT4-binding agent comprises a heavy chain variable region of SEQ ID NO:144 and/or a light chain variable region of SEQ ID NO:145. In some embodiments, the ILT2/ILT4-binding agent comprises a heavy chain variable region of SEQ ID NO:144 and a light chain variable region of SEQ ID NO:145.

In some embodiments, an ILT2/ILT4-binding agent comprises a heavy chain variable region CDR1, CDR2, and CDR3 from the amino acid sequence of SEQ ID NO:143 and/or a light chain variable region CDR1, CDR2, and CDR3 from the amino acid sequence of SEQ ID NO:142. In some embodiments, an ILT2/ILT4-binding agent comprises a heavy chain variable region comprising a heavy chain variable region CDR1, CDR2, and CDR3 from the amino acid sequence of SEQ ID NO:143 and/or a light chain variable region comprising a light chain variable region CDR1, CDR2, and CDR3 from the amino acid sequence of SEQ ID NO:142. In some embodiments, an ILT2/ILT4-binding agent comprises a heavy chain variable region CDR1, CDR2, and CDR3 from the amino acid sequence of SEQ ID NO:144 and/or a light chain variable region CDR1, CDR2, and CDR3 from the amino acid sequence of SEQ ID NO:145. In some embodiments, an ILT2/ILT4-binding agent comprises a heavy chain variable region comprising a heavy chain variable region CDR1, CDR2, and CDR3 from the amino acid sequence of SEQ ID NO:144 and/or a light chain variable region comprising a light chain variable region CDR1, CDR2, and CDR3 from the amino acid sequence of SEQ ID NO:145.

In another aspect of the disclosure, provided herein is an agent that competes for binding to ILT2, ILT4, or ILT2/ILT4 with any of the ILT-binding agents described herein. In some embodiments, the agent competes for binding to both human ILT2 and human ILT4 with any of the ILT-binding agents described herein. In some embodiments, the agent competes for binding to human ILT2 with any of the ILT-binding agents described herein. In some embodiments, the agent competes for binding to human ILT4 with any of the ILT-binding agents described herein. In some embodiments, the agent is antibody. In some embodiment, the agent is an antibody fragment.

In some embodiments of each of the aforementioned aspects and embodiments, as well as other aspects and embodiments described herein, the ILT-binding agents are antibodies. In some embodiments, the antibodies are recombinant antibodies. In some embodiments, the antibodies are humanized antibodies. In some embodiments, the antibodies are human antibodies. In some embodiments, the antibody are chimeric antibodies. In some embodiments, the antibody are whole or intact antibodies. In some embodiments, the antibodiesare bispecific antibodies or a multispecific antibodies. In some embodiments, the antibodies are antibody fragments comprising at least one antigen-binding site. In some embodiments, the antibodies are a Fab, Fab', F(ab')$_2$, Fv, scFv, (scFv)$_2$, single chain antibody, dual variable region antibody, single variable region antibody, linear antibody, diabody, nanobody, or a V region antibody. In some embodiments, the antibodies are IgG antibodies. In some embodiments, the antibodies are IgG1 antibodies, IgG2 antibodies, IgG3 antibodies, or IgG4 antibodies. In some embodiments, the antibodies each comprises a kappa light chain. In some embodiments, the antibodies each comprises a lambda light chain. In some instances, the antibodies each comprises a human IgG1 constant region. In some instances, the antibodies each comprises a human kappa light chain constant region. In some instances, the antibodies each comprises a human IgG1 constant region and a human kappa light chain constant region. In certain instances, the human IgG1 constant region comprises one or more mutations that reduce or eliminate Fc effector functions. In certain instances, the human IgG1 constant region comprises a N297G mutation that reduces effector function.

In some embodiments of each of the aforementioned aspects and embodiments, as well as other aspects and embodiments described herein, the ILT-binding agents each is attached (either directly or indirectly) to a half-life extending moiety.

In some embodiments of each of the aforementioned aspects and embodiments, as well as other aspects and embodiments described herein, the ILT-binding agents described herein are antagonists of ILT2. In some embodiments, the ILT-binding agents inhibit ILT2 activity. In some embodiments, the ILT-binding agents are antagonistic antibodies. In some embodiments, the ILT-binding agents are antibodies that inhibit ILT2-induced immune cell suppression. In some embodiments, the ILT-binding agents are antibodies that inhibit ILT2-induced myeloid cell suppression.

In some embodiments of each of the aforementioned aspects and embodiments, as well as other aspects and embodiments described herein, the ILT-binding agents described herein are antagonists of ILT4. In some embodiments, the ILT-binding agents inhibit ILT4 activity. In some embodiments, the ILT-binding agents are antagonistic antibodies. In some embodiments, the ILT-binding agents are antibodies that inhibit ILT4-induced immune cell suppression. In some embodiments, the ILT-binding agents are antibodies that inhibit ILT4-induced myeloid cell suppression.

In some embodiments of each of the aforementioned aspects and embodiments, as well as other aspects and embodiments described herein, the ILT-binding agents described herein are antagonists of human ILT2 and ILT4. In some embodiments, the ILT-binding agents inhibit ILT2 activity and ILT4 activity. In some embodiments, the ILT-binding agents are antagonistic antibodies. In some embodiments, the ILT-binding agents are antibodies that inhibit ILT2-induced and ILT4-induced immune cell suppression. In some embodiments, the ILT-binding agents are antibodies that inhibit ILT2-induced and ILT4-induced myeloid cell suppression.

In some embodiments, the ILT-binding agents are antibodies that reactivate tolerogenic dendritic cells. In some embodiments, the ILT-binding agents are antibodies that inhibit the activity of myeloid-derived suppressor cells (MDSCs). In some embodiments, the ILT-binding agents are antibodies that enhance cytolytic T-cell lymphocyte (CTL) activity. In some embodiments, the ILT-binding agents are antibodies that enhances CD8+ T-cell cytolytic activity. In some embodiments, the ILT-binding agents are antibodies that enhance natural killer (NK) cell activity. In some embodiments, the ILT-binding agents are antibodies that enhance macrophage phagocytosis. In some embodiments, the ILT-binding agents desuppress or activate Fc receptor signaling in myeloid cells. In some embodiments, the ILT-binding agents act synergistically with an immune checkpoint inhibitor.

In another aspect, the disclosure provides compositions comprising an ILT-binding agent described herein. In some embodiments, a composition comprises an anti-ILT antibody described herein. In some embodiments, a composition comprises a recombinant anti-ILT antibody described herein. In some embodiments, a composition comprises the anti-ILT2 antibody 27F9. In some embodiments, a composition comprises the anti-ILT4 antibody 47C8 or antibody 48A5. In some embodiments, a composition comprises an anti-ILT2/ILT4 antibody selected from the group consisting of: 47H6, Hz47H6.v2, 51A1, 64A12, Hz64A12, 73C4, 73D1, and Hz73D1.v1.

In some instances, pharmaceutical compositions are provided, which comprise (a) a means for inhibiting the interaction between ILT2 and/or ILT4 and MHC Class I (e.g., on tumor cells); and (b) a pharmaceutically acceptable carrier. In some embodiments, the means for inhibiting the interaction between ILT2 and/or ILT4 and MHC Class I comprises an antibody comprising a heavy chain variable region comprising VH-CDR1, VH-CDR2, and VH-CDR3 and a light chain variable region comprising VL-CDR1, VL-CDR2, and VL-CDR3 from any one of 27F9, 47C8, 48A5, 47H6, Hz47H6.v2, 51A1, 64A12, Hz64A12, 73C4, 73D1, and Hz73D1.v1.

In some embodiments of each of the aforementioned aspects, as well as other aspects and/or embodiments described elsewhere herein, the ILT-binding agent is isolated. In some embodiments, the ILT-binding agent is substantially pure.

In another aspect, the disclosure provides polynucleotides comprising a polynucleotide that encodes an ILT-binding agent described herein. In some embodiments, a polynucleotide encodes an anti-ILT2 antibody described herein. In some embodiments, a polynucleotide encodes an anti-ILT4 antibody described herein. In some embodiments, a polynucleotide encodes an anti-ILT2/ILT4 antibody described herein. In some embodiments, the polynucleotide is isolated. In some embodiments, a vector comprises a polynucleotide that encodes an ILT-binding agent described herein. In some embodiments, an isolated cell comprises a polynucleotide that encodes an ILT-binding agent described herein. In some embodiments, an isolated cell comprises a vector comprising a polynucleotide that encodes an ILT-binding agent described herein. In some embodiments, a cell comprises an ILT-binding agent described herein. In some embodiments, a cell produces an ILT-binding agent described herein. In some embodiments, a cell produces an anti-ILT antibody described herein. In some embodiments, a cell is a monoclonal cell line. In some embodiments, a cell is a hybridoma.

In another aspect, the disclosure provides methods of using the ILT-binding agents described herein. In some embodiments, the methods comprise using a composition comprising an ILT2-binding agent described herein. In some embodiments, the methods comprise using a composition comprising an ILT4-binding agent described herein. In some embodiments, the methods comprise using a composition comprising an ILT2/ILT4-binding agent described herein. In some embodiments, the methods comprise using a pharmaceutical composition comprising an ILT2-binding agent described herein. In some embodiments, the methods comprise using a pharmaceutical composition comprising an ILT4-binding agent described herein. In some embodiments, the methods comprise using a pharmaceutical composition comprising an ILT2/ILT4-binding agent described herein.

In some embodiments, a method of disrupting, inhibiting, or blocking the binding of ILT2 and/or ILT4 to a ligand and/or binding partner is provided. In some embodiments, a method of disrupting, inhibiting, or blocking the binding of ILT2 and/or ILT4 to one or more MHC I molecules is provided. In some embodiments, a method of disrupting, inhibiting, or blocking the binding of ILT2 and/or ILT4 to a MHC I molecule in a mixture of cells comprises contacting the cells with an ILT2-binding agent, an ILT4-binding agent, or an ILT2/ILT4-binding agent described herein.

In some embodiments, a method of disrupting, inhibiting, or blocking ILT2 and/or ILT4 activity is provided. In some embodiments, a method of disrupting, inhibiting, or blocking ILT2 activity in a mixture of cells comprises contacting the cells with an ILT2-binding agent or an ILT2/ILT4-binding agent described herein. In some embodiments, a method of disrupting, inhibiting, or blocking ILT4 activity in a mixture of cells comprises contacting the cells with an ILT4-binding agent or an ILT2/ILT4-binding agent described herein. In some embodiments, a method of disrupting, inhibiting, or blocking ILT2 and ILT4 activity in a mixture of cells comprises contacting the cells with an ILT2/ILT4-binding agent described herein.

In some embodiments, a method of disrupting, inhibiting, or blocking MHC I-induced ILT2 and/or ILT4 activity is provided. In some embodiments, a method of disrupting, inhibiting, or blocking MHC I-induced ILT2 activity in a mixture of cells comprises contacting the cells with an ILT2-binding agent or an ILT2/ILT4-binding agent described herein. In some embodiments, a method of disrupting, inhibiting, or blocking MHC I-induced ILT4 activity in a mixture of cells comprises contacting the cells with an ILT4-binding agent or an ILT2/ILT4-binding agent described herein. In some embodiments, a method of disrupting, inhibiting, or blocking MHC I-induced ILT2 and ILT4 activity in a mixture of cells comprises contacting the cells with an ILT2/ILT4-binding agent described herein. In some embodiments, the MHC I molecule is HLA-A, HLA-B, HLA-C, HLA-E, and/or HLA-G.

In some embodiments, a method of disrupting, inhibiting, or blocking ILT2-induced and/or ILT4-induced suppression of myeloid cells is provided. In some embodiments, a method of disrupting, inhibiting, or blocking ILT2-induced and/or ILT4-induced suppression of myeloid cells comprises contacting the myeloid cells with an ILT2-binding agent, an ILT4-binding agent, or an ILT2/ILT4-binding agent described herein. In some embodiments, a method of disrupting, inhibiting, or blocking ILT2-induced suppression of myeloid cells comprises contacting the myeloid cells with an ILT2-binding agent or an ILT2/ILT4-binding agent described herein. In some embodiments, a method of disrupting, inhibiting, or blocking ILT4-induced suppression of myeloid cells comprises contacting the myeloid cells with an ILT4-binding agent or an ILT2/ILT4-binding agent described herein. In some embodiments, a method of disrupting, inhibiting, or blocking ILT2-induced and ILT4-induced suppression of myeloid cells comprises contacting the myeloid cells with an ILT2/ILT4-binding agent described herein.

In some embodiments, a method of disrupting, inhibiting, or blocking ILT2-induced and/or ILT4-induced suppression of myeloid cell activity comprises contacting the myeloid cell with an ILT2-binding agent, an ILT4-binding agent, or an ILT2/ILT4-binding agent described herein. In some embodiments, a method of disrupting, inhibiting, or blocking ILT2-induced or ILT4-induced suppression of myeloid cell activity comprises contacting the myeloid cell with an ILT2/ILT4-binding agent described herein. In some embodiments, a method of disrupting, inhibiting, or blocking ILT2-induced and/or ILT4-induced suppression of myeloid cell activity restores FcR activity in myeloid cells. In some embodiments, a method of disrupting, inhibiting, or blocking ILT2-induced and/or ILT4-induced suppression of myeloid activity enhances, increases, or restores chemokine/cytokine production in myeloid cells. In some embodiments, a method of disrupting, inhibiting, or blocking ILT2-induced and/or ILT4-induced suppression of myeloid cell activity enhances, increases, or restores myeloid cell proliferation activity. In some embodiments, a method of disrupting, inhibiting, or blocking ILT2-induced and/or ILT4-induced suppression of myeloid cell activity enhances, increases, or restores phagocytic activity of the myeloid cell. In some embodiments, the myeloid cells are monocytes. In some embodiments, the myeloid cells are macrophages. In some embodiments, the myeloid cells are dendritic cells. In some embodiments, the myeloid cells are tolerogenic dendritic cells. In some embodiments, the myeloid cells are APCs.

In some embodiments, a method of enhancing or increasing NK cell activity is provided. In some embodiments, a method of enhancing or increasing NK cell activity comprises contacting the NK cell with an ILT2-binding agent, or an ILT2/ILT4-binding agent described herein. In some embodiments, a method of enhancing or increasing NK cell activity comprises contacting the NK cell with an ILT2/ILT4-binding agent described herein.

In some embodiments, a method of enhancing or increasing cytotoxic T lymphocyte (CTL) activity is provided. In some embodiments, a method of enhancing or increasing CTL activity comprises contacting the CTL with an ILT2-binding agent, or an ILT2/ILT4-binding agent described herein. In some embodiments, a method of enhancing or increasing CTL activity comprises contacting the CTL with an ILT2/ILT4-binding agent described herein.

In some embodiments, a method of enhancing or increasing macrophage phagocytosis is provided. In some embodiments, a method of enhancing or increasing phagocytosis comprises contacting the macrophage with an ILT2-binding agent, or an ILT2/ILT4-binding agent described herein. In some embodiments, a method of enhancing or increasing phagocytosis comprises contacting the macrophage with an ILT2/ILT4-binding agent described herein.

In some embodiments, a method of inhibiting the activity of myeloid-derived suppressor cells (MDSCs) is provided. In some embodiments, a method of inhibiting the activity of MDSCs comprises contacting the MDSCs with an ILT4-binding agent, or an ILT2/ILT4-binding agent described herein. In some embodiments, a method inhibiting the activity of MDSCs comprises contacting the MDSCs with an ILT2/ILT4-binding agent described herein.

In some embodiments of each of the aforementioned aspects and embodiments, as well as other aspects and embodiments described herein, the methods can be in vitro, ex vivo, or in vivo.

In some embodiments, a method of disrupting, inhibiting, or blocking the binding of ILT2 or ILT4 to a MHC I molecule in a subject, comprises administering to the subject an effective amount of an ILT2-binding agent, an ILT4-binding agent, or an ILT2/ILT4-binding agent described herein. In some embodiments, a method of disrupting, inhibiting, or blocking the binding of ILT2 or ILT4 to a MHC I molecule in a subject, comprises administering to the subject an effective amount of an ILT2/ILT4-binding agent described herein. In some embodiments of the methods described herein, the MHC I molecule is HLA-A, HLA-B, HLA-C, HLA-E, and/or HLA-G.

In some embodiments, a method of disrupting, inhibiting, or blocking MHC I-induced ILT2 and/or ILT4 activity in a subject, comprises administering to the subject an effective amount of an ILT2-binding agent, an ILT4-binding agent, or an ILT2/ILT4-binding agent. In some embodiments, a method of disrupting, inhibiting, or blocking MHC I-induced ILT2 activity in a subject, comprises administering to the subject an effective amount of an ILT2-binding agent or an ILT2/ILT4-binding agent described herein. In some embodiments, a method of disrupting, inhibiting, or blocking MHC I-induced ILT4 activity in a subject, comprises administering to the subject an effective amount of an ILT4-binding agent or an ILT2/ILT4-binding agent described herein. In some embodiments, a method of disrupting, inhibiting, or blocking MHC I-induced ILT2 and/or ILT4 activity in a subject, comprises administering to the subject an effective amount of an ILT2/ILT4-binding agent described herein. In some embodiments of the methods described herein, the MHC I molecule is HLA-A, HLA-B, HLA-C, HLA-E, and/or HLA-G.

In some embodiments, a method of disrupting, inhibiting, or blocking ILT2-induced suppression of myeloid cells in a subject, comprises administering to the subject an effective amount of an ILT2-binding agent or an ILT2/ILT4-binding agent described herein. In some embodiments, a method of disrupting, inhibiting, or blocking ILT4-induced suppression of myeloid cell activity in a subject, comprises administering to the subject an effective amount of an ILT4-binding agent or an ILT2/ILT4-binding agent described herein.

In some embodiments, a method of inhibiting or decreasing MDSC activity in a subject comprises administering to the subject an effective amount of an ILT4-binding agent, or an ILT2/ILT4-binding agent described herein.

In some embodiments, a method of enhancing or increasing NK cell activity in a subject comprises administering to the subject an effective amount of an ILT2-binding agent, or an ILT2/ILT4-binding agent described herein. In some embodiments, a method of enhancing or increasing NK cell activity in a subject comprises administering to the subject an effective amount of an ILT2/ILT4-binding agent described herein.

In some embodiments, a method of enhancing or increasing CTL activity in a subject comprises administering to the subject an effective amount of an ILT2-binding agent, or an ILT2/ILT4-binding agent described herein. In some embodiments, a method of enhancing or increasing CTL activity in a subject comprises administering to the subject an ILT2/ILT4-binding agent described herein.

In some embodiments, a method of enhancing or increasing macrophage phagocytosis in a subject comprises administering to the subject an effective amount of an ILT2-binding agent, or an ILT2/ILT4-binding agent described herein. In some embodiments, a method of enhancing or increasing macrophage phagocytosis in a subject comprises administering to the subject an ILT2/ILT4-binding agent described herein.

In some embodiments, a method of treating cancer in a subject comprises administering to the subject a therapeutically effective amount of an ILT2-binding agent, an ILT4-binding agent, or an ILT2/ILT4-binding agent described herein. In some embodiments, the cancer is mesothelioma, glioblastoma, renal cell carcinoma (including cancer arising from the clear cell type and papillary cell type), non-small cell lung cancer, melanoma, pancreatic ductal adenocarcinoma, gastric cancer, squamous cell carcinoma of the head and neck, biliary duct cancer, breast cancer, ovarian cancer, cervical cancer, endocervical cancer, colorectal cancer, or esophageal cancer. In some embodiments, the cancer is an advanced solid tumor.

In some embodiments, the cancer is pancreatic cancer, lung cancer, head and neck cancer, prostate cancer, skin cancer, stomach cancer, intestinal cancer, ovarian cancer, cervical cancer, uterine cancer, endometrial cancer, urinary bladder cancer, brain cancer, liver cancer, kidney cancer, or testicular cancer. In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia. In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML.

In some embodiments, a method of inhibiting tumor growth in a subject comprises administering to the subject a therapeutically effective amount of an ILT2-binding agent, an ILT4-binding agent, or an ILT2/ILT4-binding agent described herein. In some embodiments, a method of increasing or enhancing an immune response to a tumor or tumor cells in a subject comprises administering to the subject a therapeutically effective amount of an ILT2-binding agent, an ILT4-binding agent, or an ILT2/ILT4-binding agent described herein. In some embodiments, a method of activating or enhancing a persistent or long-term immune response to a tumor or tumor cells in a subject comprises administering to the subject a therapeutically effective amount of an ILT2-binding agent, an ILT4-binding agent, or an ILT2/ILT4-binding agent described herein. In some embodiments, a method of inhibiting tumor relapse or tumor regrowth in a subject comprises administering to the subject a therapeutically effective amount of an ILT2-binding agent, an ILT4-binding agent, or an ILT2/ILT4-binding agent described herein. In some embodiments a method of inducing a persistent or long-term immunity that inhibits tumor relapse or tumor regrowth in a subject comprises administering to the subject a therapeutically effective amount of an ILT2-binding agent, an ILT4-binding agent, or an ILT2/ILT4-binding agent described herein. In some embodiments, the tumor is a a pancreatic tumor, a breast tumor, a lung tumor, a non-small cell lung tumor, a head and neck tumor, a colorectal tumor, a prostate tumor, a skin tumor, a melanoma, a gastric tumor, a colorectal tumor, an ovarian tumor, a cervical tumor, a uterine tumor, an endometrial tumor, an endocervical tumor, a bladder tumor, a brain tumor, an esophageal tumor, a liver tumor, a kidney tumor, a renal tumor, mesothelioma, glioblastoma, a biliary duct tumor, or a testicular tumor.

In some embodiments, a method of activating myeloid cells in the tumor microenvironment in a subject with a tumor comprises administering to the subject a therapeutically effective amount of an ILT2-binding agent, an ILT4-binding agent, or an ILT2/ILT4-binding agent described herein. In some embodiments, the myeloid cells are primary dendritic cells or tolerogenic dendritic cells. In some embodiments, the myeloid cells are monocytes or macrophages.

In some embodiments, a method of reactivating tolerogenic dendritic cells in a subject comprises administering to the subject a therapeutically effective amount of an ILT2-binding agent, an ILT4-binding agent, or an ILT2/ILT4-binding agent described herein. In some embodiments, the tolerogenic dendritic cells are found in the tumor microenvironment.

In some embodiments of all the methods described herein, the ILT-binding agent is administered to a subject as part of a combination therapy. In some embodiments, the combination therapy comprises at least one additional therapeutic agent. In some embodiments, the combination therapy comprises an immune checkpoint inhibitor, such as an anti-PD-1 antibody or an anti-PD-L1 antibody. In some embodiments, the anti-PD-1 antibody is Pembrolizumab (MK-3475; KEYTRUDA), Pidilizumab (CT-011), Nivolumab (OPDIVO), Durvalumab (MEDI0680), Cemiplimab (REGN2810), Tislelizumab (BGB-A317), Spartalizumab (PDR-001), or STI-A1110.

Also disclosed is the use of an ILT-binding agent described herein in the manufacture of a medicament for the treatment of cancer. In some embodiments, an ILT-binding agent described herein is for use in the treatment of cancer. In some embodiments, an ILT-binding agent described herein is for use in inhibition of tumor growth.

In some embodiments of all the aforementioned methods, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

BRIEF DESCRIPTION OF THE FIGURES

FIGS. 23A-23C. Synergetic effects of an anti-ILT2/ILT4 antibody and anti-PD-1 antibody on T cell activation and cytokine release from T cells.

DETAILED DESCRIPTION

Figure 1:
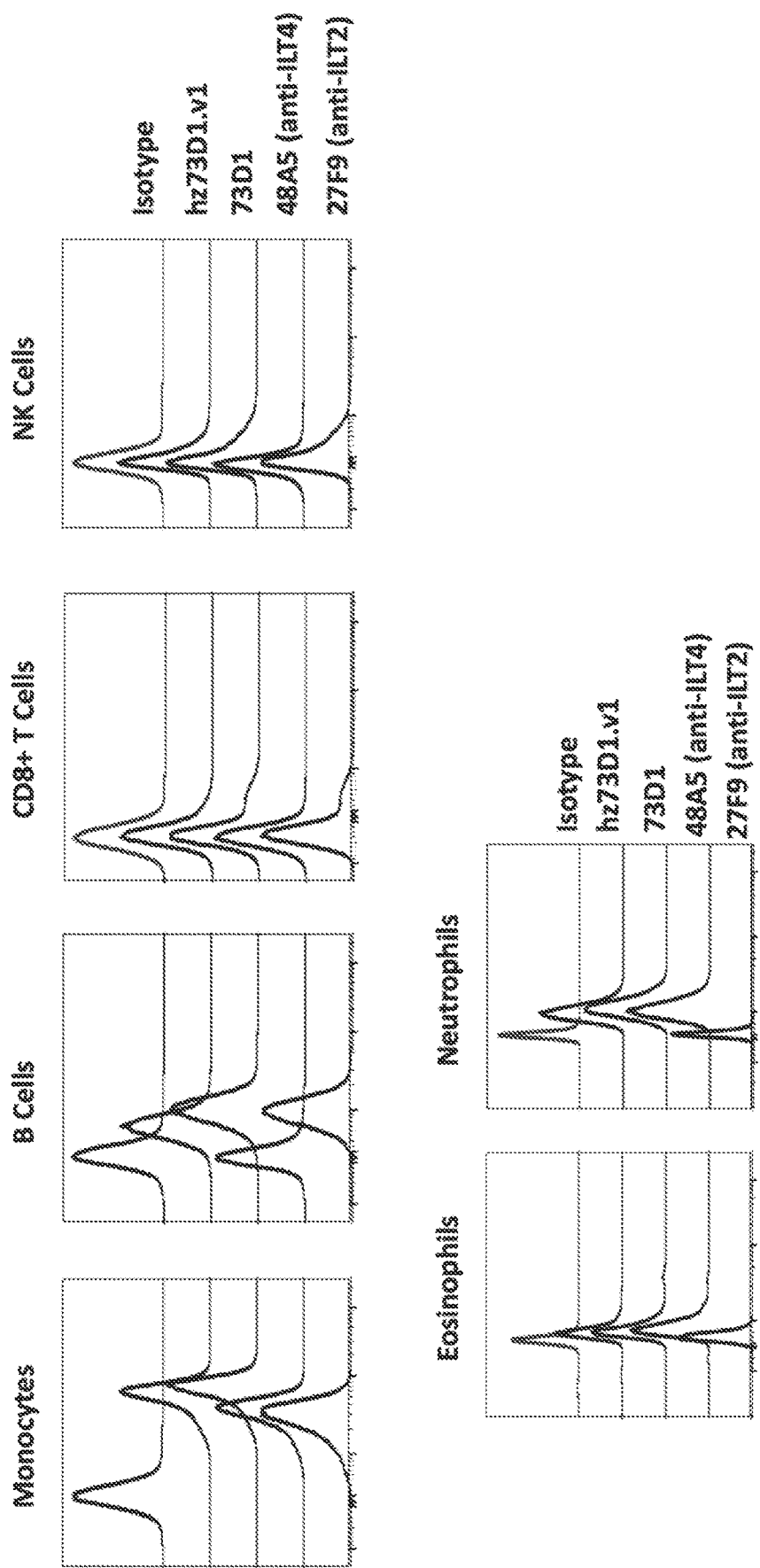
FIG. 1. Expression of ILT2 and ILT4 in various immune cells assayed by flow cytometry.

The present disclosure provides novel agents, including but not limited to polypeptides such as antibodies, that bind immunoglobulin-like transcript 2 (ILT2), immunoglobulin-like transcript 4 (ILT4), or both ILT2 and ILT4. As used herein the term "ILT-binding agents" refers to ILT2-binding agents, ILT4-binding agents, and ILT2/ILT4-binding agents. As used herein "ILT2/ILT4-binding agents" refers to agents that bind both ILT2 and ILT4, and may also be referred to as ILT2/ILT4 dual binders. The ILT-binding agents include, but are not limited to, polypeptides, antibodies (including antigen-binding fragments thereof), scaffold proteins, and heterodimeric molecules. ILT-binding agents include, but are not limited to, antagonists of ILT2 and/or ILT4 activity, inhibitors of ILT2 and/or ILT4 activity, and/or agents that inhibit ILT2 and/or ILT4 suppressive activity. Related polypeptides, polynucleotides, vectors, compositions comprising the agents, cells comprising the related polynucleotides or vectors, and methods of making the agents are also provided. Methods of using the novel ILT-binding agents are also provided.

I. Definitions

Unless otherwise defined herein, technical and scientific terms used in the present description have the meanings that are commonly understood by those of ordinary skill in the art. Whenever appropriate, terms used in the singular will also include the plural and vice versa. In the event that any description of a term set forth conflicts with any document incorporated herein by reference, the description of the term set forth below shall control.

The term "binding agent" as used herein refers to a molecule that binds a specific antigen or target (e.g., ILT2 and/or ILT4). A binding agent may comprise a protein, peptide, nucleic acid, carbohydrate, lipid, or small molecular weight compound. In some embodiments, a binding agent comprises a full-length antibody. In some embodiments, a binding agent is an antigen-binding fragment of an antibody. In some embodiments, a binding agent comprises an alternative protein scaffold or artificial scaffold (e.g., a non-immunoglobulin backbone). In some embodiments, a binding agent is a fusion protein comprising an antigen-binding site. In some embodiments, a binding agent is a bispecific or multispecific molecule comprising at least one antigen-binding site.

The term "antibody" is used herein in the broadest sense and encompasses various antibody structures, including but not limited to, an immunoglobulin molecule that recognizes and binds a target through at least one antigen-binding site, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, and antibody fragments as long as they exhibit the desired antigen-binding activity.

The term "intact antibody" or "full-length antibody" refers to an antibody having a structure substantially similar to a native antibody structure. This includes, for example, an antibody comprising two light chains each comprising a variable region and a light chain constant region (CL) and two heavy chains each comprising a variable region and at least heavy chain constant regions CH1, CH2, and CH3. Generally, an intact antibody includes a hinge region (or a portion thereof) between the CH1 and CH2 regions.

The term "antibody fragment" or "antibody fragments" as used herein refers to a molecule other than an intact antibody that comprises a portion of an antibody and generally an antigen-binding site. Examples of antibody fragments include, but are not limited to, Fab, Fab', F(ab')2, Fv, single chain antibody molecules (e.g., scFv), sc(Fv)$_2$, disulfide-linked scFv (dsscFv), diabodies, tribodies, tetrabodies, minibodies, dual variable domain antibodies (DVD), single variable domain antibodies (e.g., camelid antibodies), and multispecific antibodies formed from antibody fragments.

The term "monoclonal antibody" as used herein refers to a substantially homogenous antibody population involved in the highly specific recognition and binding of a single antigenic determinant or epitope. The term "monoclonal antibody" encompasses intact and full-length monoclonal antibodies as well as antibody fragments (e.g., Fab, Fab', F(ab')$_2$, Fv), single chain antibodies (e.g., scFv), fusion proteins comprising an antibody fragment, and any other modified immunoglobulin molecule comprising at least one antigen-binding site. Furthermore, "monoclonal antibody"

refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a first source or species, while the remainder of the heavy and/or light chain is derived from a different source or species.

The term "humanized antibody" as used herein refers to an antibody that comprises a human heavy chain variable region and a light chain variable region wherein the native CDR amino acid residues are replaced by residues from corresponding CDRs from a nonhuman antibody (e.g., mouse, rat, rabbit, or nonhuman primate), wherein the nonhuman antibody has the desired specificity, affinity, and/or activity. In some embodiments, one or more framework region amino acid residues of the human heavy chain or light chain variable regions are replaced by corresponding residues from the nonhuman antibody. Furthermore, humanized antibodies can comprise amino acid residues that are not found in the human antibody or in the nonhuman antibody. In some embodiments, these modifications are made to further refine and/or optimize antibody characteristics. In some embodiments, the humanized antibody comprises at least a portion of a human immunoglobulin constant region (e.g., CH1, CH2, CH3, Fc, and/or hinge region).

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but are not limited to, phage display libraries, yeast display libraries, transgenic animals, recombinant protein production, and B-cell hybridoma technology.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

The term "specifically binds" as used herein refers to an agent that interacts more frequently, more rapidly, with greater duration, with greater affinity, or with some combination of the above to a particular antigen, epitope, protein, or target molecule than with alternative substances. A binding agent that specifically binds an antigen can be identified, for example, by immunoassays, ELISAs, surface plasmon resonance (SPR), or other techniques known to those of skill in the art. In some embodiments, an agent that specifically binds an antigen (e.g., human ILT2) can bind related antigens (e.g., rhesus ILT2 and/or cyno ILT2). In some embodiments, an agent that specifically binds an antigen (e.g., human ILT2) can bind a second antigen (e.g., human ILT4) and is referred to herein as a "dual binder". In some embodiments, a binding agent that specifically binds an antigen can bind the target antigen at a higher affinity than its affinity for a different antigen. The different antigen can be a related antigen. In some embodiments, a binding agent that specifically binds an antigen can bind the target antigen with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different antigen. In some embodiments, a binding agent that specifically binds a particular antigen binds a different antigen at such a low affinity that binding cannot be detected using an assay described herein or otherwise known in the art. In some embodiments, affinity is measured using SPR technology in a Biacore system as described herein or as known to those of skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 20-40, at least about 40-60, at least about 60-80 nucleotides or amino acid residues in length, or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of an alanine for a valine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct that is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition that is in a form not found in nature. An "isolated" antibody is substantially free of material from the cellular source from which it is derived. In some embodiments, isolated polypeptides, soluble proteins, antibodies, polynucleotides, vectors, cells, or compositions are those that have been purified to a degree that they are no longer in a form in which they are found in nature. In some embodiments, a polypeptide, soluble protein, antibody, polynucleotide, vector, cell, or composition that is isolated is substantially pure. A polypeptide, soluble protein, antibody, polynucleotide, vector, cell, or composition can be isolated from a natural source (e.g., tissue) or from a source such as an engineered cell line.

The term "substantially pure" as used herein refers to material that is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent, and that is generally safe, non-toxic, and has no effect on the pharmacological activity of the therapeutic agent. In general, those of skill in the art and government agencies consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent to be effective. A pharmaceutical formulation or composition generally comprises additional components, such as a pharmaceutically acceptable excipient, carrier, adjuvant, buffers, etc.

The term "effective amount" or "therapeutically effective amount" as used herein refers to the amount of an agent that is sufficient to reduce and/or ameliorate the severity and/or duration of (i) a disease, disorder or condition in a subject, and/or (ii) a symptom in a subject. The term also encompasses an amount of an agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding agents provided herein).

The term "therapeutic effect" as used herein refers to the effect and/or ability of an agent to reduce and/or ameliorate the severity and/or duration of (i) a disease, disorder, or condition in a subject, and/or (ii) a symptom in a subject. The term also encompasses the ability of an agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding agents provided herein).

The term "treat" or "treatment" or "treating" or "to treat" or "alleviate" or "alleviation" or "alleviating" or "to alleviate" as used herein refers to therapeutic measures that aim to slow down, lessen symptoms of, and/or halt progression of a pathologic condition or disorder. Thus, those in need of treatment include those already with the disorder.

The term "prevent" or "prevention" or "preventing" as used herein refers to the partial or total inhibition of the development, recurrence, onset, or spread of a disease, disorder, or condition, or a symptom thereof in a subject.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, dendritic cells, etc.

As used herein, reference to "about" or "approximately" a value or parameter includes (and describes) embodiments that are directed to that value or parameter. For example, a description referring to "about X" includes description of "X".

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. ILT-Binding Agents

Amino acid (aa) sequences for human ILT2 (UniProtKB No. Q8NHL6), human ILT4 (UniProtKB No. Q8N423), rhesus macaque ("rhesus") ILT2 (NCBI Ref No. XP_028694980.1), and cynomolgus monkey ("cyno") ILT2 (in house sequence has 98% identity to UniProtKB No. A0A2K5VN04) are provided herein as SEQ ID NO:1, SEQ ID NO:8, SEQ ID NO:15, and SEQ ID NO:166, respectively. As used herein, reference to amino acid positions of ILT2 or ILT4 refer to the numbering of amino acid sequences including the signal sequence.

A genomic orthologue for human ILT2 is found in the monkey genome, however, no genomic orthologue for human ILT4 appears to exist. Expression patterns of the monkey ILT2 orthologue are comparable to the combined expression patterns of human ILT2 and human ILT4. Without being bound by theory, it is believed that the ILT2 orthologue in monkeys may have biological/functional capabilities that are equivalent to a combination of the biological functions of human ILT2 and human ILT4.

ILT2 is a single pass type I transmembrane protein with a predicted molecular weight of approximately 71 kDa. ILT2 (human, rhesus, and cyno) is characterized by an extracellular domain comprising four Ig-like C2 type domains, a transmembrane domain, and a long cytoplasmic domain containing 4 ITIM domains (see, e.g., Borges et al., 1997, *J. Immunol.*, 159:5192-5196). The four Ig-like C2-type domains may be referred to herein as Domain 1 (D1), Domain 2 (D2), Domain 3 (D3), and Domain 4 (D4). D1 is situated at the N-terminal portion of the protein, then D2, D3, with D4 situated closest to the transmembrane region. As characterized within UniProtKB, human ILT2 is a protein of 650 amino acids (aa)—the signal sequence is aa 1-23, the extracellular domain is aa 24-461, the transmembrane region is aa 462-482, and the cytoplasmic domain is aa 483-650. Within the extracellular domain, D1 is aa 27-115, D2 is aa 116-221, D3 is aa 222-312, D4 is aa 313-409, and the "stem region" is aa 410-461. Within the cytoplasmic domain, ITIMs are aa 531-536, 560-565, 612-617, and 642-647. Rhesus ILT2 is a protein of 639 amino acids (aa)—as compared to structural characterization of human ILT2 the signal sequence is aa 1-23, the extracellular domain is aa 24-460, the transmembrane region is aa 461-481, and the cytoplasmic domain is aa 482-639. Within the extracellular domain, D1 is aa 27-114, D2 is aa 115-220, D3 is aa 221-311, D4 is aa 312-408, and the "stem region" is aa 409-460. Within the cytoplasmic domain, ITIMs are aa 530-535, 559-564, 601-606, and 631-636. Cyno ILT2 is a protein of 651 amino acids (aa)—as compared to structural characterization of human ILT2 the signal sequence is aa 1-23, the extracellular domain is aa 24-461, the transmembrane region is aa 462-482, and the cytoplasmic domain is aa 483-651. Within the extracellular domain, D1 is aa 27-114, D2 is aa 115-220, D3 is aa 221-311, D4 is aa 312-408, and the "stem region" is aa 409-461. Within the cytoplasmic domain, ITIMs are aa 531-536, 561-566, 613-618, and 643-648. ILT2 is expressed (to varying degrees) on natural killer (NK) cells, monocytes, macrophages, eosinophils, basophils, dendritic cells (DCs), subset of T-cells, and B-cells. Various ligands are known to interact with ILT2, including HLA class I molecules (e.g., HLA-A, HLA-B, HLA-C, HLA-E, HLA-F, and HLA-G). ILT2 appears to bind more strongly with the "non-classical" MHC I molecule HLA-G than to classical HLA class I molecules.

ILT4 has a structure very similar to ILT2. It is a single pass type I transmembrane protein with a predicted molecular weight of approximately 65 kDa. ILT4 is characterized by an extracellular domain comprising four Ig-like C2 type domains, a transmembrane domain, and a long cytoplasmic domain containing 3 ITIM domains (see, e.g., Borges et al., 1997, *J. Immunol.*, 159:5192-5196). As described for ILT2, the four Ig-like C2-type domains may be referred to herein as D1, D2, D3, and D4. D1 is situated at the N-terminal portion of the protein, then D2, D3, with D4 situated closest to the transmembrane region. As characterized within UniProtKB, human ILT4 is a protein of 598 amino acids (aa)—the signal sequence is aa 1-21, the extracellular domain is aa 22-461, the transmembrane region is aa 462-482, and the cytoplasmic domain is aa 483-598. Within the extracellular domain, D1 is aa 27-110, D2 is aa 111-229, D3 is aa 230-318, D4 is aa 330-419, and the "stem region" is aa 420-461. Within the cytoplasmic domain, ITIMs are aa 531-536, 560-565, and 590-595. ILT4 is expressed on myeloid cells such as monocytes, macrophages, dendritic cells, but not on lymphoid cells. ILT4 has been observed to bind a variety of ligands, notably HLA class I molecules, ANGPTL proteins, myelin inhibitors, and β-amyloid.

It is understood that the domains of ILT2 or ILT4 (e.g., human ILT2, rhesus ILT2, cyno ILT2, or human ILT4) may be defined differently by those of skill in the art, therefore the N-terminal amino acids and the C-terminal amino acids of any ILT2 or ILT4 domain or region may vary by 1, 2, 3, 4, 5, or more amino acid residues.

The present disclosure provides agents that bind ILT2, ILT4, or ILT2 and ILT4, i.e., ILT-binding agents. The agents that bind both ILT2 and ILT4 (ILT2/ILT4-binding agents) may be referred to herein as "dual binders". In some embodiments, an ILT2-binding agent or an ILT2/ILT4-binding agent binds ILT2 or a fragment of ILT2. In some embodiments, a fragment of ILT2 comprises the extracellular domain of ILT2. In some embodiments, a fragment of ILT2 comprises one or more of the Ig-like C2 type domains (e.g., D1, D2, D3, and/or D4). In some embodiments, a fragment of ILT2 comprises D1 and D2. In some embodiments, a fragment of ILT2 comprises D2 and D3. In some embodiments, a fragment of ILT2 comprises D3 and D4. In some embodiments, a fragment of ILT2 comprises D1, D2, and D3. In some embodiments, a fragment of ILT2 comprises D2, D3, and D4. In some embodiments, a fragment of ILT2 comprises one or more of the Ig-like C2 type domains and the stem region. In some embodiments, a fragment of ILT2 comprises D4-stem, D3-D4-stem, or D2-D3-D4-stem.

In some embodiments, the extracellular domain of human ILT2 comprises amino acids 24-461 of SEQ ID NO:1. In some embodiments, D1 of human ILT2 comprises amino acids 27-115 of SEQ ID NO:1. In some embodiments, D2 of human ILT2 comprises amino acids 116-221 of SEQ ID NO:1. In some embodiments, D3 of human ILT2 comprises amino acids 222-312 of SEQ ID NO:1. In some embodiments, D4 of human ILT2 comprises amino acids 313-409 of SEQ ID NO:1. In some embodiments, D1-D2 of human ILT2 comprises amino acids 27-221 of SEQ ID NO:1. In some embodiments, D2-D3 of human ILT2 comprises amino acids 116-312 of SEQ ID NO:1. In some embodiments, D3-D4 of human ILT2 comprises amino acids 222-409 of SEQ ID NO:1. In some embodiments, D1-D2-D3 of human ILT2 comprises amino acids 27-312 of SEQ ID NO:1. In some embodiments, D2-D3-D4 of human ILT2 comprises amino acids 116-409 of SEQ ID NO:1. In some embodiments, D4-stem of human ILT2 comprises amino acids 313-461 of SEQ ID NO:1. In some embodiments, D3-D4-stem of human ILT2 comprises amino acids 222-461 of SEQ ID NO:1. In some embodiments, D2-D3-D4-stem of human ILT2 comprises amino acids 116-461 of SEQ ID NO:1. In some embodiments, a fragment of human ILT2 comprises the amino acid sequence of SEQ ID NO:3. In some embodiments, a fragment of human ILT2 comprises the amino acid sequence of SEQ ID NO:4. In some embodiments, a fragment of human ILT2 comprises the amino acid sequence of SEQ ID NO:5. In some embodiments, a fragment of human ILT2 comprises the amino acid sequence of SEQ ID NO:6. In some embodiments, a fragment of human ILT2 comprises the amino acid sequence of SEQ ID NO:7. In some embodiments, a fragment of human ILT2 comprises the amino acid sequence of SEQ ID NO:4 and SEQ ID NO:5. In some embodiments, a fragment of human ILT2 comprises the amino acid sequence of SEQ ID NO:5 and SEQ ID NO:6. In some embodiments, a fragment of human ILT2 comprises the amino acid sequence of SEQ ID NO:6 and SEQ ID NO:7. In some embodiments, a fragment of human ILT2 comprises the amino acid sequence of SEQ ID NO:4, SEQ ID NO:5, and SEQ ID NO:6. In some embodiments, a fragment of human ILT2 comprises the amino acid sequence of SEQ ID NO:5, SEQ ID NO:6, and SEQ ID NO:7.

In some embodiments, the extracellular domain of rhesus ILT2 comprises amino acids 24-460 of SEQ ID NO:15. In some embodiments, D1 of rhesus ILT2 comprises amino acids 27-114 of SEQ ID NO:15. In some embodiments, D2 of rhesus ILT2 comprises amino acids 115-220 of SEQ ID NO:15. In some embodiments, D3 of rhesus ILT2 comprises amino acids 221-311 of SEQ ID NO:15. In some embodiments, D4 of rhesus ILT2 comprises amino acids 312-408 of SEQ ID NO:15. In some embodiments, D1-D2 of rhesus ILT2 comprises amino acids 27-220 of SEQ ID NO:15. In some embodiments, D2-D3 of rhesus ILT2 comprises amino acids 115-311 of SEQ ID NO:15. In some embodiments, D3-D4 of rhesus ILT2 comprises amino acids 221-408 of SEQ ID NO:15. In some embodiments, D1-D2-D3 of rhesus ILT2 comprises amino acids 27-311 of SEQ ID NO:15. In some embodiments, D2-D3-D4 of rhesus ILT2 comprises amino acids 115-408 of SEQ ID NO:15. In some embodiments, D4-stem of rhesus ILT2 comprises amino acids 312-460 of SEQ ID NO:15. In some embodiments, D3-D4-stem of rhesus ILT2 comprises amino acids 221-460 of SEQ ID NO:15. In some embodiments, D2-D3-D4-stem of rhesus ILT2 comprises amino acids 115-460 of SEQ ID NO:15. In some embodiments, a fragment of rhesus ILT2 comprises the amino acid sequence of SEQ ID NO:17. In some embodiments, a fragment of rhesus ILT2 comprises the amino acid sequence of SEQ ID NO:18. In some embodiments, a fragment of rhesus ILT2 comprises the amino acid sequence of SEQ ID NO:19. In some embodiments, a fragment of rhesus ILT2 comprises the amino acid sequence of SEQ ID NO:20. In some embodiments, a fragment of rhesus ILT2 comprises the amino acid sequence of SEQ ID NO:21. In some embodiments, a fragment of rhesus ILT2 comprises the amino acid sequence of SEQ ID NO:18 and SEQ ID NO:19. In some embodiments, a fragment of human ILT2 comprises the amino acid sequence of SEQ ID NO:19 and SEQ ID NO:20. In some embodiments, a fragment of human ILT2 comprises the amino acid sequence of SEQ ID NO:20 and SEQ ID NO:21. In some embodiments, a fragment of human ILT2 comprises the amino acid sequence of SEQ ID NO:18, SEQ ID NO:19, and SEQ ID NO:20. In some embodiments, a fragment of human ILT2 comprises the amino acid sequence of SEQ ID NO:19, SEQ ID NO:20, and SEQ ID NO:21.

In some embodiments, the extracellular domain of cyno ILT2 comprises amino acids 24-461 of SEQ ID NO:166. In some embodiments, D1 of cyno ILT2 comprises amino acids 27-114 of SEQ ID NO:166. In some embodiments, D2 of cyno ILT2 comprises amino acids 115-220 of SEQ ID NO:166. In some embodiments, D3 of cyno ILT2 comprises amino acids 221-311 of SEQ ID NO:166. In some embodiments, D4 of cyno ILT2 comprises amino acids 312-408 of SEQ ID NO:166. In some embodiments, D1-D2 of cyno ILT2 comprises amino acids 27-220 of SEQ ID NO:166. In some embodiments, D2-D3 of cyno ILT2 comprises amino acids 115-311 of SEQ ID NO:166. In some embodiments, D3-D4 of cyno ILT2 comprises amino acids 221-408 of SEQ ID NO:166. In some embodiments, D1-D2-D3 of cyno ILT2 comprises amino acids 27-311 of SEQ ID NO:166. In some embodiments, D2-D3-D4 of cyno ILT2 comprises amino acids 115-408 of SEQ ID NO:166. In some embodiments, D4-stem of cyno ILT2 comprises amino acids 312-461 of SEQ ID NO:166. In some embodiments, D3-D4-stem of cyno ILT2 comprises amino acids 221-461 of SEQ ID NO:166. In some embodiments, D2-D3-D4-stem of cyno ILT2 comprises amino acids 115-461 of SEQ ID NO:166. In some embodiments, a fragment of cyno ILT2 comprises the amino acid sequence of SEQ ID NO:168. In some embodiments, a fragment of cyno ILT2 comprises the amino acid sequence of SEQ ID NO:169. In some embodiments, a fragment of cyno ILT2 comprises the amino acid sequence of SEQ ID NO:170. In some embodiments, a fragment of cyno ILT2 comprises the amino acid sequence of SEQ ID NO:171. In some embodiments, a fragment of cyno ILT2 comprises the amino acid sequence of SEQ ID NO:172. In some embodiments, a fragment of cyno ILT2 comprises the amino acid sequence of SEQ ID NO:169 and SEQ ID NO:170. In some embodiments, a fragment of human ILT2 comprises the amino acid sequence of SEQ ID NO:170 and SEQ ID NO:171. In some embodiments, a fragment of human ILT2 comprises the amino acid sequence of SEQ ID NO:171 and SEQ ID NO:172. In some embodiments, a fragment of human ILT2 comprises the amino acid sequence of SEQ ID NO:169, SEQ ID NO:170, and SEQ ID NO:171. In some embodiments, a fragment of human ILT2 comprises the amino acid sequence of SEQ ID NO:170, SEQ ID NO:171, and SEQ ID NO:172.

In some embodiments, an ILT2-binding agent or an ILT2/ILT4-binding agent binds a fragment of ILT2 (e.g., human ILT2, rhesus ILT2, and/or cyno ILT2). In some embodiments, an ILT2-binding agent or an ILT2/ILT4-binding agent binds within a specific region of ILT2. In some embodiments, an ILT2-binding agent or an ILT2/ILT4-binding agent binds within the extracellular domain of ILT2. In some embodiments, an ILT2-binding agent or an ILT2/ILT4-binding agent binds within the D1 domain of ILT2. In some embodiments, an ILT2-binding agent or an ILT2/ILT4-binding agent binds within the D2 domain of ILT2. In some embodiments, an ILT2-binding agent or an ILT2/ILT4-binding agent binds within the D3 domain of ILT2. In some embodiments, an ILT2-binding agent or an ILT2/ILT4-binding agent binds within the D4 domain of ILT2. In some embodiments, an ILT2-binding agent or an ILT2/ILT4-binding agent binds within the D4-stem region of ILT2. In some embodiments, an ILT2-binding agent or an ILT2/ILT4-binding agent binds within the D1-D2 domains of ILT2. In some embodiments, an ILT2-binding agent or an ILT2/ILT4-binding agent binds within the D2-D3 domains of ILT2. In some embodiments, an ILT2-binding agent or an ILT2/ILT4-binding agent binds within the D3-D4 domains of ILT2. In some embodiments, an ILT2-binding agent or an ILT2/ILT4-binding agent binds within the D1-D2-D3 domains of ILT2. In some embodiments, an ILT2-binding agent or an ILT2/ILT4-binding agent binds within the D2-D3-D4 domains of ILT2. In some embodiments, an ILT2-binding agent or an ILT2/ILT4-binding agent binds an epitope on ILT2. In some embodiments, an ILT2-binding agent or an ILT2/ILT4-binding agent binds a conformational epitope on ILT2. In some embodiments, an ILT2-binding agent does not bind other human LILRB proteins (e.g., ILT3, ILT4, ILT5, or LILRB5). In some embodiments, an ILT2/ILT4-binding agent does not bind other human LILRB proteins (e.g., ILT3, ILT5, or LILRB5). In some embodiments, an ILT2-binding agent or an ILT2/ILT4-binding agent does not bind one or more of the human LILRA proteins (e.g., LILRA1, LILRA2, LILRA4, LILRA5, or LILRA6). In some embodiments, an ILT2-binding agent or an ILT2/ILT4-binding agent does not bind LILRA2, LILRA4, LILRA5, or LILRA6.

In some embodiments, an ILT2-binding agent or an ILT2/ILT4-binding agent binds human ILT2. In some embodiments, an ILT2-binding agent or an ILT2/ILT4-binding agent binds cyno ILT2 and/or rhesus ILT2. In some embodiments, an ILT2-binding agent or an ILT2/ILT4-binding agent binds human ILT2, cyno ILT2, and rhesus ILT2. In some embodiments, an ILT2-binding agent or an ILT2/ILT4-binding agent binds SEQ ID NO:1. In some embodiments, an ILT2-binding agent or an ILT2/ILT4-binding agent binds SEQ ID NO:2. In some embodiments, an ILT2-binding agent or an ILT2/ILT4-binding agent binds SEQ ID NO:3. In some embodiments, an ILT2-binding agent or an ILT2/ILT4-binding agent binds a fragment comprising amino acids 24-461 of SEQ ID NO:1. In some embodiments, an ILT2-binding agent or an ILT2/ILT4-binding agent binds a fragment comprising amino acids 27-115 of SEQ ID NO:1. In some embodiments, an ILT2-binding agent or an ILT2/ILT4-binding agent binds a fragment comprising amino acids 116-221 of SEQ ID NO:1. In some embodiments, an ILT2-binding agent or an ILT2/ILT4-binding agent binds a fragment comprising amino acids 222-312 of SEQ ID NO:1. In some embodiments, an ILT2-binding agent or an ILT2/ILT4-binding agent binds a fragment comprising amino acids 313-409 of SEQ ID NO:1. In some embodiments, an ILT2-binding agent or an ILT2/ILT4-binding agent binds a fragment comprising amino acids 27-221 of SEQ ID NO:1. In some embodiments, an ILT2-binding agent or an ILT2/ILT4-binding agent binds a fragment comprising amino acids 116-312 of SEQ ID NO:1. In some embodiments, an ILT2-binding agent or an ILT2/ILT4-binding agent binds a fragment comprising amino acids 222-409 of SEQ ID NO:1. In some embodiments, an ILT2-binding agent or an ILT2/ILT4-binding agent binds SEQ ID NO:4. In some embodiments, an ILT2-binding agent or an ILT2/ILT4-binding agent binds SEQ ID NO:5. In some embodiments, an ILT2-binding agent or an ILT2/ILT4-binding agent binds SEQ ID NO:6. In some embodiments, an ILT2-binding agent or an ILT2/ILT4-binding agent binds SEQ ID NO:7.

In some embodiments, an ILT2-binding agent or an ILT2/ILT4-binding agent binds SEQ ID NO:15. In some embodiments, an ILT2-binding agent or an ILT2/ILT4-binding agent binds SEQ ID NO:16. In some embodiments, an ILT2-binding agent or an ILT2/ILT4-binding agent binds SEQ ID NO:17. In some embodiments, an ILT2-binding agent or an ILT2/ILT4-binding agent binds a fragment comprising amino acids 24-460 of SEQ ID NO:15. In some embodiments, an ILT2-binding agent or an ILT2/ILT4-binding agent binds a fragment comprising amino acids 27-114 of SEQ ID NO:15. In some embodiments, an ILT2-binding agent or an ILT2/ILT4-binding agent binds a fragment comprising amino acids 115-220 of SEQ ID NO:15. In some embodiments, an ILT2-binding agent or an ILT2/ILT4-binding agent binds a fragment comprising amino acids 221-311 of SEQ ID NO:15. In some embodiments, an ILT2-binding agent or an ILT2/ILT4-binding agent binds a fragment comprising amino acids 312-408 of SEQ ID NO:15. In some embodiments, an ILT2-binding agent or an ILT2/ILT4-binding agent binds a fragment comprising amino acids 27-220 of SEQ ID NO:15. In some embodiments, an ILT2-binding agent or an ILT2/ILT4-binding agent binds a fragment comprising amino acids 115-311 of SEQ ID NO:15. In some embodiments, an ILT2-binding agent or an ILT2/ILT4-binding agent binds a fragment comprising amino acids 221-408 of SEQ ID NO:15. In some embodiments, an ILT2-binding agent or an ILT2/ILT4-binding agent binds SEQ ID NO:18. In some embodiments, an ILT2-binding agent or an ILT2/ILT4-binding agent binds SEQ ID NO:19. In some embodiments, an ILT2-binding agent or an ILT2/ILT4-binding agent binds SEQ ID NO:20. In some embodiments, an ILT2-binding agent or an ILT2/ILT4-binding agent binds SEQ ID NO:21.

In some embodiments, an ILT2-binding agent or an ILT2/ILT4-binding agent binds SEQ ID NO:166. In some embodiments, an ILT2-binding agent or an ILT2/ILT4-binding agent binds SEQ ID NO:167. In some embodiments, an ILT2-binding agent or an ILT2/ILT4-binding agent binds SEQ ID NO:168. In some embodiments, an ILT2-binding agent or an ILT2/ILT4-binding agent binds a fragment comprising amino acids 24-461 of SEQ ID NO:166. In some embodiments, an ILT2-binding agent or an ILT2/ILT4-binding agent binds a fragment comprising amino acids 27-114 of SEQ ID NO:166. In some embodiments, an ILT2-binding agent or an ILT2/ILT4-binding agent binds a fragment comprising amino acids 115-220 of SEQ ID NO:166. In some embodiments, an ILT2-binding agent or an ILT2/ILT4-binding agent binds a fragment comprising amino acids 221-311 of SEQ ID NO:166. In some embodiments, an ILT2-binding agent or an ILT2/ILT4-binding agent binds a fragment comprising amino acids 312-408 of SEQ ID NO:166. In some embodiments, an ILT2-binding agent or an ILT2/ILT4-binding agent binds a fragment comprising amino acids 27-220 of SEQ ID NO:166. In some embodiments, an ILT2-binding agent or an ILT2/ILT4-binding agent binds a fragment comprising amino acids 115-311 of SEQ ID NO:166. In some embodiments, an ILT2-binding agent or an ILT2/ILT4-binding agent binds a fragment comprising amino acids 221-408 of SEQ ID NO:166. In some embodiments, an ILT2-binding agent or an ILT2/ILT4-binding agent binds SEQ ID NO:169. In some embodiments, an ILT2-binding agent or an ILT2/ILT4-binding agent binds SEQ ID NO:170. In some embodiments, an ILT2-binding agent or an ILT2/ILT4-binding agent binds SEQ ID NO:171. In some embodiments, an ILT2-binding agent or an ILT2/ILT4-binding agent binds SEQ ID NO:172.

In some embodiments, an ILT2-binding agent or an ILT2/ILT4-binding agent binds a polypeptide comprising the amino acid sequence of SEQ ID NO:2. In some embodiments, an ILT2-binding agent or an ILT2/ILT4-binding agent binds a polypeptide comprising the amino acid sequence of SEQ ID NO:3. In some embodiments, an ILT2-binding agent or an ILT2/ILT4-binding agent binds a polypeptide comprising the amino acid sequence of SEQ ID NO:4. In some embodiments, an ILT2-binding agent or an ILT2/ILT4-binding agent binds a polypeptide comprising the amino acid sequence of SEQ ID NO:5. In some embodiments, an ILT2-binding agent or an ILT2/ILT4-binding agent binds a polypeptide comprising the amino acid sequence of SEQ ID NO:6. In some embodiments, an ILT2-binding agent or an ILT2/ILT4-binding agent binds a polypeptide comprising the amino acid sequence of SEQ ID NO:7. In some embodiments, an ILT2-binding agent or an ILT2/ILT4-binding agent binds a polypeptide comprising the amino acid sequence of SEQ ID NO:16. In some embodiments, an ILT2-binding agent or an ILT2/ILT4-binding agent binds a polypeptide comprising the amino acid sequence of SEQ ID NO:17. In some embodiments, an ILT2-binding agent or an ILT2/ILT4-binding agent binds a polypeptide comprising the amino acid sequence of SEQ ID NO:18. In some embodiments, an ILT2-binding agent or an ILT2/ILT4-binding agent binds a polypeptide comprising the amino acid sequence of SEQ ID NO:19. In some embodiments, an ILT2-binding agent or an ILT2/ILT4-binding agent binds a polypeptide comprising the amino acid sequence of SEQ ID NO:20. In some embodiments, an ILT2-binding agent or an ILT2/ILT4-binding agent binds a polypeptide comprising the amino acid sequence of SEQ ID NO:21. In some embodiments, an ILT2-binding agent or an ILT2/ILT4-binding agent binds a polypeptide comprising the amino acid sequence of SEQ ID NO:167. In some embodiments, an ILT2-binding agent or an ILT2/ILT4-binding agent binds a polypeptide comprising the amino acid sequence of SEQ ID NO:168. In some embodiments, an ILT2-binding agent or an ILT2/ILT4-binding agent binds a polypeptide comprising the amino acid sequence of SEQ ID NO:169. In some embodiments, an ILT2-binding agent or an ILT2/ILT4-binding agent binds a polypeptide comprising the amino acid sequence of SEQ ID NO:170. In some embodiments, an ILT2-binding agent or an ILT2/ILT4-binding agent binds a polypeptide comprising the amino acid sequence of SEQ ID NO:171. In some embodiments, an ILT2-binding agent or an ILT2/ILT4-binding agent binds a polypeptide comprising the amino acid sequence of SEQ ID NO:172.

In some embodiments, an ILT2-binding agent or an ILT2/ILT4-binding agent binds an epitope comprising amino acids within SEQ ID NO:2. In some embodiments, an ILT2-binding agent or an ILT2/ILT4-binding agent binds an epitope comprising amino acids within SEQ ID NO:3. In some embodiments, an ILT2-binding agent or an ILT2/ILT4-binding agent binds an epitope comprising amino acids within SEQ ID NO:4. In some embodiments, an ILT2-binding agent or an ILT2/ILT4-binding agent binds an epitope comprising amino acids within SEQ ID NO:5. In some embodiments, an ILT2-binding agent or an ILT2/ILT4-binding agent binds an epitope comprising amino acids within SEQ ID NO:6. In some embodiments, an ILT2-binding agent or an ILT2/ILT4-binding agent binds an epitope comprising amino acids within SEQ ID NO:7. In some embodiments, an ILT2-binding agent or an ILT2/ILT4-binding agent binds an epitope comprising amino acids within SEQ ID NO:16 In some embodiments, an ILT2-binding agent or an ILT2/ILT4-binding agent binds an epitope comprising amino acids within SEQ ID NO:17. In some embodiments, an ILT2-binding agent or an ILT2/ILT4-binding agent binds an epitope comprising amino acids within SEQ ID NO:18. In some embodiments, an ILT2-binding agent or an ILT2/ILT4-binding agent binds an epitope comprising amino acids within SEQ ID NO:19. In some embodiments, an ILT2-binding agent or an ILT2/ILT4-binding agent binds an epitope comprising amino acids within SEQ ID NO:20. In some embodiments, an ILT2-binding agent or an ILT2/ILT4-binding agent binds an epitope comprising amino acids within SEQ ID NO:21. In some embodiments, an ILT2-binding agent or an ILT2/ILT4-binding agent binds an epitope comprising amino acids within SEQ ID NO:167 In some embodiments, an ILT2-binding agent or an ILT2/ILT4-binding agent binds an epitope comprising amino acids within SEQ ID NO:168. In some embodiments, an ILT2-binding agent or an ILT2/ILT4-binding agent binds an epitope comprising amino acids within SEQ ID NO:169. In some embodiments, an ILT2-binding agent or an ILT2/ILT4-binding agent binds an epitope comprising amino acids within SEQ ID NO:170. In some embodiments, an ILT2-binding agent or an ILT2/ILT4-binding agent binds an epitope comprising amino acids within SEQ ID NO:171. In some embodiments, an ILT2-binding agent or an ILT2/ILT4-binding agent binds an epitope comprising amino acids within SEQ ID NO:172.

In some embodiments, an ILT4-binding agent or an ILT2/ILT4-binding agent binds ILT4 or a fragment of ILT4. In some embodiments, a fragment of ILT4 comprises the extracellular domain of ILT4. In some embodiments, a fragment of ILT4 comprises one or more of the Ig-like C2 type domains (e.g., D1, D2, D3, and/or D4). In some embodiments, a fragment of ILT4 comprises D1 and D2. In some embodiments, a fragment of ILT4 comprises D2 and D3. In some embodiments, a fragment of ILT4 comprises D3 and D4. In some embodiments, a fragment of ILT4 comprises D1, D2, and D3. In some embodiments, a fragment of ILT4 comprises D2, D3, and D4. In some embodiments, a fragment of ILT4 comprises one or more of the Ig-like C2 type domains and the stem region. In some embodiments, a fragment of ILT4 comprises D4-stem, D3-D4-stem, or D2-D3-D4-stem. In some embodiments, the extracellular domain of human ILT4 comprises amino acids 22-461 of SEQ ID NO:8. In some embodiments, D1 of human ILT4 comprises amino acids 27-110 of SEQ ID NO:8. In some embodiments, D2 of human ILT4 comprises amino acids 111-229 of SEQ ID NO:8. In some embodiments, D3 of human ILT4 comprises amino acids 230-318 of SEQ ID NO:8. In some embodiments, D4 of human ILT4 comprises amino acids 330-419 of SEQ ID NO:8. In some embodiments, D1-D2 of human ILT4 comprises amino acids 27-229 of SEQ ID NO:8. In some embodiments, D2-D3 of human ILT4 comprises amino acids 111-318 of SEQ ID NO:8. In some embodiments, D3-D4 of human ILT4 comprises amino acids 230-419 of SEQ ID NO:8. In some embodiments, D1-D2-D3 of human ILT4 comprises amino acids 27-318 of SEQ ID NO:8. In some embodiments, D2-D3-D4 of human ILT4 comprises amino acids 111-419 of SEQ ID NO:8. In some embodiments, D4-stem of human ILT4 comprises amino acids 330-461 of SEQ ID NO:8. In some embodiments, D3-D4-stem of human ILT4 comprises amino acids 230-461 of SEQ ID NO:8. In some embodiments, D2-D3-D4-stem of human ILT4 comprises amino acids 111-461 of SEQ ID NO:8.

In some embodiments, an ILT4-binding agent or an ILT2/ILT4-binding agent binds a fragment of ILT4. In some embodiments, an ILT4-binding agent or an ILT2/ILT4-binding agent binds within a specific region of ILT4. In some embodiments, an ILT4-binding agent or an ILT2/ILT4- binding agent binds within the extracellular domain of ILT4. In some embodiments, an ILT4-binding agent or an ILT2/ILT4-binding agent binds within the D1 domain of ILT4. In some embodiments, an ILT4-binding agent or an ILT2/ILT4-binding agent binds within the D2 domain of ILT4. In some embodiments, an ILT4-binding agent or an ILT2/ILT4-binding agent binds within the D3 domain of ILT4. In some embodiments, an ILT4-binding agent or an ILT2/ILT4-binding agent binds within the D4 domain of ILT4. In some embodiments, an ILT4-binding agent or an ILT2/ILT4-binding agent binds within the D4-stem region of ILT4. In some embodiments, an ILT4-binding agent or an ILT2/ILT4-binding agent binds within the D1-D2 domains of ILT4. In some embodiments, an ILT4-binding agent or an ILT2/ILT4-binding agent binds within the D2-D3 domains of ILT4. In some embodiments, an ILT4-binding agent or an ILT2/ILT4-binding agent binds within the D3-D4 domains of ILT4. In some embodiments, an ILT4-binding agent or an ILT2/ILT4-binding agent binds within the D1-D2-D3 domains of ILT4. In some embodiments, an ILT4-binding agent or an ILT2/ILT4-binding agent binds within the D2-D3-D4 domains of ILT4. In some embodiments, an ILT4-binding agent or an ILT2/ILT4-binding agent binds an epitope on ILT4. In some embodiments, an ILT4-binding agent or an ILT2/ILT4-binding agent binds a conformational epitope on ILT4. In some embodiments, an ILT4-binding agent does not bind other human LILRB proteins (e.g., ILT2, ILT3, ILT5, or LILRB5). In some embodiments, an ILT2/ILT4-binding agent does not bind other human LILRB proteins (e.g., ILT3, ILT5, or LILRB5). In some embodiments, an ILT4-binding agent or an ILT2/ILT4-binding agent does not bind one or more of the human LILRA proteins (e.g., LILRA1, LILRA2, LILRA4, LILRA5, or LILRA6). In some embodiments, an ILT4-binding agent or an ILT2/ILT4-binding agent does not bind LILRA2, LILRA4, LILRA5, or LILRA6.

In some embodiments, an ILT4-binding agent or an ILT2/ILT4-binding agent binds human ILT4. In some embodiments, an ILT4-binding agent or an ILT2/ILT4-binding agent binds SEQ ID NO:8. In some embodiments, an ILT4-binding agent or an ILT2/ILT4-binding agent binds SEQ ID NO:9. In some embodiments, an ILT4-binding agent or an ILT2/ILT4-binding agent binds SEQ ID NO:10. In some embodiments, an ILT4-binding agent or an ILT2/ILT4-binding agent binds a fragment comprising amino acids 22-461 of SEQ ID NO:8. In some embodiments, an ILT4-binding agent or an ILT2/ILT4-binding agent binds a fragment comprising amino acids 27-110 of SEQ ID NO:8. In some embodiments, an ILT4-binding agent or an ILT2/ILT4-binding agent binds a fragment comprising amino acids 111-229 of SEQ ID NO:8. In some embodiments, an ILT4-binding agent or an ILT2/ILT4-binding agent binds a fragment comprising amino acids 230-318 of SEQ ID NO:8. In some embodiments, an ILT4-binding agent or an ILT2/ILT4-binding agent binds a fragment comprising amino acids 330-419 of SEQ ID NO:8. In some embodiments, an ILT4-binding agent or an ILT2/ILT4-binding agent binds a fragment comprising amino acids 27-229 of SEQ ID NO:8. In some embodiments, an ILT4-binding agent or an ILT2/ILT4-binding agent binds a fragment comprising amino acids 111-318 of SEQ ID NO:8. In some embodiments, an ILT4-binding agent or an ILT2/ILT4-binding agent binds a fragment comprising amino acids 230-419 of SEQ ID NO:8. In some embodiments, an ILT4-binding agent or an ILT2/ILT4-binding agent binds SEQ ID NO:11. In some embodiments, an ILT4-binding agent or an ILT2/ILT4-binding agent binds SEQ ID NO:12. In some embodiments, an ILT4-binding agent or an ILT2/ILT4-binding agent binds SEQ ID NO:13. In some embodiments, an ILT4-binding agent or an ILT2/ILT4-binding agent binds SEQ ID NO:14. In some embodiments, an ILT4-binding agent or an ILT2/ILT4-binding agent binds SEQ ID NO:11 and SEQ ID NO:12. In some embodiments, an ILT4-binding agent or an ILT2/ILT4-binding agent binds SEQ ID NO:12 and SEQ ID NO:13. In some embodiments, an ILT4-binding agent or an ILT2/ILT4-binding agent binds SEQ ID NO:13 and SEQ ID NO:14. In some embodiments, an ILT4-binding agent or an ILT2/ILT4-binding agent binds SEQ ID NO:11, SEQ ID NO:12, and SEQ ID NO:13. In some embodiments, an ILT4-binding agent or an ILT2/ILT4-binding agent binds SEQ ID NO:12, SEQ ID NO:13, and SEQ ID NO:14.

In some embodiments, an ILT4-binding agent or an ILT2/ILT4-binding agent binds a polypeptide comprising the amino acid sequence of SEQ ID NO:9. In some embodiments, an ILT4-binding agent or an ILT2/ILT4-binding agent binds a polypeptide comprising the amino acid sequence of SEQ ID NO:10. In some embodiments, an ILT4-binding agent or an ILT2/ILT4-binding agent binds a polypeptide comprising the amino acid sequence of SEQ ID NO:11. In some embodiments, an ILT4-binding agent or an ILT2/ILT4-binding agent binds a polypeptide comprising the amino acid sequence of SEQ ID NO:12. In some embodiments, an ILT4-binding agent or an ILT2/ILT4-binding agent binds a polypeptide comprising the amino acid sequence of SEQ ID NO:13. In some embodiments, an ILT4-binding agent or an ILT2/ILT4-binding agent binds a polypeptide comprising the amino acid sequence of SEQ ID NO:14.

In some embodiments, an ILT4-binding agent or an ILT2/ILT4-binding agent binds an epitope comprising amino acids within SEQ ID NO:9. In some embodiments, an ILT4-binding agent or an ILT2/ILT4-binding agent binds an epitope comprising amino acids within SEQ ID NO:10. In some embodiments, an ILT4-binding agent or an ILT2/ILT4-binding agent binds an epitope comprising amino acids within SEQ ID NO:11. In some embodiments, an ILT4-binding agent or an ILT2/ILT4-binding agent binds an epitope comprising amino acids within SEQ ID NO:12. In some embodiments, an ILT4-binding agent or an ILT2/ILT4-binding agent binds an epitope comprising amino acids within SEQ ID NO:13. In some embodiments, an ILT4-binding agent or an ILT2/ILT4-binding agent binds an epitope comprising amino acids within SEQ ID NO:14.

In some embodiments, an ILT-binding agent binds human ILT2, human ILT4, or both human ILT2/ILT4, and has at least one or more of the following properties: (i) binds rhesus ILT2; (ii) binds cyno ILT2; (iii) does not bind ILT3, ILT5, and LILRB5; (iv) does not bind LILRA2, LILRA4, LILRA5, and LILRA6; (v) is an ILT2 antagonist; (vi) is an ILT4 antagonist, (vii) inhibits ILT2 activity; (viii) inhibits ILT4 activity; (ix) inhibits ILT2 signaling in cells that express ILT2; (x) inhibits ILT4 signaling in cells that express ILT4; (xi) inhibits binding of ILT2 to MHC I molecules; (xii) inhibits binding of ILT4 to MHC I molecules; (xiii) inhibits ILT2-induced suppression of myeloid cells; (xiv) inhibits ILT4-induced suppression of myeloid cells; (xv) inhibits ILT2-induced suppression of myeloid cell activity; (xvi) inhibits ILT4-induced suppression of myeloid cell activity; (xvii) restores FcR activation in myeloid cells; (xviii) enhances NK cell activity; (xix) enhances CTL activity; and/or (xx) enhances macrophage phagocytosis.

In some embodiments, an ILT-binding agent is an antibody. In some embodiments, an ILT2-binding agent is an antibody. In some embodiments, an ILT4-binding agent is an antibody. In some embodiments, an ILT2/ILT4-binding agent is an antibody. In some embodiments, an ILT-binding agent is an anti-ILT2 antibody. In some embodiments, an ILT-binding agent is an anti-ILT4 antibody. In some embodiments, an ILT-binding agent is an anti-ILT2/ILT4 antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody comprises an IgG heavy chain. In some embodiments, the antibody comprises an IgG1 heavy chain. In some embodiments, the antibody comprises an IgG2 heavy chain. In some embodiments, the antibody comprises an IgG4 heavy chain. In some embodiments, the antibody comprises a human IgG heavy chain. In some embodiments, the antibody comprises a human IgG1 heavy chain. In some embodiments, the antibody comprises a human IgG2 heavy chain. In some embodiments, the antibody comprises a human IgG4 heavy chain. In some embodiments, the antibody comprises a kappa light chain. In some embodiments, the antibody comprises a kappa light chain constant region. In some embodiments, the antibody comprises a human kappa light chain constant region. In some embodiments, the antibody comprises a lambda light chain. In some embodiments, the antibody comprises a lambda light chain constant region. In some embodiments, the antibody comprises a human lambda light chain constant region. In some embodiments, the antibody is an antibody fragment comprising at least one antigen-binding site. In some embodiments, the antibody is a scFv. In some embodiments, the antibody is a disulfide-linked scFv. In some embodiments, the antibody is a disulfide-linked sc(Fv)$_2$. In some embodiments, the antibody is a Fab, Fab', or a F(ab)$_2$ antibody. In some embodiments, the antibody is a diabody. In some embodiments, the antibody is a nanobody. In some embodiments, the antibody is a monospecific antibody. In some embodiments, the antibody is a bispecific antibody. In some embodiments, the antibody is a multispecific antibody. In some embodiments, the antibody is a monovalent antibody. In some embodiments, the antibody is a bivalent antibody. In some embodiments, the antibody is a tetravalent antibody.

In some embodiments, the antibody is isolated. In some embodiments, the antibody is substantially pure.

In some embodiments, an ILT-binding agent (e.g., an ILT2-binding agent, an ILT4-binding agent, or an ILT2/ILT4 binding agent) is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, an ILT-binding agent (e.g., an ILT2-binding agent, an ILT4-binding agent, or an ILT2/ILT4 binding agent) is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof. In some embodiments, the immunizing antigen is a rhesus protein or a fragment thereof. In some embodiments, the immunizing antigen is a cyno protein or a fragment thereof. In some embodiments, the immunizing antigen is a combination of two or more (e.g., 2, 3, 4) related proteins or fragments thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies against a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. In some embodiments, high-throughput methods are used to distribute single cell hybridoma cells into plates. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, an ILT-binding agent (e.g., an ILT2-binding agent, an ILT4-binding agent, or an ILT2/ILT4 binding agent) is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region to use for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, an ILT-binding agent (e.g., an ILT2-binding agent, an ILT4-binding agent, or an ILT2/ILT4 binding agent) is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized human donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, an ILT-binding agent (e.g., an ILT2-binding agent, an ILT4-binding agent, or an ILT2/ILT4 binding agent) is an antibody fragment. As used herein, the term "antibody fragment" refers to a molecule other than an intact antibody that comprises a portion of an antibody and generally at least one antigen-binding site. Examples of antibody fragments include, but are not limited to, Fab, Fab', F(ab')2, Fv, single chain antibody molecules (e.g., scFv), disulfide-linked scFv (dsscFv), nanobodies, diabodies, tribodies, tetrabodies, minibodies, dual variable domain antibodies (DVD), single variable domain antibodies (e.g., camelid antibodies), and multispecific antibodies formed from antibody fragments.

In some embodiments, an ILT-binding agent is a scFv antibody. In some embodiments, the scFv is a disulfide-linked scFv (dsscFv), which is a scFv comprising an engineered disulfide bond between the light chain variable region and heavy chain variable region of the scFv. In some embodiments, the disulfide bond increases stability of the scFv molecule. In some embodiments, the disulfide bond increases thermostability of the scFv molecule.

In some embodiments, an ILT-binding agent is a Fv. In some embodiments, an ILT-binding agent is a Fab. In some embodiments, an ILT-binding agent is a F(ab')$_2$. In some embodiments, an ILT-binding agent is a F(ab').

Antibody fragments can be made by various techniques, including but not limited to proteolytic digestion of an intact antibody. The antibody fragments described herein can be produced using recombinant technologies known in the art (e.g., *E. coli* or phage expression).

In some embodiments, an ILT-binding agent (e.g., an ILT2-binding agent, an ILT4-binding agent, or an ILT2/ILT4 binding agent) is a bispecific antibody. Bispecific antibodies are capable of recognizing and binding at least two different antigens or epitopes. The different epitopes can either be within the same molecule (e.g., two epitopes on ILT2) or on different molecules (e.g., one epitope on ILT2 and a second epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Many techniques for making bispecific antibodies are known to those skilled in the art. In some embodiments, a bispecific antibody comprises heavy chain constant regions with modifications in the amino acids that are part of the interface between the two heavy chains. These modifications are made to enhance heterodimer formation and generally reduce or eliminate homodimer formation. In some embodiments, the bispecific antibody is generated using a knobs-into-holes (KIH) strategy. In some embodiments, the bispecific antibody comprises variant hinge regions incapable of forming disulfide linkages between identical heavy chains (e.g., reduce homodimer formation). In some embodiments, the bispecific antibody comprises heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

In some embodiments, an ILT-binding agent is an antibody that binds ILT2. In some embodiments, an anti-ILT antibody binds human ILT2. In some embodiments, an anti-ILT antibody binds cyno ILT2. In some embodiments, an anti-ILT antibody binds rhesus ILT2. In some embodiments, an anti-ILT antibody binds human ILT2 and cyno ILT2. In some embodiments, an anti-ILT antibody binds human ILT2 and rhesus ILT2. In some embodiments, an anti-ILT antibody binds human ILT2, rhesus ILT2, and cyno ILT2. In some embodiments, an anti-ILT2 antibody binds an ILT2 epitope. In some embodiments, an anti-ILT2 antibody binds an ILT2 epitope within the extracellular domain of human ILT2. In some embodiments, an anti-ILT2 antibody binds an ILT2 epitope within the extracellular domain of cyno ILT2. In some embodiments, an anti-ILT2 antibody binds an ILT2 epitope within the extracellular domain of rhesus ILT2. In some embodiments, an anti-ILT2 antibody binds an epitope comprising at least one amino acid (e.g., 1, 2, 3, 4, 5, 6, 7, 8, 9) within amino acids 24-461 of SEQ ID NO:1. In some embodiments, an anti-ILT2 antibody binds an epitope comprising at least one amino acid (e.g., 1, 2, 3, 4, 5, 6, 7, 8, 9) within amino acids 27-115 of SEQ ID NO:1. In some embodiments, an anti-ILT2 antibody binds an epitope comprising at least one amino acid (e.g., 1, 2, 3, 4, 5, 6, 7, 8, 9) within amino acids 116-221 of SEQ ID NO:1. In some embodiments, an anti-ILT2 antibody binds an epitope comprising at least one amino acid (e.g., 1, 2, 3, 4, 5, 6, 7, 8, 9) within amino acids 222-312 of SEQ ID NO:1. In some embodiments, an anti-ILT2 antibody binds an epitope comprising at least one amino acid (e.g., 1, 2, 3, 4, 5, 6, 7, 8, 9) within amino acids 313-409 of SEQ ID NO:1. In some embodiments, an anti-ILT2 antibody binds an epitope comprising amino acids within SEQ ID NO:3. In some embodiments, an anti-ILT2 antibody binds an epitope comprising amino acids within SEQ ID NO:4. In some embodiments, an anti-ILT2 antibody binds an epitope comprising amino acids within SEQ ID NO:5. In some embodiments, an anti-ILT2 antibody binds an epitope comprising amino acids within SEQ ID NO:6. In some embodiments, an anti-ILT2 antibody binds an epitope comprising amino acids within SEQ ID NO:7. In some embodiments, an anti-ILT2 antibody binds an epitope comprising at least one amino acid (e.g., 1, 2, 3, 4, 5, 6, 7, 8, 9) within amino acids 24-460 of SEQ ID NO:15. In some embodiments, an anti-ILT2 antibody binds an epitope comprising at least one amino acid (e.g., 1, 2, 3, 4, 5, 6, 7, 8, 9) within amino acids 27-114 of SEQ ID NO:15. In some embodiments, an anti-ILT2 antibody binds an epitope comprising at least one amino acid (e.g., 1, 2, 3, 4, 5, 6, 7, 8, 9) within amino acids 115-220 of SEQ ID NO:15. In some embodiments, an anti-ILT2 antibody binds an epitope comprising at least one amino acid (e.g., 1, 2, 3, 4, 5, 6, 7, 8, 9) within amino acids 221-311 of SEQ ID NO:15. In some embodiments, an anti-ILT2 antibody binds an epitope comprising at least one amino acid (e.g., 1, 2, 3, 4, 5, 6, 7, 8, 9) within amino acids 312-408 of SEQ ID NO:15. In some embodiments, an anti-ILT2 antibody binds an epitope comprising amino acids within SEQ ID NO:17. In some embodiments, an anti-ILT2 antibody binds an epitope comprising amino acids within SEQ ID NO:18. In some embodiments, an anti-ILT2 antibody binds an epitope comprising amino acids within SEQ ID NO:19. In some embodiments, an anti-ILT2 antibody binds an epitope comprising amino acids within SEQ ID NO:20. In some embodiments, an anti-ILT2 antibody binds an epitope comprising amino acids within SEQ ID NO:21. In some embodiments, an anti-ILT2 antibody binds an epitope comprising at least one amino acid (e.g., 1, 2, 3, 4, 5, 6, 7, 8, 9) within amino acids 24-461 of SEQ ID NO:166. In some embodiments, an anti-ILT2 antibody binds an epitope comprising at least one amino acid (e.g., 1, 2, 3, 4, 5, 6, 7, 8, 9) within amino acids 27-114 of SEQ ID NO:166. In some embodiments, an anti-ILT2 antibody binds an epitope comprising at least one amino acid (e.g., 1, 2, 3, 4, 5, 6, 7, 8, 9) within amino acids 115-220 of SEQ ID NO:166. In some embodiments, an anti-ILT2 antibody binds an epitope comprising at least one amino acid (e.g., 1, 2, 3, 4, 5, 6, 7, 8, 9) within amino acids 221-311 of SEQ ID NO:166. In some embodiments, an anti-ILT2 antibody binds an epitope comprising at least one amino acid (e.g., 1, 2, 3, 4, 5, 6, 7, 8, 9) within amino acids 312-408 of SEQ ID NO:166. In some embodiments, an anti-ILT2 antibody binds an epitope comprising amino acids within SEQ ID NO:168. In some embodiments, an anti-ILT2 antibody binds an epitope comprising amino acids within SEQ ID NO:169. In some embodiments, an anti-ILT2 antibody binds an epitope comprising amino acids within SEQ ID NO:170. In some embodiments, an anti-ILT2 antibody binds an epitope comprising amino acids within SEQ ID NO:171. In some embodiments, an anti-ILT2 antibody binds an epitope comprising amino acids within SEQ ID NO:172. In some embodiments, the epitope is a conformational epitope. In some embodiments, the epitope is a linear epitope.

In some embodiments, an ILT-binding agent is an antibody that binds ILT4. In some embodiments, an anti-ILT antibody binds human ILT4. In some embodiments, an anti-ILT4 antibody binds an ILT4 epitope. In some embodiments, an anti-ILT4 antibody binds an ILT4 epitope within the extracellular domain of human ILT4. In some embodiments, an anti-ILT4 antibody binds an epitope comprising at least one amino acid (e.g., 1, 2, 3, 4, 5, 6, 7, 8, 9) within amino acids 22-461 of SEQ ID NO:8. In some embodiments, an anti-ILT4 antibody binds an epitope comprising at least one amino acid (e.g., 1, 2, 3, 4, 5, 6, 7, 8, 9) within amino acids 27-110 of SEQ ID NO:8. In some embodiments, an anti-ILT4 antibody binds an epitope comprising at least one amino acid (e.g., 1, 2, 3, 4, 5, 6, 7, 8, 9) within amino acids 111-229 of SEQ ID NO:8. In some embodiments, an anti-ILT4 antibody binds an epitope comprising at least one amino acid (e.g., 1, 2, 3, 4, 5, 6, 7, 8, 9) within amino acids 230-318 of SEQ ID NO:8. In some embodiments, an anti-ILT4 antibody binds an epitope comprising at least one amino acid (e.g., 1, 2, 3, 4, 5, 6, 7, 8, 9) within amino acids 330-419 of SEQ ID NO:8. In some embodiments, an anti-ILT4 antibody binds an epitope comprising amino acids within SEQ ID NO:9. In some embodiments, an anti-ILT4 antibody binds an epitope comprising amino acids within SEQ ID NO:10. In some embodiments, an anti-ILT4 antibody binds an epitope comprising amino acids within SEQ ID NO:11. In some embodiments, an anti-ILT4 antibody binds an epitope comprising amino acids within SEQ ID NO:12. In some embodiments, an anti-ILT4 antibody binds an epitope comprising amino acids within SEQ ID NO:13. In some embodiments, an anti-ILT4 antibody binds an epitope comprising amino acids within SEQ ID NO:14. In some embodiments, the epitope is a conformational epitope. In some embodiments, the epitope is a linear epitope.

In some embodiments, an ILT-binding agent is an antibody that binds ILT2 and ILT4. It is understood by those of skill in the art that an antibody that binds ILT2 and ILT4, described as a dual binder, comprises at least one antigen-binding site that binds an epitope on both ILT2 and ILT4, in contrast to a bispecific antibody which would comprise one antigen-binding site that binds an epitope on ILT2 and a second antigen-binding site that binds a different epitope on ILT4. In some embodiments, an anti-ILT2/ILT4 antibody binds human ILT2 and human ILT4. In some embodiments, anti-ILT2/ILT4 antibody binds human ILT2, human ILT4, cyno ILT2, and rhesus ILT2. In some embodiments, an anti-ILT2/ILT4 antibody binds an ILT2 epitope and ILT4 epitope. In some embodiments, an anti-ILT2/ILT4 antibody binds an epitope within the extracellular domain of human ILT2 and an epitope within the extracellular domain of human ILT4, wherein the ILT2 epitope and the ILT4 epitope are the same or essentially the same. In some embodiments, an anti-ILT2/ILT4 antibody binds an ILT2 epitope within the extracellular domain of human ILT2, an ILT4 epitope within the extracellular domain of human ILT4, an ILT2 epitope within the extracellular domain of cyno ILT2, and an ILT2 epitope within the extracellular domain of rhesus ILT2. In some embodiments, an anti-ILT2/ILT4 antibody binds an epitope comprising at least one amino acid (e.g., 1, 2, 3, 4, 5, 6, 7, 8, 9) within amino acids 24-461 of SEQ ID NO:1 and the same or essentially the same epitope within amino acids 22-461 of SEQ ID NO:8. In some embodiments, an anti-ILT2/ILT4 antibody binds an epitope comprising at least one amino acid (e.g., 1, 2, 3, 4, 5, 6, 7, 8, 9) within amino acids 27-115 of SEQ ID NO:1 and the same or essentially the same epitope within amino acids 27-110 of SEQ ID NO:8. In some embodiments, an anti-ILT2/ILT4 antibody binds an epitope comprising at least one amino acid (e.g., 1, 2, 3, 4, 5, 6, 7, 8, 9) within amino acids 116-221 of SEQ ID NO:1 and the same or essentially the same epitope within amino acids 111-229 of SEQ ID NO:8. In some embodiments, an anti-ILT2/ILT4 antibody binds an epitope comprising at least one amino acid (e.g., 1, 2, 3, 4, 5, 6, 7, 8, 9) within amino acids 222-312 of SEQ ID NO:1 and the same or essentially the same epitope within amino acids 230-318 of SEQ ID NO:8. In some embodiments, an anti-ILT2/ILT4 antibody binds an epitope comprising at least one amino acid (e.g., 1, 2, 3, 4, 5, 6, 7, 8, 9) within amino acids 313-409 of SEQ ID NO:1 and the same or essentially the same epitope within amino acids 330-419 of SEQ ID NO:8. In some embodiments, the epitope is a conformational epitope. In some embodiments, the epitope is a linear epitope.

In some embodiments, an ILT-binding agent is an anti-ILT2 antibody, an anti-ILT4 antibody, or an anti-ILT2/ILT4 antibody described herein. In some embodiments, the ILT-binding agent is a variant of an anti-ILT2 antibody, an anti-ILT4 antibody, or an anti-ILT2/ILT4 antibody described herein. In some embodiments, a variant of an anti-ILT antibody comprises one to thirty amino acid substitutions. In some embodiments, a variant of the anti-ILT antibody comprises one to twenty-five amino acid substitutions. In some embodiments, a variant of the anti-ILT antibody comprises one to twenty amino acid substitutions. In some embodiments, a variant of the anti-ILT antibody comprises one to fifteen amino acid substitutions. In some embodiments, a variant of the anti-ILT antibody comprises one to ten amino acid substitutions. In some embodiments, a variant of the anti-ILT antibody comprises one to five amino acid substitutions. In some embodiments, the variant of the anti-ILT antibody comprises one to three amino acid substitutions. In some embodiments, the amino acid substitution(s) is in a CDR of the antibody. In some embodiments, the amino acid substitution(s) is not in a CDR of the antibody. In some embodiments, the amino acid substitution(s) is in a framework region of the antibody. In some embodiments, the amino acid substitution(s) is a conservative amino acid substitution.

CDRs of an antibody are defined using a variety of methods/systems by those skilled in the art. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary definition). However, it will be understood that reference to a heavy chain variable region CDR or CDRs and/or a light chain variable region CDR or CDRs of a specific antibody will encompass all CDR definitions as known to those of skill in the art.

In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the Kabat definition. In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the Chothia definition. In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the AbM definition. In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the IMGT definition. In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the Contact definition. In some embodiments, an anti-ILT antibody described herein comprises the six CDRs of antibody 27F9, 47C8, 48A5, 47H6, Hz47H6.v2, 51A1, 64A12, Hz64A12, 73C4, 73D1, or Hz73D1.v1 based on the Exemplary definition.

In some embodiments, an ILT-binding agent is an anti-ILT antibody (e.g., an anti-ILT2 antibody, an anti-ILT4 antibody, or an anti-ILT2/ILT4 antibody) that comprises one, two, three, four, five, and/or six CDRs of any one of the antibodies described herein. In some embodiments, an anti-ILT2 antibody comprises (i) a heavy chain variable region comprising one, two, and/or three heavy chain variable region CDRs from Table 1, and/or (ii) a light chain variable region comprising one, two, and/or three light chain variable region CDRs from Table 1. In some embodiments, an anti-ILT4 antibody comprises (i) a heavy chain variable region comprising one, two, and/or three heavy chain variable region CDRs from Table 2, and/or (ii) a light chain variable region comprising one, two, and/or three light chain variable region CDRs from Table 2. In some embodiments, an anti-ILT4 antibody comprises (i) a heavy chain variable region comprising one, two, and/or three heavy chain variable region CDRs from Table 3, and/or (ii) a light chain variable region comprising one, two, and/or three light chain variable region CDRs from Table 3. In some embodiments, an anti-ILT2/ILT4 antibody comprises (i) a heavy chain variable region comprising one, two, and/or three heavy chain variable region CDRs from Table 4A or Table 4B, and/or (ii) a light chain variable region comprising one, two, and/or three light chain variable region CDRs from Table 4A or Table 4B. In some embodiments, an anti-ILT2/ILT4 antibody comprises (i) a heavy chain variable region comprising one, two, and/or three heavy chain variable region CDRs from Table 5, and/or (ii) a light chain variable region comprising one, two, and/or three light chain variable region CDRs from Table 5. In some embodiments, an anti-ILT2/ILT4 antibody comprises (i) a heavy chain variable region comprising one, two, and/or three heavy chain variable region CDRs from Table 6A or Table 6B, and/or (ii) a light chain variable region comprising one, two, and/or three light chain variable region CDRs from Table 6A or Table 6B. In some embodiments, an anti-ILT2/ILT4 antibody comprises (i) a heavy chain variable region comprising one, two, and/or three heavy chain variable region CDRs from Table 7, and/or (ii) a light chain variable region comprising one, two, and/or three light chain variable region CDRs from Table 7. In some embodiments, an anti-ILT2/ILT4 antibody comprises (i) a heavy chain variable region comprising one, two, and/or three heavy chain variable region CDRs from Table 8A or Table 8B, and/or (ii) a light chain variable region comprising one, two, and/or three light chain variable region CDRs from Table 8A or Table 8B. In some embodiments, an anti-ILT2 antibody comprises (i) a heavy chain variable region comprising three heavy chain variable region CDRs from Table 1, and (ii) a light chain variable region comprising three light chain variable region CDRs from Table 1. In some embodiments, an anti-ILT4 antibody comprises (i) a heavy chain variable region comprising three heavy chain variable region CDRs from Table 2, and (ii) a light chain variable region comprising three light chain variable region CDRs from Table 2. In some embodiments, an anti-ILT4 antibody comprises (i) a heavy chain variable region comprising three heavy chain variable region CDRs from Table 3, and (ii) a light chain variable region comprising three light chain variable region CDRs from Table 3. In some embodiments, an anti-ILT2/ILT4 antibody comprises (i) a heavy chain variable region comprising three heavy chain variable region CDRs from Table 4A, and (ii) a light chain variable region comprising three light chain variable region CDRs from Table 4A. In some embodiments, an anti-ILT2/ILT4 antibody comprises (i) a heavy chain variable region comprising three heavy chain variable region CDRs from Table 4B, and (ii) a light chain variable region comprising three light chain variable region CDRs from Table 4B. In some embodiments, an anti-ILT2/ILT4 antibody comprises (i) a heavy chain variable region comprising three heavy chain variable region CDRs from Table 5, and (ii) a light chain variable region comprising three light chain variable region CDRs from Table 5. In some embodiments, an anti-ILT2/ILT4 antibody comprises (i) a heavy chain variable region comprising three heavy chain variable region CDRs from Table 6A, and (ii) a light chain variable region comprising three light chain variable region CDRs from Table 6A. In some embodiments, an anti-ILT2/ILT4 antibody comprises (i) a heavy chain variable region comprising three heavy chain variable region CDRs from Table 6B, and (ii) a light chain variable region comprising three light chain variable region CDRs from Table 6B. In some embodiments, an anti-ILT2/ILT4 antibody comprises (i) a heavy chain variable region comprising three heavy chain variable region CDRs from Table 7, and (ii) a light chain variable region comprising three light chain variable region CDRs from Table 7. In some embodiments, an anti-ILT2/ILT4 antibody comprises (i) a heavy chain variable region comprising three heavy chain variable region CDRs from Table 8A, and (ii) a light chain variable region comprising three light chain variable region CDRs from Table 8B. In some embodiments, an anti-ILT2/ILT4 antibody comprises (i) a heavy chain variable region comprising three heavy chain variable region CDRs from Table 8B, and (ii) a light chain variable region comprising three light chain variable region CDRs from Table 8B.

TABLE 1

Anti-ILT2 Antibody 27F9 Sequences

| | Exemplary | Chothia | AbM | Kabat | Contact |
|---|---|---|---|---|---|
| Heavy Chain variable region CDR1 | GFSLTNYGVS (SEQ ID NO: 22) | GFSLTNY (SEQ ID NO: 28) | GFSLTNYGVS (SEQ ID NO: 22) | NYGVS (SEQ ID NO: 31) | TNYGVS (SEQ ID NO: 32) |
| Heavy Chain variable region CDR2 | IIWGDGSTNYHSALIS (SEQ ID NO: 23) | WGDGS (SEQ ID NO: 29) | IIWGDGSTN (SEQ ID NO: 30) | IIWGDGSTNYHSALIS (SEQ ID NO: 23) | WLGIIWGDGSTN (SEQ ID NO: 33) |
| Heavy Chain variable region CDR3 | PNWDTYAMDF (SEQ ID NO: 24) | PNWDTYAMDF (SEQ ID NO: 24) | PNWDTYAMDF (SEQ ID NO: 24) | PNWDTYAMDF (SEQ ID NO: 24) | AKPNWDTYAMD (SEQ ID NO: 34) |

TABLE 1-continued

Anti-ILT2 Antibody 27F9 Sequences

| | Exemplary | Chothia | AbM | Kabat | Contact |
|---|---|---|---|---|---|
| Light Chain variable region CDR1 | RASQDISNFLN (SEQ ID NO: 25) | RASQDISNFLN (SEQ ID NO: 25) | RASQDISNFLN (SEQ ID NO: 25) | RASQDISNFLN (SEQ ID NO: 25) | SNFLNWY (SEQ ID NO: 35) |
| Light Chain variable region CDR2 | CTSKLHS (SEQ ID NO: 26) | CTSKLHS (SEQ ID NO: 26) | CTSKLHS (SEQ ID NO: 26) | CTSKLHS (SEQ ID NO: 26) | LLIYCTSKLH (SEQ ID NO: 36) |
| Light Chain variable region CDR3 | QQGNTLPPT (SEQ ID NO: 27) | QQGNTLPPT (SEQ ID NO: 27) | QQGNTLPPT (SEQ ID NO: 27) | QQGNTLPPT (SEQ ID NO: 27) | QQGNTLPP (SEQ ID NO: 37) |

27F9 Heavy chain variable region (SEQ ID NO: 125)
QVQLKESGPGLVAPSQSLSITCTVSGFSLTNYGVSWVRQPPGKGLEWLGIIWGDGSTNYH
SALISRLSISKDNSKSQVFLKLNSLQADDTATYYCAKPNWDTYAMDFWGQGTSVTVSS 27F9 Light chain variable region (SEQ ID NO: 126)
DIQMTQTTSSLSASLGDRVTISCRASQDISNFLNWYQQKPDGTVKLLIYCTSKLHSGVPS
RFSGSGSETDYSLTISNLEQEDIATYFCQQGNTLPPTFGGGTKLEII

TABLE 2

Anti-ILT4 Antibody 47C8 Sequences

| | Exemplary | Chothia | AbM | Kabat | Contact |
|---|---|---|---|---|---|
| Heavy Chain variable region CDR1 | GYSFTGYYMEI (SEQ ID NO: 38) | GYSFTGY (SEQ ID NO: 44) | GYSFTGYYMEI (SEQ ID NO: 38) | GYYMH (SEQ ID NO: 47) | TGYYMH (SEQ ID NO: 48) |
| Heavy Chain variable region CDR2 | RVYPNNGDTSYNQKFKV (SEQ ID NO: 39) | YPNNGD (SEQ ID NO: 45) | RVYPNNGDTS (SEQ ID NO: 46) | RVYPNNGDTSYNQKFKV (SEQ ID NO: 39) | WIGRVYPNNGDTS (SEQ ID NO: 49) |
| Heavy Chain variable region CDR3 | GATVVESLFAY (SEQ ID NO: 40) | GATVVESLFAY (SEQ ID NO: 40) | GATVVESLFAY (SEQ ID NO: 40) | GATVVESLFAY (SEQ ID NO: 40) | ARGATVVESLFA (SEQ ID NO: 50) |
| Light Chain variable region CDR1 | RASESVDNYGNNFLH (SEQ ID NO: 41) | RASESVDNYGNNFLH (SEQ ID NO: 41) | RASESVDNYGNNFLH (SEQ ID NO: 41) | RASESVDNYGNNFLH (SEQ ID NO: 41) | DNYGNNFLHWY (SEQ ID NO: 51) |
| Light Chain variable region CDR2 | RTSNLES (SEQ ID NO: 42) | RTSNLES (SEQ ID NO: 42) | RTSNLES (SEQ ID NO: 42) | RTSNLES (SEQ ID NO: 42) | LLIYRTSNLE (SEQ ID NO: 52) |
| Light Chain variable region CDR3 | QQSNEDPYT (SEQ ID NO: 43) | QQSNEDPYT (SEQ ID NO: 43) | QQSNEDPYT (SEQ ID NO: 43) | QQSNEDPYT (SEQ ID NO: 43) | QQSNEDPY (SEQ ID NO: 53) |

47C8 Heavy chain variable region (SEQ ID NO: 127)
EVQLQQSGPDLVKPGASVKISCKASGYSFTGYYMEIWVKQSHGKSLEWIGRVYPNNGDTSY
NQKFKVKAILTVDKSSSTAYMELRSLTSEDSAVYYCARGATVVESLFAYWGQGTLVTVSA 47C8 Light chain variable region (SEQ ID NO: 128)
DIVLTQSPASLAVSLGQRATISCRASESVDNYGNNFLHWYQQKPGQPPKLLIYRTSNLES
GIPARFSGSGSRTDFTLTINPVEADDVATYYCQQSNEDPYTFGGGTKLEIK

TABLE 3

Anti-ILT4 Antibody 48A5 Sequences

| | Exemplary | Chothia | AbM | Kabat | Contact |
|---|---|---|---|---|---|
| Heavy Chain variable region CDR1 | GYTFTNYGMN (SEQ ID NO: 54) | GYTFTNY (SEQ ID NO: 60) | GYTFTNYGMN (SEQ ID NO: 54) | NYGMN (SEQ ID NO: 63) | TNYGMN (SEQ ID NO: 64) |

TABLE 3-continued

Anti-ILT4 Antibody 48A5 Sequences

| | Exemplary | Chothia | AbM | Kabat | Contact |
|---|---|---|---|---|---|
| Heavy Chain variable region CDR2 | WINTYIGEPIYADDFK G (SEQ ID NO: 55) | NTYIGE (SEQ ID NO: 61) | WINTYIGEPI (SEQ ID NO: 62) | WINTYIGEPIYADDFK G (SEQ ID NO: 55) | WMGWINTYIGEPI (SEQ ID NO: 65) |
| Heavy Chain variable region CDR3 | RSDYDGYAMDY (SEQ ID NO: 56) | RSDYDGYAMDY (SEQ ID NO: 56) | RSDYDGYAMDY (SEQ ID NO: 56) | RSDYDGYAMDY (SEQ ID NO: 56) | ARRSDYDGYAMD (SEQ ID NO: 66) |
| Light Chain variable region CDR1 | KSSQSLLYSGNQKNY LA (SEQ ID NO: 57) | KSSQSLLYSGNQKNY LA (SEQ ID NO: 57) | KSSQSLLYSGNQKNY LA (SEQ ID NO: 57) | KSSQSLLYSGNQKNY LA (SEQ ID NO: 57) | LYSGNQKNYLAWY (SEQ ID NO: 67) |
| Light Chain variable region CDR2 | WASTRES (SEQ ID NO: 58) | WASTRES (SEQ ID NO: 58) | WASTRES (SEQ ID NO: 58) | WASTRES (SEQ ID NO: 58) | LLIYWASTRE (SEQ ID NO: 68) |
| Light Chain variable region CDR3 | QQHDSYPT (SEQ ID NO: 59) | QQHDSYPT (SEQ ID NO: 59) | QQHDSYPT (SEQ ID NO: 59) | QQHDSYPT (SEQ ID NO: 59) | QQHDSYP (SEQ ID NO: 69) |

48A5 Heavy chain variable region (SEQ ID NO: 129)
QIQLVQSGPELKKPGETVKISCKASGYTFTNYGMNWVKQAPGKGLKWMGWINTYIGEPIY
ADDFKGRFAFSLETSASTAYLQINNLKNEDMATYFCARRSDYDGYAMDYWGQGTSVTVSS 48A5 Light chain variable region (SEQ ID NO: 130)
DIVMSQSPSSLAVSVGERVTMSCKSSQSLLYSGNQKNYLAWYQQKPGQSPKLLIYWASTR
ESGVPDRFTGSGSGTDFTLTISSVKAEDLAVYYCQQHDSYPTFGGGSRLEIK

TABLE 4A

Anti-ILT2/1LT4 Antibody 47H6 Sequences

| | Exemplary | Chothia | AbM | Kabat | Contact |
|---|---|---|---|---|---|
| Heavy Chain variable region CDR1 | GYTFTDYYMN (SEQ ID NO: 70) | GYTFTDY (SEQ ID NO: 76) | GYTFTDYYMN (SEQ ID NO: 70) | DYYMN (SEQ ID NO: 79) | TDYYMN (SEQ ID NO: 80) |
| Heavy Chain variable region CDR2 | DFNPNNGGTTYNQKF EG (SEQ ID NO: 71) | NPNNGG (SEQ ID NO: 77) | DFNPNNGGTT (SEQ ID NO: 78) | DFNPNNGGTTYNQKFE G (SEQ ID NO: 71) | WIGDFNPNNGGTT (SEQ ID NO: 81) |
| Heavy Chain variable region CDR3 | GRFYYGSLYSFDY (SEQ ID NO: 72) | GRFYYGSLYSFDY (SEQ ID NO: 72) | GRFYYGSLYSFDY (SEQ ID NO: 72) | GRFYYGSLYSFDY (SEQ ID NO: 72) | ARGRFYYGSLYSFD (SEQ ID NO: 82) |
| Light Chain variable region CDR1 | RASGNIHNYLA (SEQ ID NO: 73) | RASGNIHNYLA (SEQ ID NO: 73) | RASGNIHNYLA (SEQ ID NO: 73) | RASGNIHNYLA (SEQ ID NO: 73) | HNYLAWY (SEQ ID NO: 83) |
| Light Chain variable region CDR2 | NAKTLAD (SEQ ID NO: 74) | NAKTLAD (SEQ ID NO: 74) | NAKTLAD (SEQ ID NO: 74) | NAKTLAD (SEQ ID NO: 74) | LLVYNAKTLA (SEQ ID NO: 84) |
| Light Chain variable region CDR3 | QHFWTSIT (SEQ ID NO: 75) | QHFWTSIT (SEQ ID NO: 75) | QHFWTSIT (SEQ ID NO: 75) | QHFWTSIT (SEQ ID NO: 75) | QHFWTSI (SEQ ID NO: 85) |

47H6 Heavy chain variable region (SEQ ID NO: 131)
EVQLQQSGPELVKPGASVKISCKASGYTFTDYYMNWVKQSHGKSLEWIGDFNPNNGGTTY
NQKFEGKATLTVDKSSNTAYMDLRSLTSEDSAVYYCARGRFYYGSLYSFDYWGQGTTLTVSS 47H6 Light chain variable region (SEQ ID NO: 132)
DIQMTQSPASLSASVGETVTITCRASGNIHNYLAWYQQKQGKSPHLLVYNAKTLADGVPS
RFSGSGSGTQYSLKINNLQPEDFGSYYCQHFWTSITFGAGTKLDLK

TABLE 4B

Anti-ILT2/ILT4 Antibody Hz47H6.v2 Sequences

| | Exemplary | Chothia | AbM | Kabat | Contact |
|---|---|---|---|---|---|
| Heavy Chain variable region CDR1 | GYTFTDYYMN (SEQ ID NO: 70) | GYTFTDY (SEQ ID NO: 76) | GYTFTDYYMN (SEQ ID NO: 70) | DYYMN (SEQ ID NO: 79) | TDYYMN (SEQ ID NO: 80) |
| Heavy Chain variable region CDR2 | DFNPNNAGTTYNQKF EG (SEQ ID NO: 118) | NPNNAG (SEQ ID NO: 119) | DFNPNNAGTT (SEQ ID NO: 120) | DFNPNNAGTTYNQKFE G (SEQ ID NO: 118) | WIGDFNPNNAGTT (SEQ ID NO: 121) |
| Heavy Chain variable region CDR3 | GRFYYGSLYSFDY (SEQ ID NO: 72) | GRFYYGSLYSFDY (SEQ ID NO: 72) | GRFYYGSLYSFDY (SEQ ID NO: 72) | GRFYYGSLYSFDY (SEQ ID NO: 72) | ARGRFYYGSLYSFD (SEQ ID NO: 82) |
| Light Chain variable region CDR1 | RASGNIHNYLA (SEQ ID NO: 73) | RASGNIHNYLA (SEQ ID NO: 73) | RASGNIHNYLA (SEQ ID NO: 73) | RASGNIHNYLA (SEQ ID NO: 73) | HNYLAWY (SEQ ID NO: 83) |
| Light Chain variable region CDR2 | NAKTLAD (SEQ ID NO: 74) | NAKTLAD (SEQ ID NO: 74) | NAKTLAD (SEQ ID NO: 74) | NAKTLAD (SEQ ID NO: 74) | LLIYNAKTLA (SEQ ID NO: 122) |
| Light Chain variable region CDR3 | QHFWTSIT (SEQ ID NO: 75) | QHFWTSIT (SEQ ID NO: 75) | QHFWTSIT (SEQ ID NO: 75) | QHFWTSIT (SEQ ID NO: 75) | QHFWTSI (SEQ ID NO: 85) |

Hz47H6.v2 Heavy chain variable region (SEQ ID NO: 133)
QVQLVQSGAEVKKPGASVKVSCKASGYTFTDYYMNWVRQAPGQRLEWIGDFNPNNAGTTYN
QKFEGRVTITVDKSASTAYMELSSLRSEDTAVYYCARGRFYYGSLYSFDYWGQGTLVTVSS Hz47H6.v2 Light chain variable region (SEQ ID NO: 134)
DIQMTQSPSSLSASVGDRVTITCRASGNIHNYLAWYQQKPGKAPKLLIYNAKTLADGVPSR
FSGSGSGTDFTLTISSLQPEDFATYYCQHFWTSITFGPGTKVDIK

TABLE 5

Anti-ILT2/ILT4 Antibody 51A1 Sequences

| | Exemplary | Chothia | AbM | Kabat | Contact |
|---|---|---|---|---|---|
| Heavy Chain variable region CDR1 | GFTFNTYAMH (SEQ ID NO: 86) | GFTFNTY (SEQ ID NO: 92) | GFTFNTYAMH (SEQ ID NO: 86) | TYAMH (SEQ ID NO: 95) | NTYAMH (SEQ ID NO: 96) |
| Heavy Chain variable region CDR2 | RIRSKSSNYATYYADS VKD (SEQ ID NO: 87) | RSKSSNYA (SEQ ID NO: 93) | RIRSKSSNYATY (SEQ ID NO: 94) | RIRSKSSNYATYYADS VKD (SEQ ID NO: 87) | WVARIRSKSSNYATY (SEQ ID NO: 97) |
| Heavy Chain variable region CDR3 | DGIYYYGTMYYYAM DY (SEQ ID NO: 88) | DGIYYYGTMYYYAM DY (SEQ ID NO: 88) | DGIYYYGTMYYYA MDY (SEQ ID NO: 88) | DGIYYYGTMYYYAMD Y (SEQ ID NO: 88) | VRDGIYYYGTMYYY AMD (SEQ ID NO: 98) |
| Light Chain variable region CDR1 | RASESVDYYGNSFMY (SEQ ID NO: 89) | RASESVDYYGNSFMY (SEQ ID NO: 89) | RASESVDYYGNSFM Y (SEQ ID NO: 89) | RASESVDYYGNSFMY (SEQ ID NO: 89) | DYYGNSFMYWY (SEQ ID NO: 99) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

51A1 Heavy chain variable region (SEQ ID NO: 135)
EVQLVESGGGLVQPKGSLKLSCAASGFTFNTYAMHWVRQAPGKGLEWVARIRSKSSNYAT
YYADSVKDRFTISRDDSQSMLYLQMNNLKTEDTAMYYCVRDGIYYYGTMYYYAMDYWGQGTSVTVSS 51A1 Light chain variable region (SEQ ID NO: 136)
NIVLTQSPASLAVSLGQRATISCRASESVDYYGNSFMYWYQQKPGQPPKLLIYFASNLES
GVPARFSGSGSRTDFTLTIDPVEAADAASYYCQQNNEDPWTFGGGTKLEIK

TABLE 6A

Anti-ILT2/ILT4 Antibody 64A12 Sequences

| | Exemplary | Chothia | AbM | Kabat | Contact |
|---|---|---|---|---|---|
| Heavy Chain variable region CDR1 | GFTFNTYAMH (SEQ ID NO: 86) | GFTFNTY (SEQ ID NO: 92) | GFTFNTYAMH (SEQ ID NO: 86) | TYAMH (SEQ ID NO: 95) | NTYAMH (SEQ ID NO: 96) |
| Heavy Chain variable region CDR2 | RIRSKSSNYATYYADSVKD (SEQ ID NO: 87) | RSKSSNYA (SEQ ID NO: 93) | RIRSKSSNYATY (SEQ ID NO: 94) | RIRSKSSNYATYYADSVKD (SEQ ID NO: 87) | WVARIRSKSSNYATY (SEQ ID NO: 97) |
| Heavy Chain variable region CDR3 | DGIYYYDTMYYYAMDY (SEQ ID NO: 102) | DGIYYYDTMYYYAMDY (SEQ ID NO: 102) | DGIYYYDTMYYYAMDY (SEQ ID NO: 102) | DGIYYYDTMYYYAMDY (SEQ ID NO: 102) | VRDGIYYYDTMYYYAMD (SEQ ID NO: 104) |
| Light Chain variable region CDR1 | RASESVDYYGNSFIY (SEQ ID NO: 103) | RASESVDYYGNSFIY (SEQ ID NO: 103) | RASESVDYYGNSFIY (SEQ ID NO: 103) | RASESVDYYGNSFIY (SEQ ID NO: 103) | DYYGNSFIYWY (SEQ ID NO: 105) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

64A12 Heavy chain variable region (SEQ ID NO: 137)
EVQLVESGGGLVQPKGSLKLSCAASGFTFNTYAMHWVRQAPGKGLEWVARIRSKSSNYAT
YYADSVKDRFTISRDDSQSMLYLQMNNLKTEDTAMYYCVRDGIYYYDTMYYYAMDYWGQGTSVTVSS 64A12 Light chain variable region (SEQ ID NO: 138)
NIVLTQSPASLAVSLGQRATISCRASESVDYYGNSFIYWYQQKPGQPPKWYFASNLES
GVPARFSGSGSRTDFTLTIDPVEAADAASYYCQQNNEDPWTFGGGTKLEIK

TABLE 6B

Anti-ILT2/ILT4 Antibody Hz64A12 Sequences

| | Exemplary | Chothia | AbM | Kabat | Contact |
|---|---|---|---|---|---|
| Heavy Chain variable region CDR1 | GFTFNTYAMH (SEQ ID NO: 86) | GFTFNTY (SEQ ID NO: 92) | GFTFNTYAMH (SEQ ID NO: 86) | TYAMH (SEQ ID NO: 95) | NTYAMH (SEQ ID NO: 96) |
| Heavy Chain variable region CDR2 | RIRSKSSNYATYYADSVKD (SEQ ID NO: 87) | RSKSSNYA (SEQ ID NO: 93) | RIRSKSSNYATY (SEQ ID NO: 94) | RIRSKSSNYATYYADSVKD (SEQ ID NO: 87) | WVARIRSKSSNYATY (SEQ ID NO: 97) |
| Heavy Chain variable region CDR3 | DGIYYYDTMYYYAMDY (SEQ ID NO: 102) | DGIYYYDTMYYYAMDY (SEQ ID NO: 102) | DGIYYYDTMYYYAMDY (SEQ ID NO: 102) | DGIYYYDTMYYYAMDY (SEQ ID NO: 102) | ARDGIYYYDTMYYYAMD (SEQ ID NO: 123) |
| Light Chain variable region CDR1 | RASESVDYYGNSFIY (SEQ ID NO: 103) | RASESVDYYGNSFIY (SEQ ID NO: 103) | RASESVDYYGNSFIY (SEQ ID NO: 103) | RASESVDYYGNSFIY (SEQ ID NO: 103) | DYYGNSFIYWY (SEQ ID NO: 105) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

Hz64A12 Heavy chain variable region (SEQ ID NO: 139)
EVQLVESGGGLVQPGGSLRLSCAASGFTFNTYAMHWVRQAPGKGLEWVARIRSKSSNYAT
YYADSVKDRFTISRDDAKNSLYLQMNSLRAEDTAVYYCARDGIYYYDTMYYYAMDYWGQGTLVTVSS Hz64A12 Light chain variable region (SEQ ID NO: 140)
NIVLTQSPDSLAVSLGERATINCRASESVDYYGNSFIYWYQQKPGQPPKLLIYFASNLES
GVPDRFSGSGSGTDFTLTISSLQAEDVAVYYCQQNNEDPWTFGGGTKVEIK

TABLE 7

Anti-ILT2/1LT4 Antibody 73C4 Sequences

| | Exemplary | Chothia | AbM | Kabat | Contact |
|---|---|---|---|---|---|
| Heavy Chain variable region CDR1 | GYTFTDYYMN (SEQ ID NO: 70) | GYTFTDY (SEQ ID NO: 76) | GYTFTDYYMN (SEQ ID NO: 70) | DYYMN (SEQ ID NO: 79) | TDYYMN (SEQ ID NO: 80) |
| Heavy Chain variable region CDR2 | NVNPNNGGTSYNQKFKG (SEQ ID NO: 106) | NPNNGG (SEQ ID NO: 77) | NVNPNNGGTS (SEQ ID NO: 108) | NVNPNNGGTSYNQKFKG (SEQ ID NO: 106) | WIGNVNPNNGGTS (SEQ ID NO: 109) |
| Heavy Chain variable region CDR3 | REIYFYGTIYYYAMDY (SEQ ID NO: 107) | REIYFYGTIYYYAMDY (SEQ ID NO: 107) | REIYFYGTIYYYAMDY (SEQ ID NO: 107) | REIYFYGTIYYYAMDY (SEQ ID NO: 107) | ARREIYFYGTIYYYAMD (SEQ ID NO: 110) |
| Light Chain variable region CDR1 | RASESVDYYGNSFMY (SEQ ID NO: 89) | RASESVDYYGNSFMY (SEQ ID NO: 89) | RASESVDYYGNSFMY (SEQ ID NO: 89) | RASESVDYYGNSFMY (SEQ ID NO: 89) | DYYGNSFMYWY (SEQ ID NO: 99) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

73C4 Heavy chain variable region (SEQ ID NO: 141)
AVQLQQSGPELVKPGASVKISCKASGYTFTDYYMNWVKQSHGKSLEWIGNVNPNNGGTSY
NQKFKGKATLTVDKSSSTAYMELRSLTSEDSAVYYCARREIYFYGTIYYYAMDYWGQGTSVTVSS 73C4 Light chain variable region (SEQ ID NO: 142)
DIVLTQSPASLAVSLGQRATISCRASESVDYYGNSFMYWYQQKPGRPPNLLIYFASNLES
GVPARFSGSGSRTDFTLTIDPVEADDAATYYCQQNNEDPWTFGGGTKLEIK

TABLE 8A

Anti-ILT2/1LT4 Antibody 73D1 Sequences

| | Exemplary | Chothia | AbM | Kabat | Contact |
|---|---|---|---|---|---|
| Heavy Chain variable region CDR1 | GYTFTDYYIN (SEQ ID NO: 111) | GYTFTDY (SEQ ID NO: 76) | GYTFTDYYIN (SEQ ID NO: 111) | DYYIN (SEQ ID NO: 115) | TDYYIN (SEQ ID NO: 116) |
| Heavy Chain variable region CDR2 | NVNPNDGGTTYNQKFKG (SEQ ID NO: 112) | NPNDGG (SEQ ID NO: 113) | NVNPNDGGTT (SEQ ID NO: 114) | NVNPNDGGTTYNQKFKG (SEQ ID NO: 112) | WIGNVNPNDGGTT (SEQ ID NO: 117) |
| Heavy Chain variable region CDR3 | REIYFYGTIYYYAMDY (SEQ ID NO: 107) | REIYFYGTIYYYAMDY (SEQ ID NO: 107) | REIYFYGTIYYYAMDY (SEQ ID NO: 107) | REIYFYGTIYYYAMDY (SEQ ID NO: 107) | ARREIYFYGTIYYYAMD (SEQ ID NO: 110) |
| Light Chain variable region CDR1 | RASESVDYYGNSFMY (SEQ ID NO: 89) | RASESVDYYGNSFMY (SEQ ID NO: 89) | RASESVDYYGNSFMY (SEQ ID NO: 89) | RASESVDYYGNSFMY (SEQ ID NO: 89) | DYYGNSFMYWY (SEQ ID NO: 99) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

73D1 Heavy chain variable region (SEQ ID NO: 143)
AVQLQQSGPELVKPGASVKISCKASGYTFTDYYINWVKQSHGKSLQWIGNVNPNDGGTTY
NQKFKGKATLTVDKSSSTAYMELRSLTSEDSAVYYCARREIYFYGTIYYYAMDYWGQGTSVTVSS 73D1 Light chain variable region (SEQ ID NO: 142)
DIVLTQSPASLAVSLGQRATISCRASESVDYYGNSFMYWYQQKPGRPPNLLIYFASNLES
GVPARFSGSGSRTDFTLTIDPVEADDAATYYCQQNNEDPWTFGGGTKLEIK

TABLE 8B

Anti-ILT2/1LT4 Antibody Hz73D1.v1 Sequences

| | Exemplary | Chothia | AbM | Kabat | Contact |
|---|---|---|---|---|---|
| Heavy Chain variable region CDR1 | GYTFTDYYIN (SEQ ID NO: 111) | GYTFTDY (SEQ ID NO: 76) | GYTFTDYYIN (SEQ ID NO: 111) | DYYIN (SEQ ID NO: 115) | TDYYIN (SEQ ID NO: 116) |
| Heavy Chain variable region CDR2 | NVNPNDGGTTYNQKF KG (SEQ ID NO: 112) | NPNDGG (SEQ ID NO: 113) | NVNPNDGGTT (SEQ ID NO: 114) | NVNPNDGGTTYNQKF KG (SEQ ID NO: 112) | WMGNVNPNDGGTT (SEQ ID NO: 124) |
| Heavy Chain variable region CDR3 | REIYFYGTIYYYAMD Y (SEQ ID NO: 107) | REIYFYGTIYYYAM DY (SEQ ID NO: 107) | REIYFYGTIYYYAM DY (SEQ ID NO: 107) | REIYFYGTIYYYAMDY (SEQ ID NO: 107) | ARREIYFYGTIYYY (SEQ ID NO: 110) |
| Light Chain variable region CDR1 | RASESVDYYGNSFMY (SEQ ID NO: 89) | RASESVDYYGNSF MY (SEQ ID NO: 89) | RASESVDYYGNSF MY (SEQ ID NO: 89) | RASESVDYYGNSFMY (SEQ ID NO: 89) | DYYGNSFMYWY (SEQ ID NO: 99) |
| Light Chain variable region CDR2 | FASNLES (SEQ ID NO: 90) | FASNLES (SEQ ID NO: 90) | FASNLES (SEQ ID NO: 90) | FASNLES (SEQ ID NO: 90) | LLIYFASNLE (SEQ ID NO: 100) |
| Light Chain variable region CDR3 | QQNNEDPWT (SEQ ID NO: 91) | QQNNEDPWT (SEQ ID NO: 91) | QQNNEDPWT (SEQ ID NO: 91) | QQNNEDPWT (SEQ ID NO: 91) | QQNNEDPW (SEQ ID NO: 101) |

Hz73D1.v1 Heavy chain variable region (SEQ ID NO: 144)
QVQLVQSGAEVKKPGASVKVSCKASGYTFTDYYINWVRQAPGQGLEWMGNVNPNDGGTTY
NQKFKGRVTMTTDTSTSTAYMELRSLRSDDTAVYYCARREIYFYGTIYYYAMDYWGQGTLVTVSS Hz73D1.v1 Light chain variable region (SEQ ID NO: 145)
DIQLTQSPSFLSASVGDRVTITCRASESVDYYGNSFMYWYQQKPGKAPKLLIYFASNLES
GVPSRFSGSGSGTEFTLTISSLQPEDFATYYCQQNNEDPWTFGGGTKVEIK In some embodiments, an ILT-binding agent (e.g., an ILT2-binding agent, an ILT4-binding agent, or an ILT2/ILT4 binding agent) comprises a heavy chain variable region CDR1, CDR2, and CDR3 and/or a light chain variable region CDR1, CDR2, and CDR3 from an antibody described herein. In some embodiments, an ILT-binding agent comprises a heavy chain variable region CDR1, CDR2, and CDR3 and a light chain variable region CDR1, CDR2, and CDR3 from an antibody described herein. In some embodiments, an ILT-binding agent comprises: (a) a heavy chain variable region comprising a heavy chain variable region CDR1, CDR2, and CDR3; and (b) a light chain variable region comprising a light chain variable region CDR1, CDR2, and CDR3 from an antibody described herein.

In some embodiments, an ILT-binding agent (e.g., an anti-ILT2 antibody, an anti-ILT4 antibody, or an anti-ILT2/ILT4 antibody) comprises one or more (e.g., 1, 2, 3, 4, etc.) amino acid substitutions in a CDR of an antibody described herein. In some embodiments, the amino acid substitutions are conservative substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the CDR is a heavy chain variable region CDR1. In some embodiments, the CDR is a heavy chain variable region CDR2. In some embodiment, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, an ILT-binding agent (e.g., an ILT2-binding agent, an ILT4-binding agent, or an ILT2/ILT4 binding agent) comprises one or more heavy chain variable region CDRs or light chain variable region CDRs that have been modified to reduce deamidation within the CDR sequence. Deamidation is a chemical reaction in which an amide functional group in the side chain of the amino acids asparagine (Asn or N) or glutamine (Gln or Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity. In some embodiments, the heavy chain variable region CDR1, CDR2, and/or CDR3 of an antibody described herein is modified to reduce deamidation. In some embodiments, the light chain variable region CDR1, CDR2, and/or CDR3 of an antibody described herein is modified to reduce deamidation.

In some embodiments, an ILT-binding agent (e.g., an ILT2-binding agent, an ILT4-binding agent, or an ILT2/ILT4 binding agent) comprises one or more heavy chain variable region CDRs or light chain variable region CDRs that have been modified to reduce isomerization. Isomerization is a chemical process by which a compound is transformed into any of its isomeric forms, i.e., forms with the same chemical composition but with different structure or configuration and, potentially with different physical and chemical properties. Studies have shown that asparatate (Asp or D) isomerization within a CDR can impact antibody binding and/or stability. In some embodiments, the heavy chain variable region CDR1, CDR2, and/or CDR3 of an antibody described herein is modified to reduce isomerization. In some embodiments, the light chain variable region CDR1, CDR2, and/or CDR3 is modified to reduce isomerization.

In some embodiments, an ILT-binding agent (e.g., an ILT2-binding agent, an ILT4-binding agent, or an ILT2/ILT4 binding agent) comprises one or more heavy chain variable region CDRs or light chain variable region CDRs that have been modified to reduce oxidation. Oxidation is a chemical process by which an oxygen is added to an atom, for example, methionine is converted to methionine sulfoxide by addition of an oxygen to the sulfur atom. Oxidation of one or more amino acids can potentially affect the physical and chemical properties of a protein. Studies have shown that oxidation of methionine (Met or M) within a CDR has the potential to impact antibody binding and/or stability. In some embodiments, the heavy chain variable region CDR1, CDR2, and/or CDR3 of an antibody described herein is modified to reduce oxidation (e.g., methionine oxidation). In some embodiments, the light chain variable region CDR1, CDR2, and/or CDR3 of an antibody described herein is modified to reduce oxidation (e.g., methionine oxidation).

In some embodiments, an ILT2-binding agent comprises a heavy chain variable region CDR1, CDR2, and CDR3 and/or a light chain variable region CDR1, CDR2, and CDR3 from antibody 27F9, a humanized version thereof, or variants thereof. In some embodiments, an ILT2-binding agent comprises a heavy chain variable region comprising a heavy chain variable region CDR1, a heavy chain variable region CDR2, and a heavy chain variable region CDR3 from antibody 27F9. In other embodiments, an ILT2-binding agent comprises a light chain variable region comprising a light chain variable region CDR1, a light chain variable region CDR2, and a light chain variable region CDR3 from antibody 27F9 In some embodiments, an ILT2-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 27F9. In some embodiments, an ILT2-binding agent is a humanized version of antibody 27F9. In some embodiments, an ILT2-binding agent is a variant of antibody 27F9 or humanized 27F9.

In some embodiments, an ILT2-binding agent comprises: (a) a heavy chain variable region comprising a heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24), and a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27); (b) a heavy chain variable region comprising a heavy chain variable region CDR1 comprising the amino acid sequence GFSLTNY (SEQ ID NO:28), a heavy chain variable region CDR2 comprising the amino acid sequence WGDGS (SEQ ID NO:29), and a heavy chain variable region CDR3 comprising the amino acid sequence PNWDTYAMDF (SEQ ID NO:24), and a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27); (c) a heavy chain variable region comprising a heavy chain variable region CDR1 comprising the amino acid sequence GFSLTNYGVS (SEQ ID NO:22), a heavy chain variable region CDR2 comprising the amino acid sequence IIWGDGSTN (SEQ ID NO:30), and a heavy chain variable region CDR3 comprising the amino acid sequence PNWDTYAMDF (SEQ ID NO:24), and a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27); (d) a heavy chain variable region comprising a heavy chain variable region CDR1 comprising the amino acid sequence NYGVS (SEQ ID NO:31), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24), and a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27); or (e) a heavy chain variable region comprising a heavy chain variable region CDR1 comprising the amino acid sequence TNYGVS (SEQ ID NO:32), a heavy chain variable region CDR2 comprising the amino acid sequence WLGIIWGDGSTN (SEQ ID NO:33), and a heavy chain variable region CDR3 comprising the amino acid sequence AKPNWDTYAMD (SEQ ID NO:34), and a light chain variable region comprising a light chain variable region CDR1 comprising the amino acid sequence SNFLNWY (SEQ ID NO:35), a light chain variable region CDR2 comprising the amino acid sequence LLIYCTSKLH (SEQ ID NO:36), and a light chain variable region CDR3 comprising the amino acid sequence QQGNTLPP (SEQ ID NO:37).

In some embodiments, an ILT2-binding agent comprises: (a) a heavy chain variable region comprising heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24), and/or (b) a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27). In some embodiments, the ILT2-binding agent comprises a heavy chain variable region comprising heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24). In some embodiments, the ILT2-binding agent comprises a light chain variable region comprising a light chain variable region CDR1 comprising the amino acid sequence RASQDISNFLN (SEQ ID NO:25), a light chain variable region CDR2 comprising the amino acid sequence CTSK-LHS (SEQ ID NO:26), and a light chain variable region CDR3 comprising the amino acid sequence QQGNTLPPT (SEQ ID NO:27). In some embodiments, the ILT2-binding agent comprises: (a) a heavy chain variable region comprising heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMDF (SEQ ID NO:24), and (b) a light chain variable region comprising a light chain variable region CDR1 comprising the amino acid sequence RASQDISNFLN (SEQ ID NO:25), a light chain variable region CDR2 comprising the amino acid sequence CTSK-LHS (SEQ ID NO:26), and a light chain variable region CDR3 comprising the amino acid sequence QQGNTLPPT (SEQ ID NO:27).

In some embodiments, an anti-ILT2 binding agent comprises a heavy chain variable region comprising the amino acid sequence of heavy chain variable region CDR1, CDR2, and CDR3 of antibody 27F9 and which has at least 75%, at least 80%, at least 85%, at least 90%, at least 95%, at least 96%, at least 97%, at least 98%, at least 99%, or 100% identity to the sequence of SEQ ID NO:125 and a light chain variable region comprising the amino acid sequence of light chain variable region CDR1, CDR2, and CDR3 of antibody 27F9 and which has at least 75%, at least 80%, at least 85%, at least 90%, at least 95%, at least 96%, at least 97%, at least 98%, at least 99%, or 100% identity to the sequence of SEQ ID NO:126.

In some embodiments, an ILT2-binding agent comprises a heavy chain variable region having at least 80%, at least 85%, at least 90%, at least 95%, at least 97%, or at least 99% identity to the sequence of SEQ ID NO:125. In some embodiments, an ILT2-binding agent comprises a light chain variable region having at least 80%, at least 85%, at least 90%, at least 95%, at least 97%, or at least 99% identity to the sequence of SEQ ID NO:126. In some embodiments, an ILT2-binding agent comprises a heavy chain variable region comprising an amino acid sequence of SEQ ID NO:125. In some embodiments, an ILT2-binding agent comprises a light chain variable region comprising an amino acid sequence of SEQ ID NO:126.

In some embodiments, an ILT2-binding agent comprises a heavy chain variable region having at least 80% sequence identity to SEQ ID NO:125 and a light chain variable region having at least 80% sequence identity to SEQ ID NO:126. In some embodiments, an ILT2-binding agent comprises a heavy chain variable region having at least 90% sequence identity to SEQ ID NO:125 and a light chain variable region having at least 90% sequence identity to SEQ ID NO:126. In some embodiments, an ILT2-binding agent comprises a heavy chain variable region having at least 95% sequence identity to SEQ ID NO:125 and a light chain variable region having at least 95% sequence identity to SEQ ID NO:126. In some embodiments, an ILT2-binding agent comprises a heavy chain variable region comprising an amino acid sequence of SEQ ID NO:125 and a light chain variable region comprising an amino acid sequence of SEQ ID NO:126.

In some embodiments, an ILT4-binding agent comprises a heavy chain variable region CDR1, CDR2, and CDR3 and/or a light chain variable region CDR1, CDR2, and CDR3 from antibody 47C8, a humanized version thereof, or variants thereof. In some embodiments, an ILT4-binding agent comprises a heavy chain variable region comprising a heavy chain variable region CDR1, a heavy chain variable region CDR2, and a heavy chain variable region CDR3 from antibody 47C8. In other embodiments, an ILT4-binding agent comprises a light chain variable region comprising a light chain variable region CDR1, a light chain variable region CDR2, and a light chain variable region CDR3 from antibody 47C8 In some embodiments, an ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 47C8. In some embodiments, an ILT4-binding agent is a humanized version of antibody 47C8. In some embodiments, an ILT4-binding agent is a variant of antibody 47C8 or humanized 47C8.

In some embodiments, an ILT4-binding agent comprises: (a) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40), and a light chain variable region comprising a light chain variable region CDR1 comprising the amino acid sequence RAS-ESVDNYGNNFLH (SEQ ID NO:41), a light chain variable region CDR2 comprising the amino acid sequence RTSN-LES (SEQ ID NO:42), and a light chain variable region CDR3 comprising the amino acid sequence QQSNEDPYT (SEQ ID NO:43); (b) a heavy chain variable region comprising a heavy chain variable region CDR1 comprising the amino acid sequence GYSFTGY (SEQ ID NO:44), a heavy chain variable region CDR2 comprising the amino acid sequence YPNNGD (SEQ ID NO:45), and a heavy chain variable region CDR3 comprising the amino acid sequence GATVVESLFAY (SEQ ID NO:40), and a light chain variable region comprising a light chain variable region CDR1 comprising the amino acid sequence RASESVDNYGNN-FLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43); (c) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTS (SEQ ID NO:46), and a heavy chain variable region CDR3 comprising the amino acid sequence GATVVESLFAY (SEQ ID NO:40), and a light chain variable region comprising a light chain variable region CDR1 comprising the amino acid sequence RASESVDNYGNN-FLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43); (d) a heavy chain variable region comprising a heavy chain variable region CDR1 comprising the amino acid sequence GYYMH (SEQ ID NO:47), a heavy chain variable region CDR2 comprising the amino acid sequence RVYPNNGDT-SYNQKFKV (SEQ ID NO:39), and a heavy chain variable region CDR3 comprising the amino acid sequence GATVVESLFAY (SEQ ID NO:40), and a light chain variable region comprising a light chain variable region CDR1 comprising the amino acid sequence RASESVDNYGNN-FLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43); or (e) a heavy chain variable region comprising a heavy chain variable region CDR1 comprising the amino acid sequence TGYYMH (SEQ ID NO:48), a heavy chain variable region CDR2 comprising the amino acid sequence WIGRVYPNNGDTS (SEQ ID NO:49), and a heavy chain variable region CDR3 comprising the amino acid sequence ARGATVVESLFA (SEQ ID NO:50), and a light chain variable region comprising a light chain variable region CDR1 comprising the amino acid sequence DNYGNN-FLHWY (SEQ ID NO:51), a light chain variable region CDR2 comprising the amino acid sequence LLIYRTSNLE (SEQ ID NO:52), and a light chain variable region CDR3 comprising the amino acid sequence QQSNEDPY (SEQ ID NO:53).

In some embodiments, an ILT4-binding agent comprises: (a) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40), and/or (b) a light chain variable region comprising a light chain variable region CDR1 comprising the amino acid sequence RAS-ESVDNYGNNFLH (SEQ ID NO:41), a light chain variable region CDR2 comprising the amino acid sequence RTSN-LES (SEQ ID NO:42), and a light chain variable region CDR3 comprising the amino acid sequence QQSNEDPYT (SEQ ID NO:43). In some embodiments, the ILT4-binding agent comprises a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40). In some embodiments, the ILT4-binding agent comprises a light chain variable region comprising a light chain variable region CDR1 comprising the amino acid sequence RAS-ESVDNYGNNFLH (SEQ ID NO:41), a light chain variable region CDR2 comprising the amino acid sequence RTSN-LES (SEQ ID NO:42), and a light chain variable region CDR3 comprising the amino acid sequence QQSNEDPYT (SEQ ID NO:43). In some embodiments, the ILT4-binding agent comprises: (a) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40), and (b) a light chain variable region comprising a light chain variable region CDR1 comprising the amino acid sequence RASESVDNYGNNFLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43).

In some embodiments, an anti-ILT4 binding agent comprises a heavy chain variable region comprising the amino acid sequence of heavy chain variable region CDR1, CDR2, and CDR3 of antibody 47C8 and which has at least 75%, at least 80%, at least 85%, at least 90%, at least 95%, at least 96%, at least 97%, at least 98%, at least 99%, or 100% identity to the sequence of SEQ ID NO:127 and a light chain variable region comprising the amino acid sequence of light chain variable region CDR1, CDR2, and CDR3 of antibody 47C8 and which has at least 75%, at least 80%, at least 85%, at least 90%, at least 95%, at least 96%, at least 97%, at least 98%, at least 99%, or 100% identity to the sequence of SEQ ID NO:128.

In some embodiments, an ILT4-binding agent comprises a heavy chain variable region having at least 80%, at least 85%, at least 90%, at least 95%, at least 97%, or at least 99% identity to the sequence of SEQ ID NO:127. In some embodiments, an ILT4-binding agent comprises a light chain variable region having at least 80%, at least 85%, at least 90%, at least 95%, at least 97%, or at least 99% identity to the sequence of SEQ ID NO:128. In some embodiments, an ILT4-binding agent comprises a heavy chain variable region comprising an amino acid sequence of SEQ ID NO:127. In some embodiments, an ILT4-binding agent comprises a light chain variable region comprising an amino acid sequence of SEQ ID NO:128.

In some embodiments, an ILT4-binding agent comprises a heavy chain variable region having at least 80% sequence identity to SEQ ID NO:127 and a light chain variable region having at least 80% sequence identity to SEQ ID NO:128. In some embodiments, an ILT4-binding agent comprises a heavy chain variable region having at least 90% sequence identity to SEQ ID NO:127 and a light chain variable region having at least 90% sequence identity to SEQ ID NO:128. In some embodiments, an ILT4-binding agent comprises a heavy chain variable region having at least 95% sequence identity to SEQ ID NO:127 and a light chain variable region having at least 95% sequence identity to SEQ ID NO:128. In some embodiments, an ILT4-binding agent comprises a heavy chain variable region comprising an amino acid sequence of SEQ ID NO:127 and a light chain variable region comprising an amino acid sequence of SEQ ID NO:128.

In some embodiments, an ILT4-binding agent comprises a heavy chain variable region CDR1, CDR2, and CDR3 and/or a light chain variable region CDR1, CDR2, and CDR3 from antibody 48A5, a humanized version thereof, or variants thereof. In some embodiments, an ILT4-binding agent comprises a heavy chain variable region comprising a heavy chain variable region CDR1, a heavy chain variable region CDR2, and a heavy chain variable region CDR3 from antibody 48A5. In other embodiments, an ILT4-binding agent comprises a light chain variable region comprising a light chain variable region CDR1, a light chain variable region CDR2, and a light chain variable region CDR3 from antibody 48A5 In some embodiments, an ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 48A5. In some embodiments, an ILT4-binding agent is a humanized version of antibody 48A5. In some embodiments, an ILT4-binding agent is a variant of antibody 48A5 or humanized 48A5.

In some embodiments, an ILT4-binding agent comprises: (a) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59); (b) a heavy chain variable region comprising a heavy chain variable region CDR1 comprising the amino acid sequence GYTFTNY (SEQ ID NO:60), a heavy chain variable region CDR2 comprising the amino acid sequence NTYIGE (SEQ ID NO:61), and a heavy chain variable region CDR3 comprising the amino acid sequence RSDYDGYAMDY (SEQ ID NO:56), and a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59); (c) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPI (SEQ ID NO:62), and a heavy chain variable region CDR3 comprising the amino acid sequence RSDYDGYAMDY (SEQ ID NO:56), and a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59); (d) a heavy chain variable region comprising a heavy chain variable region CDR1 comprising the amino acid sequence NYGMN (SEQ ID NO:63), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59); or (e) a heavy chain variable region comprising a heavy chain variable region CDR1 comprising the amino acid sequence TNYGMN (SEQ ID NO:64), a heavy chain variable region CDR2 comprising the amino acid sequence WMGWINTYIGEPI (SEQ ID NO:65), and a heavy chain variable region CDR3 comprising the amino acid sequence ARRSDYDGYAMD (SEQ ID NO:66), and a light chain variable region comprising a light chain variable region CDR1 comprising the amino acid sequence LYSGNQKNYLAWY (SEQ ID NO:67), a light chain variable region CDR2 comprising the amino acid sequence LLIYWASTRE (SEQ ID NO:68), and a light chain variable region CDR3 comprising the amino acid sequence QQHDSYP (SEQ ID NO:69).

In some embodiments, an ILT4-binding agent comprises: (a) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and/or (b) a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59). In some embodiments, the ILT4-binding agent comprises a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56). In some embodiments, the ILT4-binding agent comprises a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59). In some embodiments, the ILT4-binding agent comprises: (a) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and (b) a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59).

In some embodiments, an anti-ILT4 binding agent comprises a heavy chain variable region comprising the amino acid sequence of heavy chain variable region CDR1, CDR2, and CDR3 of antibody 48A5 and which has at least 75%, at least 80%, at least 85%, at least 90%, at least 95%, at least 96%, at least 97%, at least 98%, at least 99%, or 100% identity to the sequence of SEQ ID NO:129 and a light chain variable region comprising the amino acid sequence of light chain variable region CDR1, CDR2, and CDR3 of antibody 48A5 and which has at least 75%, at least 80%, at least 85%, at least 90%, at least 95%, at least 96%, at least 97%, at least 98%, at least 99%, or 100% identity to the sequence of SEQ ID NO:130.

In some embodiments, an ILT4-binding agent comprises a heavy chain variable region having at least 80%, at least 85%, at least 90%, at least 95%, at least 97%, or at least 99% identity to the sequence of SEQ ID NO:129. In some embodiments, an ILT4-binding agent comprises a light chain variable region having at least 80%, at least 85%, at least 90%, at least 95%, at least 97%, or at least 99% identity to the sequence of SEQ ID NO:130. In some embodiments, an ILT4-binding agent comprises a heavy chain variable region comprising an amino acid sequence of SEQ ID NO:129. In some embodiments, an ILT4-binding agent comprises a light chain variable region comprising an amino acid sequence of SEQ ID NO:130.

In some embodiments, an ILT4-binding agent comprises a heavy chain variable region having at least 80% sequence identity to SEQ ID NO:129 and a light chain variable region having at least 80% sequence identity to SEQ ID NO:130. In some embodiments, an ILT4-binding agent comprises a heavy chain variable region having at least 90% sequence identity to SEQ ID NO:129 and a light chain variable region having at least 90% sequence identity to SEQ ID NO:130. In some embodiments, an ILT4-binding agent comprises a heavy chain variable region having at least 95% sequence identity to SEQ ID NO:129 and a light chain variable region having at least 95% sequence identity to SEQ ID NO:130. In some embodiments, an ILT4-binding agent comprises a heavy chain variable region comprising an amino acid sequence of SEQ ID NO:129 and a light chain variable region comprising an amino acid sequence of SEQ ID NO:130.

In some embodiments, an ILT2/ILT4-binding agent (e.g., a dual binder) comprises a heavy chain variable region CDR1, CDR2, and CDR3 and/or a light chain variable region CDR1, CDR2, and CDR3 from antibody 47H6, a humanized version thereof (e.g., Hz47H6.v2), or variants thereof. In some embodiments, an ILT2/ILT4-binding agent comprises a heavy chain variable region comprising a heavy chain variable region CDR1, a heavy chain variable region CDR2, and a heavy chain variable region CDR3 from antibody 47H6 or antibody Hz47H6.v2. In other embodiments, an ILT2/ILT4-binding agent comprises a light chain variable region comprising a light chain variable region CDR1, a light chain variable region CDR2, and a light chain variable region CDR3 from antibody 47H6 or antibody Hz47H6.v2. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 47H6. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody Hz47H6.v2. In some embodiments, an ILT2/ILT4-binding agent is a humanized version of antibody 47H6. In some embodiments, an ILT2/ILT4-binding agent is a variant of antibody 47H6. In some embodiments, an ILT2/ILT4-binding agent is a variant of antibody Hz47H6.v2.

In some embodiments, an ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75); (b) a heavy chain variable region comprising a heavy chain variable region CDR1 comprising the amino acid sequence GYTFTDY (SEQ ID NO:76), a heavy chain variable region CDR2 comprising the amino acid sequence NPNNGG (SEQ ID NO:77) or the amino acid sequence NPNNAG (SEQ ID NO:119), and a heavy chain variable region CDR3 comprising the amino acid sequence GRFYYGSLYSFDY (SEQ ID NO:72), and a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75); (c) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTT (SEQ ID NO:78) or the amino acid sequence DFNPNNAGTT (SEQ ID NO:120), and a heavy chain variable region CDR3 comprising the amino acid sequence GRFYYGSLYSFDY (SEQ ID NO:72), and a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75); (d) a heavy chain variable region comprising a heavy chain variable region CDR1 comprising the amino acid sequence DYYMN (SEQ ID NO:79), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75); or (e) a heavy chain variable region comprising a heavy chain variable region CDR1 comprising the amino acid sequence TDYYMN (SEQ ID NO:80), a heavy chain variable region CDR2 comprising the amino acid sequence WIGDFNPNNGGTT (SEQ ID NO:81) or the amino acid sequence WIGDFNPNNAGTT (SEQ ID NO:121), and a heavy chain variable region CDR3 comprising the amino acid sequence ARGRFYYGSLYSFD (SEQ ID NO:82), and a light chain variable region comprising a light chain variable region CDR1 comprising the amino acid sequence HNYLAWY (SEQ ID NO:83), a light chain variable region CDR2 comprising the amino acid sequence LLVYNAKTLA (SEQ ID NO:84) or the amino acid sequence LLIYNAKTLA (SEQ ID NO:122), and a light chain variable region CDR3 comprising the amino acid sequence QHFWTSI (SEQ ID NO:85).

In some embodiments, an ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPN- NAGTTYNQKFEG (SEQ ID NO:118), and a heavy chain variable region CDR3 comprising the amino acid sequence GRFYYGSLYSFDY (SEQ ID NO:72), and/or (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, the ILT2/ILT4-binding agent comprises a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71), and a heavy chain variable region CDR3 comprising the amino acid sequence GRFYYGSLYSFDY (SEQ ID NO:72). In some embodiments, the ILT2/ILT4-binding agent comprises a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNAGTTYNQKFEG (SEQ ID NO:118), and a heavy chain variable region CDR3 comprising the amino acid sequence GRFYYGSLYSFDY (SEQ ID NO:72). In some embodiments, the ILT2/ILT4-binding agent comprises a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, the ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, the ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNAGTTYNQKFEG (SEQ ID NO:118), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75).

In some embodiments, an ILT2/ILT4-binding agent comprises a heavy chain variable region comprising the amino acid sequence of heavy chain variable region CDR1, CDR2, and CDR3 of antibody 47H6 and which has at least 75%, at least 80%, at least 85%, at least 90%, at least 95%, at least 96%, at least 97%, at least 98%, at least 99%, or 100% identity to the sequence of SEQ ID NO:131 and a light chain variable region comprising the amino acid sequence of light chain variable region CDR1, CDR2, and CDR3 of antibody 47H6 and which has at least 75%, at least 80%, at least 85%, at least 90%, at least 95%, at least 96%, at least 97%, at least 98%, at least 99%, or 100% identity to the sequence of SEQ ID NO:132.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:131. In some embodiments, an ILT2/ILT4-binding agent comprises a light chain variable region having at least 80%, at least 85%, at least 90%, at least 95%, at least 97%, or at least 99% identity to the sequence of SEQ ID NO:132. In some embodiments, an ILT2/ILT4-binding agent comprises a heavy chain variable region comprising an amino acid sequence of SEQ ID NO:131. In some embodiments, an ILT2/ILT4-binding agent comprises a light chain variable region comprising an amino acid sequence of SEQ ID NO:132.

In some embodiments, an ILT2/ILT4-binding agent comprises a heavy chain variable region having at least 80% sequence identity to SEQ ID NO:131 and a light chain variable region having at least 80% sequence identity to SEQ ID NO:132. In some embodiments, an ILT2/ILT4-binding agent comprises a heavy chain variable region having at least 90% sequence identity to SEQ ID NO:131 and a light chain variable region having at least 90% sequence identity to SEQ ID NO:132. In some embodiments, an ILT2/ILT4-binding agent comprises a heavy chain variable region having at least 95% sequence identity to SEQ ID NO:131 and a light chain variable region having at least 95% sequence identity to SEQ ID NO:132. In some embodiments, an ILT2/ILT4-binding agent comprises a heavy chain variable region comprising an amino acid sequence of SEQ ID NO:131 and a light chain variable region comprising an amino acid sequence of SEQ ID NO:132.

In some embodiments, an ILT2/ILT4-binding agent comprises a heavy chain variable region comprising the amino acid sequence of heavy chain variable region CDR1, CDR2, and CDR3 of antibody Hz47H6.v2 and which has at least 75%, at least 80%, at least 85%, at least 90%, at least 95%, at least 96%, at least 97%, at least 98%, at least 99%, or 100% identity to the sequence of SEQ ID NO:133 and a light chain variable region comprising the amino acid sequence of light chain variable region CDR1, CDR2, and CDR3 of antibody Hz47H6.v2 and which has at least 75%, at least 80%, at least 85%, at least 90%, at least 95%, at least 96%, at least 97%, at least 98%, at least 99%, or 100% identity to the sequence of SEQ ID NO:134.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:133. In some embodiments, an ILT2/ILT4-binding agent comprises a light chain variable region having at least 80%, at least 85%, at least 90%, at least 95%, at least 97%, or at least 99% identity to the sequence of SEQ ID NO:134. In some embodiments, an ILT2/ILT4-binding agent comprises a heavy chain variable region comprising an amino acid sequence of SEQ ID NO:133. In some embodiments, an ILT2/ILT4-binding agent comprises a light chain variable region comprising an amino acid sequence of SEQ ID NO:134.

In some embodiments, an ILT2/ILT4-binding agent comprises a heavy chain variable region having at least 80% sequence identity to SEQ ID NO:133 and a light chain variable region having at least 80% sequence identity to SEQ ID NO:134. In some embodiments, an ILT2/ILT4-binding agent comprises a heavy chain variable region having at least 90% sequence identity to SEQ ID NO:133 and a light chain variable region having at least 90% sequence identity to SEQ ID NO:134. In some embodiments, an ILT2/ILT4-binding agent comprises a heavy chain variable region having at least 95% sequence identity to SEQ ID NO:133 and a light chain variable region having at least 95% sequence identity to SEQ ID NO:134. In some embodiments, an ILT2/ILT4-binding agent comprises a heavy chain variable region comprising an amino acid sequence of SEQ ID NO:133 and a light chain variable region comprising an amino acid sequence of SEQ ID NO:134.

In some embodiments, an ILT2/ILT4-binding agent comprises a heavy chain comprising a heavy chain variable region CDR1 comprising GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and a light chain comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75), wherein the heavy chain comprises at least 80%, at least 85%, at least 90%, at least 95%, at least 97%, at least 98%, at least 99%, or 100% identity to the sequence of SEQ ID NO:148, and wherein the light chain comprises at least 80%, at least 85%, at least 90%, at least 95%, at least 97%, at least 98%, at least 99%, or 100% identity to the sequence of SEQ ID NO:149. In some embodiments, an ILT2/ILT4-binding agent comprises a heavy chain comprising a heavy chain variable region CDR1 comprising GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and a light chain comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75), wherein the heavy chain comprises at least 95% identity to the sequence of SEQ ID NO:148, and wherein the light chain comprises at least 95% identity to the sequence of SEQ ID NO:149. In some embodiments, an ILT2/ILT4-binding agent comprises (a) a heavy chain comprising the amino acids of SEQ ID NO:148 and (b) a light chain comprising a light chain variable region CDR1 comprising RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75), wherein the light chain comprises at least 80%, at least 85%, at least 90%, at least 95%, at least 97%, at least 98%, at least 99%, or 100% identity to the sequence of SEQ ID NO:149. In some embodiments, an ILT2/ILT4-binding agent comprises (a) a heavy chain comprising the amino acids of SEQ ID NO:148 and (b) a light chain comprising a light chain variable region CDR1 comprising RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, an ILT2/ILT4-binding agent comprises (a) a heavy chain comprising a heavy chain variable region CDR1 comprising GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), wherein the heavy chain comprises at least 80%, at least 85%, at least 90%, at least 95%, at least 97%, at least 98%, at least 99%, or 100% identity to the sequence of SEQ ID NO:148, and (b) a light chain comprising the amino acid sequence of SEQ ID NO:149. In some embodiments, an ILT2/ILT4-binding agent comprises (a) a heavy chain comprising a heavy chain variable region CDR1 comprising GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and (b) a light chain comprising the amino acid sequence of SEQ ID NO:149. In some embodiments, an ILT2/ILT4-binding agent is an antibody comprising a heavy chain comprising the amino acid sequence of SEQ ID NO:148 and a light chain comprising the amino acid sequence of SEQ ID NO:149.

In some embodiments, an ILT2/ILT4-binding agent comprises a heavy chain having at least 80%, at least 85%, at least 90%, or at least 95% identity to the amino acid sequence of SEQ ID NO:148. In some embodiments, an ILT2/ILT4-binding agent comprises a light chain having at least 80%, at least 85%, at least 90%, or at least 95% identity to the amino acid sequence of SEQ ID NO:149. In some embodiments, an ILT2/ILT4-binding agent comprises a heavy chain having at least 80%, at least 85%, at least 90%, or at least 95% identity to the amino acid sequence of SEQ ID NO:148 and a light chain having at least 80%, at least 85%, at least 90%, or at least 95% identity to the amino acid sequence of SEQ ID NO:149. In some embodiments, an ILT2/ILT4-binding agent comprises a heavy chain having at least 90% identity to the amino acid sequence of SEQ ID NO:148. In some embodiments, an ILT2/ILT4-binding agent comprises a light chain having at least 90% identity to the amino acid sequence of SEQ ID NO:149. In some embodiments, an ILT2/ILT4-binding agent comprises a heavy chain having at least 90% identity to the amino acid sequence of SEQ ID NO:148 and a light chain having at least 90% identity to the amino acid sequence of SEQ ID NO:149. In some embodiments, an ILT2/ILT4-binding agent comprises a heavy chain comprising the amino acid sequence of SEQ ID NO:148. In some embodiments, an ILT2/ILT4-binding agent comprises a light chain comprising the amino acid sequence of SEQ ID NO:149. In some embodiments, an ILT2/ILT4-binding agent comprises a heavy chain comprising the amino acid sequence of SEQ ID NO:148 and a light chain comprising the amino acid sequence of SEQ ID NO:149. In some embodiments, an ILT2/ILT4-binding agent is an antibody that comprises a heavy chain of SEQ ID NO:148 and/or a light chain of SEQ ID NO:149. In some embodiments, an ILT2/ILT4-binding agent is an antibody that comprises a heavy chain of SEQ ID NO:148. In some embodiments, an ILT2/ILT4-binding agent is an antibody that comprises a light chain of SEQ ID NO:149. In some embodiments, an ILT2/ILT4-binding agent is an antibody that comprises a heavy chain of SEQ ID NO:148 and a light chain of SEQ ID NO:149.

In some embodiments, an ILT2/ILT4-binding agent (e.g., a dual binder) comprises a heavy chain variable region CDR1, CDR2, and CDR3 and/or a light chain variable region CDR1, CDR2, and CDR3 from antibody 51A1, a humanized version thereof, or variants thereof. In some embodiments, an ILT2/ILT4-binding agent comprises a heavy chain variable region comprising a heavy chain variable region CDR1, a heavy chain variable region CDR2, and a heavy chain variable region CDR3 from antibody 51A1. In other embodiments, an ILT2/ILT4-binding agent comprises a light chain variable region comprising a light chain variable region CDR1, a light chain variable region CDR2, and a light chain variable region CDR3 from antibody 51A1. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 51A1. In some embodiments, an ILT2/ILT4-binding agent is a humanized version of antibody 51A1. In some embodiments, an ILT2/ILT4-binding agent is a variant of antibody 51A1 or humanized 51A1.

In some embodiments, an ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (b) a heavy chain variable region comprising a heavy chain variable region CDR1 comprising the amino acid sequence GFTFNTY (SEQ ID NO:92), a heavy chain variable region CDR2 comprising the amino acid sequence RSKSSNYA (SEQ ID NO:93), and a heavy chain variable region CDR3 comprising the amino acid sequence DGIYYYGTMYYYAMDY (SEQ ID NO:88), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (c) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATY (SEQ ID NO:94), and a heavy chain variable region CDR3 comprising the amino acid sequence DGIYYYGTMYYYAMDY (SEQ ID NO:88), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (d) a heavy chain variable region comprising a heavy chain variable region CDR1 comprising the amino acid sequence TYAMH (SEQ ID NO:95), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); or (e) a heavy chain variable region comprising a heavy chain variable region CDR1 comprising the amino acid sequence NTYAMH (SEQ ID NO:96), a heavy chain variable region CDR2 comprising the amino acid sequence WVARIRSKSSNYATY (SEQ ID NO:97), and a heavy chain variable region CDR3 comprising the amino acid sequence VRDGIYYYGTMYYYAMD (SEQ ID NO:98), and a light chain variable region comprising a light chain variable region CDR1 comprising the amino acid sequence DYYGNSFMYWY (SEQ ID NO:99), a light chain variable region CDR2 comprising the amino acid sequence LLIYFASNLE (SEQ ID NO:100), and a light chain variable region CDR3 comprising the amino acid sequence QQNNEDPW (SEQ ID NO:101).

In some embodiments, an ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88). In some embodiments, the ILT2/ILT4-binding agent comprises a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91).

In some embodiments, an ILT2/ILT4-binding agent comprises a heavy chain variable region comprising the amino acid sequence of heavy chain variable region CDR1, CDR2, and CDR3 of antibody 51A1 and which has at least 75%, at least 80%, at least 85%, at least 90%, at least 95%, at least 96%, at least 97%, at least 98%, at least 99%, or 100% identity to the sequence of SEQ ID NO:135 and a light chain variable region comprising the amino acid sequence of light chain variable region CDR1, CDR2, and CDR3 of antibody 51A1 and which has at least 75%, at least 80%, at least 85%, at least 90%, at least 95%, at least 96%, at least 97%, at least 98%, at least 99%, or 100% identity to the sequence of SEQ ID NO:136.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:135. In some embodiments, an ILT2/ILT4-binding agent comprises a light chain variable region having at least 80%, at least 85%, at least 90%, at least 95%, at least 97%, or at least 99% identity to the sequence of SEQ ID NO:136. In some embodiments, an ILT2/ILT4-binding agent comprises a heavy chain variable region comprising an amino acid sequence of SEQ ID NO:135. In some embodiments, an ILT2/ILT4-binding agent comprises a light chain variable region comprising an amino acid sequence of SEQ ID NO:136.

In some embodiments, an ILT2/ILT4-binding agent comprises a heavy chain variable region having at least 80% sequence identity to SEQ ID NO:135 and a light chain variable region having at least 80% sequence identity to SEQ ID NO:136. In some embodiments, an ILT2/ILT4-binding agent comprises a heavy chain variable region having at least 90% sequence identity to SEQ ID NO:135 and a light chain variable region having at least 90% sequence identity to SEQ ID NO:136. In some embodiments, an ILT2/ILT4-binding agent comprises a heavy chain variable region having at least 95% sequence identity to SEQ ID NO:135 and a light chain variable region having at least 95% sequence identity to SEQ ID NO:136. In some embodiments, an ILT2/ILT4-binding agent comprises a heavy chain variable region comprising an amino acid sequence of SEQ ID NO:135 and a light chain variable region comprising an amino acid sequence of SEQ ID NO:136.

In some embodiments, an ILT2/ILT4-binding agent (e.g., a dual binder) comprises a heavy chain variable region CDR1, CDR2, and CDR3 and/or a light chain variable region CDR1, CDR2, and CDR3 from antibody 64A12, a humanized version thereof (e.g., Hz64A12), or variants thereof. In some embodiments, an ILT2/ILT4-binding agent comprises a heavy chain variable region comprising a heavy chain variable region CDR1, a heavy chain variable region CDR2, and a heavy chain variable region CDR3 from antibody 64A12 or Hz64A12. In other embodiments, an ILT2/ILT4-binding agent comprises a light chain variable region comprising a light chain variable region CDR1, a light chain variable region CDR2, and a light chain variable region CDR3 from antibody 64A12 or Hz64A12. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 64A12 or Hz64A12. In some embodiments, an ILT2/ILT4-binding agent is a humanized version of antibody 64A12. In some embodiments, an ILT2/ILT4-binding agent is a variant of antibody 64A12. In some embodiments, an ILT2/ILT4-binding agent is a variant of antibody Hz64A12.

In some embodiments, an ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91); (b) a heavy chain variable region comprising a heavy chain variable region CDR1 comprising the amino acid sequence GFTFNTY (SEQ ID NO:92), a heavy chain variable region CDR2 comprising the amino acid sequence RSKSSNYA (SEQ ID NO:93), and a heavy chain variable region CDR3 comprising the amino acid sequence DGIYYYDTMYYYAMDY (SEQ ID NO:102), and a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91); (c) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATY (SEQ ID NO:94), and a heavy chain variable region CDR3 comprising the amino acid sequence DGIYYYDTMYYYAMDY (SEQ ID NO:102), and a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91); (d) a heavy chain variable region comprising a heavy chain variable region CDR1 comprising the amino acid sequence TYAMH (SEQ ID NO:95), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91); or (e) a heavy chain variable region comprising a heavy chain variable region CDR1 comprising the amino acid sequence NTYAMH (SEQ ID NO:96), a heavy chain variable region CDR2 comprising the amino acid sequence WVARIRSKSSNYATY (SEQ ID NO:97), and a heavy chain variable region CDR3 comprising the amino acid sequence VRDGIYYYDTMYYYAMD (SEQ ID NO:104), and a light chain variable region comprising a light chain variable region CDR1 comprising the amino acid sequence DYYGNSFIYWY (SEQ ID NO:105), a light chain variable region CDR2 comprising the amino acid sequence LLIYFASNLE (SEQ ID NO:100), and a light chain variable region CDR3 comprising the amino acid sequence QQNNEDPW (SEQ ID NO:101).

In some embodiments, an ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and/or (b) a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102). In some embodiments, the ILT2/ILT4-binding agent comprises a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and (b) a light chain variable region comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91).

In some embodiments, an ILT2/ILT4-binding agent comprises a heavy chain variable region comprising the amino acid sequence of heavy chain variable region CDR1, CDR2, and CDR3 of antibody 64A12 and which has at least 75%, at least 80%, at least 85%, at least 90%, at least 95%, at least 96%, at least 97%, at least 98%, at least 99%, or 100% identity to the sequence of SEQ ID NO:137 and a light chain variable region comprising the amino acid sequence of light chain variable region CDR1, CDR2, and CDR3 of antibody 64A12 and which has at least 75%, at least 80%, at least 85%, at least 90%, at least 95%, at least 96%, at least 97%, at least 98%, at least 99%, or 100% identity to the sequence of SEQ ID NO:138.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:137. In some embodiments, an ILT2/ILT4-binding agent comprises a light chain variable region having at least 80%, at least 85%, at least 90%, at least 95%, at least 97%, or at least 99% identity to the sequence of SEQ ID NO:138. In some embodiments, an ILT2/ILT4-binding agent comprises a heavy chain variable region comprising an amino acid sequence of SEQ ID NO:137. In some embodiments, an ILT2/ILT4-binding agent comprises a light chain variable region comprising an amino acid sequence of SEQ ID NO:138.

In some embodiments, an ILT2/ILT4-binding agent comprises a heavy chain variable region having at least 80% sequence identity to SEQ ID NO:137 and a light chain variable region having at least 80% sequence identity to SEQ ID NO:138. In some embodiments, an ILT2/ILT4-binding agent comprises a heavy chain variable region having at least 90% sequence identity to SEQ ID NO:137 and a light chain variable region having at least 90% sequence identity to SEQ ID NO:138. In some embodiments, an ILT2/ILT4-binding agent comprises a heavy chain variable region having at least 95% sequence identity to SEQ ID NO:137 and a light chain variable region having at least 95% sequence identity to SEQ ID NO:138. In some embodiments, an ILT2/ILT4-binding agent comprises a heavy chain variable region comprising an amino acid sequence of SEQ ID NO:137 and a light chain variable region comprising an amino acid sequence of SEQ ID NO:138.

In some embodiments, an ILT2/ILT4-binding agent comprises a heavy chain variable region comprising the amino acid sequence of heavy chain variable region CDR1, CDR2, and CDR3 of antibody Hz64A12 and which has at least 75%, at least 80%, at least 85%, at least 90%, at least 95%, at least 96%, at least 97%, at least 98%, at least 99%, or 100% identity to the sequence of SEQ ID NO:139 and a light chain variable region comprising the amino acid sequence of light chain variable region CDR1, CDR2, and CDR3 of antibody Hz64A12 and which has at least 75%, at least 80%, at least 85%, at least 90%, at least 95%, at least 96%, at least 97%, at least 98%, at least 99%, or 100% identity to the sequence of SEQ ID NO:140.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:139. In some embodiments, an ILT2/ILT4-binding agent comprises a light chain variable region having at least 80%, at least 85%, at least 90%, at least 95%, at least 97%, or at least 99% identity to the sequence of SEQ ID NO:140. In some embodiments, an ILT2/ILT4-binding agent comprises a heavy chain variable region comprising an amino acid sequence of SEQ ID NO:139. In some embodiments, an ILT2/ILT4-binding agent comprises a light chain variable region comprising an amino acid sequence of SEQ ID NO:140.

In some embodiments, an ILT2/ILT4-binding agent comprises a heavy chain variable region having at least 80% sequence identity to SEQ ID NO:139 and a light chain variable region having at least 80% sequence identity to SEQ ID NO:140. In some embodiments, an ILT2/ILT4-binding agent comprises a heavy chain variable region having at least 90% sequence identity to SEQ ID NO:139 and a light chain variable region having at least 90% sequence identity to SEQ ID NO:140. In some embodiments, an ILT2/ILT4-binding agent comprises a heavy chain variable region having at least 95% sequence identity to SEQ ID NO:139 and a light chain variable region having at least 95% sequence identity to SEQ ID NO:140. In some embodiments, an ILT2/ILT4-binding agent comprises a heavy chain variable region comprising an amino acid sequence of SEQ ID NO:139 and a light chain variable region comprising an amino acid sequence of SEQ ID NO:140.

In some embodiments, an ILT2/ILT4-binding agent comprises a heavy chain comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and a light chain comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain comprises at least 80%, at least 85%, at least 90%, at least 95%, at least 97%, at least 98%, at least 99%, or 100% identity to the sequence of SEQ ID NO:152, and wherein the light chain comprises at least 80%, at least 85%, at least 90%, at least 95%, at least 97%, at least 98%, at least 99%, or 100% identity to the sequence of SEQ ID NO:153. In some embodiments, an ILT2/ILT4-binding agent comprises a heavy chain comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and a light chain comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain comprises at least 95% identity to the sequence of SEQ ID NO:152, and wherein the light chain comprises at least 95% identity to the sequence of SEQ ID NO:153. In some embodiments, an ILT2/ILT4-binding agent comprises (a) a heavy chain comprising the amino acids of SEQ ID NO:152 and (b) a light chain comprising a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises (a) a heavy chain comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), wherein the heavy chain comprises at least 80%, at least 85%, at least 90%, at least 95%, at least 97%, at least 98%, at least 99%, or 100% identity to the sequence of SEQ ID NO:152, and (b) a light chain comprising the amino acid sequence of SEQ ID NO:153. In some embodiments, an ILT2/ILT4-binding agent comprises (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and (b) a light chain comprising the amino acid sequence of SEQ ID NO:153. In some embodiments, an ILT2/ILT4-binding agent is an antibody comprising a heavy chain comprising the amino acid sequence of SEQ ID NO:152 and a light chain comprising the amino acid sequence of SEQ ID NO:153.

In some embodiments, an ILT2/ILT4-binding agent comprises a heavy chain having at least 80%, at least 85%, at least 90%, or at least 95% identity to the amino acid sequence of SEQ ID NO:152. In some embodiments, an ILT2/ILT4-binding agent comprises a light chain having at least 80%, at least 85%, at least 90%, or at least 95% identity to the amino acid sequence of SEQ ID NO:153. In some embodiments, an ILT2/ILT4-binding agent comprises a heavy chain having at least 80%, at least 85%, at least 90%, or at least 95% identity to the amino acid sequence of SEQ ID NO:152 and a light chain having at least 80%, at least 85%, at least 90%, or at least 95% identity to the amino acid sequence of SEQ ID NO:153. In some embodiments, an ILT2/ILT4-binding agent comprises a heavy chain having at least 90% identity to the amino acid sequence of SEQ ID NO:152. In some embodiments, an ILT2/ILT4-binding agent comprises a light chain having at least 90% identity to the amino acid sequence of SEQ ID NO:153. In some embodiments, an ILT2/ILT4-binding agent comprises a heavy chain having at least 90% identity to the amino acid sequence of SEQ ID NO:152 and a light chain having at least 90% identity to the amino acid sequence of SEQ ID NO:153. In some embodiments, an ILT2/ILT4-binding agent comprises a heavy chain comprising the amino acid sequence of SEQ ID NO:152. In some embodiments, an ILT2/ILT4-binding agent comprises a light chain comprising the amino acid sequence of SEQ ID NO:153. In some embodiments, an ILT2/ILT4-binding agent comprises a heavy chain comprising the amino acid sequence of SEQ ID NO:152 and a light chain comprising the amino acid sequence of SEQ ID NO:153. In some embodiments, an ILT2/ILT4-binding agent is an antibody that comprises a heavy chain of SEQ ID NO:152 and/or a light chain of SEQ ID NO:153. In some embodiments, an ILT2/ILT4-binding agent is an antibody that comprises a heavy chain of SEQ ID NO:152. In some embodiments, an ILT2/ILT4-binding agent is an antibody that comprises a light chain of SEQ ID NO:153. In some embodiments, an ILT2/ILT4-binding agent is an antibody that comprises a heavy chain of SEQ ID NO:152 and a light chain of SEQ ID NO:153.

In some embodiments, an ILT2/ILT4-binding agent (e.g., a dual binder) comprises a heavy chain variable region CDR1, CDR2, and CDR3 and/or a light chain variable region CDR1, CDR2, and CDR3 from antibody 73C4, a humanized version thereof, or variants thereof. In some embodiments, an ILT2/ILT4-binding agent comprises a heavy chain variable region comprising a heavy chain variable region CDR1, a heavy chain variable region CDR2, and a heavy chain variable region CDR3 from antibody 73C4. In other embodiments, an ILT2/ILT4-binding agent comprises a light chain variable region comprising a light chain variable region CDR1, a light chain variable region CDR2, and a light chain variable region CDR3 from antibody 73C4. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 73C4. In some embodiments, an ILT2/ILT4-binding agent is a humanized version of antibody 73C4. In some embodiments, an ILT2/ILT4-binding agent is a variant of antibody 73C4 or humanized 73C4.

In some embodiments, an ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (b) a heavy chain variable region comprising a heavy chain variable region CDR1 comprising the amino acid sequence GYTFTDY (SEQ ID NO:76), a heavy chain variable region CDR2 comprising the amino acid sequence NPNNGG (SEQ ID NO:77), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (c) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTS (SEQ ID NO:108), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (d) a heavy chain variable region comprising a heavy chain variable region CDR1 comprising the amino acid sequence DYYMN (SEQ ID NO:79), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); or (e) a heavy chain variable region comprising a heavy chain variable region CDR1 comprising the amino acid sequence TDYYMN (SEQ ID NO:80), a heavy chain variable region CDR2 comprising the amino acid sequence WIGNVNPNNGGTS (SEQ ID NO:109), and a heavy chain variable region CDR3 comprising the amino acid sequence ARREIYFYGTIYYYAMD (SEQ ID NO:110), and a light chain variable region comprising a light chain variable region CDR1 comprising the amino acid sequence DYYGNSFMYWY (SEQ ID NO:99), a light chain variable region CDR2 comprising the amino acid sequence LLIYFASNLE (SEQ ID NO:100), and a light chain variable region CDR3 comprising the amino acid sequence QQNNEDPW (SEQ ID NO:101).

In some embodiments, an ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107). In some embodiments, the ILT2/ILT4-binding agent comprises a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91).

In some embodiments, an ILT2/ILT4-binding agent comprises a heavy chain variable region comprising the amino acid sequence of heavy chain variable region CDR1, CDR2, and CDR3 of antibody 73C4 and which has at least 75%, at least 80%, at least 85%, at least 90%, at least 95%, at least 96%, at least 97%, at least 98%, at least 99%, or 100% identity to the sequence of SEQ ID NO:141 and a light chain variable region comprising the amino acid sequence of light chain variable region CDR1, CDR2, and CDR3 of antibody 73C4 and which has at least 75%, at least 80%, at least 85%, at least 90%, at least 95%, at least 96%, at least 97%, at least 98%, at least 99%, or 100% identity to the sequence of SEQ ID NO:142.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:141. In some embodiments, an ILT2/ILT4-binding agent comprises a light chain variable region having at least 80%, at least 85%, at least 90%, at least 95%, at least 97%, or at least 99% identity to the sequence of SEQ ID NO:142. In some embodiments, an ILT2/ILT4-binding agent comprises a heavy chain variable region comprising an amino acid sequence of SEQ ID NO:141. In some embodiments, an ILT2/ILT4-binding agent comprises a light chain variable region comprising an amino acid sequence of SEQ ID NO:142.

In some embodiments, an ILT2/ILT4-binding agent comprises a heavy chain variable region having at least 80% sequence identity to SEQ ID NO:141 and a light chain variable region having at least 80% sequence identity to SEQ ID NO:142. In some embodiments, an ILT2/ILT4-binding agent comprises a heavy chain variable region having at least 90% sequence identity to SEQ ID NO:141 and a light chain variable region having at least 90% sequence identity to SEQ ID NO:142. In some embodiments, an ILT2/ILT4-binding agent comprises a heavy chain variable region having at least 95% sequence identity to SEQ ID NO:141 and a light chain variable region having at least 95% sequence identity to SEQ ID NO:142. In some embodiments, an ILT2/ILT4-binding agent comprises a heavy chain variable region comprising an amino acid sequence of SEQ ID NO:141 and a light chain variable region comprising an amino acid sequence of SEQ ID NO:142.

In some embodiments, an ILT2/ILT4-binding agent (e.g., a dual binder) comprises a heavy chain variable region CDR1, CDR2, and CDR3 and/or a light chain variable region CDR1, CDR2, and CDR3 from antibody 73D1, a humanized version thereof (e.g., Hz73D1), or variants thereof. In some embodiments, an ILT2/ILT4-binding agent comprises a heavy chain variable region comprising a heavy chain variable region CDR1, a heavy chain variable region CDR2, and a heavy chain variable region CDR3 from antibody 73D1 or antibody Hz73D1.v1. In other embodiments, an ILT2/ILT4-binding agent comprises a light chain variable region comprising a light chain variable region CDR1, a light chain variable region CDR2, and a light chain variable region CDR3 from antibody 73D1 or antibody Hz73D1.v1. In some embodiments, an ILT2/ILT4-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 73D1 or antibody Hz73D1.v1. In some embodiments, an ILT2/ILT4-binding agent is a humanized version of antibody 73D1. In some embodiments, an ILT2/ILT4-binding agent is a variant of antibody 73D1. In some embodiments, an ILT2/ILT4-binding agent is a variant of antibody Hz73D1.v1.

In some embodiments, an ILT2/ILT4-binding agent comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (b) a heavy chain variable region comprising a heavy chain variable region CDR1 comprising the amino acid sequence GYTFTDY (SEQ ID NO:76), a heavy chain variable region CDR2 comprising the amino acid sequence NPNDGG (SEQ ID NO:113), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (c) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTT (SEQ ID NO:114), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); (d) a heavy chain variable region comprising a heavy chain variable region CDR1 comprising the amino acid sequence DYYIN (SEQ ID NO:115), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91); or (e) a heavy chain variable region comprising a heavy chain variable region CDR1 comprising the amino acid sequence TDYYIN (SEQ ID NO:116), a heavy chain variable region CDR2 comprising the amino acid sequence WIGNVNPNDGGTT (SEQ ID NO:117) or the amino acid sequence WMGNVNPNDGGTT (SEQ ID NO:124), and a heavy chain variable region CDR3 comprising the amino acid sequence ARREIYFYGTIYYYAMD (SEQ ID NO:110), and a light chain variable region comprising a light chain variable region CDR1 comprising the amino acid sequence DYYGNSFMYWY (SEQ ID NO:99), a light chain variable region CDR2 comprising the amino acid sequence LLIYFASNLE (SEQ ID NO:100), and a light chain variable region CDR3 comprising the amino acid sequence QQNNEDPW (SEQ ID NO:101).

In some embodiments, an ILT2/ILT4-binding agent comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and/or (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107). In some embodiments, the ILT2/ILT4-binding agent comprises a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, the ILT2/ILT4-binding agent comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91).

In some embodiments, an ILT2/ILT4-binding agent comprises: (a) a heavy chain variable region comprising a heavy chain variable region CDR1 comprising the amino acid sequence GYTFTDYYIN (SEQ ID NO:111), or a variant thereof comprising 1, 2, 3, or 4 amino acid substitutions; a heavy chain variable region CDR2 comprising the amino acid sequence NVNPNDGGTTYNQKFKG (SEQ ID NO:112), or a variant thereof comprising 1, 2, 3, or 4 amino acid substitutions; and a heavy chain variable region CDR3 comprising the amino acid sequence REIYFYGTIYYYAMDY (SEQ ID NO:107), or a variant thereof comprising 1, 2, 3, or 4 amino acid substitutions; and (b) a light chain variable region comprising a light chain variable region CDR1 comprising the amino acid sequence RASESVDYYGNSFMY (SEQ ID NO:89), or a variant thereof comprising 1, 2, 3, or 4 amino acid substitutions; a light chain variable region CDR2 comprising the amino acid sequence FASNLES (SEQ ID NO:90), or a variant thereof comprising 1, 2, 3, or 4 amino acid substitutions; and a light chain variable region CDR3 comprising the amino acid sequence QQNNEDPWT (SEQ ID NO:91), or a variant thereof comprising 1, 2, 3, or 4 amino acid substitutions.

In some embodiments, an ILT2/ILT4-binding agent comprises a heavy chain variable region comprising the amino acid sequence of heavy chain variable region CDR1, CDR2, and CDR3 of antibody 73D1 and which has at least 75%, at least 80%, at least 85%, at least 90%, at least 95%, at least 96%, at least 97%, at least 98%, at least 99%, or 100% identity to the sequence of SEQ ID NO:143 and a light chain variable region comprising the amino acid sequence of light chain variable region CDR1, CDR2, and CDR3 of antibody 73D1 and which has at least 75%, at least 80%, at least 85%, at least 90%, at least 95%, at least 96%, at least 97%, at least 98%, at least 99%, or 100% identity to the sequence of SEQ ID NO:142.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:143. In some embodiments, an ILT2/ILT4-binding agent comprises a light chain variable region having at least 80%, at least 85%, at least 90%, at least 95%, at least 97%, or at least 99% identity to the sequence of SEQ ID NO:142. In some embodiments, an ILT2/ILT4-binding agent comprises a heavy chain variable region comprising an amino acid sequence of SEQ ID NO:143. In some embodiments, an ILT2/ILT4-binding agent comprises a light chain variable region comprising an amino acid sequence of SEQ ID NO:142.

In some embodiments, an ILT2/ILT4-binding agent comprises a heavy chain variable region having at least 80% sequence identity to SEQ ID NO:143 and a light chain variable region having at least 80% sequence identity to SEQ ID NO:142. In some embodiments, an ILT2/ILT4-binding agent comprises a heavy chain variable region having at least 90% sequence identity to SEQ ID NO:143 and a light chain variable region having at least 90% sequence identity to SEQ ID NO:142. In some embodiments, an ILT2/ILT4-binding agent comprises a heavy chain variable region having at least 95% sequence identity to SEQ ID NO:143 and a light chain variable region having at least 95% sequence identity to SEQ ID NO:142. In some embodiments, an ILT2/ILT4-binding agent comprises a heavy chain variable region comprising an amino acid sequence of SEQ ID NO:143 and a light chain variable region comprising an amino acid sequence of SEQ ID NO:142.

In some embodiments, an ILT2/ILT4-binding agent comprises a heavy chain variable region comprising the amino acid sequence of heavy chain variable region CDR1, CDR2, and CDR3 of antibody Hz73D1.v1 and which has at least 75%, at least 80%, at least 85%, at least 90%, at least 95%, at least 96%, at least 97%, at least 98%, at least 99%, or 100% identity to the sequence of SEQ ID NO:144 and a light chain variable region comprising the amino acid sequence of light chain variable region CDR1, CDR2, and CDR3 of antibody Hz73D1.v1 and which has at least 75%, at least 80%, at least 85%, at least 90%, at least 95%, at least 96%, at least 97%, at least 98%, at least 99%, or 100% identity to the sequence of SEQ ID NO:145.

In some embodiments, an ILT2/ILT4-binding agent comprises a heavy chain variable region having at least 80%, at least 85%, at least 90%, at least 95%, at least 97%, or at least 99% identity to the sequence of SEQ ID NO:144. In some embodiments, an ILT2/ILT4-binding agent comprises a light chain variable region having at least 80%, at least 85%, at least 90%, at least 95%, at least 97%, or at least 99% identity to the sequence of SEQ ID NO:145. In some embodiments, an ILT2/ILT4-binding agent comprises a heavy chain variable region comprising an amino acid sequence of SEQ ID NO:144. In some embodiments, an ILT2/ILT4-binding agent comprises a light chain variable region comprising an amino acid sequence of SEQ ID NO:145.

In some embodiments, an ILT2/ILT4-binding agent comprises a heavy chain variable region having at least 80% sequence identity to SEQ ID NO:144 and a light chain variable region having at least 80% sequence identity to SEQ ID NO:145. In some embodiments, an ILT2/ILT4-binding agent comprises a heavy chain variable region having at least 90% sequence identity to SEQ ID NO:144 and a light chain variable region having at least 90% sequence identity to SEQ ID NO:145. In some embodiments, an ILT2/ILT4-binding agent comprises a heavy chain variable region having at least 95% sequence identity to SEQ ID NO:144 and a light chain variable region having at least 95% sequence identity to SEQ ID NO:145. In some embodiments, an ILT2/ILT4-binding agent comprises a heavy chain variable region comprising an amino acid sequence of SEQ ID NO:144 and a light chain variable region comprising an amino acid sequence of SEQ ID NO:145.

In some embodiments, an ILT2/ILT4-binding agent comprises a heavy chain variable region comprising a heavy chain variable region CDR1 comprising GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain variable region comprises at least 80%, at least 85%, at least 90%, at least 95%, at least 97%, at least 98% identity to the sequence of SEQ ID NO:143, and wherein the light chain variable region comprises at least 80%, at least 85%, at least 90%, at least 95%, at least 97%, at least 98% identity to the sequence of SEQ ID NO:142. In some embodiments, an ILT2/ILT4-binding agent comprises a heavy chain variable region comprising a heavy chain variable region CDR1 comprising GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain variable region comprises at least 80%, at least 85%, at least 90%, at least 95%, at least 97%, at least 98% identity to the sequence of SEQ ID NO:144, and wherein the light chain variable region comprises at least 80%, at least 85%, at least 90%, at least 95%, at least 97%, at least 98% identity to the sequence of SEQ ID NO:145.

In some embodiments, an ILT2/ILT4-binding agent comprises a heavy chain comprising a heavy chain variable region CDR1 comprising GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain comprises at least 80%, at least 85%, at least 90%, at least 95%, at least 97%, at least 98%, at least 99%, or 100% identity to the sequence of SEQ ID NO:156, and wherein the light chain comprises at least 80%, at least 85%, at least 90%, at least 95%, at least 97%, at least 98%, at least 99%, or 100% identity to the sequence of SEQ ID NO:157. In some embodiments, an ILT2/ILT4-binding agent comprises a heavy chain comprising a heavy chain variable region CDR1 comprising GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and a light chain comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the heavy chain comprises at least 95% identity to the sequence of SEQ ID NO:156, and wherein the light chain comprises at least 95% identity to the sequence of SEQ ID NO:157. In some embodiments, an ILT2/ILT4-binding agent comprises (a) a heavy chain comprising the amino acids of SEQ ID NO:156 and (b) a light chain comprising a light chain variable region CDR1 comprising RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91), wherein the light chain comprises at least 80%, at least 85%, at least 90%, at least 95%, at least 97%, at least 98%, at least 99%, or 100% identity to the sequence of SEQ ID NO:157. In some embodiments, an ILT2/ILT4-binding agent comprises (a) a heavy chain comprising the amino acids of SEQ ID NO:156 and (b) a light chain comprising a light chain variable region CDR1 comprising RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises: (a) a heavy chain comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), wherein the heavy chain comprises at least 80%, at least 85%, at least 90%, at least 95%, at least 97%, at least 98%, at least 99%, or 100% identity to the sequence of SEQ ID NO:156, and (b) a light chain comprising the amino acid sequence of SEQ ID NO:157. In some embodiments, an ILT2/ILT4-binding agent comprises: (a) a heavy chain comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and (b) a light chain comprising the amino acid sequence of SEQ ID NO:157. In some embodiments, an ILT2/ILT4-binding agent is an antibody comprising a heavy chain comprising the amino acid sequence of SEQ ID NO:156 and a light chain comprising the amino acid sequence of SEQ ID NO:157.

In some embodiments, an ILT2/ILT4-binding agent comprises a heavy chain having at least 80%, at least 85%, at least 90%, or at least 95% identity to the amino acid sequence of SEQ ID NO:156. In some embodiments, an ILT2/ILT4-binding agent comprises a light chain having at least 80%, at least 85%, at least 90%, or at least 95% identity to the amino acid sequence of SEQ ID NO:157. In some embodiments, an ILT2/ILT4-binding agent comprises a heavy chain having at least 80%, at least 85%, at least 90%, or at least 95% identity to the amino acid sequence of SEQ ID NO:156 and a light chain having at least 80%, at least 85%, at least 90%, or at least 95% identity to the amino acid sequence of SEQ ID NO:157. In some embodiments, an ILT2/ILT4-binding agent comprises a heavy chain having at least 90% identity to the amino acid sequence of SEQ ID NO:156. In some embodiments, an ILT2/ILT4-binding agent comprises a light chain having at least 90% identity to the amino acid sequence of SEQ ID NO:157. In some embodiments, an ILT2/ILT4-binding agent comprises a heavy chain having at least 90% identity to the amino acid sequence of SEQ ID NO:156 and a light chain having at least 90% identity to the amino acid sequence of SEQ ID NO:157. In some embodiments, an ILT2/ILT4-binding agent comprises a heavy chain comprising the amino acid sequence of SEQ ID NO:156. In some embodiments, an ILT2/ILT4-binding agent comprises a light chain comprising the amino acid sequence of SEQ ID NO:157. In some embodiments, an ILT2/ILT4-binding agent comprises a heavy chain comprising the amino acid sequence of SEQ ID NO:156 and a light chain comprising the amino acid sequence of SEQ ID NO:157. In some embodiments, an ILT2/ILT4-binding agent is an antibody that comprises a heavy chain of SEQ ID NO:156 and/or a light chain of SEQ ID NO:157. In some embodiments, an ILT2/ILT4-binding agent is an antibody that comprises a heavy chain of SEQ ID NO:156. In some embodiments, an ILT2/ILT4-binding agent is an antibody that comprises a light chain of SEQ ID NO:157. In some embodiments, an ILT2/ILT4-binding agent is an antibody that comprises a heavy chain of SEQ ID NO:156 and a light chain of SEQ ID NO:157.

In some embodiments, the ILT2/ILT4-binding agent is antibody 73D1. In some embodiments, the ILT2/ILT4-binding agent is antibody Hz73D1.v1.

Provided herein are agents that compete with one or more of the binding agents described herein for binding to ILT2, ILT4, or both ILT2 and ILT4. In some embodiments, an agent competes with one or more of the antibodies described herein for binding to ILT2, ILT4, or both ILT2 and ILT4. In some embodiments, an agent that competes with one or more of the antibodies described herein is an antibody. In some embodiments, an agent binds the same epitope as one of the antibodies described herein. In some embodiments, an agent binds an epitope overlapping with an epitope bound by one of the antibodies described herein. Antibodies and antigen-binding fragments that compete with or bind the same epitope as the antibodies described herein are expected to show similar functional properties.

In some embodiments, an agent competes for binding to human ILT2, ILT4, or both ILT2 and ILT4 with a reference antibody, wherein the reference antibody comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an agent competes for binding to human ILT2 with a reference antibody, wherein the reference antibody comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91).

In some embodiments, an agent competes for binding to human ILT2, ILT4, or both ILT2 and ILT4 with a reference antibody, wherein the reference antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, an agent competes for binding to human ILT4 with a reference antibody, wherein the reference antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75).

In some embodiments, an ILT-binding agent (e.g., an ILT2-binding agent, an ILT4, binding agent, or an ILT2/ILT4 binding agent) described herein comprises an antibody in which at least one or more of the constant regions of the antibody has been modified or deleted. In some embodiments, an antibody comprises one or more modifications to one or more of the three heavy chain constant regions (CH1, CH2 or CH3) and/or to the light chain constant region (CL). In some embodiments, an antibody comprises one or more modifications to the hinge region. In some embodiments, the heavy chain constant region of the modified antibody comprises at least one human constant region. In some embodiments, the heavy chain constant region of the modified antibody comprises more than one human constant region. In some embodiments, modifications to the constant region comprise additions, deletions, or substitutions of one or more amino acids in one or more regions. In some embodiments, one or more regions are partially or entirely deleted from the constant regions of a modified antibody. In some embodiments, the entire CH2 domain has been removed from an antibody (ΔCH2 constructs). In some embodiments, one or more regions are partially or entirely deleted from the hinge region of a modified antibody. In some embodiments, a deleted constant region is replaced by a short amino acid spacer that provides some of the molecular flexibility typically imparted by the absent constant region. In some embodiments, a deleted hinge region is replaced by a short amino acid spacer that provides some of the molecular flexibility typically imparted by the absent hinge region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a Fc receptor (FcR) on the surface of a cell. There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an ILT-binding agent comprises a variant Fc region. The amino acid sequences of the Fc region of human IgG1, IgG2, IgG3, and IgG4 are known to those of ordinary skill in the art (e.g., a representative human IgG1 region is SEQ ID NO:158). In some cases, Fc regions with amino acid variations have been identified in native antibodies. In some embodiments, a variant Fc region is engineered with substitutions at specific amino acid positions as compared to a native Fc region. Variant Fc regions are well-known in the art and include, but are not limited to, SEQ ID NO:159, SEQ ID NO:160, SEQ ID NO:161, SEQ ID NO:162, and SEQ ID NO:163.

In some embodiments, a modified antibody provides for altered effector functions that, in turn, affect the biological profile of the antibody. For example, in some embodiments, the deletion or inactivation (through point mutations or other means) of a constant region reduces Fc receptor binding of a modified antibody as it circulates. In some embodiments, constant region modifications increase the serum half-life of an antibody. In some embodiments, constant region modifications reduce the serum half-life of an antibody. In some embodiments, constant region modifications decrease or remove ADCC and/or complement-dependent cytotoxicity (CDC) of an antibody. In some embodiments, specific amino acid substitutions in a human IgG1 Fc region with corresponding IgG2 or IgG4 residues reduce effector functions (e.g., ADCC and CDC) in a modified antibody. In some embodiments, a modified antibody does not have one or more effector functions. In some embodiments, a modified antibody does not have any detectable effector functions (e.g., "effectorless" antibodies). In some embodiments, a modified antibody has no ADCC activity and/or no CDC activity. In some embodiments, a modified antibody does not bind an Fc receptor and/or complement factors. In some embodiments, a modified antibody has no effector function(s). In some embodiments, constant region modifications increase or enhance ADCC and/or CDC of an antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

Modifications to the constant region of antibodies described herein may be made using well-known biochemical or molecular engineering techniques. In some embodiments, antibody variants are prepared by introducing appropriate nucleotide changes into the encoding DNA, and/or by synthesis of the desired antibody or polypeptide. Using these engineering techniques to modify an antibody it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations may be generated by the substitution, deletion, or insertion of one or more nucleotides into a polynucleotide encoding the antibody or polypeptide that results in a change in an amino acid or the amino acid sequence as compared with the native antibody or polypeptide sequence. In some embodiments, amino acid substitutions are the result of replacing one amino acid with another amino acid having similar structural and/or chemical properties, such as the replacement of a leucine with a serine (i.e., conservative amino acid replacements). In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein to create a fusion protein. In some embodiments, a variant is engineered to be detectable and may comprise a detectable label and/or protein (e.g., a fluorescent tag, a fluorescent protein, or an enzyme).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell epitopes (known or predicted) without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, an ILT-binding agent (e.g., an ILT2-binding agent, an ILT4-binding agent, or an ILT2/ILT4-binding agent) described herein is chemically modified. In some embodiments, an ILT-binding agent is (i) an anti-ILT2 antibody, (ii) an anti-ILT4 antibody, or (iii) an anti-ILT2/ILT4 antibody that is chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques. In some embodiments, an ILT-binding agent is an antibody fragment (e.g., scFv, Fv, Fab, F(ab')$_2$, or F(ab')), wherein the antibody fragment is attached (either directly or indirectly) to a half-life extending moiety including, but not limited to, polyethylene glycol (PEG), a PEG mimetic, XTEN®, serum albumin, polysialic acid, N-(2-hydroxypropyl)methacrylamide, or dextran.

The present disclosure encompasses ILT-binding agents built upon non-immunoglobulin backbones, wherein the agents bind the same epitope or essentially the same epitope as an anti-ILT antibody disclosed herein. In some embodiments, a non-immunoglobulin-based binding agent is an agent that competes with (i) an anti-ILT2 antibody, (ii) an anti-ILT4 antibody, and/or (iii) an anti-ILT2/ILT4 antibody described herein in a competitive binding assay. In some embodiments, alternative ILT-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the 10$^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid anti-parallel β-strand protein fold; and Kunitz domain inhibitor scaffolds, which are based upon a structure that contains three disulfide bonds and three loops.

In some embodiments, an ILT2-binding agent comprises an engineered scaffold protein comprising a heavy chain variable region CDR1, CDR2, and CDR3 and a light chain variable region CDR1, CDR2, and CDR3 shown in Table 1. In some embodiments, an ILT2-binding agent comprises an engineered scaffold protein comprising a heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), a heavy chain variable region CDR3 comprising the amino acid sequence PNWDTYAIVIDF (SEQ ID NO:24), a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27). In some embodiments, an ILT2-binding agent comprises an engineered scaffold protein comprising a heavy chain variable region CDR1, CDR2, and CDR3 and a light chain variable region CDR1, CDR2, and CDR3 from antibody 27F9.

In some embodiments, an ILT4-binding agent comprises an engineered scaffold protein comprising a heavy chain variable region CDR1, CDR2, and CDR3 and a light chain variable region CDR1, CDR2, and CDR3 shown in Table 2. In some embodiments, an ILT4-binding agent comprises an engineered scaffold protein comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), a heavy chain variable region CDR3 comprising the amino acid sequence GATVVESLFAY (SEQ ID NO:40), a light chain variable region CDR1 comprising the amino acid sequence RASESVDNYGNNFLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43). In some embodiments, an ILT4-binding agent comprises an engineered scaffold protein comprising a heavy chain variable region CDR1, CDR2, and CDR3 and a light chain variable region CDR1, CDR2, and CDR3 from antibody 47C8.

In some embodiments, an ILT4-binding agent comprises an engineered scaffold protein comprising a heavy chain variable region CDR1, CDR2, and CDR3 and a light chain variable region CDR1, CDR2, and CDR3 shown in Table 3. In some embodiments, an ILT4-binding agent comprises an engineered scaffold protein comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), a heavy chain variable region CDR3 comprising the amino acid sequence RSDYDGYAMDY (SEQ ID NO:56), a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59). In some embodiments, an ILT4-binding agent comprises an engineered scaffold protein comprising a heavy chain variable region CDR1, CDR2, and CDR3 and a light chain variable region CDR1, CDR2, and CDR3 from antibody 48A5.

In some embodiments, an ILT2/ILT4-binding agent comprises an engineered scaffold protein comprising a heavy chain variable region CDR1, CDR2, and CDR3 and a light chain variable region CDR1, CDR2, and CDR3 shown in Table 4A or Table 4B. In some embodiments, an ILT2/ILT4-binding agent comprises an engineered scaffold protein comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), a heavy chain variable region CDR3 comprising the amino acid sequence GRFYYGSLYSFDY (SEQ ID NO:72), a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments, an ILT2/ILT4-binding agent comprises an engineered scaffold protein comprising a heavy chain variable region CDR1, CDR2, and CDR3 and a light chain variable region CDR1, CDR2, and CDR3 from antibody 47H6 or antibody Hz47H6.v2.

In some embodiments, an ILT2/ILT4-binding agent comprises an engineered scaffold protein comprising a heavy chain variable region CDR1, CDR2, and CDR3 and a light chain variable region CDR1, CDR2, and CDR3 shown in Table 5. In some embodiments, an ILT2/ILT4-binding agent comprises an engineered scaffold protein comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), a heavy chain variable region CDR3 comprising the amino acid sequence DGIYYYGTMYYYAMDY (SEQ ID NO:88), a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises an engineered scaffold protein comprising a heavy chain variable region CDR1, CDR2, and CDR3 and a light chain variable region CDR1, CDR2, and CDR3 from antibody 51A1.

In some embodiments, an ILT2/ILT4-binding agent comprises an engineered scaffold protein comprising a heavy chain variable region CDR1, CDR2, and CDR3 and a light chain variable region CDR1, CDR2, and CDR3 shown in Table 6A or Table 6B. In some embodiments, an ILT2/ILT4-binding agent comprises an engineered scaffold protein comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), a heavy chain variable region CDR3 comprising the amino acid sequence DGIYYYDTMYYYAMDY (SEQ ID NO:102), a light chain variable region CDR1 comprising the amino acid sequence RASESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises an engineered scaffold protein comprising a heavy chain variable region CDR1, CDR2, and CDR3 and a light chain variable region CDR1, CDR2, and CDR3 from antibody 64A12.

In some embodiments, an ILT2/ILT4-binding agent comprises an engineered scaffold protein comprising a heavy chain variable region CDR1, CDR2, and CDR3 and a light chain variable region CDR1, CDR2, and CDR3 shown in Table 7. In some embodiments, an ILT2/ILT4-binding agent comprises an engineered scaffold protein comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), a heavy chain variable region CDR3 comprising the amino acid sequence REIYFYGTIYYYAMDY (SEQ ID NO:107), a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises an engineered scaffold protein comprising a heavy chain variable region CDR1, CDR2, and CDR3 and a light chain variable region CDR1, CDR2, and CDR3 from antibody 73C4.

In some embodiments, an ILT2/ILT4-binding agent comprises an engineered scaffold protein comprising a heavy chain variable region CDR1, CDR2, and CDR3 and a light chain variable region CDR1, CDR2, and CDR3 shown in Table 8A or Table 8B. In some embodiments, an ILT2/ILT4-binding agent comprises an engineered scaffold protein comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), a heavy chain variable region CDR3 comprising the amino acid sequence REIYFYGTIYYYAMDY (SEQ ID NO:107), a light chain variable region CDR1 comprising the amino acid sequence RASESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments, an ILT2/ILT4-binding agent comprises an engineered scaffold protein comprising a heavy chain variable region CDR1, CDR2, and CDR3 and a light chain variable region CDR1, CDR2, and CDR3 from antibody 73D1 or antibody Hz73D1.v1.

In some embodiments, a composition comprises an ILT-binding agent described herein. In some embodiments, a composition comprises an ILT2-binding agent described herein. In some embodiments, a composition comprises an ILT4-binding agent described herein. In some embodiments, a composition comprises an ILT2/ILT4-binding agent described herein. In some embodiments, a composition comprises an anti-ILT2 antibody described herein. In some embodiments, a composition comprises a monoclonal anti-ILT2 antibody described herein. In some embodiments, a composition comprises an anti-ILT4 antibody described herein. In some embodiments, a composition comprises a monoclonal anti-ILT4 antibody described herein. In some embodiments, a composition comprises an anti-ILT2/ILT4 antibody described herein. In some embodiments, a composition comprises a monoclonal anti-ILT2/ILT4 antibody described herein. In some embodiments, a composition comprises an antibody selected from the group consisting of: antibody 27F9, antibody 47C8, antibody 48A5, antibody 47H6, antibody 51A1, antibody 64A12, antibody 73C4, or antibody 73D1, or humanized versions thereof.

In some embodiments, a pharmaceutical composition comprises an ILT-binding agent described herein and a pharmaceutically acceptable carrier. In some embodiments, a pharmaceutical composition comprises an ILT2-binding agent described herein and a pharmaceutically acceptable carrier. In some embodiments, a pharmaceutical composition comprises an ILT4-binding agent described herein and a pharmaceutically acceptable carrier. In some embodiments, a pharmaceutical composition comprises an ILT2/ILT4-binding agent described herein and a pharmaceutically acceptable carrier. In some embodiments, a pharmaceutical composition comprises an anti-ILT2 antibody described herein and a pharmaceutically acceptable carrier. In some embodiments, a composition comprises a monoclonal anti-ILT2 antibody described herein and a pharmaceutically acceptable carrier. In some embodiments, a pharmaceutical composition comprises an anti-ILT4 antibody described herein and a pharmaceutically acceptable carrier. In some embodiments, a composition comprises a monoclonal anti-ILT4 antibody described herein and a pharmaceutically acceptable carrier. In some embodiments, a pharmaceutical composition comprises an anti-ILT2/ILT4 antibody described herein and a pharmaceutically acceptable carrier. In some embodiments, a composition comprises a monoclonal anti-ILT2/ILT4 antibody described herein and a pharmaceutically acceptable carrier. In some embodiments, a pharmaceutical composition comprises an antibody selected from the group consisting of: antibody 27F9, antibody 47C8, antibody 48A5, antibody 47H6, antibody 51A1, antibody 64A12, antibody 73C4, or antibody 73D1, or humanized versions thereof and a pharmaceutically acceptable carrier. In some embodiments, a pharmaceutical composition comprises antibody Hz73D1.v1 and a pharmaceutically acceptable carrier.

In some embodiments, an ILT-binding agent is isolated. In some embodiments, an ILT-binding agent is substantially pure.

Generally speaking, antigen-antibody interactions are non-covalent and reversible, formed by a combination of hydrogen bonds, hydrophobic interactions, and electrostatic and van der Waals forces. When describing the strength of an antigen-antibody complex, the terms affinity and/or avidity are commonly used. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology (e.g., using a Biacore system). Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, an ILT-binding agent binds ILT2, ILT4, or both ILT2 and ILT4 with a dissociation constant ($K_D$) of 1 µM or less, 100 nM or less, 40 nM or less, 20 nM or less, 10 nM or less, 1 nM or less, 0.1 nM or less, 50 pM or less, 10 pM or less, or 1 pM or less. In some embodiments, an ILT-binding agent binds ILT2, ILT4, or both ILT2 and ILT4 with a $K_D$ of about 20 nM or less. In some embodiments, an ILT-binding agent binds ILT2, ILT4, or both ILT2 and ILT4 with a $K_D$ of 10 nM or less. In some embodiments, an ILT-binding agent binds ILT2, ILT4, or both ILT2 and ILT4 with a $K_D$ of 5 nM or less. In some embodiments, an ILT-binding agent binds ILT2, ILT4, or both ILT2 and ILT4 with a $K_D$ of 3 nM or less. In some embodiments, an ILT-binding agent binds ILT2, ILT4, or both ILT2 and ILT4 with a $K_D$ of 2 nM or less. In some embodiments, an ILT-binding agent binds ILT2, ILT4, or both ILT2 and ILT4 with a $K_D$ of 1 nM or less. In some embodiments, an ILT-binding agent binds ILT2, ILT4, or both ILT2 and ILT4 with a $K_D$ of 0.5 nM or less. In some embodiments, an ILT-binding agent binds ILT2, ILT4, or both ILT2 and ILT4 with a $K_D$ of 0.1 nM or less. In some embodiments, an ILT-binding agent binds ILT2, ILT4, or both ILT2 and ILT4 with a $K_D$ of 50 pM or less. In some embodiments, an ILT-binding agent binds ILT2, ILT4, or both ILT2 and ILT4 with a $K_D$ of 25 pM or less. In some embodiments, an ILT-binding agent binds ILT2, ILT4, or both ILT2 and ILT4 with a $K_D$ of 10 pM or less. In some embodiments, an ILT-binding agent binds ILT2, ILT4, or both ILT2 and ILT4 with a $K_D$ of 1 pM or less. In some embodiments, an ILT-binding agent binds ILT2, ILT4, or both ILT2 and ILT4 with a $K_D$ of 0.01 nM to 2.5 nM. In some embodiments, an ILT-binding agent binds ILT2, ILT4, or both ILT2 and ILT4 with a $K_D$ of 0.1 nM to 5 nM. In some embodiments, an ILT-binding agent binds ILT2, ILT4, or both ILT2 and ILT4 with a $K_D$ of 1 nM to 5 nM. In some embodiments, the dissociation constant of the binding agent for ILT2 and/or ILT4 is the dissociation constant determined using an ILT protein (e.g., ILT2 or ILT4) immobilized on a Biacore chip and the binding agent flowed over the chip. In some embodiments, the dissociation constant of the binding agent for ILT2 and/or ILT4 is the dissociation constant determined using the binding agent captured by an anti-human IgG antibody on a Biacore chip and soluble ILT2 or ILT4 flowed over the chip.

In some embodiments, an ILT-binding agent binds ILT2, ILT4, or both ILT2 and ILT4 with a half maximal effective concentration (EC50) of 1 µM or less, 100 nM or less, 40 nM or less, 20 nM or less, 10 nM or less, 1 nM or less, or 0.1 nM or less. In some embodiments, an ILT-binding agent binds human ILT2, ILT4, or both ILT2 and ILT4 with an EC50 of 1 µM or less, 100 nM or less, 40 nM or less, 20 nM or less, 10 nM or less, 1 nM or less, or 0.1 nM or less. In some embodiments, an ILT-binding agent binds cyno or rhesus ILT2 with an EC50 of 40 nM or less, 20 nM or less, 10 nM or less, 1 nM or less or 0.1 nM or less. In some embodiments, an ILT-binding agent binds ILT2 and/or ILT4 with an EC50 of 0.1 nM to about 3 nM, 0.1 nM to 2 nM, 0.1 nM to 1 nM, 0.5 nM to 3 nM, 0.5 nM to 2 nM, or 0.5 nM to 1 nM.

In some embodiments, an ILT-binding agent binds human ILT2 and human ILT4 and has at least one or more of the following properties: (i) binds rhesus ILT2/4; (ii) binds cyno ILT2/4; (iii) does not bind ILT3, ILT5, and LILRB5; (iv) does not bind LILRA2, LILRA4, LILRA5, and LILRA6; (v) is an ILT2 antagonist; (vi) is an ILT4 antagonist, (vii) inhibits ILT2 activity; (viii) inhibits ILT4 activity; (ix) inhibits ILT2 signaling in cells that express ILT2; (x) inhibits ILT4 signaling in cells that express ILT4; (xi) inhibits binding of ILT2 to MHC I molecules; (xii) inhibits binding of ILT4 to MHC molecules; (xiii) inhibits ILT2-induced suppression of myeloid cells; (xiv) inhibits ILT4-induced suppression of myeloid cells; (xv) inhibits ILT2-induced suppression of myeloid cell activity; (xvi) inhibits ILT4-induced suppression of myeloid cell activity; (xvii) restores FcR activation in myeloid cells; (xviii) enhances NK cell activity; (xix) enhances CTL activity; and/or (xx) enhances macrophage phagocytosis.

The ILT-binding agents (e.g., ILT2-binding agents, ILT4-binding agents, or ILT2/ILT4-binding agents) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host.

In some embodiments, recombinant expression vectors are used to amplify and express DNA encoding the ILT-binding agents described herein. For example, recombinant expression vectors can be replicable DNA constructs which have synthetic or cDNA-derived DNA fragments encoding a polypeptide chain of an ILT-binding agent, such as an anti-ILT2/ILT4 antibody, or antigen-binding fragment thereof, operatively linked to suitable transcriptional and/or translational regulatory elements derived from mammalian, microbial, viral, or insect genes. A transcriptional unit generally comprises an assembly of (1) a genetic element or elements having a regulatory role in gene expression, for example, transcriptional promoters and/or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

In some embodiments, an ILT-binding agent (e.g., an ILT2-binding agent, an ILT4-binding agent, or an ILT2/ILT4-binding agent) of the present disclosure is expressed from one or more vectors. In some embodiments, a heavy chain variable region is expressed by one vector and a light chain variable region is expressed by a second vector. In some embodiments, a heavy chain variable region and a light chain variable region are expressed by one vector. In some embodiments, a vector encodes a heavy chain variable region of an ILT-binding agent described herein. In some embodiments, a vector encodes a light chain variable region of an ILT-binding agent described herein. In some embodiments, a vector encodes a heavy chain variable region and a light chain variable region of an ILT-binding agent described herein. In some embodiments, a heavy chain polypeptide is expressed by one vector and a light chain polypeptide is expressed by a second vector. In some embodiments, a heavy chain polypeptide and a light chain polypeptide are expressed by one vector. In some embodiments, a vector encodes a heavy chain polypeptide of an ILT-binding agent described herein. In some embodiments, a vector encodes a light chain polypeptide of an ILT-binding agent described herein. In some embodiments, a vector encodes a heavy chain polypeptide and a light chain polypeptide of an ILT-binding agent described herein.

Suitable host cells for expression of an ILT-binding agent (e.g., ILT2-binding agents, ILT4-binding agents, or ILT2/ILT4-binding agents) or a ILT2 or ILT4 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning vectors and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the ILT-binding agents described herein. In some embodiments, the cells produce the ILT-binding agents described herein. In some embodiments, the cells produce an antibody. In some embodiments, the cells produce an antibody that binds human ILT2. In some embodiments, the cells produce an antibody that binds human ILT4. In some embodiments, the cells produce an antibody that binds human ILT2 and ILT4. In some embodiments, the cells produce an antibody that binds human ILT2 and cyno ILT2. In some embodiments, the cells produce an anti-ILT2 antibody designated 27F9. In some embodiments, the cells produce an anti-ILT4 antibody designated 47C8. In some embodiments, the cells produce an anti-ILT4 antibody designated 48A5. In some embodiments, the cells produce an anti-ILT2/ILT4 antibody designated 47H6. In some embodiments, the cells produce a humanized anti-ILT2/ILT4 antibody designated Hz47H6.v2. In some embodiments, the cells produce an anti-ILT2/ILT4 antibody designated 51A1. In some embodiments, the cells produce an anti-ILT2/ILT4 antibody designated 64A12. In some embodiments, the cells produce a humanized anti-ILT2/ILT4 antibody designated Hz64A12. In some embodiments, the cells produce an anti-ILT2/ILT4 antibody designated 73C4. In some embodiments, the cells produce an anti-ILT2/ILT4 antibody designated 73D1. In some embodiments, the cells produce a humanized anti-ILT2/ILT4 antibody designated Hz73D1.v1. In some embodiments, the cell is a prokaryotic cell. In some embodiments, the cell is an eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexahistidine (His6; SEQ ID NO:173), maltose binding domain, influenza coat sequence, and glutathione-S-transferase can be attached to the protein to allow easy purification by passage over an appropriate affinity column. Affinity chromatography methods used for purifying immunoglobulins can include, but are not limited to, Protein A, Protein G, and Protein L chromatography. Isolated proteins can be physically characterized using techniques that include, but are not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT).

In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques.

Some or all of the foregoing purification steps, in various combinations, can be employed to provide a homogeneous recombinant protein.

ILT-binding agents (e.g., ILT2-binding agents, ILT4-binding agents, or ILT2/ILT4-binding agents) of the present disclosure may be analyzed for their physical/chemical properties and/or biological activities by various assays known in the art. In some embodiments, an anti-ILT2 antibody is tested for its ability to bind ILT2 (e.g., human ILT2 and/or cyno/rhesus ILT2). In some embodiments, an anti-ILT4 antibody is tested for its ability to bind ILT4 (e.g., human ILT4). In some embodiments, an anti-ILT2/ILT4 antibody is tested for its ability to bind ILT2 and ILT4 (e.g., human ILT2, human ILT4, and cyno/rhesus ILT2). Binding assays include, but are not limited to, SPR (e.g., Biacore), ELISA, and FACS. In some embodiments, an anti-ILT2 antibody is tested for its ability to inhibit, reduce, or block ILT2 binding to MHC class I antigens. In some embodiments, an anti-ILT4 antibody is tested for its ability to inhibit, reduce, or block ILT4 binding to MHC class I antigens. In some embodiments, an anti-ILT2/ILT4 antibody is tested for its ability to inhibit, reduce, or block ILT2 and ILT4 binding to MHC class I antigens. In addition, antibodies may be evaluated for solubility, stability, thermostability, viscosity, expression levels, expression quality, and/or purification efficiency.

In some embodiments, monoclonal antibodies generated against ILT2, ILT4, or ILT2 and ILT4 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of a second antibody and antigen is flowed over the immobilized first antibody. In tandem, the antigen is immobilized on a surface and the two antibodies are flowed over the immobilized antigen and compete to bind. Using these techniques, antibodies that block one another can be identified. A competitive blocking profile is created for each antibody relative to the other antibodies. The blocking results determine which bin each antibody is placed in. High-throughput methods of epitope binning are known in the art and allow for screening and characterization of large numbers of antibodies within a short period of time. Antibodies that bind similar epitopes often share similar functions and/or capabilities. Conversely, antibodies that bind different epitopes may have different functional activities.

In some embodiments, an epitope bin comprises at least one antibody from the group consisting of: 27F9, 47C8, 48A5, 47H6, 51A1, 64A12, 73C4, and 73D1. In some embodiments, an epitope bin comprises at least antibodies 27F9 and 73D1. In some embodiments, an epitope bin comprises at least antibodies 27F9, 73C4, and 73D1. In some embodiments, an epitope bin comprises at least antibodies 48A5 and 47H6.

Epitope mapping is the process of identifying the binding site, or epitope on a target protein/antigen where an antibody (or other binding agent) binds. A variety of methods are known in the art for mapping epitopes on target proteins. These methods include (i) mutagenesis, including but not limited to, shotgun mutagenesis, site-directed mutagenesis, and alanine scanning; (ii) domain or fragment scanning; (iii) peptide scanning (e.g., Pepscan technology); (iv) display methods, including but not limited to, phage display, microbial display, and ribosome/mRNA display; (v) methods involving proteolysis and mass spectroscopy; (vi) methods involving amide hydrogen/deuterium exchange; and (vii) structural determination, including but not limited to, x-ray crystallography and NMR.

In some embodiments, purified anti-ILT antibodies (e.g., anti-ILT2 antibodies, anti-ILT4 antibodies, or anti-ILT2/ILT4 antibodies) are characterized by assays including, but not limited to, N-terminal sequencing, amino acid analysis, HPLC, mass spectrometry, differential scanning fluorimetry (DSF), nanoDSF, capillary isoelectric focusing (cIEF), ion exchange chromatography, and papain digestion.

In vitro assays that characterize immune cell function include, but are not limited to, cell activation assays (e.g., cell proliferation assays), cytotoxic T-cell (CTL) assays, T-cell suppression assays, MDSC assays, natural killer (NK) cell assays, mixed lymphocyte reaction (MLR) assays, cytokine/chemokine production assays, FcR binding assays, phagocytosis assays, and cell migration assays. In some embodiments, assays are provided for identifying anti-ILT antibodies that affect ILT activity. "Affect or affecting ILT activity" may include, for example, inhibiting, reducing, blocking, antagonizing, suppressing, and/or interfering with ILT2 activity, ILT4 activity, or ILT2 and ILT4 activity. As ILT2 and ILT4 generally act as negative regulator/inhibitory molecules, in some embodiments, inhibiting, reducing, blocking, antagonizing, suppressing, and/or interfering with ILT2 and/or ILT4 activity results in a blockade of ILT2-induced and/or ILT4-induced suppression of a biological function. Those of skill in the art may refer to this ability as "releasing the brake", for example, anti-ILT antibodies described herein block the signaling of ILT2 and/or ILT4 that would otherwise send a suppressive message. Once the "brakes" are released, the immune system is able to mount a response or a stronger response to, for example, a tumor.

As described herein, ILT2 is expressed on myeloid cells, such as monocytes, macrophages, dendritic cells (DCs), and APCs, as well as NK cells, B-cells, and CD8+ T-cells (CTLs). ILT2 activity or ILT2 signaling activity includes, but is not limited to, suppression of myeloid cells, suppression of myeloid cell activity, suppression of tumor-associated myeloid cells, suppression of NK cells, and suppression of cytolytic T-cells (CTLs). In some embodiments, inhibiting, reducing, blocking, antagonizing, suppressing, and/or interfering with ILT2 activity results in a release of ILT2-induced suppression of an activation signal. In some embodiments, an anti-ILT2 antibody or an anti-ILT2/ILT4 antibody inhibits ILT2 signaling. In some embodiments, an anti-ILT2 antibody or an anti-ILT2/ILT4 antibody inhibits ILT2 signaling thereby reversing an ILT2-induced suppressive effect. In some embodiments, an anti-ILT2 antibody or an anti-ILT2/ILT4 antibody inhibits an ILT2-induced extinction signal. In some embodiments, an anti-ILT2 antibody or an anti-ILT2/ILT4 antibody increases myeloid cell activity. In some embodiments, an anti-ILT2 antibody or an anti-ILT2/ILT4 antibody increases APC activity. In some embodiments, an anti-ILT2 antibody or an anti-ILT2/ILT4 antibody increases macrophage activity. In some embodiments, an anti-ILT2 antibody or an anti-ILT2/ILT4 antibody increases macrophage phagocytosis. In some embodiments, an anti-ILT2 antibody or an anti-ILT2/ILT4 antibody increases NK cell activity. In some embodiments, an anti-ILT2 antibody or an anti-ILT2/ILT4 antibody increases CTL activity.

ILT4 is expressed on myeloid cells, such as monocytes, macrophages, dendritic cells (DCs), myeloid-derived suppressor cells (MDSCs), and APCs, as well as neutrophils and eosinophils. ILT4 activity or ILT4 signaling activity includes, but is not limited to, suppression of myeloid cells, suppression of myeloid cell activity, and suppression of tumor-associated myeloid cells. In some embodiments, inhibiting, reducing, blocking, antagonizing, suppressing, and/or interfering with ILT4 activity results in a release of ILT4-induced suppression of an activation signal. In some embodiments, an anti-ILT4 antibody or an anti-ILT2/ILT4 antibody inhibits ILT4 signaling. In some embodiments, an anti-ILT4 antibody or an anti-ILT2/ILT4 antibody inhibits ILT4 signaling thereby reversing an ILT4-induced suppressive effect. In some embodiments, an anti-ILT4 antibody or an anti-ILT2/ILT4 antibody inhibits an ILT4-induced extinction signal. In some embodiments, an anti-ILT4 antibody or an anti-ILT2/ILT4 antibody increases myeloid cell activity. In some embodiments, an anti-ILT4 antibody or an anti-ILT2/ILT4 antibody increases macrophage activity. In some embodiments, an anti-ILT4 antibody or an anti-ILT2/ILT4 antibody decreases MDSCs. In some embodiments, an anti-ILT4 antibody or an anti-ILT2/ILT4 antibody decreases suppression by MDSCs. In some embodiments, an anti-ILT4 antibody or an anti-ILT2/ILT4 antibody induces a switch of MDSCs to activated macrophages.

In some embodiments, an anti-ILT2 antibody or an anti-ILT2/ILT4 antibody disrupts the ILT2 signaling pathway. In some embodiments, an anti-ILT2 antibody or an anti-ILT2/ILT4 antibody disrupts the ILT2 signaling pathway and activates myeloid cells. In some embodiments, an anti-ILT2 antibody or an anti-ILT2/ILT4 antibody disrupts the ILT2 signaling pathway and activates APCs. In some embodiments, an anti-ILT2 antibody or an anti-ILT2/ILT4 antibody disrupts the ILT2 signaling pathway and activates dendritic cells. In some embodiments, an anti-ILT2 antibody or an anti-ILT2/ILT4 antibody disrupts the ILT2 signaling pathway and activates primary dendritic cells. In some embodiments, an anti-ILT2 antibody or an anti-ILT2/ILT4 antibody disrupts the ILT2 signaling pathway and increases NK cell activity. In some embodiments, an anti-ILT2 antibody or an anti-ILT2/ILT4 antibody disrupts the ILT2 signaling pathway and increases CTL activity.

In some embodiments, an anti-ILT4 antibody or an anti-ILT2/ILT4 antibody disrupts the ILT4 signaling pathway. In some embodiments, an anti-ILT4 antibody or an anti-ILT2/ILT4 antibody disrupts the ILT4 signaling pathway and activates myeloid cells. In some embodiments, an anti-ILT4 antibody or an anti-ILT2/ILT4 antibody disrupts the ILT4 signaling pathway and activates APCs. In some embodiments, an anti-ILT4 antibody or an anti-ILT2/ILT4 antibody disrupts the ILT4 signaling pathway and activates dendritic cells. In some embodiments, an anti-ILT4 antibody or an anti-ILT2/ILT4 antibody disrupts the ILT4 signaling pathway and activates primary dendritic cells.

In some embodiments, an anti-ILT2/ILT4 antibody disrupts the ILT2 signaling pathway and the ILT4 signaling pathway. In some embodiments, an anti-ILT2/ILT4 antibody disrupts the ILT2 signaling pathway and the ILT4 signaling pathway and activates myeloid cells. In some embodiments, an anti-ILT2/ILT4 antibody disrupts the ILT2 signaling pathway and the ILT4 signaling pathway and activates APCs. In some embodiments, an anti-ILT2/ILT4 antibody disrupts the ILT2 signaling pathway and the ILT4 signaling pathway and activates dendritic cells. In some embodiments, an anti-ILT2/ILT4 antibody disrupts the ILT2 signaling pathway and the ILT4 signaling pathway and activates primary dendritic cells. In some embodiments, an anti-ILT2/ILT4 antibody disrupts the ILT2 signaling pathway and the ILT4 signaling pathway and increases myeloid cell activity. In some embodiments, an anti-ILT2/ILT4 antibody disrupts the ILT2 signaling pathway and the ILT4 signaling pathway and increases NK cell activity. In some embodiments, an anti-ILT2/ILT4 antibody disrupts the ILT2 signaling pathway and the ILT4 signaling pathway and increases CTL activity. In some embodiments, an anti-ILT2/ILT4 antibody disrupts the ILT2 signaling pathway and the ILT4 signaling pathway and decreases MDSC activity.

In some embodiments, the terms "inhibiting", "reducing", "blocking", "antagonizing", "suppressing", and "interfering" are relative to levels and/or activity in the absence of treatment with the ILT-binding agent. In some embodiments, the terms "inhibiting", "reducing", "blocking", "antagonizing", "suppressing", and "interfering" are relative to levels and/or activity prior to treatment with the ILT-binding agent.

In some embodiments, the terms "activating", "promoting", "increasing", and "enhancing" are relative to levels and/or activity in the absence of treatment with the ILT-binding agent. In some embodiments, the terms "activating", "promoting", "increasing", and "enhancing" are relative to levels and/or activity prior to treatment with the ILT-binding agent.

In some embodiments, an anti-ILT2 antibody that inhibits ILT2 activity is antibody 27F9. In some embodiments, an anti-ILT4 antibody that inhibits ILT4 activity is antibody 47C8. In some embodiments, an anti-ILT4 antibody that inhibits ILT4 activity is antibody 48A5. In some embodiments, an anti-ILT2/ILT4 antibody that inhibits ILT2 and ILT4 activity is antibody 47H6. In some embodiments, an anti-ILT2/ILT4 antibody that inhibits ILT2 and ILT4 activity is antibody Hz47H6.v2. In some embodiments, an anti-ILT2/ILT4 antibody that inhibits ILT2 and ILT4 activity is antibody 51A1. In some embodiments, an anti-ILT2/ILT4 antibody that inhibits ILT2 and ILT4 activity is antibody 64A12. In some embodiments, an anti-ILT2/ILT4 antibody that inhibits ILT2 and ILT4 activity is antibody Hz64A12. In some embodiments, an anti-ILT2/ILT4 antibody that inhibits ILT2 and ILT4 activity is antibody 73C4. In some embodiments, an anti-ILT2/ILT4 antibody that inhibits ILT2 and ILT4 activity is antibody 73D1. In some embodiments, an anti-ILT2/ILT4 antibody that inhibits ILT2 and ILT4 activity is antibody Hz73D1.v1

The present disclosure also provides conjugates comprising an anti-ILT2, an anti-ILT4, or an anti-ILT2/ILT4 antibody described herein. In some embodiments, the antibody is attached to a second molecule. In some embodiments, the antibody is conjugated to a cytotoxic agent or moiety. In some embodiments, the antibody is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065.

A derivative of any one of these toxins may be used as long as the derivative retains the cytotoxic activity of the parent molecule.

Conjugates comprising an anti-ILT antibody (e.g., an ILT2 antibody, an ILT4 antibody, or an ILT2/ILT4 antibody) described herein may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-ILT antibody (e.g., an anti-ILT2 antibody, an anti-ILT4 antibody, or an anti-ILT2/ILT4 antibody) described herein is conjugated to a detectable substance or molecule that allows the antibody to be used for diagnosis and/or detection. In some embodiments, a labeled anti-ILT antibody is used to monitor immune cells in a tumor or in the microenvironment of a tumor. In some embodiments, a labeled anti-ILT antibody is used to monitor immune cells in a tumor or in the microenvironment of a tumor after treatment. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C $^{57}$Co, $^{51}$Cr, $^{67}$Cu $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{b}$ $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$T, $^{133}$Xe, $^{90}$Y, $^{69}$Yb, $^{175}$Yb, $^{65}$Zn; positron emitting metals; and magnetic metal ions.

In some embodiments, an anti-ILT antibody (e.g., an anti-ILT2 antibody, an anti-ILT4 antibody, or an anti-ILT2/ILT4 antibody) described herein is used in an immunoassay. Immunoassays are known to those of skill in the art and include, but are not limited to, ELISA, SPR (e.g., Biacore), FACS, and immunohistochemistry (IHC). In some embodiments, an anti-ILT antibody described herein is used on a tissue sample or a tumor sample.

An anti-ILT antibody (e.g., an anti-ILT2 antibody, an anti-ILT4 antibody, or an anti-ILT2/ILT4 antibody) described herein can also be conjugated to a second antibody to form an antibody heteroconjugate.

An anti-ILT antibody (e.g., an anti-ILT2 antibody, an anti-ILT4 antibody, or an anti-ILT2/ILT4 antibody) as described herein may be attached to a solid support. Such solid supports include, but are not limited to, glass, cellulose, polyacrylamide, nylon, polystyrene, polyvinyl chloride, or polypropylene. In some embodiments, immobilized anti-ILT antibodies are used in immunoassays. In some embodiments, immobilized anti-ILT antibodies are used in purification of the target antigen.

III. Polynucleotides

In some embodiments, the disclosure encompasses polynucleotides comprising polynucleotides that encode a polypeptide (e.g., an ILT-binding agent) described herein. The term "polynucleotides that encode a polypeptide" encompasses a polynucleotide that includes only coding sequences for the polypeptide as well as a polynucleotide that includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, a polynucleotide comprises a polynucleotide encoding a heavy chain variable region and/or a light chain variable region of an ILT2-binding agent described herein. In some embodiments, a polynucleotide comprises a polynucleotide encoding a heavy chain variable region of an ILT2-binding agent described herein. In some embodiments, a polynucleotide comprises a polynucleotide encoding a light chain variable region of an ILT2-binding agent described herein. In some embodiments, a polynucleotide comprises a polynucleotide encoding a heavy chain variable region of an ILT2-binding agent described herein and a polynucleotide encoding a light chain variable region of the ILT2-binding agent. In some embodiments, a polynucleotide comprises a polynucleotide encoding a heavy chain variable region and/or a light chain variable region of an ILT4-binding agent described herein. In some embodiments, a polynucleotide comprises a polynucleotide encoding a light chain variable region of an ILT4-binding agent described herein. In some embodiments, a polynucleotide comprises a polynucleotide encoding a heavy chain variable region of an ILT4-binding agent described herein. In some embodiments, a polynucleotide comprises a polynucleotide encoding a heavy chain variable region of an ILT4-binding agent described herein and a polynucleotide encoding a light chain variable region of the ILT4-binding agent. In some embodiments, a polynucleotide comprises a polynucleotide encoding a heavy chain variable region and/or a light chain variable region of an ILT2/ILT4-binding agent described herein. In some embodiments, a polynucleotide comprises a polynucleotide encoding a heavy chain variable region of an ILT2/ILT4-binding agent described herein. In some embodiments, a polynucleotide comprises a polynucleotide encoding a light chain variable region of an ILT2/ILT4-binding agent described herein. In some embodiments, a polynucleotide comprises a polynucleotide encoding a heavy chain variable region of an ILT2/ILT4-binding agent described herein and a polynucleotide encoding a light chain variable region of the ILT2/ILT4-binding agent.

In some embodiments, a polynucleotide comprises a polynucleotide encoding a heavy chain and/or a light chain of an ILT2-binding agent described herein. In some embodiments, a polynucleotide comprises a polynucleotide encoding a heavy chain of an ILT2-binding agent described herein. In some embodiments, a polynucleotide comprises a polynucleotide encoding a light chain of an ILT2-binding agent described herein. In some embodiments, a polynucleotide comprises a polynucleotide encoding a heavy chain of an ILT2-binding agent described herein and a polynucleotide encoding a light chain of the ILT2-binding agent. In some embodiments, a polynucleotide comprises a polynucleotide encoding a heavy chain and/or a light chain of an ILT4-binding agent described herein. In some embodiments, a polynucleotide comprises a polynucleotide encoding a heavy chain of an ILT4-binding agent described herein. In some embodiments, a polynucleotide comprises a polynucleotide encoding a light chain of an ILT4-binding agent described herein. In some embodiments, a polynucleotide comprises a polynucleotide encoding a heavy chain of an ILT4-binding agent described herein and a polynucleotide encoding a light chain of the ILT4-binding agent. In some embodiments, a polynucleotide comprises a polynucleotide encoding a heavy chain and/or a light chain of an ILT2/ILT4-binding agent described herein. In some embodiments, a polynucleotide comprises a polynucleotide encoding a heavy chain of an ILT2/ILT4-binding agent described herein. In some embodiments, a polynucleotide comprises a polynucleotide encoding a light chain of an ILT2/ILT4-binding agent described herein. In some embodiments, a polynucleotide comprises a polynucleotide encoding a heavy chain of an ILT2/ILT4-binding agent described herein and a polynucleotide encoding a light chain of the ILT2/ILT4-binding agent.

In some embodiments, the polynucleotide comprises a polynucleotide encoding a polypeptide comprising an amino acid sequence selected from the group consisting of: SEQ ID NOs:125-145. In some embodiments, the polynucleotide comprises a polynucleotide encoding a polypeptide comprising an amino acid sequence of SEQ ID NO:125. In some embodiments, the polynucleotide comprises a polynucleotide encoding a polypeptide comprising an amino acid sequence of SEQ ID NO:126. In some embodiments, the polynucleotide comprises a polynucleotide encoding a polypeptide comprising an amino acid sequence of SEQ ID NO:127. In some embodiments, the polynucleotide comprises a polynucleotide encoding a polypeptide comprising an amino acid sequence of SEQ ID NO:128. In some embodiments, the polynucleotide comprises a polynucleotide encoding a polypeptide comprising an amino acid sequence of SEQ ID NO:129. In some embodiments, the polynucleotide comprises a polynucleotide encoding a polypeptide comprising an amino acid sequence of SEQ ID NO:130. In some embodiments, the polynucleotide comprises a polynucleotide encoding a polypeptide comprising an amino acid sequence of SEQ ID NO:131. In some embodiments, the polynucleotide comprises a polynucleotide encoding a polypeptide comprising an amino acid sequence of SEQ ID NO:132. In some embodiments, the polynucleotide comprises a polynucleotide encoding a polypeptide comprising an amino acid sequence of SEQ ID NO:133. In some embodiments, the polynucleotide comprises a polynucleotide encoding a polypeptide comprising an amino acid sequence of SEQ ID NO:134. In some embodiments, the polynucleotide comprises a polynucleotide encoding a polypeptide comprising an amino acid sequence of SEQ ID NO:135. In some embodiments, the polynucleotide comprises a polynucleotide encoding a polypeptide comprising an amino acid sequence of SEQ ID NO:136. In some embodiments, the polynucleotide comprises a polynucleotide encoding a polypeptide comprising an amino acid sequence of SEQ ID NO:137. In some embodiments, the polynucleotide comprises a polynucleotide encoding a polypeptide comprising an amino acid sequence of SEQ ID NO:138. In some embodiments, the polynucleotide comprises a polynucleotide encoding a polypeptide comprising an amino acid sequence of SEQ ID NO:139. In some embodiments, the polynucleotide comprises a polynucleotide encoding a polypeptide comprising an amino acid sequence of SEQ ID NO:140. In some embodiments, the polynucleotide comprises a polynucleotide encoding a polypeptide comprising an amino acid sequence of SEQ ID NO:141. In some embodiments, the polynucleotide comprises a polynucleotide encoding a polypeptide comprising an amino acid sequence of SEQ ID NO:142. In some embodiments, the polynucleotide comprises a polynucleotide encoding a polypeptide comprising an amino acid sequence of SEQ ID NO:143. In some embodiments, the polynucleotide comprises a polynucleotide encoding a polypeptide comprising an amino acid sequence of SEQ ID NO:144. In some embodiments, the polynucleotide comprises a polynucleotide encoding a polypeptide comprising an amino acid sequence of SEQ ID NO:145.

In some embodiments, the polynucleotide comprises a polynucleotide encoding a polypeptide comprising an amino acid sequence selected from the group consisting of: SEQ ID NOs:146-157. In some embodiments, the polynucleotide comprises a polynucleotide encoding a polypeptide comprising an amino acid sequence of SEQ ID NO:146. In some embodiments, the polynucleotide comprises a polynucleotide encoding a polypeptide comprising an amino acid sequence of SEQ ID NO:147. In some embodiments, the polynucleotide comprises a polynucleotide encoding a polypeptide comprising an amino acid sequence of SEQ ID NO:148. In some embodiments, the polynucleotide comprises a polynucleotide encoding a polypeptide comprising an amino acid sequence of SEQ ID NO:149. In some embodiments, the polynucleotide comprises a polynucleotide encoding a polypeptide comprising an amino acid sequence of SEQ ID NO:150. In some embodiments, the polynucleotide comprises a polynucleotide encoding a polypeptide comprising an amino acid sequence of SEQ ID NO:151. In some embodiments, the polynucleotide comprises a polynucleotide encoding a polypeptide comprising an amino acid sequence of SEQ ID NO:152. In some embodiments, the polynucleotide comprises a polynucleotide encoding a polypeptide comprising an amino acid sequence of SEQ ID NO:153. In some embodiments, the polynucleotide comprises a polynucleotide encoding a polypeptide comprising an amino acid sequence of SEQ ID NO:154. In some embodiments, the polynucleotide comprises a polynucleotide encoding a polypeptide comprising an amino acid sequence of SEQ ID NO:155. In some embodiments, the polynucleotide comprises a polynucleotide encoding a polypeptide comprising an amino acid sequence of SEQ ID NO:156. In some embodiments, the polynucleotide comprises a polynucleotide encoding a polypeptide comprising an amino acid sequence of SEQ ID NO:157.

In some embodiments, the polynucleotide comprises a polynucleotide encoding a polypeptide comprising more than one amino acid sequence selected from the group consisting of: SEQ ID NOs:125-145. In some embodiments, the polynucleotide comprises a polynucleotide encoding (i) a polypeptide comprising an amino acid sequence of SEQ ID NO:125 and (ii) a polypeptide comprising an amino acid sequence of SEQ ID NO:126. In some embodiments, the polynucleotide comprises a polynucleotide encoding (i) a polypeptide comprising an amino acid sequence of SEQ ID NO:127 and (ii) a polypeptide comprising an amino acid sequence of SEQ ID NO:128. In some embodiments, the polynucleotide comprises a polynucleotide encoding (i) a polypeptide comprising an amino acid sequence of SEQ ID NO:129 and (ii) a polypeptide comprising an amino acid sequence of SEQ ID NO:130. In some embodiments, the polynucleotide comprises a polynucleotide encoding (i) a polypeptide comprising an amino acid sequence of SEQ ID NO:131 and (ii) a polypeptide comprising an amino acid sequence of SEQ ID NO:132. In some embodiments, the polynucleotide comprises a polynucleotide encoding (i) a polypeptide comprising an amino acid sequence of SEQ ID NO:133 and (ii) a polypeptide comprising an amino acid sequence of SEQ ID NO:134. In some embodiments, the polynucleotide comprises a polynucleotide encoding (i) a polypeptide comprising an amino acid sequence of SEQ ID NO:135 and (ii) a polypeptide comprising an amino acid sequence of SEQ ID NO:136. In some embodiments, the polynucleotide comprises a polynucleotide encoding (i) a polypeptide comprising an amino acid sequence of SEQ ID NO:137 and (ii) a polypeptide comprising an amino acid sequence of SEQ ID NO:138. In some embodiments, the polynucleotide comprises a polynucleotide encoding (i) a polypeptide comprising an amino acid sequence of SEQ ID NO:139 and (ii) a polypeptide comprising an amino acid sequence of SEQ ID NO:140. In some embodiments, the polynucleotide comprises a polynucleotide encoding (i) a polypeptide comprising an amino acid sequence of SEQ ID NO:141 and (ii) a polypeptide comprising an amino acid sequence of SEQ ID NO:142. In some embodiments, the polynucleotide comprises a polynucleotide encoding (i) a polypeptide comprising an amino acid sequence of SEQ ID NO:143 and (ii) a polypeptide comprising an amino acid sequence of SEQ ID NO:142. In some embodiments, the polynucleotide comprises a polynucleotide encoding (i) a polypeptide comprising an amino acid sequence of SEQ ID NO:144 and (ii) a polypeptide comprising an amino acid sequence of SEQ ID NO:145.

In some embodiments, the polynucleotide comprises a polynucleotide encoding a polypeptide comprising more than one amino acid sequence selected from the group consisting of: SEQ ID NOs:146-157. In some embodiments, the polynucleotide comprises a polynucleotide encoding (i) a polypeptide comprising an amino acid sequence of SEQ ID NO:146 and (ii) a polypeptide comprising an amino acid sequence of SEQ ID NO:147. In some embodiments, the polynucleotide comprises a polynucleotide encoding (i) a polypeptide comprising an amino acid sequence of SEQ ID NO:148 and (ii) a polypeptide comprising an amino acid sequence of SEQ ID NO:149. In some embodiments, the polynucleotide comprises a polynucleotide encoding (i) a polypeptide comprising an amino acid sequence of SEQ ID NO:150 and (ii) a polypeptide comprising an amino acid sequence of SEQ ID NO:151. In some embodiments, the polynucleotide comprises a polynucleotide encoding (i) a polypeptide comprising an amino acid sequence of SEQ ID NO:152 and (ii) a polypeptide comprising an amino acid sequence of SEQ ID NO:153. In some embodiments, the polynucleotide comprises a polynucleotide encoding (i) a polypeptide comprising an amino acid sequence of SEQ ID NO:154 and (ii) a polypeptide comprising an amino acid sequence of SEQ ID NO:155. In some embodiments, the polynucleotide comprises a polynucleotide encoding (i) a polypeptide comprising an amino acid sequence of SEQ ID NO:156 and (ii) a polypeptide comprising an amino acid sequence of SEQ ID NO:157.

The present disclosure also provides variants of the polynucleotides described herein, wherein a variant encodes, for example, a fragment, an analog, and/or a derivative of a polypeptide. In some embodiments, the present disclosure provides a polynucleotide comprising a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding a polypeptide described herein.

In some embodiments, a polynucleotide comprises a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding an amino acid sequence selected from the group consisting of: SEQ ID NOs:125-157. Also provided is a polynucleotide that comprises a polynucleotide that hybridizes to a polynucleotide encoding an amino acid sequence selected from the group consisting of: SEQ ID NOs:125-157. In some embodiments, the hybridization is under conditions of high stringency as is known to those skilled in the art.

As used herein, the phrase "a polynucleotide having a nucleotide sequence at least 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. It is understood by those of skill in the art that an appropriate calculation would be made for other "% identical" statements, for example, 90% identical or 85% identical. The mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, including but not limited to, PCR mutagenesis and site-directed mutagenesis. Polynucleotide variants can be produced for a variety of reasons, for example, to optimize codon expression for a particular host (e.g., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide fused in the same reading frame to a polynucleotide that aids in expression and secretion of a polypeptide from a host cell. In some embodiments, the polynucleotide that aids in expression and secretion is a leader sequence that functions as a secretory sequence for controlling transport of a polypeptide. In some embodiments, the polypeptide has a leader sequence cleaved by the host cell to form a "mature" form of the polypeptide.

In some embodiments, a polynucleotide comprises the coding sequence for a polypeptide fused in the same reading frame to a marker or tag sequence. For example, in some embodiments, a marker sequence is a hexa-histidine tag (HIS-tag; SEQ ID NO:173) that allows for efficient purification of the polypeptide fused to the marker. In some embodiments, a marker sequence is a hemagglutinin (HA) tag derived from the influenza hemagglutinin protein when a mammalian host is used. In some embodiments, the marker sequence is a FLAG™ tag. In some embodiments, a marker may be used in conjunction with other markers or tags.

In some embodiments, a polynucleotide is isolated. In some embodiments, a polynucleotide is substantially pure.

Vectors and cells comprising each and every one of the polynucleotides described herein are also provided. In some embodiments, a vector comprises a polynucleotide molecule encoding an ILT-binding agent (e.g., an ILT2-binding agent, an ILT4-binding agent, or an ILT2/ILT4-binding agent) described herein. In some embodiments, a vector comprises a polynucleotide molecule encoding a polypeptide that is part of an ILT-binding agent described herein. In some embodiments, a cell comprises a vector comprising a polynucleotide molecule encoding an ILT-binding agent described herein. In some embodiments, a cell comprises a vector comprising a polynucleotide molecule encoding a polypeptide that is part of an ILT-binding agent described herein. In some embodiments, a cell comprises a polynucleotide molecule encoding an ILT-binding agent described herein. In some embodiments, a cell comprises one or more polynucleotides encoding an ILT-binding agent described herein. In some embodiments, a cell comprises a single polynucleotide encoding an ILT-binding agent described herein. In some embodiments, a cell comprises a first polynucleotide encoding a heavy chain variable region of an ILT-binding agent described herein and a second polynucleotide encoding a light chain variable region of an ILT-binding agent described herein. In some embodiments, a cell comprises a polynucleotide encoding a heavy chain variable region and a light chain variable region of an ILT-binding agent described herein. In some embodiments, a cell comprises a first polynucleotide encoding a heavy chain of an ILT-binding agent described herein and a second polynucleotide encoding a light chain of an ILT-binding agent described herein. In some embodiments, a cell comprises a polynucleotide encoding a heavy chain and a light chain of an ILT-binding agent described herein. In some embodiments, a cell comprises one or more vectors encoding an ILT-binding agent described herein. In some embodiments, a cell comprises a vector encoding an ILT-binding agent described herein. In some embodiments, a cell comprises a first vector encoding a heavy chain variable region of an ILT-binding agent described herein and a second vector encoding a light chain variable region of an ILT-binding agent described herein. In some embodiments, a cell comprises a single vector encoding a heavy chain variable region and a light chain variable region of an ILT-binding agent described herein. In some embodiments, a cell comprises a first vector encoding a heavy chain of an ILT-binding agent described herein and a second vector encoding a light chain of an ILT-binding agent described herein. In some embodiments, a cell comprises a single vector encoding a heavy chain and a light chain of an ILT-binding agent described herein.

IV. Methods of Making Binding Agents

The disclosure provides methods for making the ILT-binding agents (e.g., ILT2-binding agents, ILT4-binding agents, or ILT2/ILT4-binding agents) described herein. In some embodiments, a method comprises providing a cell comprising one or more polynucleotides encoding a heavy chain and/or light chain of an ILT-binding agent described herein, culturing the cell under conditions that permit the expression of the binding agent, and isolating the binding agent. In some embodiments, a method further comprises purifying the binding agent. In some embodiments, a method further comprises formulating the binding gent as a pharmaceutical composition.

In some embodiments, a cell comprises one or more polynucleotides encoding the heavy chain and the light chain of an ILT-binding agent described herein. In some embodiments, a cell comprises a first polynucleotide encoding the heavy chain of an ILT-binding agent and a second polynucleotide encoding the light chain of an ILT-binding agent. In other embodiments, a cell comprises a polynucleotide encoding the heavy chain and the light chain of an ILT-binding agent described herein. In some embodiments, a polynucleotide encoding an ILT-binding agent described herein is transiently transfected into a cell. In some embodiments, a polynucleotide encoding an ILT-binding agent described herein is stably transfected into a cell.

In some embodiments, a cell comprises one or more vectors encoding the heavy chain variable region and the light chain variable region of an ILT-binding agent described herein. In some embodiments, a cell comprises a first vector encoding the heavy chain variable region of an ILT-binding agent and a second vector encoding the light chain variable region of an ILT-binding agent. In other embodiments, a cell comprises a vector encoding the heavy chain variable region and the light chain variable region of an ILT-binding agent. In some embodiments, a cell comprises one or more vectors encoding the heavy chain and the light chain of an ILT-binding agent described herein. In some embodiments, a cell comprises a first vector encoding the heavy chain of an ILT-binding agent and a second vector encoding the light chain of an ILT-binding agent. In other embodiments, a cell comprises a vector encoding the heavy chain and the light chain of an ILT-binding agent described herein.

In some embodiments, an ILT-binding agent (e.g., an ILT2-binding agent, an ILT4-binding agent, or an ILT2/ILT4-binding agent) is an antibody fragment comprising at least one antigen-binding site and the method involves providing a cell comprising a polynucleotide encoding the fragment of the anti-ILT antibody, incubating the cell under conditions that permit the expression of the antibody fragment, and isolating the antibody fragment. In some embodiments, the cell comprises a polynucleotide encoding an antibody fragment described herein. In some embodiments, the cell comprises a vector encoding an antibody fragment described herein. In some embodiments, the method comprises purifying the antibody fragment. In some embodiments, the antibody fragment is a Fab, Fab', F(ab')$_2$, Fv, scFv, (scFv)$_2$, single chain antibody, dual variable region antibody, diabody, or nanobody.

In some embodiments, the ILT-binding agent is a scFv and the method involves providing a cell comprising the scFv, incubating the cell under conditions that permit the expression of the scFv, and isolating the scFv. In some embodiments, the cell comprises a vector described herein encoding the scFv. In some embodiments, the cell comprises a polynucleotide described herein encoding the scFv. In some embodiments, the method comprises purifying the scFv.

In some embodiments, the cell used to make an ILT-binding agent is a bacterial cell. In some embodiments, the cell used to make an ILT-binding agent is a yeast cell. In some embodiments, the cell used to make an ILT-binding agent is a mammalian cell. In some embodiments, the cell used to make an ILT-binding agent is a CHO cell. In other embodiments, the cell used to make an ILT-binding agent is a HEK-293 cell.

V. Methods of Use and Pharmaceutical Compositions

The ILT-binding agents (e.g., ILT2-binding agent, ILT4-binding agents, or ILT2/ILT4-binding agents) of the disclosure are useful in a variety of applications including, but not limited to, therapeutic treatment methods, such as treatment of cancer. In some embodiments, the therapeutic treatment methods comprise immunotherapy for cancer. In some embodiments, an ILT-binding agent described herein is useful for activating, promoting, increasing, and/or enhancing an immune response to cancer or cancer cells. In some embodiments, an ILT-binding agent described herein is useful for activating, promoting, increasing, and/or enhancing an immune response to a tumor or tumor cells. The methods of use may be in vitro, ex vivo, or in vivo methods.

The present disclosure provides methods of disrupting, inhibiting, or blocking the binding of ILT2 to one or more MHC I molecules. In some embodiments, a method of disrupting, inhibiting, or blocking the binding of ILT2 to one or more MHC I molecules comprises contacting cells with an ILT2-binding agent described herein. In some embodiments, a method of disrupting, inhibiting, or blocking the binding of ILT2 to one or more MHC I molecules comprises contacting cells with an ILT2-binding agent described herein, wherein the method results in disrupting, inhibiting, or blocking MHC I-induced ILT2 activity. In some embodiments, a method of disrupting, inhibiting, or blocking the binding of ILT2 to one or more MHC I molecules comprises contacting cells with an ILT2-binding agent described herein, wherein the method results in disrupting, inhibiting, or blocking ILT2-induced suppression of myeloid cells. In some embodiments, a method of disrupting, inhibiting, or blocking the binding of ILT2 to one or more MHC I molecules comprises contacting cells with an ILT2-binding agent described herein, wherein the method results in disrupting, inhibiting, or blocking of ILT2-induced suppression of myeloid cell activity. In some embodiments, a method of disrupting, inhibiting, or blocking the binding of ILT2 to one or more MHC I molecules restores FcR signaling activity in myeloid cells. In some embodiments, the myeloid cell is a monocyte. In some embodiments, the myeloid cell is a macrophage. In some embodiments, the myeloid cell is a dendritic cell. In some embodiments, the myeloid cell is an APC. In some embodiments, a method of disrupting, inhibiting, or blocking the binding of ILT2 to one or more MHC I molecules comprises contacting cells with an ILT2-binding agent described herein, wherein the method results in increasing NK cell activity. In some embodiments, a method of disrupting, inhibiting, or blocking the binding of ILT2 to one or more MHC I molecules comprises contacting cells with an ILT2-binding agent described herein, wherein the method results in increasing CTL activity. In some embodiments of the methods described herein, the MHC I molecule is a classical MHC I molecule. In some embodiments of the methods described herein, the MHC I molecule is a non-classical MHC I molecule. In some embodiments of the methods described herein, the MHC I molecule is HLA-A, HLA-B, HLA-C, HLA-E, and/or HLA-G.

The present disclosure provides methods of disrupting, inhibiting, or blocking the binding of ILT4 to one or more MHC I molecules. In some embodiments, a method of disrupting, inhibiting, or blocking the binding of ILT4 to one or more MHC I molecules comprises contacting cells with an ILT4-binding agent described herein. In some embodiments, a method of disrupting, inhibiting, or blocking the binding of ILT4 to one or more MHC I molecules comprises contacting cells with an ILT4-binding agent described herein, wherein the method results in disrupting, inhibiting, or blocking MHC I-induced ILT4 activity. In some embodiments, a method of disrupting, inhibiting, or blocking the binding of ILT4 to one or more MHC I molecules comprises contacting cells with an ILT4-binding agent described herein, wherein the method results in disrupting, inhibiting, or blocking ILT4-induced suppression of myeloid cells. In some embodiments, a method of disrupting, inhibiting, or blocking the binding of ILT2 to one or more MHC I molecules comprises contacting cells with an ILT4-binding agent described herein, wherein the method results in disrupting, inhibiting, or blocking of ILT4-induced suppression of myeloid cell activity. In some embodiments, a method of disrupting, inhibiting, or blocking the binding of ILT4 to one or more MHC I molecules restores FcR signaling activity in myeloid cells. In some embodiments, the myeloid cell is a monocyte. In some embodiments, the myeloid cell is a macrophage. In some embodiments, the myeloid cell is a dendritic cell. In some embodiments, the myeloid cell is an APC. In some embodiments of the methods described herein, the MHC I molecule is a classical MHC I molecule. In some embodiments of the methods described herein, the MHC I molecule is a non-classical MHC I molecule. In some embodiments of the methods described herein, the MHC I molecule is HLA-A, HLA-B, HLA-C, HLA-E, and/or HLA-G.

The present disclosure provides methods of disrupting, inhibiting, or blocking the binding of ILT2 and ILT4 to one or more MHC I molecules. In some embodiments, a method of disrupting, inhibiting, or blocking the binding of ILT2 and ILT4 to one or more MHC I molecules comprises contacting cells with an ILT2/ILT4-binding agent described herein. In some embodiments, a method of disrupting, inhibiting, or blocking the binding of ILT2 and ILT4 to one or more MHC I molecules comprises contacting cells with an ILT2/ILT4-binding agent described herein, wherein the method results in disrupting, inhibiting, or blocking MHC I-induced ILT2 and/or ILT4 activity. In some embodiments, a method of disrupting, inhibiting, or blocking the binding of ILT2 and ILT4 to one or more MHC I molecules comprises contacting cells with an ILT2/ILT4-binding agent described herein, wherein the method results in disrupting, inhibiting, or blocking ILT2-induced and/or ILT4-induced suppression of myeloid cells. In some embodiments, a method of disrupting, inhibiting, or blocking the binding of ILT2 and ILT4 to one or more MHC I molecules comprises contacting cells with an ILT2/ILT4-binding agent described herein, wherein the method results in disrupting, inhibiting, or blocking of ILT2-induced and/or ILT4-induced suppression of myeloid cell activity. In some embodiments, a method of disrupting, inhibiting, or blocking the binding of ILT2 and ILT4 to one or more MHC I molecules restores FcR signaling activity in myeloid cells. In some embodiments, the myeloid cell is a monocyte. In some embodiments, the myeloid cell is a macrophage. In some embodiments, the myeloid cell is a dendritic cell. In some embodiments, the myeloid cell is an APC. In some embodiments, a method of disrupting, inhibiting, or blocking the binding of ILT2 and ILT4 to one or more MHC I molecules comprises contacting cells with an ILT2/ILT4-binding agent described herein, wherein the method results in increasing NK cell activity. In some embodiments, a method of disrupting, inhibiting, or blocking the binding of ILT2 and ILT4 to one or more MHC I molecules comprises contacting cells with an ILT2/ILT4-binding agent described herein, wherein the method results in increasing CTL activity.

The present disclosure provides methods of disrupting, inhibiting, or blocking the binding of ILT2 and/or ILT4 to MHC I molecules in a subject. In some embodiments, a method of disrupting, inhibiting, or blocking the binding of ILT2 and/or ILT4 to MHC I molecules in a subject, comprises administering to the subject an effective amount of an ILT2/ILT4-binding agent described herein. In some embodiments, a method of disrupting, inhibiting, or blocking MHC I-induced ILT2 and/or ILT4 activity in a subject comprises administering to the subject an effective amount of an ILT2/ILT4-binding agent described herein. In some embodiments, a method of disrupting, inhibiting, or blocking ILT2-induced and/or ILT4-induced suppression of myeloid cells in a subject comprises administering to the subject an effective amount of an ILT2/ILT4-binding agent described herein. In some embodiments, a method of disrupting, inhibiting, or blocking ILT2-induced and/or ILT4-induced suppression of myeloid cell activity in a subject comprises administering to the subject an effective amount of an ILT2/ILT4-binding agent described herein. In some embodiments, a method of disrupting, inhibiting, or blocking ILT2-induced and/or ILT4-induced suppression of antigen-presenting cell activity in a subject restores FcR activity in myeloid cells. In some embodiments, the myeloid cell is a monocyte. In some embodiments, the myeloid cell is a macrophage. In some embodiments, the myeloid cell is a dendritic cell. In some embodiments, the myeloid cell is an APC.

The present disclosure provides methods for activating an immune response in a subject using an ILT2/ILT4-binding agent described herein. In some embodiments, the disclosure provides methods for promoting an immune response in a subject using an ILT2/ILT4-binding agent described herein. In some embodiments, the disclosure provides methods for increasing an immune response in a subject using an ILT2/ILT4-binding agent described herein. In some embodiments, the disclosure provides methods for enhancing an immune response in a subject using an ILT2/ILT4-binding agent described herein. In some embodiments, the activating, promoting, increasing, and/or enhancing of an immune response comprises stimulating myeloid cells. In some embodiments, the activating, promoting, increasing, and/or enhancing of an immune response comprises stimulating monocytes. In some embodiments, the activating, promoting, increasing, and/or enhancing of an immune response comprises stimulating macrophages. In some embodiments, the activating, promoting, increasing, and/or enhancing of an immune response comprises stimulating dendritic cells. In some embodiments, the activating, promoting, increasing, and/or enhancing of an immune response comprises stimulating APCs. In some embodiments, the activating, promoting, increasing, and/or enhancing of an immune response comprises increasing cell-mediated immunity. In some embodiments, the activating, promoting, increasing, and/or enhancing of an immune response comprises increasing effector T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises enhancing NK cell activity. In some embodiments, the activating, promoting, increasing, and/or enhancing of an immune response comprises inhibiting or decreasing the suppressive activity of Tregs. In some embodiments, the activating, promoting, increasing, and/or enhancing of an immune response comprises inhibiting or decreasing the suppressive activity of MDSCs. In some embodiments, the immune response is a result of antigenic stimulation. In some embodiments, the antigenic stimulation is a tumor cell. In some embodiments, the antigenic stimulation is cancer.

The disclosure also provides methods of disrupting and/or inhibiting ILT2 and/or ILT4 signaling in a cell comprising contacting the cell with an effective amount of an ILT2-binding agent, an ILT4-binding agent, or an ILT2/ILT4-binding agent described herein. In some embodiments, the method of disrupting and/or inhibiting ILT2 signaling in a cell comprises contacting the cell with an effective amount of antibody 27F9, antibody 47H6, antibody 51A1, antibody 64A12, antibody 73C4, or antibody 73D1, or a humanized version thereof. In some embodiments, the method of disrupting and/or inhibiting ILT4 signaling in a cell comprises contacting the cell with an effective amount of antibody 47C8, antibody 48A5, antibody 47H6, antibody 51A1, antibody 64A12, antibody 73C4, or antibody 73D1, or a humanized version thereof. In some embodiments, the method of disrupting and/or inhibiting ILT2 signaling and ILT4 signaling in a cell comprises contacting the cell with an effective amount of antibody 47H6, antibody 51A1, antibody 64A12, antibody 73C4, or antibody 73D1, or a humanized version thereof. In some embodiments, the method of disrupting and/or inhibiting ILT2 signaling and ILT4 in a cell comprises contacting the cell with an effective amount of antibody Hz47H6.v2. In some embodiments, the method of disrupting and/or inhibiting ILT2 signaling and ILT4 in a cell comprises contacting the cell with an effective amount of antibody Hz64A12. In some embodiments, the method of disrupting and/or inhibiting ILT2 signaling and ILT4 in a cell comprises contacting the cell with an effective amount of antibody Hz73D1.v1. In some embodiments, the disclosure provides use of an ILT2-binding agent described herein in the manufacture or preparation of a medicament for disrupting and/or inhibiting ILT2 signaling in a cell. In some embodiments, the disclosure provides use of an ILT4-binding agent described herein in the manufacture or preparation of a medicament for disrupting and/or inhibiting ILT4 signaling in a cell. In some embodiments, the disclosure provides use of an ILT2/ILT4-binding agent described herein in the manufacture or preparation of a medicament for disrupting and/or inhibiting ILT2 signaling and ILT4 signaling in a cell. In some embodiments, the cell is a myeloid cell. In some embodiments, the cell is a monocyte. In some embodiments, the cell is a macrophage. In some embodiments, the cell is a dendritic cell. In some embodiments, the cell is an antigen-presenting cell. In some embodiments, the cells is a NK cell. In some embodiments, the cell is a CTL. In some embodiments, the method is an in vivo method wherein the step of contacting the cell with the agent comprises administering a therapeutically effective amount of an ILT-binding agent to a subject. In some embodiments, the method is an in vitro or ex vivo method.

The present disclosure also provides methods for inhibiting growth of a tumor using an ILT2-binding agent, an ILT4-binding agent, or an ILT2/ILT4-binding agent described herein. In some embodiments, the method of inhibiting growth of a tumor comprises using an ILT2-binding agent described herein. In some embodiments, the method of inhibiting growth of a tumor comprises using antibody 27F9 or a humanized version thereof. In some embodiments, the method of inhibiting growth of a tumor comprises using an ILT4-binding agent described herein. In some embodiments, the method of inhibiting growth of a tumor comprises using antibody 47C8 or antibody 48A5, or a humanized version thereof. In some embodiments, the method of inhibiting growth of a tumor comprises using an ILT2/ILT4-binding agent described herein. In some embodiments, the method of inhibiting growth of a tumor comprises using antibody 47H6, antibody 51A1, antibody 64A12, antibody 73C4, or antibody 73D1, or humanized versions thereof. In some embodiments, the method of inhibiting growth of a tumor comprises using antibody Hz47H6.v2. In some embodiments, the method of inhibiting growth of a tumor comprises using antibody Hz64A12. In some embodiments, the method of inhibiting growth of a tumor comprises using antibody Hz73D1.v1. In some embodiments, the method of inhibiting growth of a tumor comprises contacting a cell mixture with an ILT-binding agent in vitro. For example, an immortalized cell line or a cancer cell line mixed with immune cells (e.g., a myeloid cell) is cultured in medium to which is added a test agent that binds ILT2 and/or ILT4. In some embodiments, tumor cells are isolated from a patient sample such as, for example, a tissue biopsy, pleural effusion, or blood sample, mixed with immune cells (e.g., myeloid cells), and cultured in medium to which is added a test agent that binds ILT2 and/or ILT4. In some embodiments, the disclosure provides use of an ILT2-binding agent described herein in the manufacture or preparation of a medicament for inhibiting growth of a tumor or a tumor cell. In some embodiments, the disclosure provides use of an ILT4-binding agent described herein in the manufacture or preparation of a medicament for inhibiting growth of a tumor or a tumor cell. In some embodiments, the disclosure provides use of an ILT2/ILT4-binding agent described herein in the manufacture or preparation of a medicament for inhibiting growth of a tumor or a tumor cell. In some embodiments, an ILT2-binding agent increases, promotes, and/or enhances the activity of effector immune cells. In some embodiments, an ILT2-binding agent inhibits tumor cell growth by increasing, promoting, and/or enhancing the activity of effector immune cells. In some embodiments, an ILT4-binding agent increases, promotes, and/or enhances the activity of effector immune cells. In some embodiments, an ILT4-binding agent inhibits tumor cell growth by increasing, promoting, and/or enhancing the activity of effector immune cells. In some embodiments, an ILT2/ILT4-binding agent increases, promotes, and/or enhances the activity of effector immune cells. In some embodiments, an ILT2/ILT4-binding agent inhibits tumor cell growth by increasing, promoting, and/or enhancing the activity of effector immune cells.

In some embodiments, a method of inhibiting tumor growth comprises contacting the tumor and/or tumor microenvironment with an ILT-binding agent (e.g., an ILT2-binding agent, an ILT4-binding agent, or ILT2/ILT4-binding agent) described herein in vivo. In some embodiments, contacting a tumor and/or tumor microenvironment with an ILT-binding agent described herein is undertaken in an animal model. For example, a test agent (e.g., an ILT2/ILT4-binding agent) may be administered to mice that have tumors. In some embodiments, an ILT2/ILT4-binding agent increases, promotes, and/or enhances the activity of immune cells in the mice. In some embodiments, an ILT2/ILT4-binding agent inhibits tumor growth. In some embodiments, an ILT2/ILT4-binding agent causes a tumor to regress. In some embodiments, an ILT2/ILT4-binding agent is administered at the same time or shortly after introduction of tumor cells into the animal to prevent tumor growth ("preventative model"). In some embodiments, an ILT2/ILT4-binding agent is administered after tumors have grown to a specified size or have become "established" for treatment ("therapeutic model"). In some embodiments, an ILT2/ILT4-binding agent is administered to a transgenic animal (e.g., a transgenic mouse) that expresses human ILT2 and/or ILT4, wherein the transgenic animal has a tumor derived from human cells.

In some embodiments, a method of inhibiting tumor growth comprises administering to a subject a therapeutically effective amount of an ILT-binding agent (e.g., an ILT2-binding agent, an ILT4-binding agent, or an ILT2/ILT4-binding agent) described herein. In some embodiments, a method of inhibiting tumor growth comprises administering to a subject a therapeutically effective amount of an ILT2/ILT4-binding agent described herein. In some embodiments, a method of increasing or enhancing an immune response to a tumor or tumor cells in a subject comprises administering to the subject a therapeutically effective amount of an ILT2/ILT4-binding agent described herein. In some embodiments, a method of activating or enhancing a persistent or long-term immune response to a tumor or tumor cells in a subject comprises administering to the subject a therapeutically effective amount of an ILT2/ILT4-binding agent described herein. In some embodiments, a method of inhibiting tumor relapse or tumor regrowth in a subject comprises administering to the subject a therapeutically effective amount of an ILT2/ILT4-binding agent described herein. In some embodiments, a method of inducing a persistent or long-term immunity that inhibits tumor relapse or tumor regrowth in a subject comprises administering to the subject a therapeutically effective amount of an ILT2/ILT4-binding agent described herein. In some embodiments of the methods described herein, the tumor is a solid tumor. In some embodiments, the tumor is a pancreatic tumor, a breast tumor, a lung tumor, a non-small cell lung tumor, a head and neck tumor, a colorectal tumor, a prostate tumor, a skin tumor, a melanoma tumor, a stomach tumor, a gastric tumor, an intestinal tumor, an ovarian tumor, a cervical tumor, an uterine tumor, an endometrial tumor, a bladder tumor, a brain tumor, an esophageal tumor, a liver tumor, a kidney tumor, a renal cell carcinoma, or a testicular tumor. In some embodiments, the tumor is a pancreatic tumor. In some embodiments, the tumor is a non-small cell lung tumor. In some embodiments, the tumor is a renal cell carcinoma (RCC). In some embodiments, the subject has a tumor or the subject had a tumor that was at least partially removed. In some embodiments of the methods described herein, the subject is a human.

In some embodiments, the disclosure provides use of an ILT2-binding agent, an ILT4-binding agent, or an ILT2/ILT4-binding agent described herein in the manufacture or preparation of a medicament for inhibiting growth of a tumor or tumor cell. In some embodiments, the method of inhibiting growth of a tumor comprises administering to a subject a therapeutically effective amount of antibody 27F9, antibody 47C8, antibody 48A5, antibody 47H6, antibody 51A1, antibody 64A12, antibody 73C4, or antibody 73D1, or humanized versions thereof. In some embodiments, the method of inhibiting growth of a tumor comprises administering to a subject a therapeutically effective amount of antibody Hz47H6.v2. In some embodiments, the method of inhibiting growth of a tumor comprises administering to a subject a therapeutically effective amount of antibody Hz64A12. In some embodiments, the method of inhibiting growth of a tumor comprises administering to a subject a therapeutically effective amount of antibody Hz73D1.v1. In some embodiments of the methods described herein, the subject is a human.

The present disclosure provides methods of treating cancer. In some embodiments, a method of treating cancer comprises administering to a subject a therapeutically effective amount of an ILT2-binding agent described herein. In some embodiments, a method of treating cancer comprises administering to a subject a therapeutically effective amount of an ILT4-binding agent described herein. In some embodiments, a method of treating cancer comprises administering to a subject a therapeutically effective amount of an ILT2/ILT4-binding agent described herein. In some embodiments, an ILT2/ILT4-binding agent binds ILT2 and/or ILT4 and inhibits or reduces growth of the cancer. In some embodiments, an ILT2/ILT4-binding agent binds human ILT2-expressing cells and/or ILT4-expressing cells, enhances an immune response to a cancer, and inhibits or reduces growth of the cancer. In some embodiments, an ILT2/ILT4-binding agent binds human ILT2-expressing cells and/or ILT4-expressing cells, activates myeloid cells, enhances an immune response to a cancer, and inhibits or reduces growth of the cancer. In some embodiments, the subject is a human. In some embodiments, the subject has a cancerous tumor. In some embodiments, the subject has had the cancer at least partially removed.

In some embodiments, the disclosure provides use of an ILT2-binding agent described herein in the manufacture or preparation of a medicament for the treatment of cancer. In some embodiments, the disclosure provides use of an ILT4-binding agent described herein in the manufacture or preparation of a medicament for the treatment of cancer. In some embodiments, the disclosure provides use of an ILT2/ILT4-binding agent described herein in the manufacture or preparation of a medicament for the treatment of cancer.

In some embodiments of the methods described herein, the cancer is pancreatic cancer, breast cancer, lung cancer, non-small cell lung cancer (NSCLC), head and neck cancer, colorectal cancer, prostate cancer, skin cancer, melanoma, stomach cancer, gastric cancer, intestinal cancer, ovarian cancer, cervical cancer, uterine cancer, endometrial cancer, bladder cancer, brain cancer, esophageal cancer, liver cancer, kidney cancer, renal cell carcinoma (RCC), or testicular cancer. In some embodiments, the cancer is pancreatic cancer. In some embodiments, the cancer is breast cancer. In some embodiments, the cancer is non-small cell lung cancer. In some embodiments, the cancer is renal cell carcinoma.

In some embodiments, a method for treating cancer in a subject comprises administering to the subject a therapeutically effective amount of antibody 27F9 or a humanized version thereof. In some embodiments, a method for treating cancer in a subject comprises administering to the subject a therapeutically effective amount of antibody 47C8 or antibody 48A5, or a humanized version thereof. In some embodiments, a method for treating cancer in a subject comprises administering to the subject a therapeutically effective amount of antibody 47H6, antibody 51A1, antibody 64A12, antibody 73C4, or antibody 73D1, or a humanized version thereof. In some embodiments, a method for treating cancer in a subject comprises administering to the subject a therapeutically effective amount of antibody Hz47H6.v2. In some embodiments, a method for treating cancer in a subject comprises administering to the subject a therapeutically effective amount of antibody Hz64A12. In some embodiments, a method for treating cancer in a subject comprises administering to the subject a therapeutically effective amount of antibody Hz73D1.v1.

In some embodiments, the disclosure provides methods of activating myeloid cells in the tumor microenvironment. In some embodiments, a method of activating myeloid cells in the tumor microenvironment in a subject with a tumor comprises administering to the subject a therapeutically effective amount of an ILT2-binding agent, an ILT4-binding agent, or an ILT2/ILT4-binding agent described herein. In some embodiments, a method of activating myeloid cells in the tumor microenvironment in a subject with a tumor comprises administering to the subject a therapeutically effective amount of an ILT2/ILT4-binding agent described herein. In some embodiments, the myeloid cells are primary dendritic cells. In some embodiments, the myeloid cells are monocytes. In some embodiments, the myeloid cells are macrophages. In some embodiments, the myeloid cells are APCs.

In some embodiments, the disclosure provides methods of activating NK cells in the tumor microenvironment. In some embodiments, a method of activating NK cells in the tumor microenvironment in a subject with a tumor comprises administering to the subject a therapeutically effective amount of an ILT2-binding agent or an ILT2/ILT4-binding agent described herein. In some embodiments, a method of activating NK cells in the tumor microenvironment in a subject with a tumor comprises administering to the subject a therapeutically effective amount of an ILT2-binding agent described herein. In some embodiments, a method of activating NK cells in the tumor microenvironment in a subject with a tumor comprises administering to the subject a therapeutically effective amount of an ILT2/ILT4-binding agent described herein.

In some embodiments, the disclosure provides methods of activating CTLs in the tumor microenvironment. In some embodiments, a method of activating CTLs in the tumor microenvironment in a subject with a tumor comprises administering to the subject a therapeutically effective amount of an ILT2-binding agent or an ILT2/ILT4-binding agent described herein. In some embodiments, a method of activating CTLs in the tumor microenvironment in a subject with a tumor comprises administering to the subject a therapeutically effective amount of an ILT2-binding agent described herein. In some embodiments, a method of activating CTLs in the tumor microenvironment in a subject with a tumor comprises administering to the subject a therapeutically effective amount of an ILT2/ILT4-binding agent described herein.

In some embodiments of the methods described herein, an ILT2-binding agent comprises a heavy chain variable region CDR1, CDR2, and CDR3 and a light chain variable region CDR1, CDR2, and CDR3 of antibody 27F9.

In some embodiments of the method described herein, an ILT2-binding agent is an anti-ILT2 antibody. In some embodiments of the methods described herein, the anti-ILT2 antibody comprises: (a) a heavy chain variable region comprising a heavy chain variable region CDR1 comprising the amino acid sequence GFSLTNYGVS (SEQ ID NO:22), a heavy chain variable region CDR2 comprising the amino acid sequence IIWGDGSTNYHSALIS (SEQ ID NO:23), and a heavy chain variable region CDR3 comprising the amino acid sequence PNWDTYAMIDF (SEQ ID NO:24), and (b) a light chain variable region comprising a light chain variable region CDR1 comprising the amino acid sequence RASQDISNFLN (SEQ ID NO:25), a light chain variable region CDR2 comprising the amino acid sequence CTSKLHS (SEQ ID NO:26), and a light chain variable region CDR3 comprising the amino acid sequence QQGNTLPPT (SEQ ID NO:27). In some embodiments of the methods described herein, the anti-ILT2 antibody comprises: (a) a heavy chain variable region of SEQ ID NO:125 and (b) a light chain variable region of SEQ ID NO:126. In some embodiments of the methods described herein, the anti-ILT2 antibody is antibody 27F9. In some embodiments of the methods described herein, the anti-ILT2 antibody is a humanized version of 27F9.

In some embodiments of the methods described herein, the ILT4-binding agent comprises a heavy chain variable region CDR1, CDR2, and CDR3 and a light chain variable region CDR1, CDR2, and CDR3 of antibody 47C8.

In some embodiments of the method described herein, an ILT4-binding agent is an anti-ILT4 antibody. In some embodiments of the methods described herein, the anti-ILT4 antibody comprises: (a) a heavy chain variable region comprising a heavy chain variable region CDR1 comprising the amino acid sequence GYSFTGYYMH (SEQ ID NO:38), a heavy chain variable region CDR2 comprising the amino acid sequence RVYPNNGDTSYNQKFKV (SEQ ID NO:39), and a heavy chain variable region CDR3 comprising the amino acid sequence GATVVESLFAY (SEQ ID NO:40), and (b) a light chain variable region comprising a light chain variable region CDR1 comprising the amino acid sequence RASESVDNYGNNFLH (SEQ ID NO:41), a light chain variable region CDR2 comprising the amino acid sequence RTSNLES (SEQ ID NO:42), and a light chain variable region CDR3 comprising the amino acid sequence QQSNEDPYT (SEQ ID NO:43). In some embodiments of the methods described herein, the anti-ILT4 antibody comprises: (a) a heavy chain variable region of SEQ ID NO:127 and (b) a light chain variable region of SEQ ID NO:128. In some embodiments of the methods described herein, the anti-ILT4 antibody is antibody 47C8. In some embodiments of the methods described herein, the anti-ILT4 antibody is a humanized version of antibody 47C8.

In some embodiments of the methods described herein, the ILT4-binding agent comprises a heavy chain variable region CDR1, CDR2, and CDR3 and a light chain variable region CDR1, CDR2, and CDR3 of antibody 48A5.

In some embodiments of the method described herein, an ILT4-binding agent is an anti-ILT4 antibody. In some embodiments of the methods described herein, the anti-ILT4 antibody comprises: (a) a heavy chain variable region comprising a heavy chain variable region CDR1 comprising the amino acid sequence GYTFTNYGMN (SEQ ID NO:54), a heavy chain variable region CDR2 comprising the amino acid sequence WINTYIGEPIYADDFKG (SEQ ID NO:55), and a heavy chain variable region CDR3 comprising the amino acid sequence RSDYDGYAMDY (SEQ ID NO:56), and (b) a light chain variable region comprising a light chain variable region CDR1 comprising the amino acid sequence KSSQSLLYSGNQKNYLA (SEQ ID NO:57), a light chain variable region CDR2 comprising the amino acid sequence WASTRES (SEQ ID NO:58), and a light chain variable region CDR3 comprising the amino acid sequence QQHDSYPT (SEQ ID NO:59). In some of the methods described herein, the anti-ILT4 antibody comprises: (a) a heavy chain variable region of SEQ ID NO:129 and (b) a light chain variable region of SEQ ID NO:130. In some embodiments of the methods described herein, the anti-ILT4 antibody is antibody 48A5. In some embodiments of the methods described herein, the anti-ILT4 antibody is a humanized version of antibody 48A5.

In some embodiments of the methods described herein, the ILT2/ILT4-binding agent comprises a heavy chain variable region CDR1, CDR2, and CDR3 and a light chain variable region CDR1, CDR2, and CDR3 of antibody 47H6 or antibody Hz47H6.v2.

In some embodiments of the method described herein, an ILT2/ILT4-binding agent is an anti-ILT2/ILT4 antibody. In some embodiments of the methods described herein, the anti-ILT2/ILT4 antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71) or DFNPNNAGTTYNQKFEG (SEQ ID NO:118), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments of the methods described herein, the anti-ILT2/ILT4 antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNGGTTYNQKFEG (SEQ ID NO:71), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments of the methods described herein, the anti-ILT2/ILT4 antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence DFNPNNAGTTYNQKFEG (SEQ ID NO:118), and a heavy chain variable region CDR3 comprising the amino acid sequence GRFYYGSLYSFDY (SEQ ID NO:72), and (b) a light chain variable region comprising a light chain variable region CDR1 comprising the amino acid sequence RASGNIHNYLA (SEQ ID NO:73), a light chain variable region CDR2 comprising the amino acid sequence NAKTLAD (SEQ ID NO:74), and a light chain variable region CDR3 comprising the amino acid sequence QHFWTSIT (SEQ ID NO:75). In some embodiments of the methods described herein, the anti-ILT2/ILT4 antibody comprises: (a) a heavy chain variable region of SEQ ID NO:131 and (b) a light chain variable region of SEQ ID NO:132. In some embodiments of the methods described herein, the anti-ILT2/ILT4 antibody comprises: (a) a heavy chain variable region of SEQ ID NO:133 and (b) a light chain variable region of SEQ ID NO:134. In some embodiments of the methods described herein, the anti-ILT2/ILT4 antibody comprises: (a) a heavy chain of SEQ ID NO:148 and (b) a light chain of SEQ ID NO:149. In some embodiments of the methods described herein, the anti-ILT2/ILT4 antibody is antibody 47H6. In some embodiments of the methods described herein, the anti-ILT2/ILT4 antibody is a humanized version of antibody 47H6. In some embodiments of the methods described herein, the anti-ILT2/ILT4 antibody is antibody Hz47H6.v2.

In some embodiments of the methods described herein, the ILT2/ILT4-binding agent comprises a heavy chain variable region CDR1, CDR2, and CDR3 and a light chain variable region CDR1, CDR2, and CDR3 of antibody 51A1 or a humanized version of antibody 51A1.

In some embodiments of the method described herein, an ILT2/ILT4-binding agent is an anti-ILT2/ILT4 antibody. In some embodiments of the methods described herein, the anti-ILT2/ILT4 antibody comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYGTMYYYAMDY (SEQ ID NO:88), and (b) a light chain variable region comprising a light chain variable region CDR1 comprising the amino acid sequence RAS-ESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments of the methods described herein, the anti-ILT2/ILT4 antibody comprises: (a) a heavy chain variable region of SEQ ID NO:135 and (b) a light chain variable region of SEQ ID NO:136. In some embodiments of the methods described herein, the anti-ILT2/ILT4 antibody is antibody 51A1. In some embodiments of the methods described herein, the anti-ILT2/ILT4 antibody is a humanized version of antibody 51A1.

In some embodiments of the methods described herein, the ILT2/ILT4-binding agent comprises a heavy chain variable region CDR1, CDR2, and CDR3 and a light chain variable region CDR1, CDR2, and CDR3 of antibody 64A12, a humanized version of antibody 64A12, or antibody Hz64A12.

In some embodiments of the method described herein, an ILT2/ILT4-binding agent is an anti-ILT2/ILT4 antibody. In some embodiments of the methods described herein, the anti-ILT2/ILT4 antibody comprises: (a) a heavy chain variable region comprising a heavy chain variable region CDR1 comprising the amino acid sequence GFTFNTYAMH (SEQ ID NO:86), a heavy chain variable region CDR2 comprising the amino acid sequence RIRSKSSNYATYYADSVKD (SEQ ID NO:87), and a heavy chain variable region CDR3 comprising the amino acid sequence DGIYYYDTMYYYAMDY (SEQ ID NO:102), and (b) a light chain variable region comprising a light chain variable region CDR1 comprising the amino acid sequence RAS-ESVDYYGNSFIY (SEQ ID NO:103), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments of the methods described herein, the anti-ILT2/ILT4 antibody comprises: (a) a heavy chain variable region of SEQ ID NO:137 and (b) a light chain variable region of SEQ ID NO:138. In some embodiments of the methods described herein, the anti-ILT2/ILT4 antibody comprises: (a) a heavy chain variable region of SEQ ID NO:139 and (b) a light chain variable region of SEQ ID NO:140. In some embodiments of the methods described herein, the anti-ILT2/ILT4 antibody comprises: (a) a heavy chain of SEQ ID NO:152 and (b) a light chain of SEQ ID NO:153. In some embodiments of the methods described herein, the anti-ILT2/ILT4 antibody is antibody 64A12. In some embodiments of the methods described herein, the anti-ILT2/ILT4 antibody is a humanized version of antibody 64A12. In some embodiments of the methods described herein, the anti-ILT2/ILT4 antibody is antibody Hz64A12.

In some embodiments of the methods described herein, the ILT2/ILT4-binding agent comprises a heavy chain variable region CDR1, CDR2, and CDR3 and a light chain variable region CDR1, CDR2, and CDR3 of antibody 73C4 or a humanized version of antibody 73C4.

In some embodiments of the method described herein, an ILT2/ILT4-binding agent is an anti-ILT2/ILT4 antibody. In some embodiments of the methods described herein, the anti-ILT2/ILT4 antibody comprises: (a) a heavy chain variable region comprising a heavy chain variable region CDR1 comprising the amino acid sequence GYTFTDYYMN (SEQ ID NO:70), a heavy chain variable region CDR2 comprising the amino acid sequence NVNPNNGGTSYNQKFKG (SEQ ID NO:106), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RAS-ESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments of the methods described herein, the anti-ILT2/ILT4 antibody comprises: (a) a heavy chain variable region of SEQ ID NO:141 and (b) a light chain variable region of SEQ ID NO:142. In some embodiments of the methods described herein, the anti-ILT2/ILT4 antibody is antibody 73C4. In some embodiments of the methods described herein, the anti-ILT2/ILT4 antibody is a humanized version of antibody 73C4.

In some embodiments of the methods described herein, the ILT2/ILT4-binding agent comprises a heavy chain variable region CDR1, CDR2, and CDR3 and a light chain variable region CDR1, CDR2, and CDR3 of antibody 73D1, a humanized version of antibody 73D1, or antibody Hz73D1.v1.

In some embodiments of the method described herein, an ILT2/ILT4-binding agent is an anti-ILT2/ILT4 antibody. In some embodiments of the methods described herein, the anti-ILT2/ILT4 antibody comprises: (a) a heavy chain variable region comprising a heavy chain variable region CDR1 comprising the amino acid sequence GYTFTDYYIN (SEQ ID NO:111), a heavy chain variable region CDR2 comprising the amino acid sequence NVNPNDGGTTYNQKFKG (SEQ ID NO:112), and a heavy chain variable region CDR3 comprising the amino acid sequence REIYFYGTIYYYAMDY (SEQ ID NO:107), and (b) a light chain variable region comprising a light chain variable region CDR1 comprising the amino acid sequence RAS-ESVDYYGNSFMY (SEQ ID NO:89), a light chain variable region CDR2 comprising the amino acid sequence FASNLES (SEQ ID NO:90), and a light chain variable region CDR3 comprising the amino acid sequence QQNNEDPWT (SEQ ID NO:91). In some embodiments of the methods described herein, the anti-ILT2/ILT4 antibody comprises: (a) a heavy chain variable region of SEQ ID NO:143 and (b) a light chain variable region of SEQ ID NO:142. In some embodiments of the methods described herein, the anti-ILT2/ILT4 antibody comprises: (a) a heavy chain variable region of SEQ ID NO:144 and (b) a light chain variable region of SEQ ID NO:145. In some embodiments of the methods described herein, the anti-ILT2/ILT4 antibody comprises: (a) a heavy chain of SEQ ID NO:156 and (b) a light chain of SEQ ID NO:157. In some embodiments of the methods described herein, the anti-ILT2/ILT4 antibody is antibody 73D1. In some embodiments of the methods described herein, the anti-ILT2/ILT4 antibody is a humanized version of antibody 73D1. In some embodiments of the methods described herein, the anti-ILT2/ILT4 antibody is antibody Hz73D1.v1.

In some embodiments of the methods described herein, a method comprises administering an ILT-binding agent (e.g., an ILT2-binding agent, an ILT4-binding agent, or an ILT2/ILT4-binding agent) described herein in combination with at least one additional therapeutic agent or therapeutic therapy. In some embodiments of the methods described herein, a method comprises administering an ILT2/ILT4-binding agent described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments of the methods described, the combination of an ILT-binding agent (e.g., an ILT2-binding agent, an ILT4-binding agent, or an ILT2/ILT4-binding agent) described herein and at least one additional therapeutic agent results in additive or synergistic results. In some embodiments, the combination therapy results in an increase in the therapeutic index of the ILT-binding agent. In some embodiments, the combination therapy results in an increase in the therapeutic index of the additional therapeutic agent(s). In some embodiments, the combination therapy results in a decrease in the toxicity and/or side effects of the ILT-binding agent. In some embodiments, the combination therapy results in a decrease in the toxicity and/or side effects of the additional therapeutic agent(s). In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, a combination treatment comprises one additional therapeutic agent. In some embodiments of the methods described herein, a combination treatment comprises at least one additional therapeutic agent. In some embodiments of the methods described herein, a combination treatment comprises two or more additional therapeutic agents.

Useful classes of therapeutic agents include, but are not limited to, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, anti-metabolites, chemotherapy sensitizers, duocarmycins, etoposides, fhiorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent is an alkylating agent, an antimetabolite, an antimitotic, a topoisomerase inhibitor, or an angiogenesis inhibitor.

Therapeutic agents that may be administered in combination with the ILT-binding agents described herein include chemotherapeutic agents. Thus, in some embodiments, the method or treatment involves the administration of an ILT-binding agent of the present disclosure in combination with a chemotherapeutic agent or in combination with a cocktail of chemotherapeutic agents.

Chemotherapeutic agents useful in the present disclosure include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT 11; topoisomerase inhibitor RFS 2000; difluoromethylornithine (DMFO); retinoic acid; esperamicins; capecitabine (XELODA); and pharmaceutically acceptable salts, acids or derivatives of any of the above.

Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

In some embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HC1, daunorubicin citrate, mitoxantrone HC1, actinomycin D, etoposide, topotecan HC1, teniposide (VM-26), and irinotecan, as well as pharmaceutically acceptable salts, acids, or derivatives of any of these. In some embodiments, the additional therapeutic agent is irinotecan.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In some embodiments, the additional therapeutic agent is gemcitabine.

In some embodiments of the methods described herein, the chemotherapeutic agent is an antimitotic agent, including, but not limited to, agents that bind tubulin. In some embodiments, the agent is a taxane. In some embodiments, the agent is paclitaxel or docetaxel, or a pharmaceutically acceptable salt, acid, or derivative of paclitaxel or docetaxel. In some embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In some embodiments, the additional therapeutic agent is paclitaxel. In some embodiments, the additional therapeutic agent is nab-paclitaxel.

In some embodiments of the methods described herein, an additional therapeutic agent comprises an agent such as a small molecule. For example, treatment can involve the combined administration of an ILT-binding agent of the present disclosure with a small molecule that acts as an inhibitor against tumor-associated antigens including, but not limited to, EGFR, HER2 (ErbB2), and/or VEGF. In some embodiments, an ILT-binding agent (e.g., an anti-ILT2 antibody, an anti-ILT4 antibody, or an anti-ILT2/ILT4 antibody) of the present disclosure is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In some embodiments of the methods described herein, an additional therapeutic agent comprises a biological molecule, such as an antibody. For example, treatment can involve the combined administration of an ILT-binding agent of the present disclosure with antibodies against tumor-associated antigens including, but not limited to, antibodies that bind EGFR, HER2/ErbB2, and/or VEGF.

In some embodiments, the additional therapeutic agent is an antibody that is an angiogenesis inhibitor (e.g., an anti-VEGF or VEGF receptor antibody). In some embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an immunotherapeutic agent. In some embodiments of the methods described herein the immunotherapeutic agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, In some embodiments of the methods described herein, an immunotherapeutic agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the additional therapeutic agent is a checkpoint inhibitor. In some embodiments, the additional therapeutic agent is an anti-PD-1 antibody, an anti-PD-L1 antibody, an anti-PD-L2 antibody, an anti-CTLA-4 antibody, or an anti-TIGIT antibody, an anti-CD28 antibody, an anti-CD80 antibody, an anti-CD86 antibody, an anti-4-1BB antibody, an anti-OX40 antibody, an anti-KIR antibody, an anti-Tim-3 antibody, an anti-LAG3 antibody, an anti-CD27 antibody, an anti-CD40 antibody, an anti-GITR antibody, an anti-TIGIT antibody, an anti-CD20 antibody, an anti-CD96 antibody, or an anti-IDO1 antibody. In some embodiments, the additional therapeutic agent is an anti-HLA-G antibody. In some embodiments, the additional therapeutic agent is B7-1 (CD80), B7-2 (CD86), 4-1BB ligand, or an anti-CD3 antibody.

In some embodiments of the methods described herein, the PD-1 antagonist is an antibody that specifically binds PD-1. In some embodiments, the antibody that binds PD-1 is Pembrolizumab (MK-3475; KEYTRUDA), Pidilizumab (CT-011), Nivolumab (OPDIVO), Durvalumab (MEDI0680), Cemiplimab (REGN2810), Tislelizumab (BGB-A317), Spartalizumab (PDR-001), or STI-A1110. Exemplary anti-PD-1 antibodies are provided, for example, in U.S. Pat. Nos. 10,316,089, 9,580,504, 9,856,320, 8,609, 089, and 8,952,136; the contents of all of which are incorporated by reference in their entirety herein. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AU P-12.

In some embodiments, the PD-L1 antagonist is an antibody that specifically binds PD-L1. In some embodiments, the antibody that binds PD-L1 is Atezolizumab (TECENTRIQ), MEDI4736, BMS-936559 (MDX-1105), Avelumab (BAVENCIO), Durvalumab (IMFINZI), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies.

In some embodiments, the CTLA-4 antagonist is an antibody that specifically binds CTLA-4. In some embodiments, the antibody that binds CTLA-4 is Ipilimumab (YERVOY) or Tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is Lirilumab.

In some embodiments, an immunotherapeutic agent is selected from the group consisting of: a CD28 agonist, a 4-1BB agonist, an OX40 agonist, a CD27 agonist, a CD80 agonist, a CD86 agonist, a CD40 agonist, and a GITR agonist.

In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MEDI0562, PF-8600, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RG-DOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is Utomilumab (PF-05082566) or Urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises a GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments of the methods described herein, the additional therapeutic agent is a biologic molecule, such as, a cytokine, a chemokine, a growth factor, an interferon, an interleukin, a lymphokine, a member of the tumor necrosis factor (TNF) family, and an immunostimulatory oligonucleotide (e.g., CpG dinucleotides). In some embodiments, the biologic molecule is selected from the group consisting of: adrenomedullin (AM), angiopoietin (Ang), BMPs, BDNF, EGF, erythropoietin (EPO), FGF, GDNF, granulocyte-macrophage colony stimulating factor (GM-CSF), macrophage colony stimulating factor (M-CSF), granulocyte colony stimulating factor (G-CSF), GDF9, HGF, HDGF, IGF, migration-stimulating factor, myostatin (GDF-8), NGF, neurotrophins, PDGF, thrombopoietin, TGF-a, TGF-β, TNF-α, VEGF, PlGF, IL-1, IL-2, IL-3, IL-4, IL-5, IL-6, IL-7, IL-12, IL-15, and IL-18.

Furthermore, treatment with an ILT-binding agent (e.g., an ILT2-binding agent, an ILT4-binding agent, or an ILT2/ILT4-binding agent) described herein can be accompanied by surgical removal of tumors, removal of cancer cells, or any other therapy deemed necessary by a treating physician.

In some embodiments, treatment with an ILT-binding agent (e.g., an ILT2-binding agent, an ILT4-binding agent, or an ILT2/ILT4-binding agent) can occur prior to, concurrently with, or subsequent to administration of the additional therapeutic agents. In some embodiments, combined administration includes co-administration, either in a single pharmaceutical formulation or using separate formulations, or consecutive administration in either order but generally within a time period such that all active agents can exert their biological activities. In some embodiments, preparation of agents and/or dosing schedules for additional therapeutic agents are according to manufacturers' instructions or as determined empirically by the skilled practitioner.

In some embodiments of the methods described herein, an ILT-binding agent (e.g., an ILT2-binding agent, an ILT4-binding agent, or an ILT2/ILT4-binding agent) is administered to a subject as part of a combination therapy.

It will be appreciated that the combination of an ILT-binding agent (e.g., an ILT2-binding agent, an ILT4-binding agent, or an ILT2/ILT4-binding agent) described herein and at least one additional therapeutic agent may be administered in any order or concurrently. In some embodiments, an ILT-binding agent is administered to subjects that have previously undergone treatment with a therapeutic agent. In some embodiments, an ILT-binding agent and a second therapeutic agent are administered substantially simultaneously or concurrently. For example, a subject may be given an ILT-binding agent while undergoing a course of treatment with a second therapeutic agent (e.g., a chemotherapeutic agent). In some embodiments, an ILT-binding agent is administered within 1 year of the treatment with a second therapeutic agent. In some embodiments, an ILT-binding agent is administered within 10, 8, 6, 4, or 2 months of any treatment with a second therapeutic agent. In some embodiments, an ILT-binding agent is administered within 4, 3, 2, or 1 weeks of any treatment with a second therapeutic agent. In some embodiments, an ILT-binding agent is administered within 5, 4, 3, 2, or 1 days of any treatment with a second therapeutic agent. It will further be appreciated that the two (or more) agents or treatments can be administered to the subject within a matter of hours or minutes (i.e., substantially simultaneously).

For the treatment of a disease, the appropriate dosage of an ILT-binding agent (e.g., an ILT2-binding agent, an ILT4-binding agent, or an ILT2/ILT4-binding agent) of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. An ILT-binding agent can be administered one time or over a series of treatments lasting from several days to several months, or until a cure is effected or a diminution of the disease state is achieved.

The present disclosure provides pharmaceutical compositions comprising an ILT-binding agent described herein and a pharmaceutically acceptable vehicle. The present disclosure also provides pharmaceutical compositions comprising an ILT2-binding agent described herein and a pharmaceutically acceptable vehicle. The present disclosure also provides pharmaceutical compositions comprising an ILT4-binding agent described herein and a pharmaceutically acceptable vehicle. The present disclosure also provides pharmaceutical compositions comprising an ILT2/ILT4-binding agent described herein and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol. (*Remington: The Science and Practice of Pharmacy*, 22$^{nd}$ Edition, 2012, Pharmaceutical Press, London.). In some embodiments, the formulation is in the form of an aqueous solution. In some embodiments, the formulation is stored in a lyophilized or in an alternative dried form.

The ILT-binding agents of the present disclosure can be formulated in any suitable form for delivery to a target cell/tissue. In some embodiments, an ILT-binding agent (e.g., an ILT2-binding agent, an ILT4-binding agent, or an ILT2/ILT4-binding agent) can be formulated as a liposome, microparticle, microcapsule, albumin microsphere, microemulsion, nanoparticle, nanocapsule, or macroemulsion.

In some embodiments, an ILT-binding agent (e.g., an ILT2-binding agent, an ILT4-binding agent, or an ILT2/ILT4-binding agent) is formulated with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, an ILT-binding agent (e.g., an ILT2-binding agent, an ILT4-binding agent, or an ILT2/ILT4-binding agent) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

EXAMPLES

Example 1

Generation of Antibodies and Screening of Antibodies

Anti-ILT antibodies were generated using the extracellular domain of human ILT2, the extracellular domain of human ILT4, and/or the extracellular domain of rhesus ILT2 as the immunogen. For examples, anti-ILT2 antibodies were generated using the extracellular domain of human ILT2. Similarly, anti-ILT4 antibodies were generated using the extracellular domain of human ILT4. Anti-ILT2/ILT4 antibodies were generated using a mixture of the extracellular domain of human ILT2, the extracellular domain of human ILT4, and the extracellular domain of rhesus ILT2. Single cell suspensions of lymphocytes were obtained from the spleens and lymph nodes of immunized mice after the individual animals had been determined to have suitable antibody titers. Lymphocytes were fused with murine myeloma cells by standard methods. Hybridoma fusions were plated onto semi-solid media for HAT selection. After 5-7 days, single colonies were selected using a ClonePix™ system and plated into 96-well plates.

ELISA assays were used to screen antibodies against human ILT2, human ILT4, and rhesus ILT2. Antibodies that bound to human ILT2 only, human ILT4 only, or human ILT2, human ILT4 and rhesus ILT2 were selected.

Example 2

Synteny Between Human and Cynomolgus Monkey ILT2 and ILT4 Genes

In rodents, paired Ig-like receptor B (PirB) and gp49B1 have been described as the potential orthologues of human LILRB family of receptors (Kang X, et al. *Cell Cycle*. (2016); 15(1):25-40). However, PirB and gp49B1 show less than 50% identity to both human ILT2 and human ILT4. Further, marked differences exist in the receptor/ligand pairing among the rodent and human LILRB family members and the biological function of the rodent receptors are unclear. Thus, rodents are not considered relevant species to test the biological effects of anti-ILT antibodies.

An analysis of genomic structure (synteny) was used to identify candidate orthologs of both human ILT2 and ILT4 in cynomolgus monkey. The genomic organization of the locus that contains the LILR family members in human (hg38) and cynomolgus monkey (*Macaca fascicularis* v5.0.95, "cyno") were compared using the gene annotations provided by Ensembl. In cases where annotations were not found, manual analysis of the intervening sequence was used to confirm lack of an open reading frame. The predicted protein sequence of genes in cynomolgus monkey without pre-annotated gene symbols was compared to all human genes using blastp tools on UniProt to find the most likely human ortholog based on the identity score.

It was found that the cynomolgus monkey genomic organization is missing a gene at the same genome location as human LILRB2 (ILT4), while retaining a gene at the same location as human LILRB1 (ILT2). A similar organization was observed with rhesus macaque. The sequence identity between human ILT2, human ILT4 and cyno ILT2 ranges from 73%-80%. The sequence identity between human ILT2 and cyno ILT2 is 73%, while sequence identity between human ILT4 and cyno ILT2 is 78%. In comparison, the sequence identity between human ILT2 and human ILT4 is 80%.

Example 3

Binding Characteristics of Anti-Human ILT2, ILT4, and ILT2/ILT4 Antibodies

The binding affinities of anti-ILT2 and anti-ILT4 antibodies were measured using a Biacore system (GE Healthcare LifeSciences). Equilibrium dissociation constant ($K_D$) measurements were carried out with purified antibodies to evaluate their binding to human ILT2, human ILT4, and rhesus ILT2. Briefly, purified anti-ILT2 antibody 27F9, anti-ILT4 antibodies 47C8 and 48A5, and anti-ILT2/ILT4 antibodies 47H6, 51A1, 64A12, 73C4, and 73D1 were captured on a Sensor Chip Protein A (GE HealthCare). The surface of the Biacore Sensor Chip Protein A consists of a carboxymethylated dextran matrix with a recombinant Protein A variant covalently attached. Soluble human ILT2-ECD, human ILT4-ECD, or rhesus ILT2-ECD were injected at a flow rate of 30 μL/min at 25° C. The ILT2 or ILT4 proteins were used at concentrations ranging from 1.6-200 nM in PBS-P buffer with 2 fold dilutions. Kinetic data were collected over time and fit using the simultaneous global fit equation to yield affinity constants ($K_D$ values) for each antibody.

Binding data is shown in Tables 9A and 9B.

TABLE 9A

| | Human ILT2 | | | Human ILT4 | | |
|---|---|---|---|---|---|---|
| Antibody | $K_{on}$ [1/Ms] | $K_{off}$ [s$^{-1}$] | $K_D$ M | $K_{on}$ [1/Ms] | $K_{off}$ [s$^{-1}$] | $K_D$ M |
| 27F9 | $2.1 \times 10^5$ | $5.4 \times 10^{-5}$ | $2.6 \times 10^{-10}$ | NB | NB | NB |
| 47C8 | NB | NB | NB | $3.4 \times 10^5$ | $2.5 \times 10^{-5}$ | $7.4 \times 10^{-11}$ |
| 48A5 | NB | NB | NB | $8.1 \times 10^5$ | $2.1 \times 10^{-5}$ | $2.6 \times 10^{-11}$ |
| 47H6 | $4.2 \times 10^4$ | $8.6 \times 10^{-5}$ | $2.1 \times 10^{-9}$ | $3.7 \times 10^4$ | $2.8 \times 10^{-5}$ | $7.6 \times 10^{-10}$ |
| 51A1 | $3.9 \times 10^4$ | $2.2 \times 10^{-4}$ | $5.8 \times 10^{-9}$ | $6.8 \times 10^4$ | $1.4 \times 10^{-5}$ | $2.0 \times 10^{-10}$ |
| 64A12[1] | $2.0 \times 10^4$ | $\sim 1.0 \times 10^{-5}$ | $<1.0 \times 10^{-10}$ | $8.2 \times 10^4$ | $\sim 1.0 \times 10^{-5}$ | $<1.0 \times 10^{-10}$ |
| 73C4[1] | $3.1 \times 10^4$ | $\sim 1.0 \times 10^{-5}$ | $<1.0 \times 10^{-10}$ | $9.7 \times 10^4$ | $\sim 1.0 \times 10^{-5}$ | $<1.0 \times 10^{-10}$ |
| 73D1 | $5.0 \times 10^4$ | $6.0 \times 10^{-5}$ | $1.2 \times 10^{-9}$ | $3.0 \times 10^5$ | $5.4 \times 10^{-5}$ | $1.8 \times 10^{-10}$ |

[1]Binding assay was performed under low resolution parameters

TABLE 9B

| | Rhesus ILT2 | | |
|---|---|---|---|
| Antibody | $K_{on}$ [1/Ms] | $K_{off}$ [s$^{-1}$] | $K_D$ M |
| 27F9 | NB | NB | NB |
| 47C8 | $5.9 \times 10^5$ | $1.4 \times 10^{-3}$ | $2.3 \times 10^{-9}$ |
| 48A5 | $1.1 \times 10^6$ | $2.6 \times 10^{-3}$ | $2.3 \times 10^{-9}$ |
| 47H6[1] | $4.7 \times 10^4$ | $\sim 1 \times 10^{-5}$ | $<1.0 \times 10^{-10}$ |
| 51A1 | $1.0 \times 10^5$ | $2.1 \times 10^{-5}$ | $2.0 \times 10^{-10}$ |
| 64A12[1] | $2.0 \times 10^4$ | $\sim 1.0 \times 10^{-5}$ | $<1.0 \times 10^{-10}$ |
| 73C4[1] | $3.1 \times 10^4$ | $\sim 1.0 \times 10^{-5}$ | $<1.0 \times 10^{-10}$ |
| 73D1 | $5.0 \times 10^4$ | $6.0 \times 10^{-5}$ | $1.2 \times 10^{-9}$ |

[1]Binding assay was performed under low resolution parameters

Example 4

Sequence Analyses of Anti-ILT2, Anti-ILT4, and Anti-ILT2/ILT4 Antibodies

Representative anti-ILT2 antibody 27F9, anti-ILT4 antibodies 47C8 and 48A5, and anti-ILT2/ILT4 antibodies 47H6, 51A1, 64A12, 73C4, and 73D1 were sequenced and the heavy chain variable region and light chain variable region amino acid sequences are disclosed herein and summarized in Table 10.

TABLE 10

| Antibody | Target | Heavy Chain Variable Region | Light Chain Variable Region |
|---|---|---|---|
| 27F9 | ILT2 | SEQ ID NO: 125 | SEQ ID NO: 126 |
| 47C8 | ILT4 | SEQ ID NO: 127 | SEQ ID NO: 128 |
| 48A5 | ILT4 | SEQ ID NO: 129 | SEQ ID NO: 130 |
| 47H6 | ILT2/ILT4 | SEQ ID NO: 131 | SEQ ID NO: 132 |
| 51A1 | ILT2/ILT4 | SEQ ID NO: 135 | SEQ ID NO: 136 |
| 64A12 | ILT2/ILT4 | SEQ ID NO: 137 | SEQ ID NO: 138 |
| 73C4 | ILT2/ILT4 | SEQ ID NO: 141 | SEQ ID NO: 142 |
| 73D1 | ILT2/ILT4 | SEQ ID NO: 143 | SEQ ID NO: 142 |

The heavy chain and light chain variable region CDRs for the individual antibodies are disclosed in Tables 1-8 and as SEQ ID NOs:22-124.

Example 5

Generation of Humanized Antibodies

Several of the anti-ILT2/ILT4 antibodies, i.e., 47H6, 64A12, and 73D1, were humanized by methods known to those skilled in the art. These humanized antibodies are referred to herein as Hz47H6.v2, Hz64A12, and Hz73D1.v1, respectively. During the humanization process for antibody 47H6, the heavy chain variable region CDR2 was modified from DFNPNNGGTTYNQKFEG (SEQ ID NO:71) to DFNPNNAGTTYNQKFEG (SEQ ID NO:118). The heavy chain variable region sequence of Hz47H6.v2 is SEQ ID NO:133 and the light chain variable region sequence of Hz47H6.v2 is SEQ ID NO:134; the heavy chain variable region sequence of Hz64A12 is SEQ ID NO:139 and the light chain variable region sequence of Hz64A12 is SEQ ID NO:140; and the heavy chain variable region sequence of Hz73D1.v1 is SEQ ID NO:144 and the light chain variable region sequence of Hz73D1.v1 is SEQ ID NO:145.

The binding affinities of the humanized antibodies to human ILT2 and human ILT4 were measured using a Biacore system as described herein. The binding affinities of antibodies Hz47H6.v2, Hz64A12, and Hz73D1.v1 are shown in Table 11 as compared with the parental antibodies.

TABLE 11

| Antibody | Human ILT2 | | | Human ILT4 | | |
|---|---|---|---|---|---|---|
| | $K_{on}$ [1/Ms] | $K_{off}$ [s$^{-1}$] | $K_D$ M | $K_{on}$ [1/Ms] | $K_{off}$ [s$^{-1}$] | $K_D$ M |
| 47H6 | $1.0 \times 10^5$ | $2.1 \times 10^{-5}$ | $2.0 \times 10^{-10}$ | $1.0 \times 10^5$ | $2.1 \times 10^{-5}$ | $2.0 \times 10^{-10}$ |
| Hz47H6.v2 | $2.3 \times 10^5$ | $9.0 \times 10^{-4}$ | $4.0 \times 10^{-9}$ | $8.7 \times 10^4$ | $1.8 \times 10^{-4}$ | $2.0 \times 10^{-9}$ |
| 64A12[1] | $2.0 \times 10^4$ | ~$1.0 \times 10^{-5}$ | <$1.0 \times 10^{-10}$ | $8.2 \times 10^4$ | ~$1.0 \times 10^{-5}$ | <$1.0 \times 10^{-10}$ |
| Hz64A12[1] | $9.3 \times 10^4$ | $1.4 \times 10^{-4}$ | $1.6 \times 10^{-9}$ | $3.0 \times 10^5$ | ~$1.0 \times 10^{-5}$ | <$1 \times 10^{-10}$ |
| 73D1 | $1.5 \times 10^5$ | $2.4 \times 10^{-4}$ | $1.8 \times 10^{-9}$ | $4.0 \times 10^5$ | $3.0 \times 10^{-5}$ | $7.4 \times 10^{-10}$ |
| Hz73D1.v1 | $8.5 \times 10^4$ | $2.5 \times 10^{-4}$ | $3.0 \times 10^{-9}$ | $3.6 \times 10^5$ | $2.7 \times 10^{-4}$ | $7.5 \times 10^{-10}$ |

[1]Binding assay was performed under low resolution parameters

These results demonstrated that the humanization process for exemplary anti-ILT2/ILT4 antibodies did not have a significant effect on the antibodies' binding capabilities to human ILT2 or human ILT4.

Cross-reactivity of humanized anti-ILT2/ILT4 antibodies with cynomolgus monkey ("cyno", *Macaca fascicularis*) ILT2 were also assayed. Similar to anti-ILT2/ILT4 antibodies, humanized anti-ILT2/ILT4 antibodies bind to cyno ILT2. Binding affinities of an exemplary clone Hz73D1.v1 measured by a Biacore system are shown in Table 12. In the Biacore system, a humanized anti-ILT2/ILT4 antibody was captured on a Protein A chip. ILT proteins were injected at different concentrations into the flow cells to evaluate kinetic parameters at 25° C. The binding affinity ($K_D$) of Hz73D1.v1 to human ILT2 and ILT4 was determined to be 1.03 and 0.205 nM, respectively. The $K_D$ of Hz73D1.v1 to cyno ILT2 was determined to be 19.1 nM.

TABLE 12

| Species of ILT | $K_D$ (nM) | $k_{on}$ (1/Ms) | $k_{off}$ (1/s) |
|---|---|---|---|
| Human ILT2 | 1.03 | $4.72 \times 10^4$ | $4.85 \times 10^{-5}$ |
| Human ILT4 | 0.205 | $2.2 \times 10^5$ | $4.6 \times 10^{-5}$ |
| Cynomolgus monkey ILT2 | 19.1 | $3.4 \times 10^6$ | 0.06 |

Example 6

ILT2 and ILT4 Expression in Subsets of Immune Cells

ILT2 and ILT4 expression has been described on various cells of hematopoietic origin, including myeloid cells, granulocytes, and lymphocytes (Colonna M et al. *J Exp Med.* (1997) December 1; 186(11): 1809-1818; Colonna M et al., *J Immunol* (1998), 160(7): 3096-3100). Anti-ILT antibodies described herein were used to further elucidate the expression of ILT2 and ILT4 on subsets of human and cyno immune cells.

Flow cytometry analysis of blood immune cells was performed on human and cyno PBMC and whole blood. PBMC were prepared from a leukopak (Allcells Inc.) by centrifugation through ficoll, washing with PBS and freezing in cryopreservation buffer in liquid nitrogen until use. Whole blood (Allcells Inc.) was obtained fresh and red blood cells (RBC) depleted using ammonium chloride RBC lysing solution (Biolegend). PBMC or whole blood samples were stained with a fluorescently labeled antibody panel to distinguish various immune subsets (monocytes, B cells, NK cells, CD4+ and CD8+ T cells, neutrophils and eosinophils). Samples were further stained with fluorescently labeled isotype, 27F9 (ILT2 specific), 48A5 (ILT4 specific), 73D1, and Hz73D1.v1. The number of ILT2 and ILT4 molecules per cell of each immune subset was estimated by incubation with Quantum Simply Cellular microspheres followed by flow cytometry analysis.

As shown in Table 13 and FIG. 1, high expression of ILT2 was observed on monocytes, B cells, a subset of NK cells (5-20% total NK cells), and a subset of CD8+ T cells (5-20% total CD8+ T cells). High expression of ILT4 was observed on monocytes, eosinophils and neutrophils. The results showed that cynomolgus monkey peripheral immune cells express ILT2 protein with a level of expression and immune cell distribution comparable with the combination of ILT2 and ILT4 in human peripheral blood.

TABLE 13

| Antigen | Monocyte | Neutrophil | B Cell | NK Cell (Subset) | CD8 T Cell (Subset) |
|---|---|---|---|---|---|
| Human ILT2 | $5.0 \times 10^4$ | 0 | $2.0 \times 10^4$ | $4.0 \times 10^3$ | $5.5 \times 10^3$ |
| Human ILT4 | $5.0 \times 10^4$ | $2.5 \times 10^4$ | 0 | 0 | 0 |

TABLE 13-continued

| Antigen | Monocyte | Neutrophil | B Cell | NK Cell (Subset) | CD8 T Cell (Subset) |
|---|---|---|---|---|---|
| Cynomolgus monkey ILT2 | $1.3 \times 10^5$ | $5.0 \times 10^4$ | $2.0 \times 10^3$ | $8.0 \times 10^3$ | $5.0 \times 10^3$ |

Example 7

Inhibition of the Interaction Between ILT2 or ILT4 and MHC I Molecules by Anti-ILT Antibodies As part of the characterization process, the ability of exemplary antibodies to inhibit or block the interaction of ILT2 or ILT4 with their natural ligands was evaluated in competition experiments using a Biacore system. As described herein, the natural ligands of ILT2 and ILT4 include, but are not limited to, HLA class I molecules, including HLA-A, HLA-B, HLA-C, HLA-E, and HLA-G. Biotinylated HLA-A*1101 was captured in high amounts on a NeutrAvidin chip surface. Antigen-antibody complexes were prepared with (i) ILT2-ECD and anti-ILT2 antibody 27F9, anti-ILT4 antibody 48A5, or anti-ILT2/ILT4 antibody Hz73D1.v1 and (ii) ILT4-ECD and anti-ILT2 antibody 27F9, anti-ILT4 antibody 48A5, or anti-ILT2/ILT4 antibody Hz73D1.v1. The antibody concentration of each antibody was titrated from 0.09-100 nM and the concentration of human ILT2-ECD or ILT4-ECD was kept constant at 20 nM. The complexes were mixed in a 96-well microplate and each was injected onto the HLA-A-coated chip surface. The measured signal (response unit, RU) was plotted against the antibody concentration.

Figure 2:
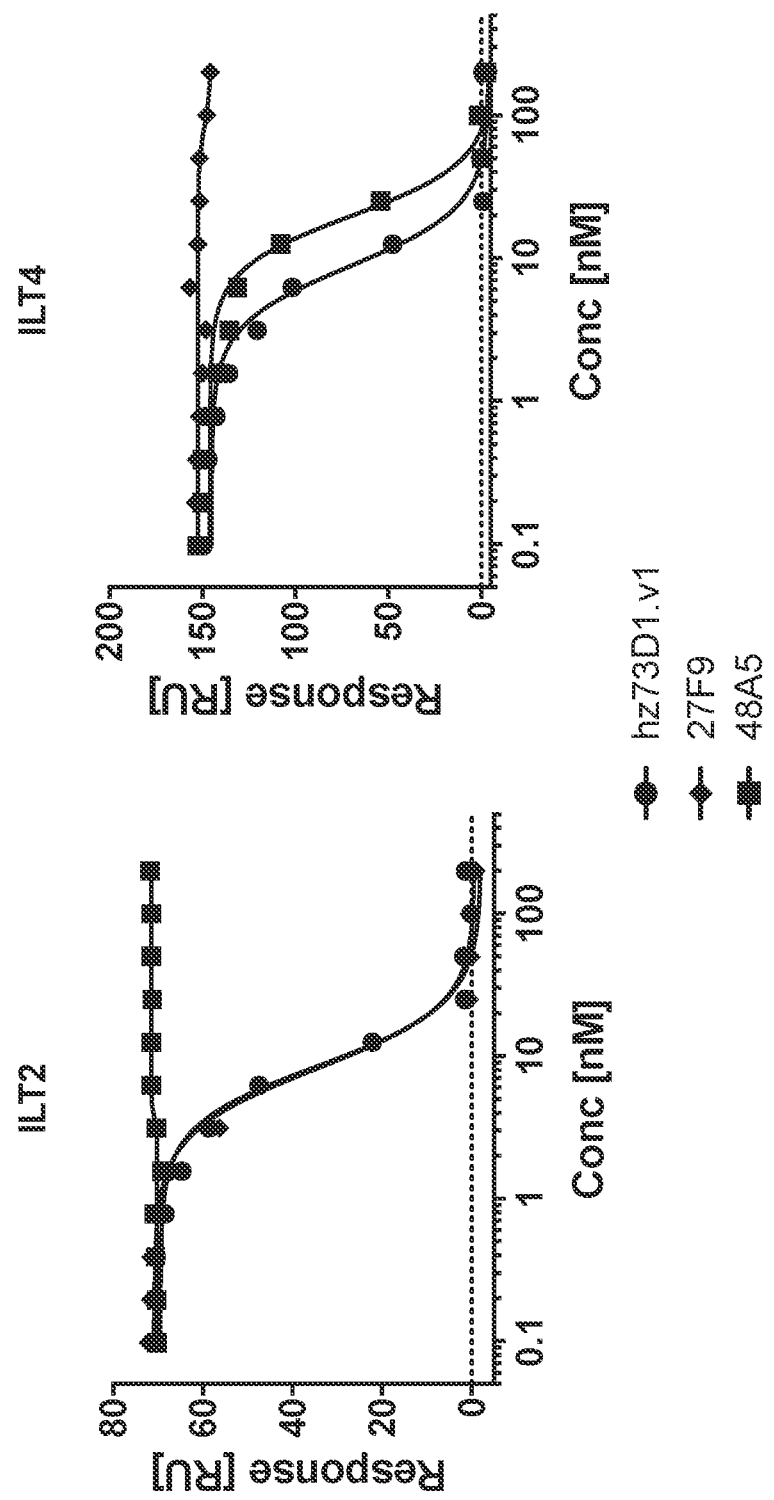
FIG. 2. Inhibition of the interaction between ILT2 or ILT4 and MHC I molecules by anti-ILT antibodies.

The results are shown in FIG. 2. A decrease in binding of ILT2 to HLA-A was observed with increasing concentrations of anti-ILT2 antibody 27F9 and anti-ILT2/ILT4 antibody Hz73D1.v1 in a dose-dependent manner. In contrast, anti-ILT4 antibody 48A5 had no effect on the binding of ILT2 to HLA-A. Similarly, a decrease in binding of ILT4 to HLA-A was observed with increasing concentrations of anti-ILT4 antibody 48A5 and anti-ILT2/ILT4 antibody Hz73D1.v1, with no effect by anti-ILT2 antibody 27F9. The antibodies were observed to inhibit the interactions at IC50s in the nanomolar range. Another set of experiments was carried out using a HLA-G-coated chip surface with similar results.

These data demonstrate that anti-ILT2 and anti-ILT2/ILT4 antibodies described herein inhibit the interactions between ILT2 and its natural ligands. In addition, anti-ILT4 and anti-ILT2/ILT4 antibodies described herein inhibit the interactions between ILT4 and its natural ligands. Importantly, this experiment also showed that the anti-ILT2/ILT4 antibody not only bound to both targets, i.e., ILT2 and ILT4, but was biologically functional in blocking the interactions of both targets with their ligands. These results show that anti-ILT2/ILT4 antibodies may be a potential therapeutic for blocking ILT2-induced and ILT4-induced suppression of immune responses.

Example 8

Binding of Anti-ILT2/ILT4 Antibody to Cells

Figure 3:
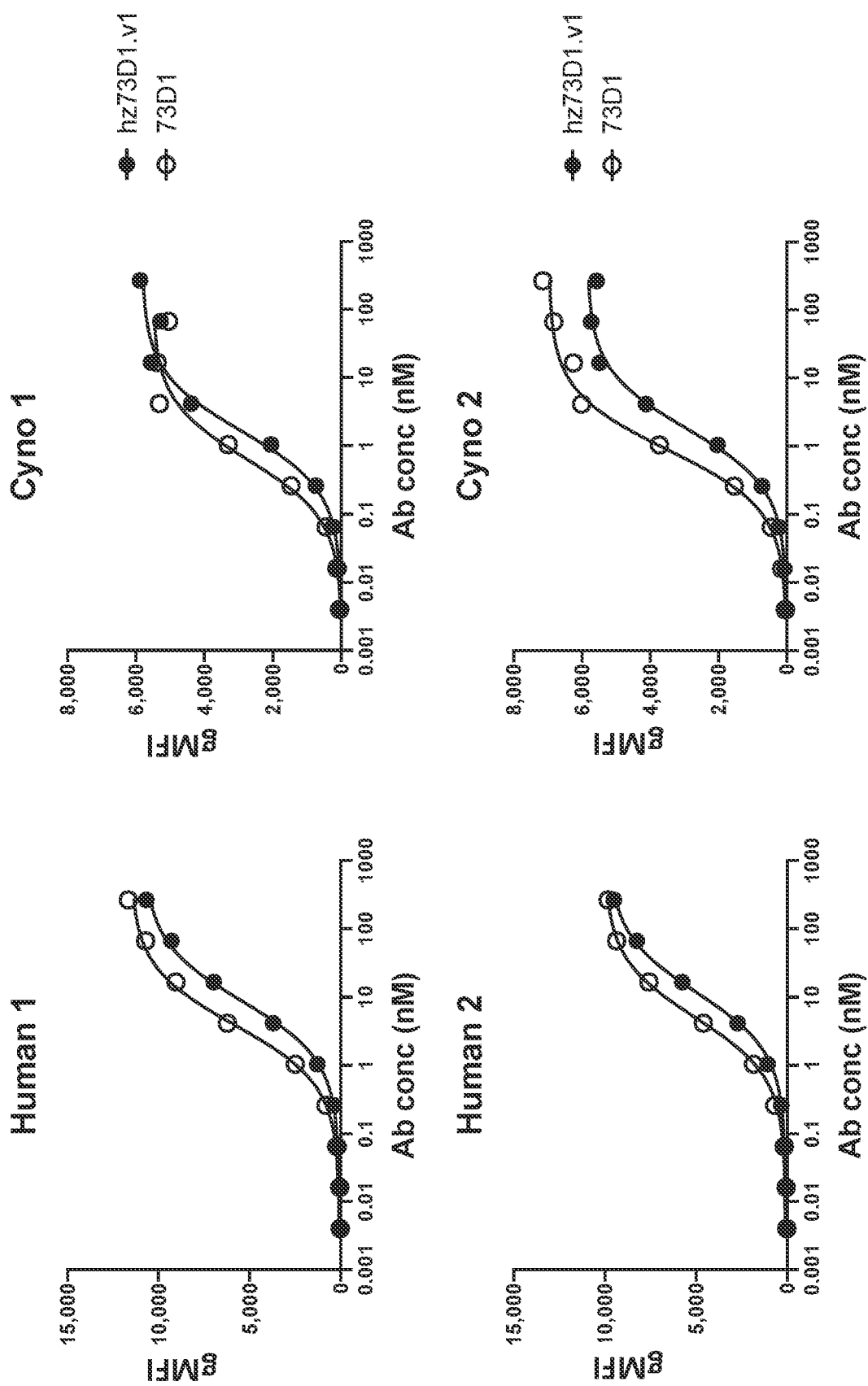
FIG. 3. Binding of anti-ILT2/ILT4 antibodies to monocytes.

The binding of anti-ILT2/ILT4 antibodies to monocytes was evaluated. The binding of exemplary anti-ILT2/ILT4 antibody 73D1 and the humanized version Hz73D1.v1 to the CD14+ monocyte population of human and cyno PBMC were determined by flow cytometry analysis. Briefly, human or cyno PBMCs (from 2 donors each) were thawed, washed in media (RPMI, 10% FBS, L-glutamine, pen/strep), and resuspended in fresh media. PBMCs were stained with a cocktail of labeled antibodies to differentiate between the different cell types. $1 \times 10^6$ cells/well were stained with fluorescently-labelled 73D1 or Hz73D1.v1 antibody and incubated on ice. The cells were washed with ice-cold reagents and immediately analyzed by flow cytometry. The geometric mean fluorescence intensity for CD14+ monocytes was calculated for each sample. As shown in FIG. 3, an increase in fluorescence was observed at increasing concentrations of antibodies 73D1 and Hz73D1.v1 in both human cells and cyno cells. Furthermore, binding of the antibodies to human cells and cyno cells was comparable. For example, the 50% effective concentration (EC50) of Hz73D1.v1 was 8.8 nM with human monocytes and 1.8 nM with cyno monocytes. Cells stained with a control antibody showed no shift in fluorescence. These results demonstrate that anti-ILT2/ILT4 antibodies recognize ILT2 and/or ILT4 on intact cells, i.e., primary monocytes. Importantly, these results show that there is comparable binding to both human and cyno monocytes, suggesting that monkeys will be a suitable model for future studies. Further, no binding of anti-ILT2/ILT4 antibodies described herein was observed to monocytes and other immune cells from rat and mouse, confirming that rodents are not an appropriate species for nonclinical testing.

In addition to binding to ILT2 and ILT4, anti-ILT2/ILT4 antibodies show cross-reactivity with LILRA1, but not with ILLRB3, ILLRB4, ILLRB5, ILLRA2, ILLRA4, ILLRA5, and ILLRA6. Binding of anti-ILT2/ILT4 antibodies to ILT family members was evaluated by fluorescent-activated cell sorting (FACS) using 293T cells expressing human and cynomolgus monkey ILT2, ILT4, LILRA1, ILLRB3, ILLRB4, ILLRB5, ILLRA2, ILLRA4, ILLRA5, and ILLRA6 respectively. The binding affinities of an exemplary anti-ILT2/ILT4 antibody Hz73D1.v1 to human ILT2, human ILT4, human LILRA1, and cyno LILRA1 expressed on 293T cells and measured by flow cytometry are shown to be 1.2 nM, 1.4 nM, 2.64 nM and 1.97 nM respectively.

Example 9

Inhibition of the Interaction Between ILT2 or ILT4 and MHC I Molecules by Anti-ILT Antibodies The ability of anti-ILT2/ILT4 antibodies to inhibit the interaction between ILT2 and/or ILT4 and MHC I molecules was evaluated using a reporter cell system. The Raji cell line was established over 50 years ago from a Burkitt lymphoma and has been shown to express MHC I and WIC II molecules. The lymphoblastoid cell line (LCL) 721.221 is a mutant of parent LCL 721, wherein LCL 721.221 does not express any MHC I molecules. LCL 721.221 cells were transfected with the non-classical WIC I molecule HLA-G and a stable cell line was established, referred to herein as 721.221-HLA-G. Raji cells or 721.221-HLA-G cells were co-cultured with cells expressing a stable reporter system and a cell surface receptor of interest ("reporter cells"). In this chimeric receptor system, the extracellular domain of the receptor of interest (e.g., ILT2 or ILT4) is fused with the transmembrane/intracellular domain of PILRβ that associates with the adaptor protein DAP12. When the chimeric receptor (e.g., ILT2 or ILT-4) is activated by binding to a ligand (e.g., MHC I molecule), DAP12 becomes phosphorylated and activates an NFAT-responsive promoter which drives GFP expression (see, e.g., Deng et al., 2014, Blood, 124:924-935).

ILT2 and ILT4 reporter cells (expressing human ILT2 or human ILT4) were stained with CellTracker Deep Red (ThermoFisher) to distinguish them from Raji or 721.221-HLA-G cells upon analysis. Reporter cells were washed after staining and resuspended at $1\times10^6$ cells/ml in X-VIVO™ 15 media (Lonza). Raji cells or 721.221-HLA-G cells were washed and resuspended in X-VIVO™ 15 media at 1'$10^6$ cell/ml. For assays with Raji cells: anti-ILT2 antibody 27F9, anti-ILT4 antibody 48A5, anti-ILT2/ILT4 antibody 73D1 and Hz73D1.v1, and a control antibody were serially diluted and 50 µl was added to each well of a 96-well flat-bottom cell culture plate. For assays with 721.221-HLA-G cells: anti-ILT4 antibody 48A5, anti-ILT2/ILT4 antibody Hz73D1.v1, and a control antibody were serially diluted and 50 µl was added to each well of a 96-well flat-bottom cell culture plate. ILT2-expressing or ILT4-expressing reporter cells (100 µl/well) were co-cultured with Raji cells or 721.221-HLA-G cells (100 µl/well). The plates were incubated overnight at 37° C. The next day, reporter cells were assayed for GFP expression by FACS.

Figure 4A:
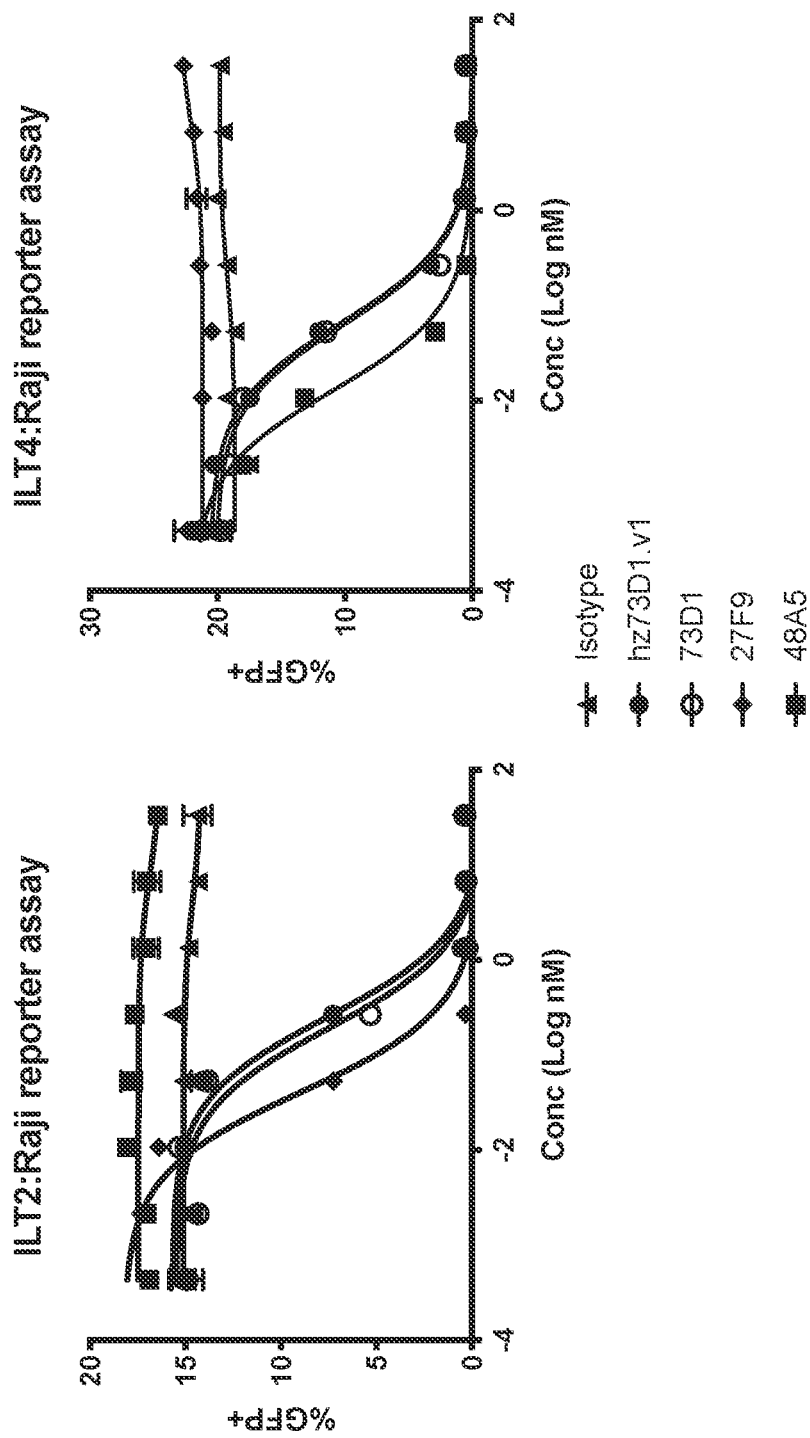
FIGS. 4A and 4B. Inhibition of the interaction between human ILT2 or ILT4 and MHC I molecules by anti-ILT antibodies.
Figure 4B:
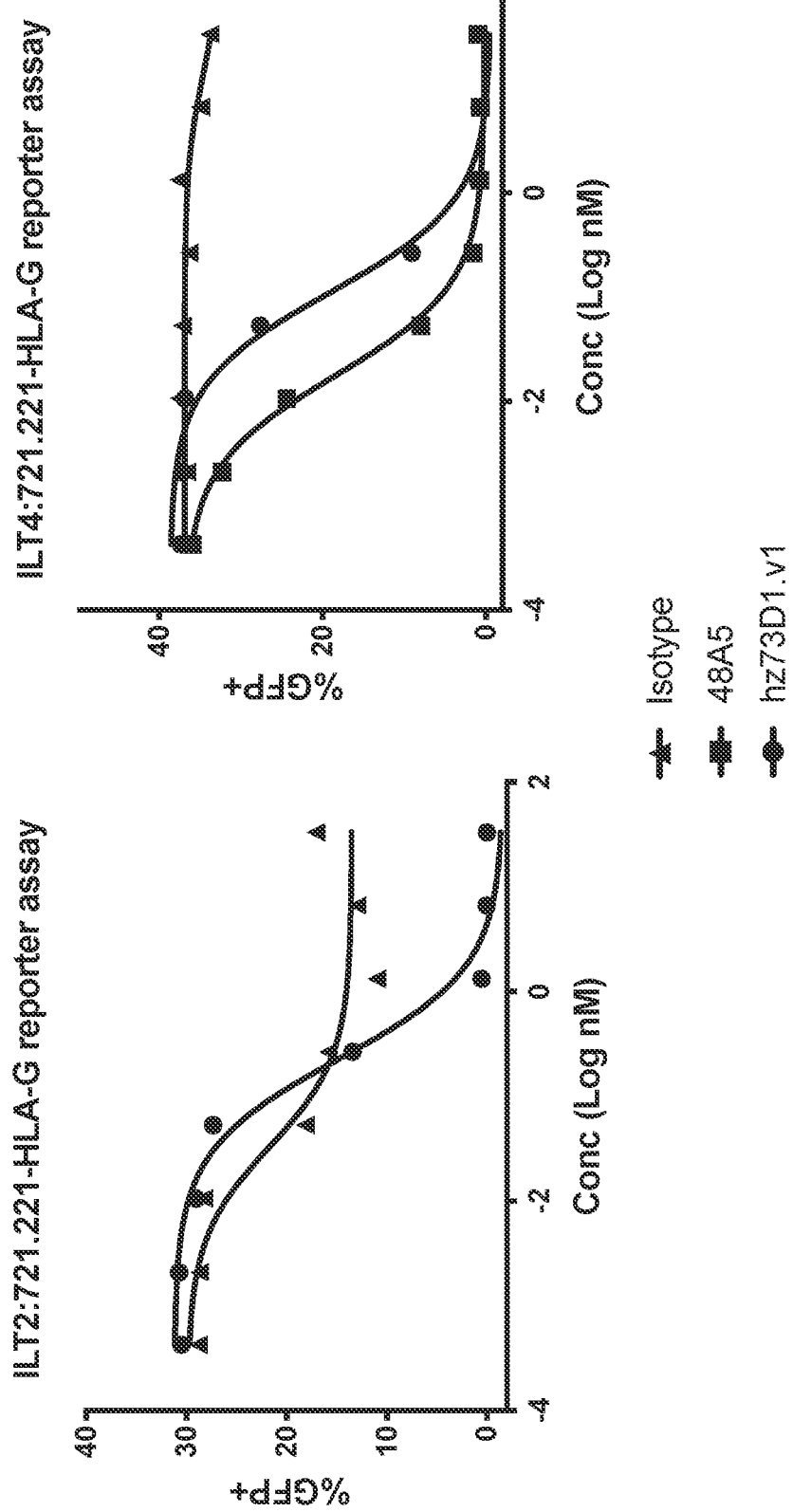

As shown in FIG. 4A, expression of GFP was induced when ILT2 or ILT4 was expressed on the surface of the reporter cells in the presence of Raji cells. With reporter cells expressing ILT2 on their cell surface, an increasing concentration of anti-ILT2 antibody 27F9 and anti-ILT2/ILT4 antibody 73D1 or Hz73D1.v1 was observed to inhibit GFP expression in a dose-dependent manner (expressed as the % GFP-positive cells). Anti-ILT4 antibody was seen to have no inhibitory effect. Similarly, with reporter cells expressing ILT4 on their cell surface, an increasing concentration of anti-ILT4 antibody 48A5 and anti-ILT2/ILT4 antibody 73D1 or Hz73D1.v1, was observed to inhibit GFP expression in a dose-dependent manner and the anti-ILT2 antibody had no effect. As shown in FIG. 4B, expression of GFP was induced when ILT2 or ILT4 was expressed on the surface of the reporter cells in the presence of 721.221-HLA-G cells. With reporter cells expressing ILT2 on their cell surface, an increasing concentration of anti-ILT2/ILT4 antibody Hz73D1.v1 was observed to inhibit GFP expression in a dose-dependent manner. With reporter cells expressing ILT4 on their cell surface, an increasing concentration of anti-ILT4 antibody 48A5 and anti-ILT2/ILT4 antibody Hz73D1.v1 was observed to inhibit GFP expression in a dose-dependent manner. Table 14 shows $IC_{50}$ of Hz73D1.v1 for blocking the interaction of human ILT2, human ILT4, and cyno ILT2 with MHC I molecules on Raji cells. Table 15 shows $IC_{50}$ of Hz73D1.v1 for blocking the interaction of human ILT2, human ILT4 with HLA-G expressed on 721.221 cells.

TABLE 14

| Reporter Construct | Raji Cell $IC_{50}$ (nM) |
|---|---|
| Human ILT2 | 0.25 |
| Human ILT4 | 0.066 |
| Cyno ILT2 | 0.094 |

TABLE 15

| Reporter Construct | 721.221-HLA-G $IC_{50}$ (nM) |
|---|---|
| Human ILT2 | 0.23 |
| Human ILT4 | 0.26 |

These results show that anti-ILT2 or anti-ILT2/ILT4 antibodies are able to inhibit and/or block the functional interaction between ILT2 and classical MHC I molecules to a high level. In parallel, these results show that anti-ILT4 or anti-ILT2/ILT4 antibodies are able to inhibit and/or block the functional interaction between ILT4 and classical and non-classical MHC I molecules (e.g., HLA-G) to a high level. These results support the idea that an antibody that binds ILT2 and ILT4 would modulate pathways induced by both of these molecules. Therefore, an anti-ILT2/ILT4 antibody may be a stronger therapeutic agent than an antibody that targets only ILT2 or only ILT4.

An additional study was undertaken with reporter cells expressing cyno ILT2. As described above, cyno ILT2 reporter cells were stained with CellTracker Deep Red, washed, and resuspended at $1\times10^6$ cells/ml in X-VIVO™ 15 media (Lonza). Raji cells were washed and resuspended in X-VIVO™ 15 media at $1\times10^6$ cell/ml. Anti-ILT2/ILT4 antibody 73D1 and Hz73D1.v1 and a control antibody were serially diluted and 50 µl was added to each well of a 96-well flat-bottom cell culture plate. ILT2-expressing reporter cells (100 µl/well) were co-cultured with Raji cells (100 µl/well). The plates were incubated overnight at 37° C. The next day, reporter cells were assayed for GFP expression by FACS.

Figure 5:
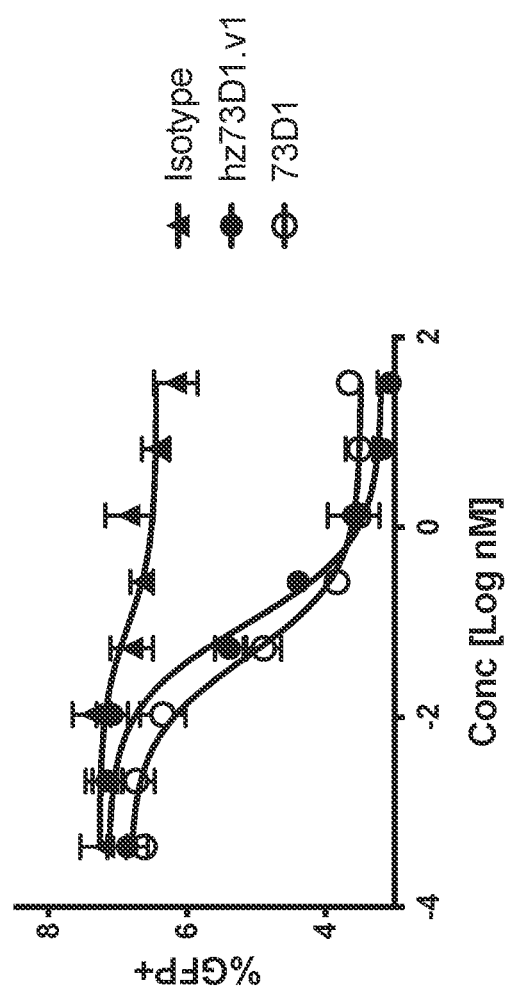
FIG. 5. Inhibition of the interaction between cyno ILT2 and MHC I molecules by anti-ILT antibodies.

As shown in FIG. 5, expression of GFP was induced when cyno ILT2/4 was expressed on the surface of the reporter cells in the presence of Raji cells. In the presence of an increasing concentration of anti-ILT2/ILT4 antibody 73D1 or Hz73D1.v1, the percentage of GFP-expressing cells was decreased in a dose-dependent manner. Table 14 shows $IC_{50}$ of Hz73D1.v1 for blocking the interaction of cyno ILT2 with MHC I molecules on Raji cells. These results are further evidence that monkeys would be a good model for testing.

In addition to the reporter cell system, the inhibitory activity of anti-ILT2/ILT4 antibodies towards the interaction between ILT2 and MHC I molecules, and the interaction between ILT4 and MHC I molecules was evaluated using the Biacore system. Human ILT2-Fc and ILT4-Fc were used as target receptors and their interaction with an exemplary MHC-I molecule (HLA-A) was assayed in the presence or absence of an exemplary anti-ILT2/ILT4 antibody Hz73D1.v1 at 25° C. Anti-human ILT2 (clone 27F9) or ILT4 (clone 48A5) antibodies were used as tool reagents to dissect ILT2- and ILT4-specific blocking activities. Anti-IL2/ILT4 antibodies produced a dose-dependent reduction in the interaction between ILT2 and HLA-A, as well as between ILT4 and HLA-A. IC50s of the antibodies tested are shown in Table 16.

TABLE 16

| Antibody | ILT2 $IC_{50}$ (nM) | ILT4 $IC_{50}$ (nM) |
|---|---|---|
| Hz73D1.v1 | 10 ± 0.36 | 9.4 ± 0.34 |
| 48A5 (ILT4 specific) | No blocking | 8.4 ± 0.46 |
| 27F9 (ILT2 specific) | 8.9 ± 0.37 | No blocking |

Example 10

Effect of Anti-ILT Antibodies on Activity of NK Cells

NKL is a human natural killer (NK) cell line established from the peripheral blood of a patient with large granular lymphocyte (LGL) leukemia and kindly provided by Dr. Louis Lanier. As disclosed herein, NK cells express ILT2 but generally do not express ILT4. 721.221 cells were transfected with plasmids expressing either HLA-G or HLA-A*0201 and high-expressing pools were enriched by antibiotic selection, generating 721.221-HLA-G and 721.221-A*0201 cell lines. 721.221-HLA-G cells (described herein) or 721.221-HLA-A*0201 cells are used as targets in cytolytic cell assays. The target cells were labeled with CellTracker Deep Red (ThermoFisher) to distinguish them from NKL cells (after co-culture) and then resuspended at $5 \times 10^5$ cells/ml in assay media (RPMI with 10% FBS, penicillin/streptomycin, L-glutamine, 5% human serum and recombinant human IL-2 (rhIL-2) at 20 ng/ml). NKL cells were suspended at $7.5 \times 10^6$ cells/ml in assay media. Serial dilutions of anti-ILT2 antibody 27F9, anti-ILT4 antibody 48A5, anti-ILT2/ILT4 antibodies 73D1 or Hz73D1.v1, and a control isotype antibody were prepared in assay media and 50 µl was added to wells of a V-bottom 96-well plate. NKL cells (50 µl) were added to each well, followed by target cells (50 µl), resulting in a target to NK ratio of 1:15. Plates were cultured for 3.5 hours at 37° C. followed by centrifugation at 360×g for 8 minutes at room temperature and removal of media. Cells were then resuspended in PBS containing a 1:1,000 dilution of Sytox Blue (ThermoFisher). Sytox Blue will stain cells with compromised cell membranes allowing live cells to be distinguished from dead or damaged cells. Cells were analyzed by FACS and the percent target cell killing was calculated based on the value of a positive control well of target cells permeabilized with detergent (100% lysis).

Figure 6:
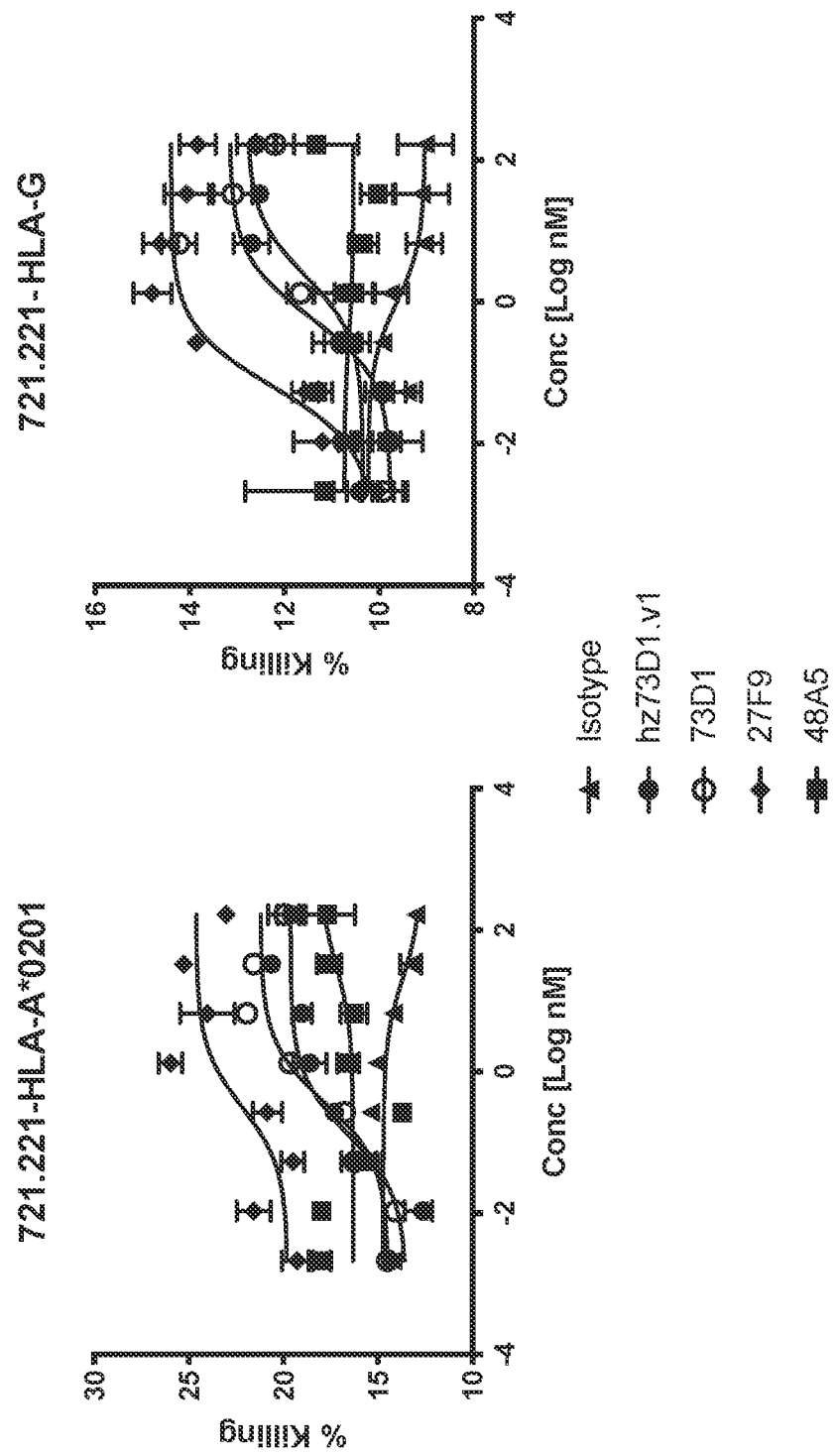
FIG. 6. Effect of anti-ILT antibodies on cytolytic activity of NKL cells.

As shown in FIG. 6, anti-ILT2 antibody 27F9 and anti-ILT2/ILT4 antibodies 73D1 and Hz73D1.v1 enhanced NK cytolytic activity in a dose-dependent manner. $EC_{50}$ values for Hz73D1.v1 were 2.4 nM for HLA-G expressing target cells and 0.13 nM for HLA-A*0201 expressing target cells. In comparison, $EC_{50}$ for 27F9 was 0.064 nM for HLA-G expressing target cells. Anti-ILT4 antibody 48A5 had little to no effect on NK cell activity. These results show that anti-ILT2 antibodies and anti-ILT2/ILT4 antibodies are able to block the functional interaction between ILT2 on NK cells and MHC I molecules on the surface of target cells, leading to the enhancement of cytolytic activity. This supports the theory that anti-ILT2/ILT4 antibodies could enhance killing of tumor cells by inhibiting ILT2-induced suppression of NK cells.

Similar experiments were undertaken using human primary NK cells. Briefly, NK cells were isolated from PBMC by negative selection, washed in assay media (RPMI with 10% FBS, pen/strep, 5% human serum, rhIL-2 (40 ng/ml), and IL-15 (50 ng/ml)), and resuspended at $7.5 \times 10^6$ cells/ml in assay media. 721.221-HLA-G target cells were labeled with CellTracker Deep Red (ThermoFisher) and resuspended at $5 \times 10^5$ cells/ml in assay media. Target cells and NK cells (50 µl each) were combined in each well of a V-bottom plate. Anti-ILT2 antibody 27F9, anti-ILT4 antibody 48A5, or anti-ILT2/ILT4 antibodies 47H6, 73D1, or 64A12 were added to wells at a final concentration of 1 µg/ml. Plates were cultured overnight at 37° C. followed by centrifugation at 360×g for 8 minutes at room temperature and removal of media. Cells were then resuspended in PBS containing a 1:1,000 dilution of Sytox Blue (ThermoFisher). Cells were analyzed by FACS and the percent target cell killing was calculated based on the value of a positive control well of target cells permeabilized with detergent (100% lysis).

Figure 7:
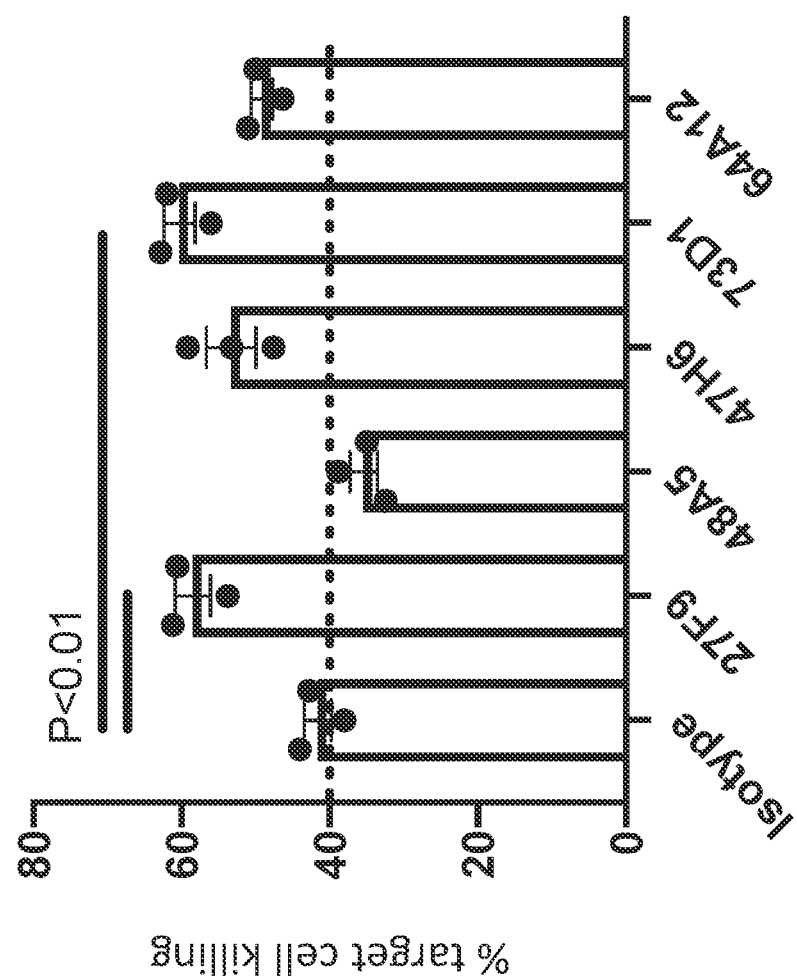
FIG. 7. Effect of anti-ILT antibodies on activity of human primary NK cells.

As shown in FIG. 7, the presence of anti-ILT2 antibody 27F9 or anti-ILT2/ILT4 antibodies 47H6, 73D1, and 64A12, enhanced killing by primary NK cells. In agreement with other experiments described herein, these results show that ILT2 mediates suppression of primary NK cells and this suppression can be reversed with antagonist antibodies inhibiting or blocking ILT2/MHC I interactions.

Figure 8:
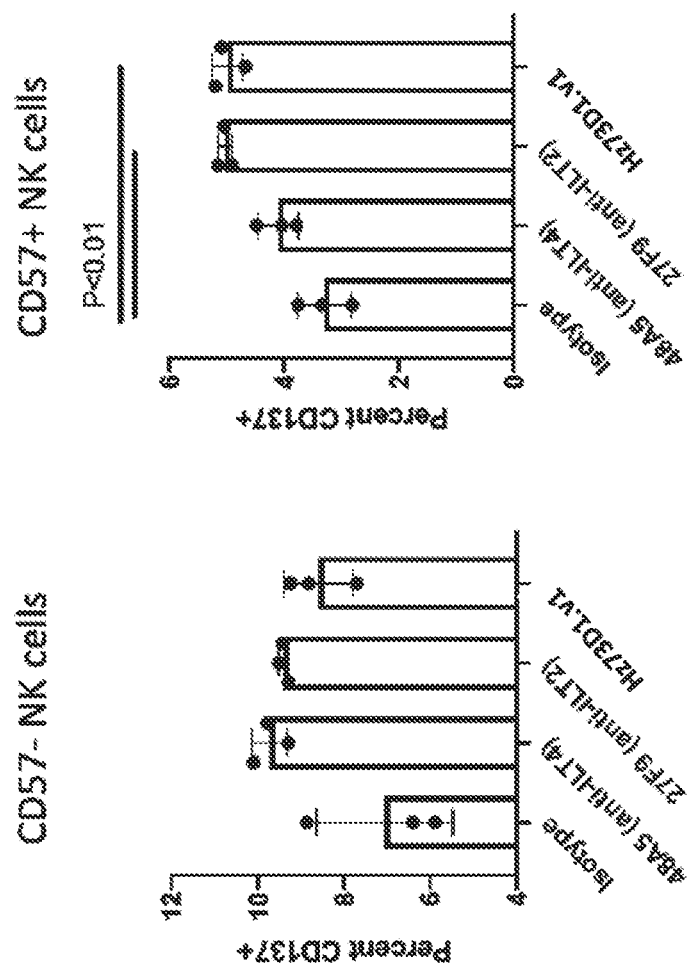
FIG. 8. Effect of anti-ILT antibodies on cytolytic activity of primary NK cells.

Further experiments were performed to evaluate NK cell cytolytic activity via analysis of CD137 expression, a marker that is upregulated on NK cells during cytolysis. NK cells were isolated from PBMC and cultured with a K562 cell line transfected to express the non-classical MHC-I molecule HLA-G. NK cell cytolytic activity was evaluated by FACS analysis of expression of activation marker CD137, gating on the CD3 negative, CD56 positive NK population. CD57 staining was performed to enrich for memory (adaptive) NK cells known to preferentially express ILT2 (Lopez-Vergès S et al, *Proc. Natl. Acad. Sci.* (2011), 108 (36) 14725-14732). CD137 is upregulated on NK cells during cytolysis, providing a surrogate measure of cell killing. Hz73D1.v1 or anti-ILT2 (27F9), but not anti-ILT4 (48A5), significantly increased the CD137+ population (FIG. 8). This effect was most pronounced in the CD57+ memory NK cell population. These data suggest that anti-IL2/ILT4 antibodies are able to block the interaction of ILT2 on primary NK cells with MHC-I on target cells, leading to enhanced activation and cytolytic activity.

Figure 9:
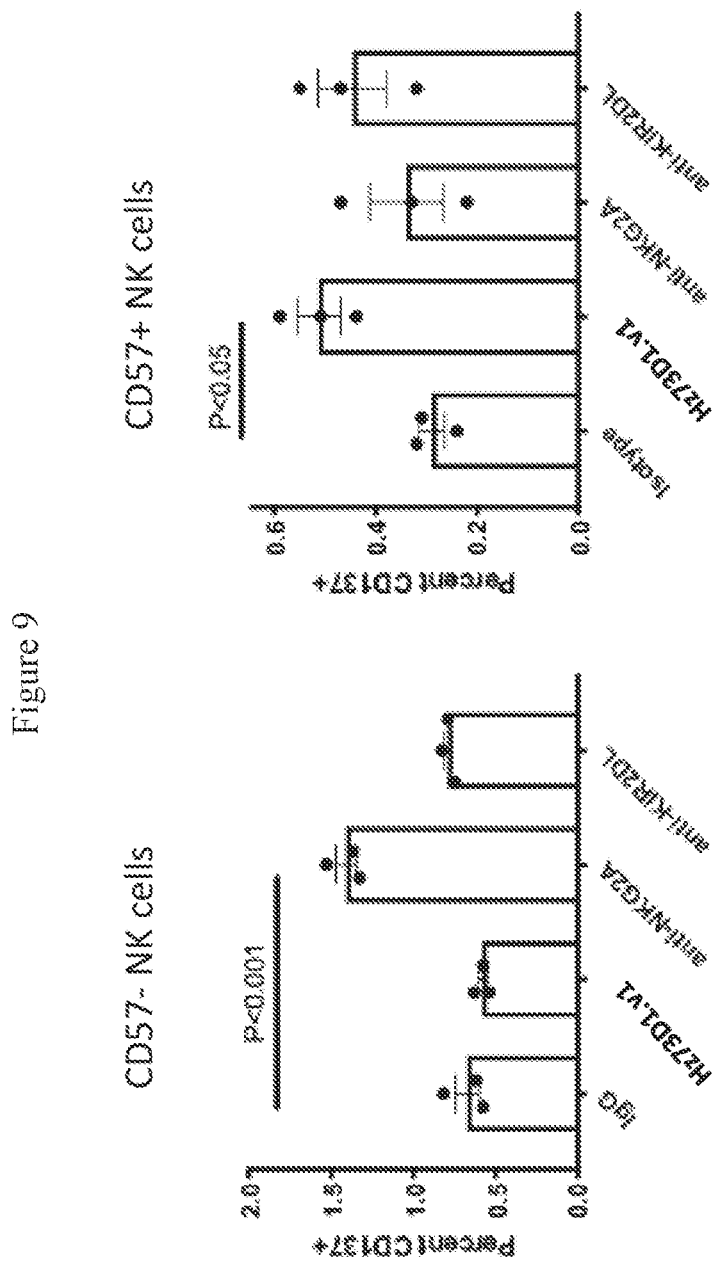
FIG. 9. Effect of anti-ILT antibodies on cytolytic activity of primary NK cells in ADCC assay with classic MHC-I-expressing target cells.

To evaluate activity of anti-IL2/ILT4 antibodies on killing of target cells naturally expressing HLA-A/B/C (classic MHC-I), an antibody dependent cellular cytotoxicity (ADCC) assay was performed. NK cells were isolated from PBMC and cultured with the CAL-27 squamous cell carcinoma cell line which expresses high levels of HLA-A, HLA-B, HLA-C and the NKG2A ligand HLA-E (data not shown). Anti-EGFR antibody was added to induce ADCC of these EGFR+ CAL-27 cells. CD137 was upregulated on NK cells during cytolysis, providing a surrogate measure of cell killing. Hz73D1.v1 or anti-ILT2 27F9, but not anti-ILT4 48A5, significantly increased the percent CD137+ NK cells in the CD57+ population (FIG. 9). By comparison, an anti-NKG2A antibody significantly increased percent CD137+ in the CD57−, but not the CD57+ population. Both antibodies induced a comparable fold increase in activation (Hz73D1.v1 increased percent CD137+ cells 1.8-fold while anti-NKG2A antibody increased percent CD137+ cells 2.1-fold). An anti-KIR2DL antibody showed no activity in this assay. These data suggest that anti-ILT2/ILT4 antibodies are able to block the interaction of ILT2 on primary NK cells with classic MHC-I on target cells, leading to enhanced activation and cytolytic activity of NK cells.

Example 11

Effect of Anti-ILT Antibodies on MDSC Activity in MLR Assay

Myeloid-derived suppressor cells (MDSC) have been shown to be critical in regulating immune responses by suppressing antigen presenting cells (APC) and T-cells. Furthermore, they have been observed to have a negative effect on anti-tumor activity by immune cells. The effect of anti-ILT antibodies on MDSC activity was investigated using a mixed lymphocyte reaction assay (MLR). To generate MDSC-like cells, human peripheral monocytes were grown in pre-conditioned X-VIVO™ 15 media (Lonza). Pre-conditioned media is generated by culture with the OVISE cell line. The OVISE cell line is an ovarian clear cell adenocarcinoma which secretes a large number of factors into its growth media. Monocytes were cultured in media consisting of 50% OVISE-conditioned media and 50% fresh X-VIVO™ 15 for 5 days; the resulting MDSC-like cells are referred to as ovMDSCs. These MDSC-like cells show MDSC functional characteristics, including increased Arg1 and IDO and suppression of T cell proliferation and pro-inflammatory cytokines in MLR (Mixed Lymphocyte Reaction) assays when compared to monocyte derived dendritic cells (data not shown). As a positive control for the assays, monocyte-derived dendritic cells (moDC) were generated by culture of human peripheral monocytes with GM-CSF and IL-4 for 5 days. To perform the MLR assay, $1\times10^5$ allogeneic T-cells were co-cultured with $2.5\times10^4$ ovMDSCs or moDCs in a 96-well round bottom cell culture plate. The cells were co-cultured in the presence of anti-ILT2 antibody 27F9, anti-ILT4 antibody 48A5, anti-ILT2/ILT4 antibodies 47H6 or 73D1, or an isotype control antibody (each at 10 μg/ml). Controls included T-cells only, moDCs only, moDCs with T-cells (positive MLR), ovMDSCs only, and ovMDSCs with T-cells. Cells were incubated at 37° C. and after 5 days 50 μl of media containing $^3$H-Thymidine was added to each well. After 18 hours of incubation, the cells from each well were harvested and analyzed for thymidine incorporation as a marker for proliferation, and the supernatants were analyzed for cytokine secretion by multiplex bead array.

Figure 10:
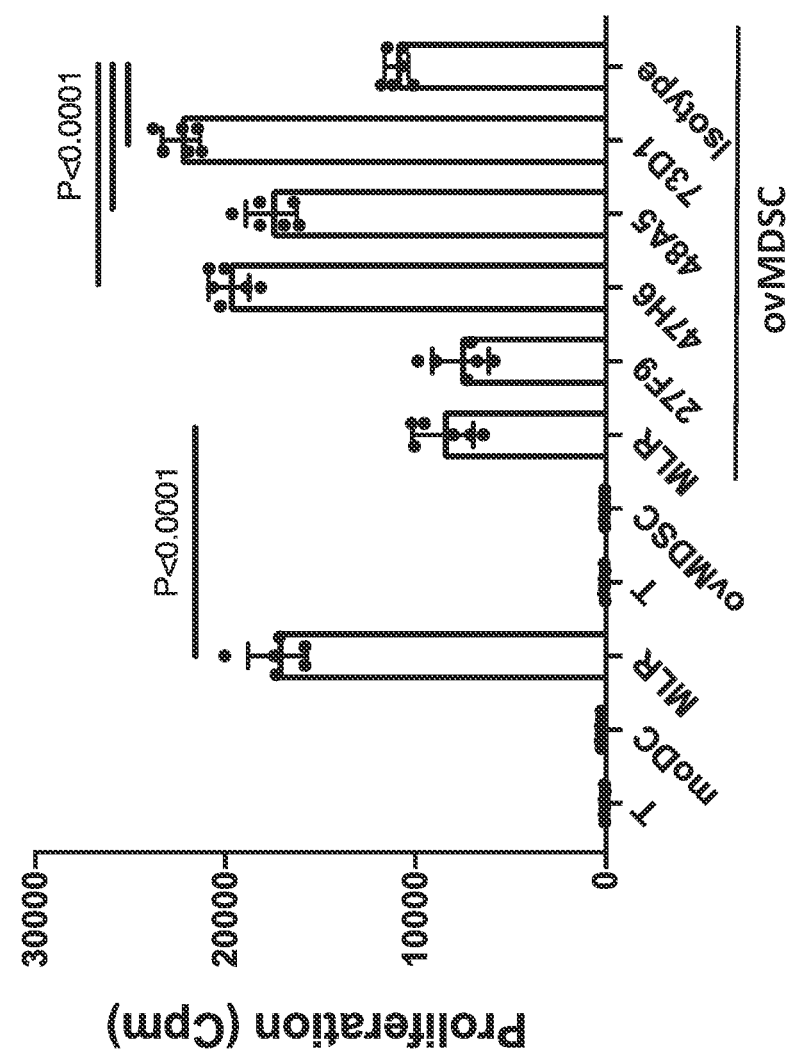
FIG. 10. Effect of anti-ILT antibodies on MDSC activity in MLR assay.

As shown in FIG. 10, T-cell proliferation was suppressed by co-culture with ovMDSCs. The presence of anti-ILT4 antibody 48A5 and anti-ILT2/ILT4 antibodies 47H6 and 73D1 increased proliferation of T-cells cultured with ovMDSC to a level equivalent to the MLR response of T-cells with moDCs. Anti-ILT2 antibody 27F9 showed no ability to enhance T-cell proliferation.

Another MLR assay was set up wherein $1\times10^5$ allogeneic T-cells were co-cultured with $2.5\times10^4$ ovMDSCs in a 96-well round bottom cell culture plate. The cells were co-cultured in the presence of serial dilutions of anti-ILT2 antibody 27F9, anti-ILT4 antibody 48A5, anti-ILT2/ILT4 antibodies 73D1 or Hz73D1.v1, or a control isotype antibody. Cells were incubated at 37° C. and after 5 days 50 μl of supernatant was harvested from each well for cytokine analysis using a Luminex system. Subsequently, 50 μl of media containing $^3$H-Thymidine was added to each well. After 18 hours of incubation, the cells from each well were harvested and analyzed for thymidine incorporation.

Figure 11A:
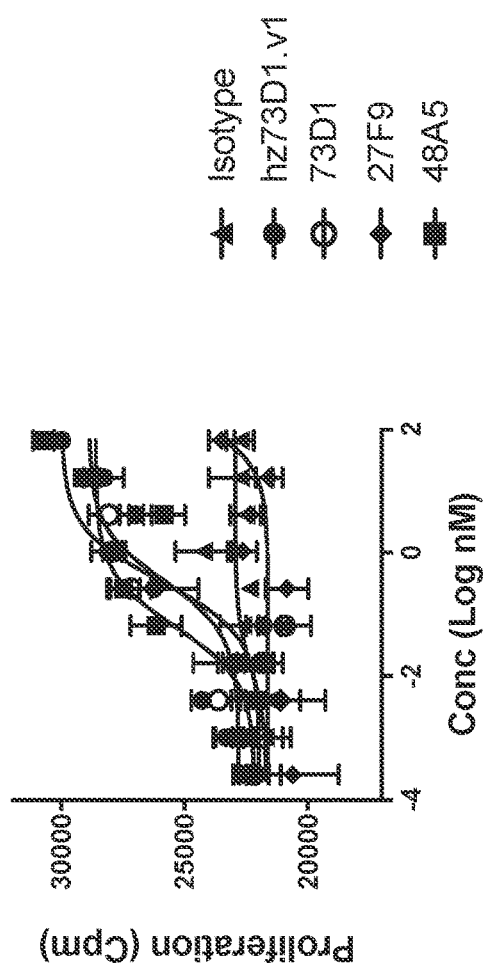
FIG. 11A-11C. Effect of anti-ILT antibodies on MDSC activity in MLR assay.
Figure 11C:
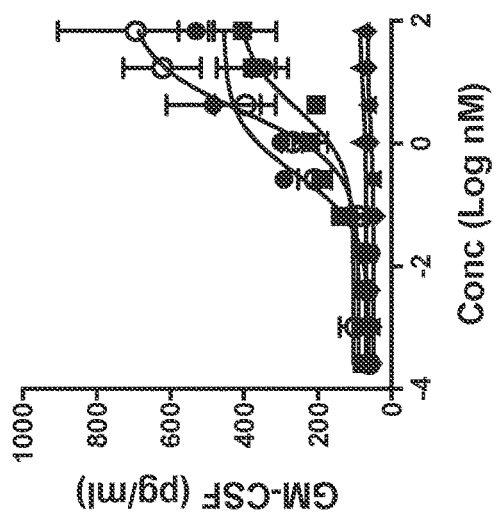
Figure 11B:
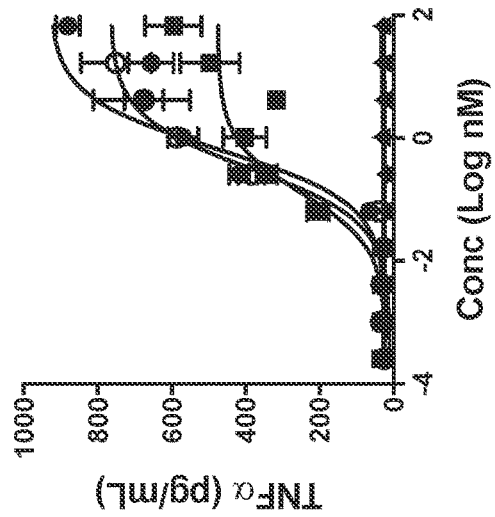

Similar to results described above, anti-ILT4 antibody 48A5 and anti-ILT2/ILT4 antibodies 73D1 and Hz73D1.v1 were shown to increase T-cell proliferation (FIG. 11A). In addition, it was determined that TNF-α secretion and GM-CSF secretion were increased in a dose-dependent manner in the presence of anti-ILT4 and anti-ILT2/ILT4 antibodies (FIG. 11B-11C). As in the previous experiment, no effect was seen with anti-ILT2 antibodies.

These results show that anti-ILT4 and anti-ILT2/ILT4 antibodies are able to inhibit and/or block the functional interaction between ILT4 on MDSCs and MHC I molecules on neighboring cells (e.g., APCs), leading to the reversal of MDSC suppression and the enhancement of T-cell activation. The reversal of MDSC-induced suppression also appears to lead to the increased secretion of pro-inflammatory cytokines such as TNF-α and GM-CSF.

Example 12

Effect of Anti-ILT2/4 Antibodies on LPS-Mediated Stimulation of Cells

Lipopolysaccharide (LPS) stimulates innate immune responses on myeloid cells via toll-like receptors 2 and 4 (TLR2 and TLR4). To determine whether anti-ILT2 and/or anti-ILT4 antibodies can enhance LPS-mediated stimulation, a PBMC/LPS assay was performed. Briefly, frozen human PBMCs were thawed, washed in media (RPMI with 10% FBS, L-glutamine and pen/strep) and counted. Anti-ILT2 antibody 27F9, anti-ILT4 antibody 48A5, anti-ILT2/ILT4 antibodies 73D1 and Hz73D1.v1, and a control isotype antibody were serially diluted in media and 50 μl added to each well of a 96-well round bottom tissue culture plate. PBMCs were added at $1\times10^6$ cells/ml in a volume of 100 μl and the plate was incubated at 37° C. for 30 minutes. LPS was added in 50 μl of media (final concentration of 30 ng/ml) and the plate were incubated at 37° C. for 2 days. Cell supernatants were removed for analysis of cytokines using a Luminex® system.

Figure 12:
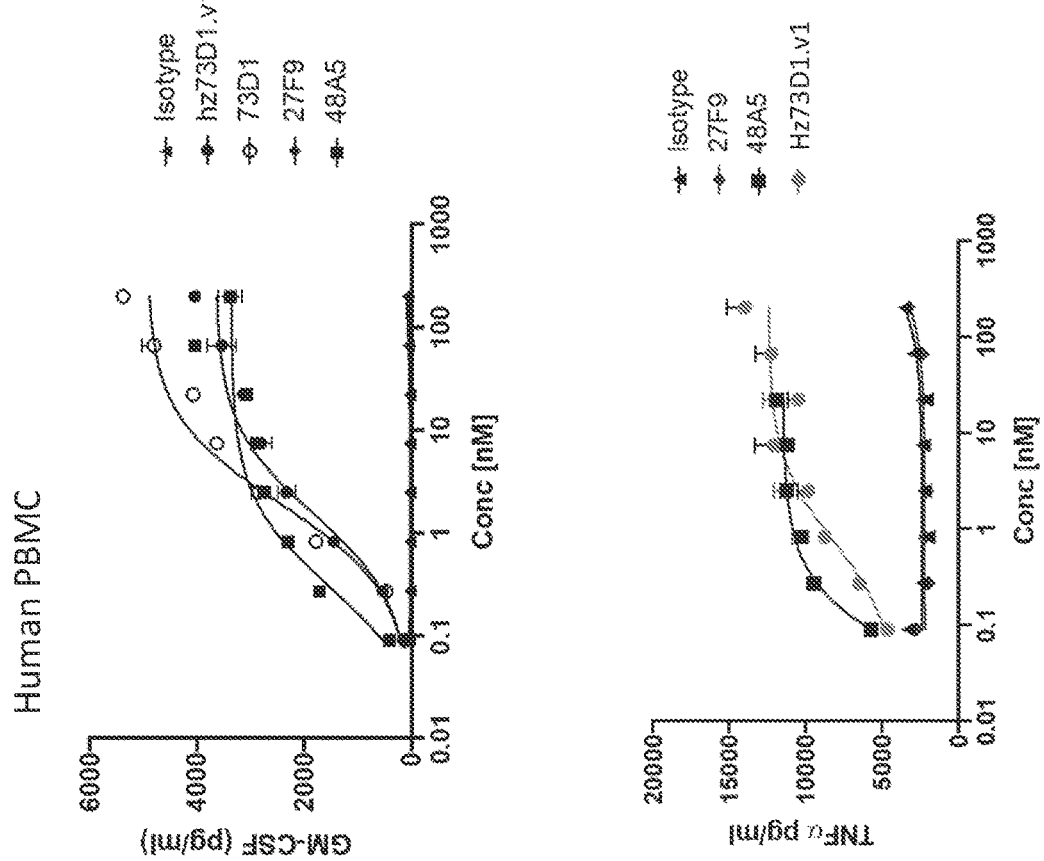
FIG. 12. Effect of anti-ILT antibodies on LPS-mediated stimulation of human PBMCs as assessed by cytokine production.

As shown in FIG. 12, the presence of anti-ILT4 and anti-ILT2/ILT4 antibodies resulted in the increased production of GM-CSF and TNFα in a dose-dependent manner. For example, the $EC_{50}$ values of Hz73D1.v1 were 0.76 nM for TNFα secretion and 1.5 nM for GM-CSF secretion. Anti-ILT2 antibody 27F9 and the control antibody showed little GM-CSF and TNFα secretion (approximately 20-40 pg/ml). These results show that the expression of ILT4 on myeloid cells in the PBMC culture can strongly suppress the production of pro-inflammatory cytokines induced by LPS, and importantly, that the suppression can be reversed by inhibiting and/or blocking ILT4/MHC I interactions.

A similar experiment was set up using cyno PMBCs. Briefly, cyno PBMCs were washed in media (RPMI with 10% FBS, L-glutamine and pen/strep) and counted. Anti-ILT2/ILT4 antibody Hz73D1.v1 or a control antibody was serially diluted in media and 50 μl added to each well of a 96-well round bottom tissue culture plate. PMBCs were added at $2\times10^6$ cells/ml in 100 μl and plates were incubated at 37° C. for 30 minutes. LPS was added in 50 μl of media (final concentration of 50 ng/ml) and plates were incubated at 37° C. for 2 days. Cell supernatants were removed for analysis of cytokines using a Luminex® system.

Figure 13:
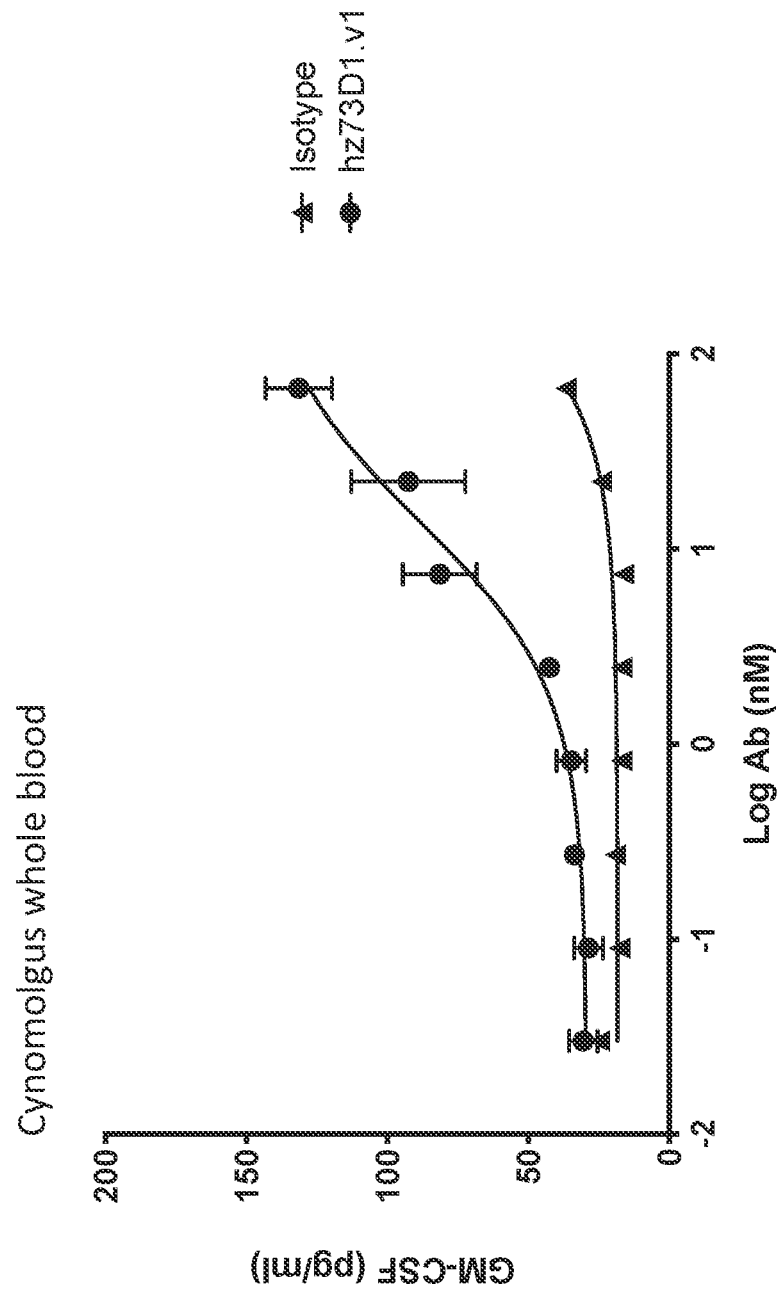
FIG. 13. Effect of anti-ILT antibodies on LPS-mediated stimulation of cyno PBMCs as assessed by cytokine production.

Similar to the results with human PBMCs, anti-ILT2/4 antibody Hz73D1.v1 enhanced GM-CSF secretion from cyno PBMCs (FIG. 13). $EC_{50}$ was determined to be 14 nM. These results show that anti-ILT2/ILT4 antibodies had a similar biological effect on cyno immune cells and human immune cells.

To further evaluate the effect of anti-ILT antibodies on cells involved in suppression of immune responses to tumor cells, a LPS assay with tolerogenic dendritic cells (tolDC) was set up. Briefly, isolated human monocytes were plated onto 10 cm tissue culture dishes at $4\times10^6$ cells/dish in a volume of 20 ml media (X-VIVO™ 15 media (Lonza) supplemented with 50 ng/mL each of recombinant GM-CSF and IL-4 (Peprotech)). The monocytes were incubated for 5-7 days at 37° C. and then the cells were harvested. For the assay, the in vitro generated DCs were suspended in fresh media containing 1:50 dilution of Fc Block (Biolegend) at a concentration of $6\times10^5$ cells/ml. DCs were seeded in 96-well tissue culture plates at 50 μl/well and anti-ILT4 antibody 48A5, anti-ILT2/ILT4 antibody Hz73D1.v1, or a control antibody were added in serial dilutions at 50 μl/well. LPS was added (6 μg/ml final concentration) together with one of a variety of tolerizing agents in a volume of 50 λl media. The tolerizing agents included: vitamin D3/dexamethasone (VitD3/Dex) at 100 nM and 10 nM respectively, cyclosporin A at 750 ng/ml, rapamycin at 100 ng/ml, prostaglandin E2 (PGE2) at 1 µg/ml, IL-6 at 20 ng/ml, IL-10 at 20 ng/ml or TGFα at 20 ng/ml. Plates were incubated at 37° C. for 2 days and supernatants were harvested for analysis using a Luminex® system.

Figure 14:
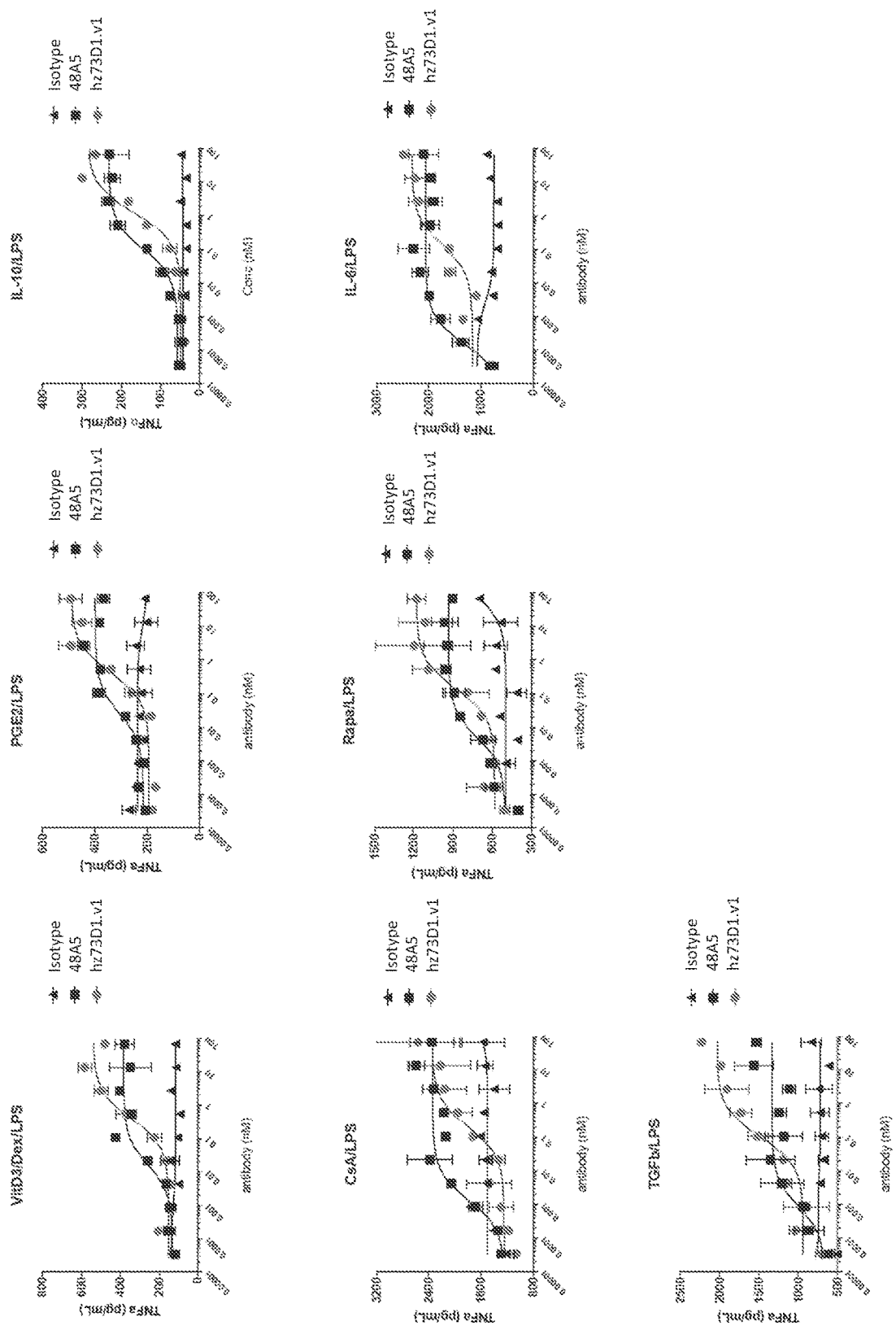
FIG. 14. Effect of anti-ILT antibodies on LPS-mediated stimulation of tolerized dendritic cells as assessed by cytokine production.

As shown in FIG. 14, anti-ILT4 and anti-ILT2/ILT4 antibodies enhanced LPS-mediated cytokine (e.g., TNFα) secretion in a dose-dependent manner. The EC50 values of Hz73D1.v1 induced TNFα secretion in the presence of LPS and an additional tolerizing agent are shown in table 17. In contrast, there was no increase of TNF-α in tolDCs treated with a control antibody and anti-ILT2 antibody (data not shown). These data show that tolDCs present within a patient's tumor would be responsive to reactivation by the presence of anti-ILT4 and/or anti-ILT2/ILT4 antibodies that inhibit or block ILT4 and MHC I molecule interactions.

TABLE 17

| Treatment | VitD3/Dex | PGE2 | IL-10 | Cyclosporine | Rapamycin | IL-6 | TGFβ |
|---|---|---|---|---|---|---|---|
| $EC_{50}$ (nM) | 0.40 | 0.44 | 1.2 | 0.20 | 0.15 | 0.14 | 0.10 |

Example 13

Effect of Anti-ILT Antibodies on HMGB1, STING and/or Anti-CD3 Stimulation of PBMCs High mobility group protein B1 (HMGB1) is a nuclear protein that can be released from cells and binds to TLRs. HMGB1 has been shown to be present at high concentrations in necrotic tumor tissue, providing a potential source of innate stimulation of tumor infiltrating DC, monocytes, and macrophages (see, e.g., Guerriero et al., 2011, *J. Immunol.*, 186:3517-3526). Experiments were designed to determine whether anti-ILT antibodies could enhance pro-inflammatory cytokine secretion from PBMCs treated with HMGB1. Briefly, anti-ILT2 antibody 27F9, anti-ILT4 antibody 48A5, anti-ILT2/ILT4 antibodies 47H6, 73D1 and 64A12, and a control isotype antibody were serially diluted in media and 50 µl added to each well of a 96-well round bottom tissue culture plate. PBMCs were added at 1×10⁶ cells/ml in a volume of 100 µl and the plate was incubated at 37° C. for 30 minutes. Recombinant HMGB1 (Biolegend) was added at a concentration of 2.5 µg/ml (a concentration anticipated to be present in the microenvironment of a tumor) and the plate was incubated at 37° C. for 2 days. Cell supernatants were removed for analysis of cytokines using a Luminex® system.

Figure 15:
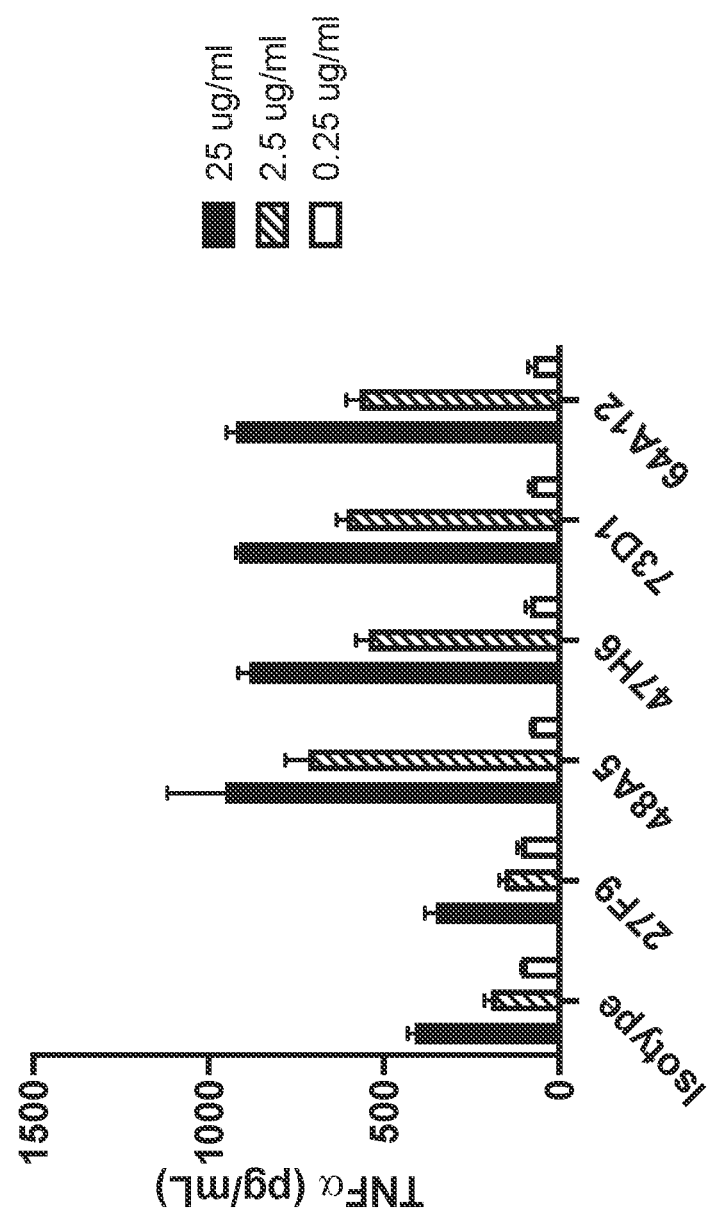
FIG. 15. Effect of anti-ILT antibodies on cytokine production from HMGB1-treated cells.

As shown in FIG. 15, anti-ILT4 antibody 48A5 and anti-ILT2/ILT4 antibodies 47H6, 73D1, and 64A12 enhanced secretion of TNF-α. These data show that anti-ILT4 and anti-ILT2/ILT4 antibodies will enhance the pro-inflammatory function of infiltrating monocytes within a tumor.

Similarly, tumor cell necrosis and/or tumor cell death from radiotherapy results in the release of nuclear DNA. Free nuclear DNA can lead to myeloid cell stimulation via STING (stimulator of interferon genes) signaling. Experiments were designed to determine whether anti-ILT antibodies could enhance inflammatory cytokine production from PBMCs treated with a STING agonist. Briefly, PBMCs were plated in 96-well round bottom tissue culture plates and anti-ILT2 antibody 27F9, anti-ILT4 antibody 48A5, and a control isotype antibody were added. After a 30-minute incubation, STING agonist 2'3'-cGAMP (Invivogen) was added at a concentration of 10 µg/ml (a concentration anticipated to be present in the microenvironment of a necrotic tumor). Cells were incubated for two days and supernatants were analyzed using a Luminex® system.

Figure 16:
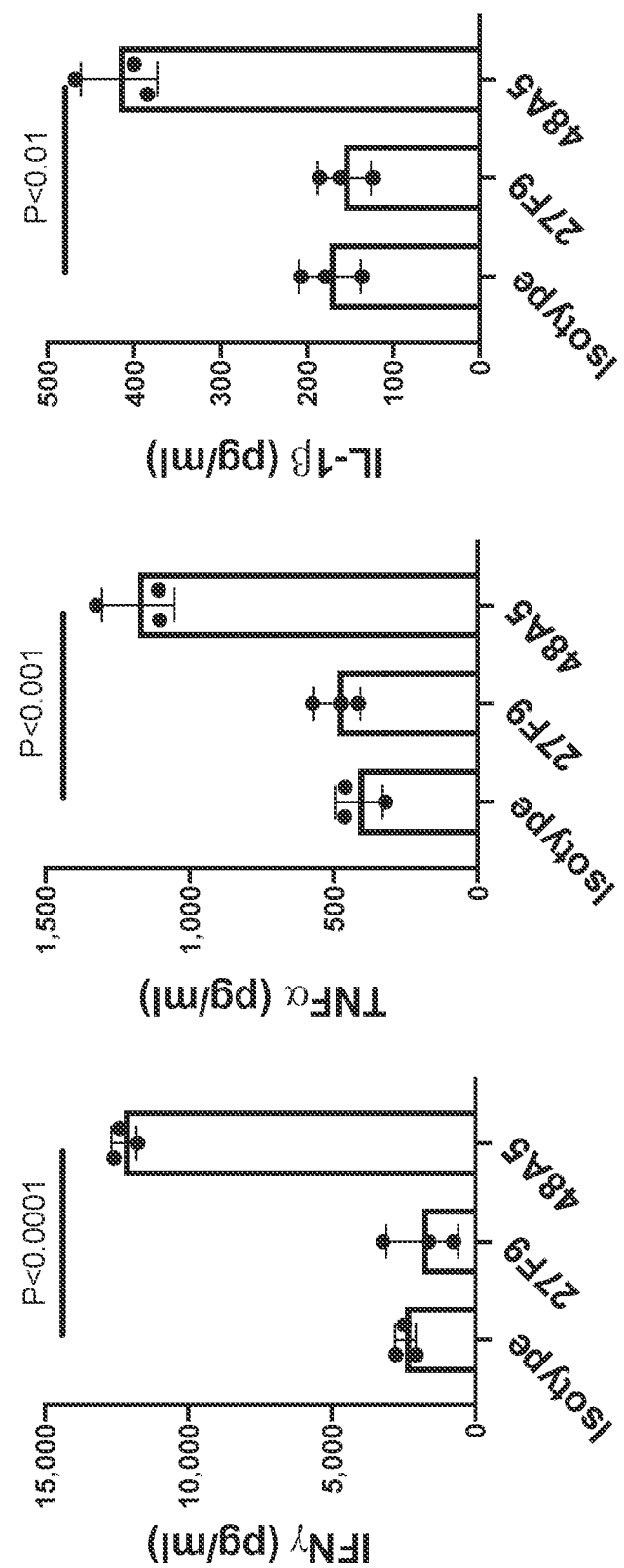
FIG. 16. Effect of anti-ILT antibodies on cytokine production from STING agonist-treated cells.

As shown in FIG. 16, exemplary anti-ILT4 antibody 48A5 enhanced secretion of IFNγ, TNF-α, and IL-1β. These data show that anti-ILT4 and anti-ILT2/ILT4 antibodies will enhance the pro-inflammatory functions of tumor infiltrating monocytes.

In addition to suppression of innate immune activators, ILT2 or ILT4 may play a role in suppression of T-cell-mediated stimulation of myeloid cells. To evaluate T-cell stimulation of myeloid cells, PBMCs were activated with an anti-CD3 antibody and recombinant IL-2. Briefly, anti-ILT2 antibody 27F9, anti-ILT4 antibody 48A5, anti-ILT2/ILT4 antibodies 47H6 and 64A12, and a control isotype antibody were serially diluted in media and 50 µl added to each well of a 96-well round bottom tissue culture plate. PBMCs were added at 1×10⁶ cells/ml in a volume of 100 µl and the plate was incubated at 37° C. for 30 minutes. Anti-CD3 antibody clone HIT3a (eBioscience) was added at a concentration of 10 ng/ml and recombinant IL-2 was added at a concentration of 100 U/ml (Peprotech). Cells were incubated for two days and supernatants were analyzed using a Luminex® system.

Figure 17:
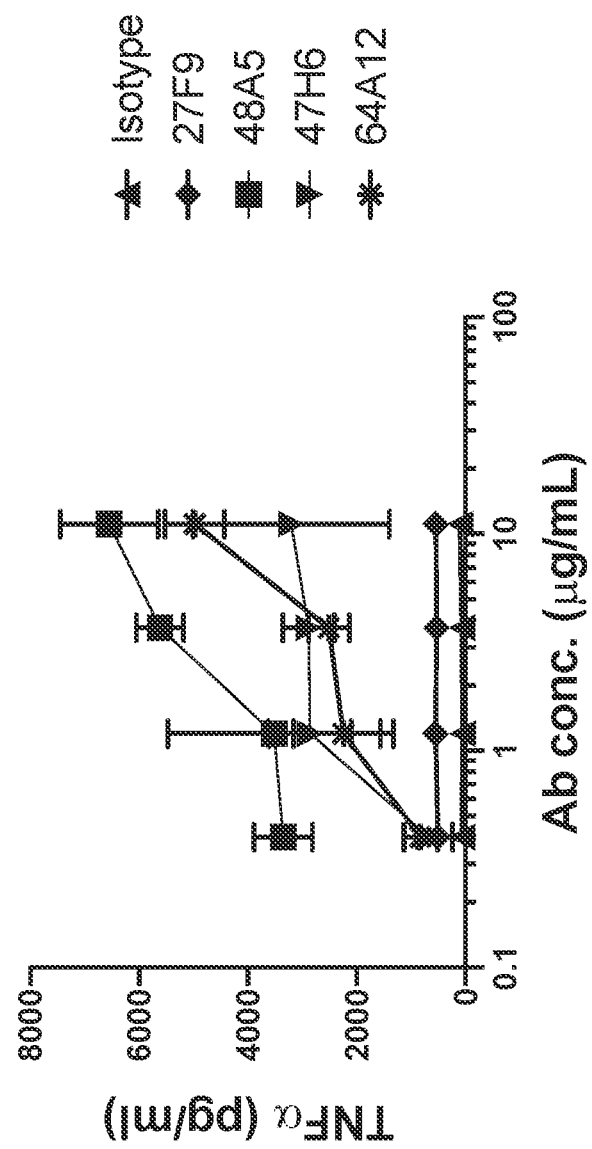
FIG. 17. Effect of anti-ILT antibodies suppression of T-cell mediated stimulation of myeloid cells.

As shown in FIG. 17, anti-ILT4 antibody 48A5 and anti-ILT2/ILT4 antibodies 47H6 and 64A12 enhanced TNF-α secretion in a dose-dependent manner. Anti-ILT2 antibody 27F9 did not have any effect of cytokine production. These data show that ILT4 blockade enhances the immune response (i.e., pro-inflammatory cytokine secretion) resulting from interaction between activated T-cells and myeloid cells.

Example 14

Effect of Anti-ILT Antibodies on Macrophage Phagocytosis

Phagocytosis assays were performed to further characterize the effect of anti-ILT2, anti-ILT4, and anti-ILT2/ILT4 antibodies on macrophage functions. Macrophages were generated by culture of isolated monocytes in media (RPMI with 10% FBS, L-glutamine and pen/strep) containing 50 ng/ml recombinant M-CSF (Peprotech) for 5 days at 37° C. in 12-well tissue culture plates. Macrophages were removed from the plate with a cell scraper and plated at 20,000 cells/well in 100 µl media in a flat bottom 96-well tissue culture plate. Macrophages were incubated overnight at 37° C. The next day, antibody was added to the macrophages at a concentration of 2.5 µg/ml together with 2.5 µg/ml of anti-CD47 antibody to induce antibody dependent phagocytosis. Raji cells were stained for 1 hour with a 1:4,000 dilution of pH Rodo Red Dye (Essen Bioscience), washed in media and added at 50,000 cells/well to macrophages. Phagocytosis was measured by mean red fluorescence on an Incucyte machine at 45 minute intervals. Test antibody was compared to isotype control antibody at the peak response timepoint (3 hours).

Figure 18:
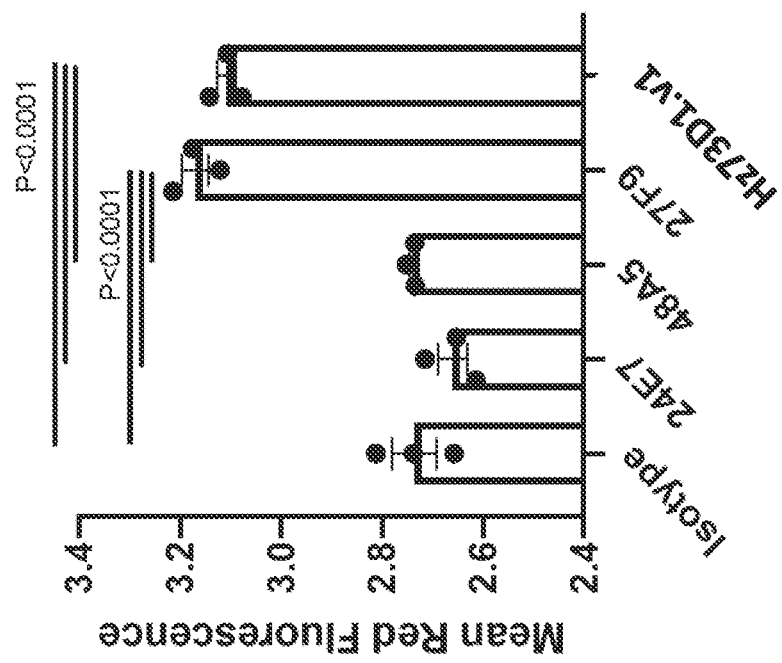
FIG. 18. Effect of anti-ILT antibodies on macrophage phagocytosis.

As shown in FIG. 18, anti-ILT2/ILT4 antibodies (e.g., Hz73D1.v1) and anti-ILT2 antibodies (e.g., 27F9) enhanced phagocytic activity of macrophages against Raji tumor cells opsonized with anti-CD47 antibody. Anti-ILT4 antibodies (e.g., 48A5) had no effect on phagocytosis by macrophages. To control for ILT2 expression by Raji cells, antibody 24E7, an ILT2 binder unable to block MHC-I interaction, was used. These data show that anti-ILT2 and anti-ILT2/ILT4 antibodies are able to enhance macrophage phagocytosis by blocking macrophage ILT2 interaction with MHC-I on tumor cells, and inhibiting ILT-2 induced suppression of macrophages, thus increasing macrophage phagocytosis of tumors. This activity of anti-ILT2 and anti-ILT2/ILT4 antibodies is specific to blocking ILT2/MHC-I interaction but not ILT4/MHC-1 interaction despite ILT4 expression on macrophages.

Example 15

Effect of Anti-ILT Antibodies on Dendritic Cells

It is believed that ILT2 and/or ILT4 act as suppressors of myeloid cell activation and that inhibition or blocking of ILT2 and/or ILT4 would inhibit ILT2 and/or ILT4-induced suppression.

Activation of myeloid cells can be achieved by the crosslinking of Fc receptors (FcR) on the cell surface and the crosslinking results in cytokine production; this is used as the basis for a myeloid cell activation assay. Dendritic cells were generated as described herein. Briefly, isolated human monocytes were plated on 10 cm tissue culture dishes with $4 \times 10^6$ cells per dish in a volume of 20 ml media (Lonza) supplemented with 50 ng/mL each of recombinant GM-CSF and IL-4 (Peprotech). The monocytes were incubated for 5-7 days at 37° C. and the resulting dendritic cells were harvested. Maxisorp 96-well ELISA plates were coated with anti-KLH antibody (5 μg/mL) and incubated overnight at 4° C. The anti-KLH antibody contains an Fc domain capable of binding Fc receptors on the dendritic cells. The plates were washed and blocked with X-VIVO™ 15 media for one hour. Dendritic cells were added at $7 \times 10^4$ cells/well. Anti-ILT2 antibody 27F9, anti-ILT4 antibody 48A5, a combination of antibodies 27F9 and 48A5, anti-ILT2/ILT4 antibody Hz73D1.v1 or a control antibody were added at serial dilutions and plates incubated at 37° C. for 2 days. Supernatants were collected and analyzed for TNF-α secretion using a Luminex® system.

Figure 19:
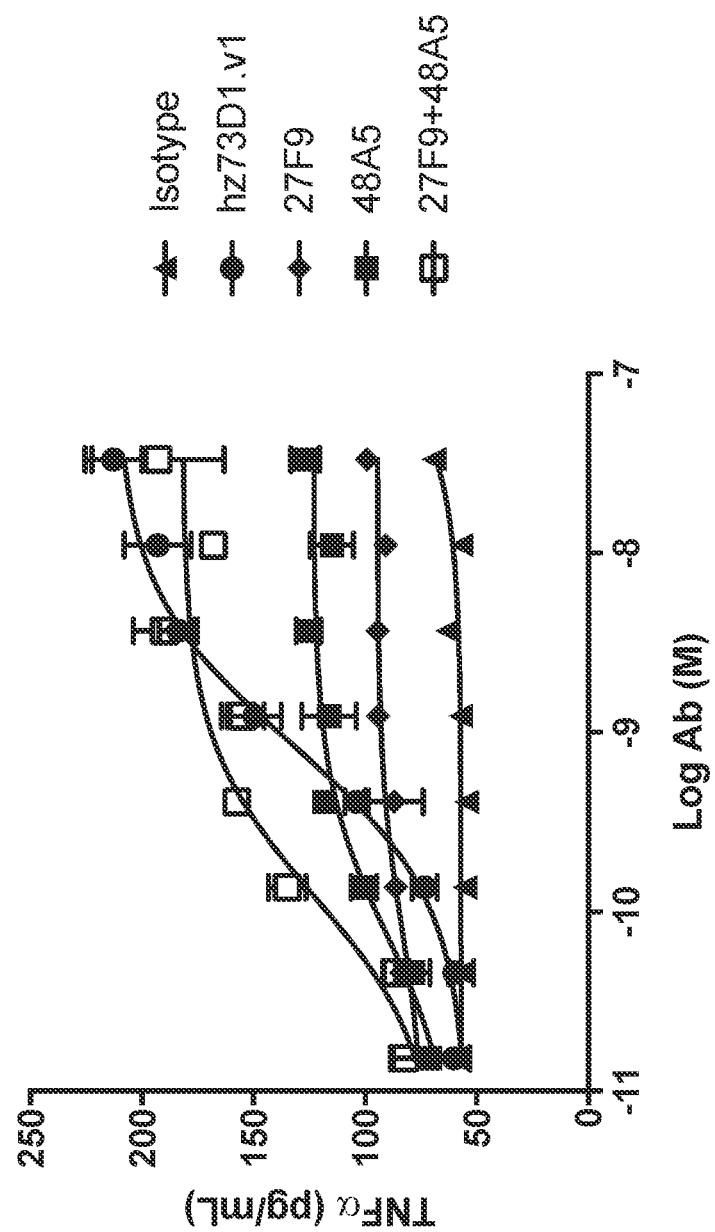
FIG. 19. Effect of anti-ILT antibodies on cytokine production by dendritic cells.

As shown in FIG. 19, a combination of anti-ILT2 antibody 27F9 and anti-ILT4 antibody 48A5 and anti-ILT2/ILT4 antibody 73D1 enhanced TNF-α secretion from dendritic cells in a dose-dependent manner. Anti-ILT2 antibody 27F9 as a single agent and anti-ILT4 antibody 48H6 as a single agent had only a small effect on increasing cytokine production. Thus the strong increase in cytokine secretion by the combination of anti-ILT2 antibody 27F9 with anti-ILT4 antibody 48A5 was surprising. This response was mirrored with the dual binding anti-ILT2/ILT4 antibody Hz73D1.v1. These data show that both ILT2 and ILT4 inhibit Fc-receptor-mediated activation of dendritic cells and that these effects are non-redundant. These data show that inhibiting the suppression of dendritic cells with agents that target both ILT2 and ILT4 (i.e., a dual binding anti-ILT2/ILT4 antibody) may result in a much better therapeutic effect than therapy with mono-specific antibodies.

Example 16

Effect of Anti-ILT Antibodies on Cytokine Secretion from Human and Cyno Blood Cells To investigate the potential for toxicity related to cytokine release (i.e., a "cytokine storm"), a variety of antibodies were cultured with human or cyno blood cells and cytokine production was analyzed. Briefly, antibodies were added at 10 μg/ml to 96-well flat-bottom plates and shaken at room temperature for 1 hour. The antibodies tested included anti-ILT4 antibody 48A5, anti-ILT2/ILT4 antibodies 47H6, 73D1, and Hz73D1.v1, superagonist anti-CD28 antibody clone 5D10 (Ancell), polyclonal anti-ILT2 antibody (R&D Systems), polyclonal anti-ILT4 antibody (R&D Systems), anti-LILRA1 antibody (R&D Systems), anti-CD3 antibody, and a control antibody. Plates were washed and blocked with culture media (RPMI with 10% FBS, L-glutamine and pen/strep) for 1 hour with shaking. Blood was obtained from healthy human donors and cyno monkeys. Red blood cells were removed from blood by lysis in RBC lysis buffer (eBioscience), followed by centrifugation, and the remaining cells were washed with culture media. $5 \times 10^5$ cells were added per well, with LPS added to replicate wells as a positive control, and plates incubated at 37° C. for 24 hours. Supernatants were collected and assayed for cytokine secretion using a Luminex® system.

Figure 20:
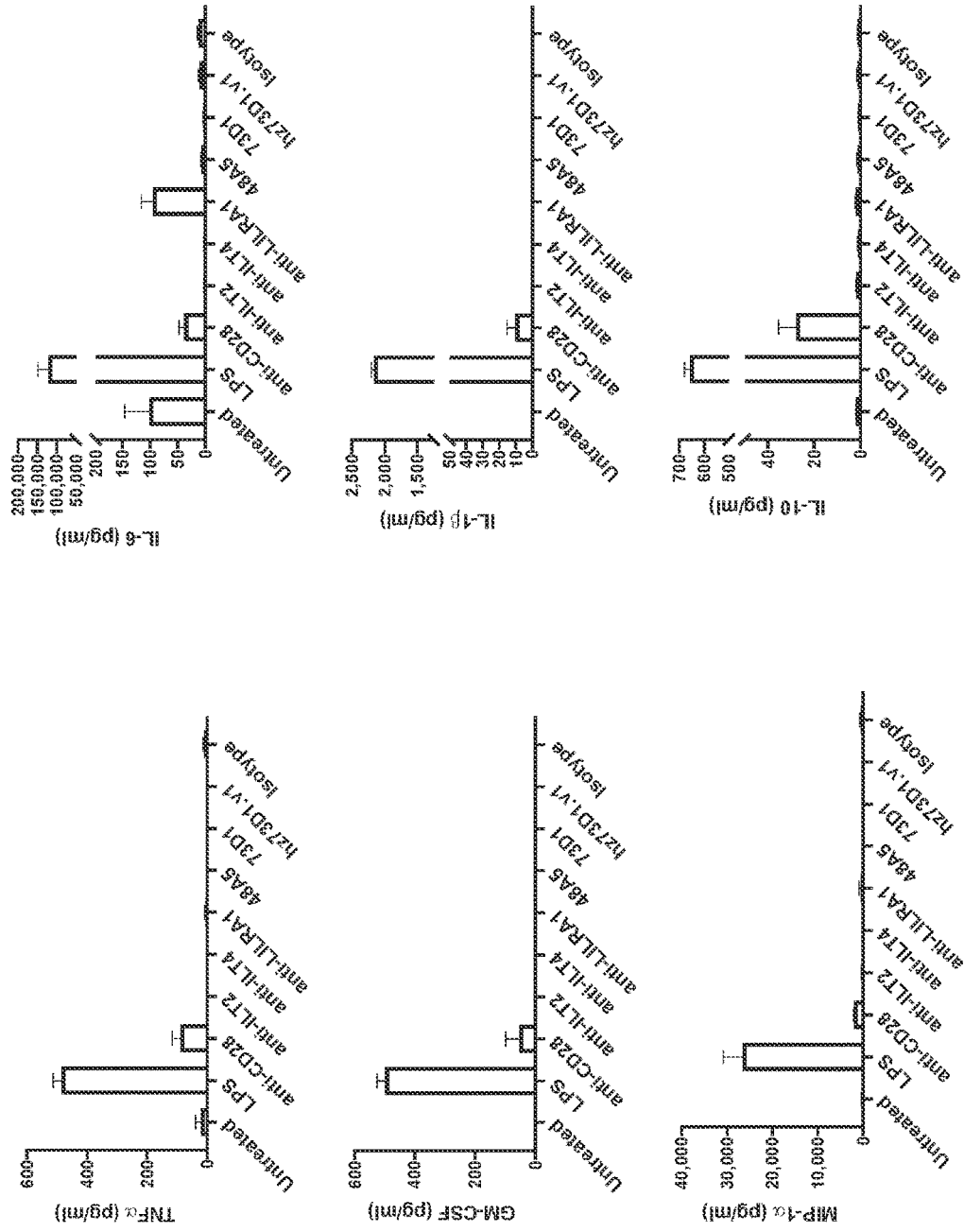
FIG. 20. Effect of anti-ILT antibodies on cytokine production from human blood cells.
Figure 21:
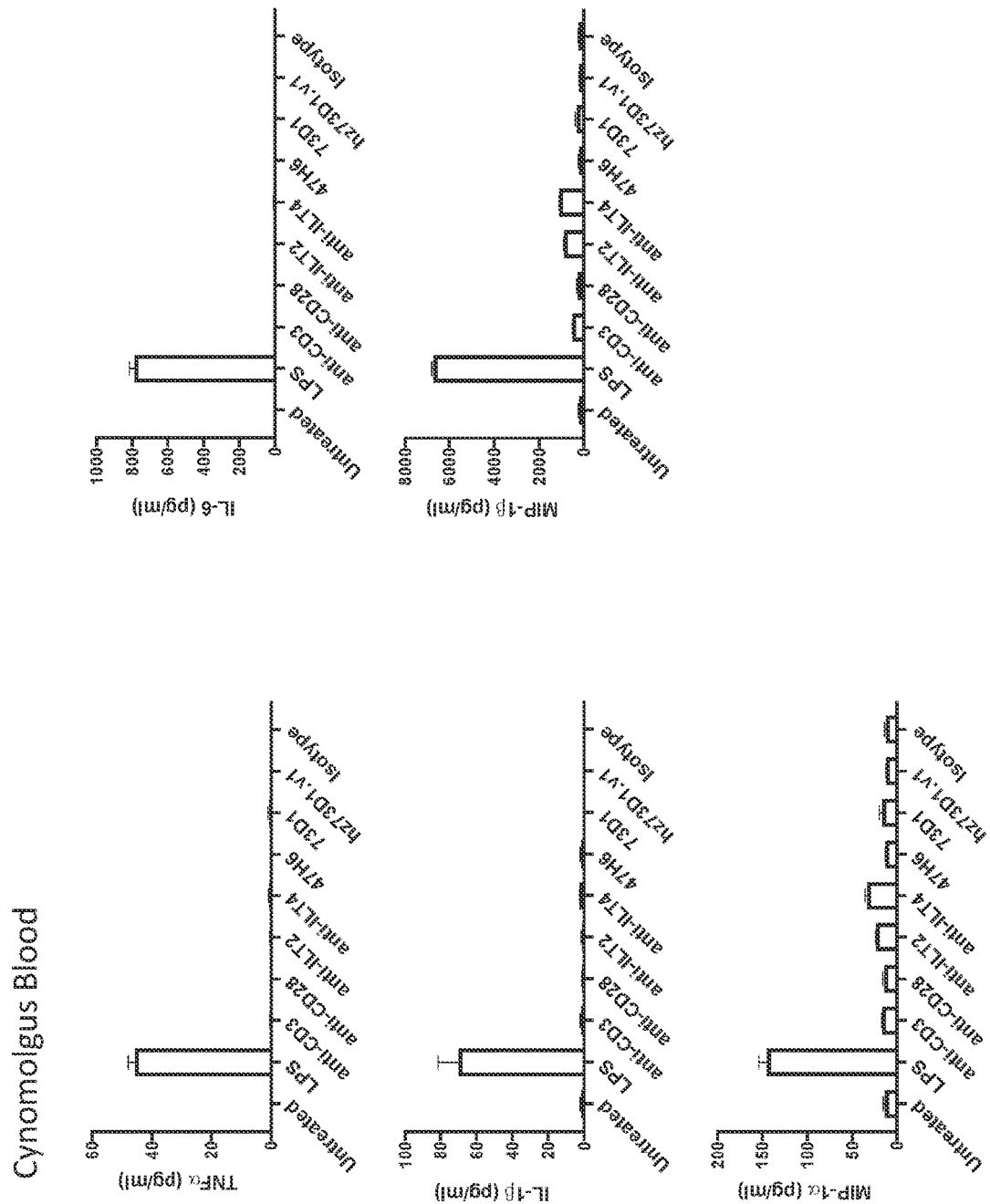
FIG. 21. Effect of anti-ILT antibodies on cytokine production from cyno blood cells.

As shown in FIG. 20, incubation of human blood cells with soluble LPS or plate-coated anti-CD28 antibody induced a significant increase in many cytokines including TNF-α, GM-CSF, MIP-1α, IL-6, IL-1β, and IL-10. In contrast, polyclonal anti-ILT2 antibody, polyclonal anti-ILT4 antibody, anti-LILRA1 antibody, anti-ILT4 antibody 48A5, and anti-ILT2/ILT4 antibodies 73D1 and Hz73D1.v1 failed to induce cytokine levels above isotype control antibody from the human blood cells. As shown in FIG. 21, incubation of cyno blood cells with soluble LPS induced a significant increase in cytokines such as TNF-α, IL-1β, MIP-1 α, IL-6 and MIP-1β. Similar to the human blood cell assay, polyclonal anti-ILT2 antibody, polyclonal anti-ILT4 antibody, anti-LILRA1 antibody, anti-CD3 antibody, and anti-ILT2/ILT4 antibodies 47H6, 73D1, and Hz73D1.v1 failed to induce cytokine levels above the level seen with the isotype control antibody from the cyno blood cells. These data show that the potential of anti-ILT2 antibodies, ILT-4 antibodies, and anti-ILT2/ILT4 antibodies to produce a toxic immune response, such as a cytokine storm, is low.

A further in vitro cytokine release assay was performed to evaluate the capacity of anti-ILT2/ILT4 antibodies to induce pro-inflammatory cytokines IL-2, TNF-α, IL-6 and IFN-γ. Whole blood samples for 10 healthy donors were used. Anti-ILT2/ILT4 antibodies were compared with a number of positive and negative controls. An anti-KLH isotype control antibody was used as a negative control. A super-agonist anti-CD28 antibody (clone ANC28.1) was used as a positive control (Walker 2011). In addition, Staphylococcus enterotoxin B (SEB) was used as a positive control for soluble antibody cultures. Two assay formats were used. In the first format, cells were cultured with an antibody (Hz73D1.v1, an isotype control antibody or anti-CD28 antibdy) or SEB at increasing concentrations. Antibodies were tested at 0.1, 1, 10 and 100 μg/ml. SEB was tested at 0.01, 0.1 and 1 μg/ml. In the second format, 96-well tissue culture plates were pre-incubated with an antibody overnight at 4° C., washed and then cells were added and cultured. Cell culture supernatant was then collected and tested for cytokine levels by cytometric bead array assay.

In the first assay format, SEB at 1 μg/mL induced high levels of all cytokines evaluated (IL-2, IL-6, TNFα and IFNγ), with cytokine levels above isotype control for all 10 donors. Soluble anti-CD28 antibody at 100 μg/mL induced cytokine levels above isotype control for IL-6, TNFα and IFNγ. Median values with Hz73D1.v1 were comparable with the isotype control (Table 18). In the second assay format, the positive control of plate-coated anti-CD28 (100 μg/ml) induced IL-6 in 5 of 10 donors. In contrast, plate-coated Hz73D1.v1 did not induce any of the 4 cytokines to a level above that of isotype control (Table 19).

TABLE 18

| | Anti-CD28 (μg/mL) | | SEB (μg/mL) | | Isotype (μg/mL) | | Hz73D1.v1 (μg/mL) | |
|---|---|---|---|---|---|---|---|---|
| | 10 | 100 | 0.1 | 1 | 10 | 100 | 10 | 100 |
| IL-6 | 1115 | 8934 | 571 | 1422 | 7 | 5 | 3 | 6 |
| IL-2 | 44 | 48 | 1309 | 3418 | 19 | 21 | 17 | 20 |
| TNFα | 52 | 605 | 614 | 1452 | 4 | 7 | 6 | 10 |
| IFNγ | 35 | 343 | 208 | 704 | 5 | 6 | 5 | 5 |

TABLE 19

| | Anti-CD28 (μg/mL) | | Isotype (μg/mL) | | Hz73D1.v1 (μg/mL) | |
|---|---|---|---|---|---|---|
| | 10 | 100 | 10 | 100 | 10 | 100 |
| IL-6 | 17 | 93 | 10 | 9 | 9 | 7 |
| IL-2 | 33 | 45 | 40 | 38 | 28 | 32 |
| TNFα | 18 | 26 | 17 | 19 | 16 | 12 |
| IFNγ | 12 | 21 | 13 | 13 | 12 | 14 |

Example 17

Effect of Anti-ILT Antibodies on T Cell Activity

ILT2 expression is known to be enriched on a population of effector memory CD45RA+ CD8+ T cells (CD8+ T EMRA cells) (Gustafson 2017). This population is only a small proportion of CD8+ T cells in healthy donors, making bulk CD8+ T cell cell-killing assays challenging. Therefore, to characterize the cytolytic activity of ILT2+ CD8 T cells, primary CD8+ T cells were transduced with ILT2 and expanded in vitro to generate sufficient numbers of ILT2+ CD8+ T cells. Cytolytic activity was then evaluated in a CD8+ T cell killing assay using fluorescently labeled 721.221-HLA-G target cells. Briefly, frozen PBMC were thawed, washed in media (RPMI with 10% FBS, L-glutamine and pen/strep) and CD8+ T cells were isolated using a CD8+ T cell positive selection kit. Isolated CD8+ T cells were cultured in basic media (Xvivo15 media with 10 mM HEPES, 2 mM Glutamine, pen/strep and 5% normal human serum) and stimulated for 24 hours at 37° C. with CD3/28 beads adding 5 μl beads per million cells. Activated T cells ($2 \times 10^5$) were then harvested and resuspended in 1 ml of Lentivirus expressing human ILT2 at a viral concentration of $1 \times 10^7$ PFU/ml in the presence of polybrene to infect cells. Infected cells were then resuspended in T cell media (basic media supplemented with 5 ng/ml IL-7, 5 ng/ml IL-15 and 25 ng/ml IL-2) and allowed to expand for two weeks. Cells were then FACS sorted for the ILT2+ population and expanded for an additional 6 weeks to generated sufficient cells for the study. For evaluation of cytolytic activity, $2.5 \times 10^4$ CellTracker deep red-labelled 721.221-HLAG cells were mixed with $2.5 \times 10^5$ ILT2-transduced CD8+ T cells at a 10:1 T cell:Target ratio and 0.1 μg/ml anti-CD3/CD19 bispecific antibody in RPMI-10% FBS media. Anti-ILT antibodies or control antibodies were added to the cells at a concentration of 10 μg/ml and incubated for 18 hours. Target cells were analyzed by FACS and percent target cell killing was calculated as the number of dead target cells divided by the total number of target cells.

Figure 22:
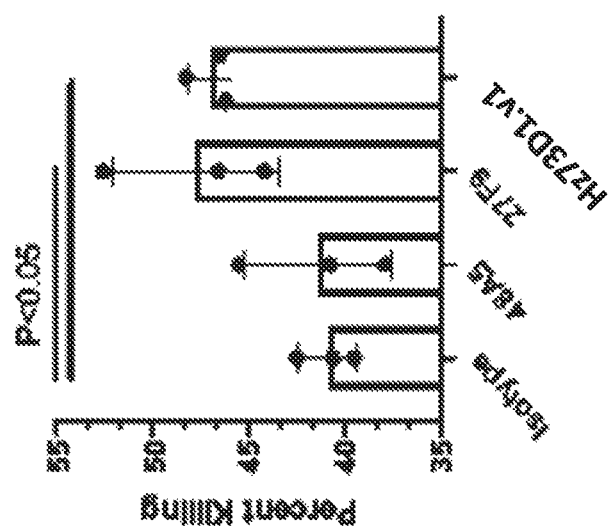
FIG. 22. Effect of anti-ILT antibodies on cytolytic activity of T cells.

As shown in FIG. 22, anti-ILT2/ILT4 antibodies (e.g., Hz73D1.v1) and anti-ILT2 antibodies (e.g., 27F9), but not anti-ILT4 antibodies (e.g., 48A5), enhanced cytolytic activity of CD8+ T cells against 721.221-HLA-G target cells. These data show that anti-ILT2 and anti-ILT2/ILT4 antibodies enhance CD8+ T cell cytolytic activity by blocking CD8+ T cell ILT2 interaction with MHC-I on target cells. As such, anti-ILT2 and anti-ILT2/ILT4 antibodies disrupt the immune suppressive activity of ILT2 on cytolytic lymphocytes, in particular effector memory T cells known to be involved in anti-tumor cell killing.

Example 18

Synergistic Effect of Anti-ILT2/ILT4 Antibodies and Anti-PD1 Antibodies on T Cell Activity A mixed leukocyte reaction assay was developed to evaluate potential synergistic or additive effects of anti-ILT2/ILT4 antibodies in combination with an anti-PD1 antibody (Pembrolizumab). Monocyte derived macrophages were generated and cultured with allogeneic CD4+ T cells from 11 different donors, together with either isotype control, Hz73D1.v1, Pembrolizumab, or the combination of Hz73D1.v1 and Pembrolizumab. Briefly, monocyte derived macrophages were generated by culturing 100,000 monocytes per well for 6 days with 50 ng/ml recombinant M-CSF. On day 6, allogeneic purified CD4+ T cells (200,000/well) were added together with either 1 μg/ml anti-KLH isotype control, 1 μg/ml Pembrolizumab, 1 μg/ml Hz73D1.v1, or the combination of anti-PD1 and Hz73D1.v1 at 1 g/ml each. Cells were cultured for an additional 6 days and supernatant collected for multiplex bead array analysis on secreted cytokines (IFN-γ, TNF-α, and GM-CSF).

As shown in FIG. 23A-23C, the anti-ILT2/ILT4 antibody or Pembrolizumab alone typically induced <2 ng/ml of interferon gamma in cultures, with 3 out of 11 donors inducing >2 ng/ml interferon gamma. In contrast, the combination of the anti-ILT2/ILT4 antibody and Pembrolizumab induced >2 ng/ml interferon gamma in 7 out of 11 CD4+ T cell donor pairs, with a greater-than-additive response compared to each reagent alone in these 7 donor pairs. Similar responses were observed with GM-CSF and TNF-α secretion. These data shows that the anti-ILT2/ILT4 antibody and pembrolizumab together have a synergistic effect on allogeneic CD4+ T cell induced cytokine secretion, possibly through a combination of anti-ILT2/ILT4 antibody-mediated stimulation of macrophage APC activity and the release of CD4+ T cell checkpoint inhibition by Pembrolizumab. Altogether, an anti-ILT2/ILT4 antibody or anti-PD-1 antibody alone modestly enhance T cell activation and increase in cytokine secretion. Combination of an anti-ILT2/ILT4 antibody or anti-PD-1 antibody leads to synergetic increase in T cell activation and cytokine secretion.

Example 19

Anti-ILT2/ILT4 Antibodies Induce M2-Like to M1-Like Polarization of Monocyte-Derived Macrophages Macrophages are traditionally characterized as either pro-inflammatory (M1) or immune suppressive (M2) based on surface expression markers CD80, CD86 (M1), CD163, CD204, and CD206 (M2). Anti-IL2/ILT4 antibodies as well as anti-IL2 and anti-ILT4 antibodies were evaluated for their ability to polarize macrophages toward an M1-like or M2-like phenotype.

Macrophages were generated by culture of monocytes in media (RPMI with 10% FBS, L-glutamine and pen/strep) containing Hz73D1.v1, 27F9, 48A5 or isotype control antibody (1 ug/ml) and 50 ng/ml recombinant M-CSF (Peprotech) for 5 days at 37° C. in 48-well tissue culture plates. On day 5 samples were analyzed by flow cytometry for various surface markers indicative of an M1-like or M2-like phenotype.

Figure 24:
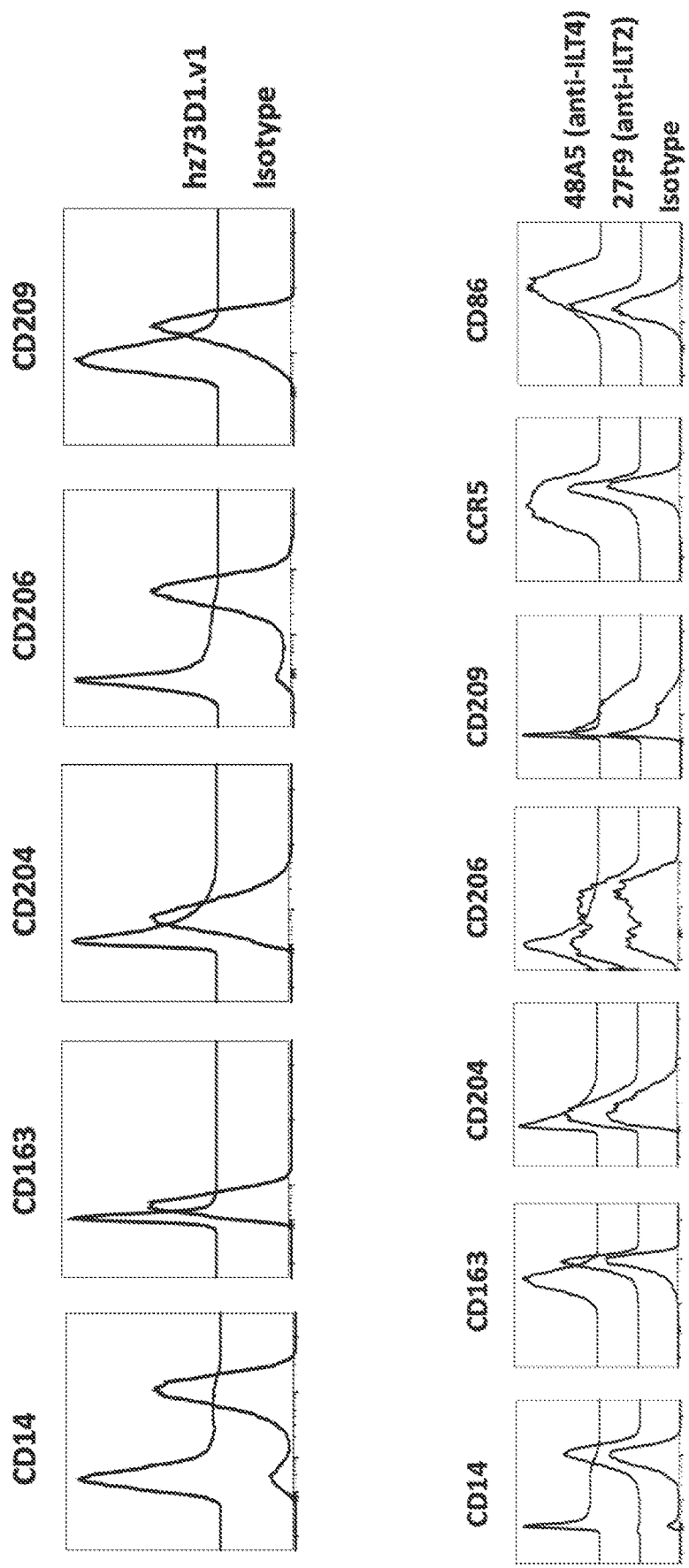
FIG. 24. Effects of anti-ILT2/ILT4 antibodies on polarization of monocyte-derived macrophages by assaying expression markers via flow cyometry.

As shown in FIG. 24, Hz73D1.v1 induced a decrease in M2-like macrophage phenotypic markers CD163, CD204, and CD206 and additional M2-like markers CD14 and CD209, consistent with an M2-like to M1-like polarization of the monocytes during differentiation. Anti-ILT4 specific antibody 48A5, but not anti-ILT2 specific antibody 27F9, induced an increase in M1-like marker CD86 and a decrease in M2-like markers CD163, CD204, and CD206, and additional M2-like markers CD14, CD209, and CCR5, consistent with an M2-like to M1-like polarization with ILT4 blockade. Overall, these data demonstrate that anti-ILT2/ILT4 antibodies induce a more pro-inflammatory M1-like phenotype during macrophage differentiation, and this response is mediated by inhibition of ILT4 interaction with MHC-I.

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application. CDR sequences are listed in Tables 1-8.

```
Human ILT2 amino acid sequence with predicted signal sequence underlined
                                                              (SEQ ID NO: 1)
MTPILTVLICLGLSLGPRTHVQAGHLPKPTLWAEPGSVITQGSPVTLRCQGGQETQEYRL

YREKKTALWITRIPQELVKKGQFPIPSITWEHAGRYRCYYGSDTAGRSESSDPLELVVTG

AYIKPTLSAQPSPVVNSGGNVILQCDSQVAFDGFSLCKEGEDEHPQCLNSQPHARGSSRA

IFSVGPVSPSRRWWYRCYAYDSNSPYEWSLPSDLLELLVLGVSKKPSLSVQPGPIVAPEE

TLTLQCGSDAGYNRFVLYKDGERDFLQLAGAQPQAGLSQANFTLGPVSRSYGGQYRCYGA

HNLSSEWSAPSDPLDILIAGQFYDRVSLSVQPGPTVASGENVTLLCQSQGWMQTFLLTKE

GAADDPWRLRSTYQSQKYQAEFPMGPVTSAHAGTYRCYGSQSSKPYLLTHPSDPLELVVS

GPSGGPSSPTTGPTSTSGPEDQPLTPTGSDPQSGLGRHLGVVIGILVAVILLLLLLLLLF

LILRHRRQGKHWTSTQRKADFQHPAGAVGPEPTDRGLQWRSSPAADAQEENLYAAVKHTQ

PEDGVEMDTRSPHDEDPQAVTYAEVKHSRPRREMASPPSPLSGEFLDTKDRQAEEDRQMD

TEAAASEAPQDVTYAQLHSLTLRREATEPPPSQEGPSPAVPSIYATLAIH

Human ILT2 amino acid sequence without predicted signal sequence
                                                              (SEQ ID NO: 2)
GHLPKPTLWAEPGSVITQGSPVTLRCQGGQETQEYRLYREKKTALWITRIPQELVKKGQF

PIPSITWEHAGRYRCYYGSDTAGRSESSDPLELVVTGAYIKPTLSAQPSPVVNSGGNVIL

QCDSQVAFDGFSLCKEGEDEHPQCLNSQPHARGSSRAIFSVGPVSPSRRWWYRCYAYDSN

SPYEWSLPSDLLELLVLGVSKKPSLSVQPGPIVAPEETLTLQCGSDAGYNRFVLYKDGER

DFLQLAGAQPQAGLSQANFTLGPVSRSYGGQYRCYGAHNLSSEWSAPSDPLDILIAGQFY

DRVSLSVQPGPTVASGENVTLLCQSQGWMQTFLLTKEGAADDPWRLRSTYQSQKYQAEFP

MGPVTSAHAGTYRCYGSQSSKPYLLTHPSDPLELVVSGPSGGPSSPTTGPTSTSGPEDQP

LTPTGSDPQSGLGRHLGVVIGILVAVILLLLLLLLLFLILRHRRQGKHWTSTQRKADFQH
```

```
PAGAVGPEPTDRGLQWRSSPAADAQEENLYAAVKHTQPEDGVEMDTRSPHDEDPQAVTYA

EVKHSRPRREMASPPSPLSGEFLDTKDRQAEEDRQMDTEAAASEAPQDVTYAQLHSLTLRREA

TEPPPSQEGPSPAVPSIYATLAIH
```

Human ILT2 extracellular domain (aa 24-461)
(SEQ ID NO: 3)
```
GHLPKPTLWAEPGSVITQGSPVTLRCQGGQETQEYRLYREKKTALWITRIPQELVKKGQF

PIPSITWEHAGRYRCYYGSDTAGRSESSDPLELVVTGAYIKPTLSAQPSPVVNSGGNVIL

QCDSQVAFDGFSLCKEGEDEHPQCLNSQPHARGSSRAIFSVGPVSPSRRWWYRCYAYDSN

SPYEWSLPSDLLELLVLGVSKKPSLSVQPGPIVAPEETLTLQCGSDAGYNRFVLYKDGER

DFLQLAGAQPQAGLSQANFTLGPVSRSYGGQYRCYGAHNLSSEWSAPSDPLDILIAGQFY

DRVSLSVQPGPTVASGENVTLLCQSQGWMQTFLLTKEGAADDPWRLRSTYQSQKYQAEFP

MGPVTSAHAGTYRCYGSQSSKPYLLTHPSDPLELVVSGPSGGPSSPTTGPTSTSGPEDQP

LTPTGSDPQSGLGRHLGV
```

Human ILT2 Ig-like C2-type domain 1 amino acid sequence (aa 27-115)
(SEQ ID NO: 4)
```
PKPTLWAEPGSVITQGSPVTLRCQGGQETQEYRLYREKKTALWITRIPQELVKKGQFPIP

SITWEHAGRYRCYYGSDTAGRSESSDPLE
```

Human ILT2 Ig-like C2-type domain 2 amino acid sequence (aa 116-221)
(SEQ ID NO: 5)
```
LVVTGAYIKPTLSAQPSPVVNSGGNVILQCDSQVAFDGFSLCKEGEDEHPQCLNSQPHAR

GSSRAIFSVGPVSPSRRWWYRCYAYDSNSPYEWSLPSDLLELLVLG
```

Human ILT2 Ig-like C2-type domain 3 amino acid sequence (aa 222-312)
(SEQ ID NO: 6)
```
VSKKPSLSVQPGPIVAPEETLTLQCGSDAGYNRFVLYKDGERDFLQLAGAQPQAGLSQAN

FTLGPVSRSYGGQYRCYGAHNLSSEWSAPSD
```

Human ILT2 Ig-like C2-type domain 4 amino acid sequence (aa 313-409)
(SEQ ID NO: 7)
```
PLDILIAGQFYDRVSLSVQPGPTVASGENVTLLCQSQGWMQTFLLTKEGAADDPWRLRST

YQSQKYQAEFPMGPVTSAHAGTYRCYGSQSSKPYLLT
```

Human ILT4 amino acid sequence with predicted signal sequence underlined
(SEQ ID NO: 8)
```
MTPIVTVLICLGLSLGPRTHVQTGTIPKPTLWAEPDSVITQGSPVTLSCQGSLEAQEYRL

YREKKSASWITRIRPELVKNGQFHIPSITWEHTGRYGCQYYSRARWSELSDPLVLVMTGA

YPKPTLSAQPSPVVTSGGRVTLQCESQVAFGGFILCKEGEEEHPQCLNSQPHARGSSRAI

FSVGPVSPNRRWSHRCYGYDLNSPYVWSSPSDLLELLVPGVSKKPSLSVQPGPVVAPGES

LTLQCVSDVGYDRFVLYKEGERDLRQLPGRQPQAGLSQANFTLGPVSRSYGGQYRCYGAH

NLSSECSAPSDPLDILITGQIRGTPFISVQPGPTVASGENVTLLCQSWRQFHTFLLTKAG

AADAPLRLRSIHEYPKYQAEFPMSPVTSAHAGTYRCYGSLNSDPYLLSHPSEPLELVVSG

PSMGSSPPPTGPISTPAGPEDQPLTPTGSDPQSGLGRHLGVVIGILVAVVLLLLLLLLLF

LILRHRRQGKHWTSTQRKADFQHPAGAVGPEPTDRGLQWRSSPAADAQEENLYAAVKDTQ

PEDGVEMDTRAAASEAPQDVTYAQLHSLTLRRKATEPPPSQEREPPAEPSIYATLAIH
```

Human ILT4 amino acid sequence without predicted signal sequence
(SEQ ID NO: 9)
```
QTGTIPKPTLWAEPDSVITQGSPVTLSCQGSLEAQEYRLYREKKSASWITRIRPELVKNG

QFHIPSITWEHTGRYGCQYYSRARWSELSDPLVLVMTGAYPKPTLSAQPSPVVTSGGRVT

LQCESQVAFGGFILCKEGEEEHPQCLNSQPHARGSSRAIFSVGPVSPNRRWSHRCYGYDL

NSPYVWSSPSDLLELLVPGVSKKPSLSVQPGPVVAPGESLTLQCVSDVGYDRFVLYKEGE
```

```
RDLRQLPGRQPQAGLSQANFTLGPVSRSYGGQYRCYGAHNLSSECSAPSDPLDILITGQI

RGTPFISVQPGPTVASGENVTLLCQSWRQFHTFLLTKAGAADAPLRLRSIHEYPKYQAEF

PMSPVTSAHAGTYRCYGSLNSDPYLLSHPSEPLELVVSGPSMGSSPPPTGPISTPAGPED

QPLTPTGSDPQSGLGRHLGVVIGILVAVVLLLLLLLLFLILRHRRQGKHWTSTQRKADF

QHPAGAVGPEPTDRGLQWRSSPAADAQEENLYAAVKDTQPEDGVEMDTRAAASEAPQDVT

YAQLHSLTLRRKATEPPPSQEREPPAEPSIYATLAIH

Human ILT4 extracellular domain (aa 22-461)
                                                    (SEQ ID NO: 10)
QTGTIPKPTLWAEPDSVITQGSPVTLSCQGSLEAQEYRLYREKKSASWITRIRPELVKNG

QFHIPSITWEHTGRYGCQYYSRARWSELSDPLVLVMTGAYPKPTLSAQPSPVVTSGGRVT

LQCESQVAFGGFILCKEGEEEHPQCLNSQPHARGSSRAIFSVGPVSPNRRWSHRCYGYDL

NSPYVWSSPSDLLELLVPGVSKKPSLSVQPGPVVAPGESLTLQCVSDVGYDRFVLYKEGE

RDLRQLPGRQPQAGLSQANFTLGPVSRSYGGQYRCYGAHNLSSECSAPSDPLDILITGQI

RGTPFISVQPGPTVASGENVTLLCQSWRQFHTFLLTKAGAADAPLRLRSIHEYPKYQAEF

PMSPVTSAHAGTYRCYGSLNSDPYLLSHPSEPLELVVSGPSMGSSPPPTGPISTPAGPED

QPLTPTGSDPQSGLGRHLGV

Human ILT4 Ig-like C2-type domain 1 amino acid sequence (aa 27-110)
                                                    (SEQ ID NO: 11)
PKPTLWAEPDSVITQGSPVTLSCQGSLEAQEYRLYREKKSASWITRIRPELVKNGQFHIP

SITWEHTGRYGCQYYSRARWSELS

Human ILT4 Ig-like C2-type domain 2 amino acid sequence (aa 111-229)
                                                    (SEQ ID NO: 12)
DPLVLVMTGAYPKPTLSAQPSPVVTSGGRVTLQCESQVAFGGFILCKEGEEEHPQCLNSQ

PHARGSSRAIFSVGPVSPNRRWSHRCYGYDLNSPYVWSSPSDLLELLVPGVSKKPSLSV

Human ILT4 Ig-like C2-type domain 3 amino acid sequence (aa 230-318)
                                                    (SEQ ID NO: 13)
QPGPVVAPGESLTLQCVSDVGYDRFVLYKEGERDLRQLPGRQPQAGLSQANFTLGPVSRS

YGGQYRCYGAHNLSSECSAPSDPLDILIT

Human ILT4 Ig-like C2-type domain 4 amino acid sequence (aa 330-419)
                                                    (SEQ ID NO: 14)
QPGPTVASGENVTLLCQSWRQFHTFLLTKAGAADAPLRLRSIHEYPKYQAEFPMSPVTSA

HAGTYRCYGSLNSDPYLLSHPSEPLELVVS

Rhesus ILT2 amino acid sequence with predicted signal sequence underlined
                                                    (SEQ ID NO: 15)
MTPILMVLICLGLSLGSRTRVQAGTFPKPTLWAEPGSMISKGSPVTLRCQGSLPVQDYRL

QREKKTASWVRRIQQELVKKGYFPIASITSEHAGQYRCQYYSHSWWSEPSDPLELVVTGA

YSKPTLSALPSPVVASGGNVTLQCDSQVAXGGFVLCKEGEDEHPQCLNSQPHTRGSSRAV

FSVGPVSPSRRWSYRCYGYDSRSPYVWSLPSDLLELLVPGVSKKPSLSVQPGPVVAPGDK

LTLQCGSDAGYNRFALYKEGERDFLQRPGRQPQAGLSQANFLLDPVRRSHGGQYRCSGAH

NLSSEWSAPSDPLDILIAGQIRGRPSLLVQPGPTVVSGENVTLLCQSSWQFHVFLLTQAG

AADAHLHLRSMYKYPKYQAEFPMSPVTSAHAGTYRCYGSHSSDSYLLSIPSDPLELVVSG

PSGGPSSPTTGPTSTCGPEDQPLTPTGSDPQSGLGRHLGVVTGVLVAFVLLLFLLLLLFL

VLRHRRQGKRWTSAQRKADFQHPAGAVEPEPRDRGLQRRSSPAANTQEENLYAAVKDTQP

EDGVELDSRPHDEDPQAVTYARVKHSRPRREMASPPSPLSEEFLDTKDTQAAASEDPQD

VTYAQLQSLTLRRETTEPPPSQEREPPVESSIYATLTIH
```

-continued

Rhesus ILT2 amino acid sequence without predicted signal sequence
(SEQ ID NO: 16)

GTFPKPTLWAEPGSMISKGSPVTLRCQGSLPVQDYRLQREKKTASWVRRIQQELVKKGYF

PIASITSEHAGQYRCQYYSHSWWSEPSDPLELVVTGAYSKPTLSALPSPVVASGGNVTLQ

CDSQVAXGGFVLCKEGEDEHPQCLNSQPHTRGSSRAVFSVGPVSPSRRWSYRCYGYDSRS

PYVWSLPSDLLELLVPGVSKKPSLSVQPGPVVAPGDKLTLQCGSDAGYNRFALYKEGERD

FLQRPGRQPQAGLSQANFLLDPVRRSHGGQYRCSGAHNLSSEWSAPSDPLDILIAGQIRG

RPSLLVQPGPTVVSGENVTLLCQSSWQFHVFLLTQAGAADAHLHLRSMYKYPKYQAEFPM

SPVTSAHAGTYRCYGSHSSDSYLLSIPSDPLELVVSGPSGGPSSPTTGPTSTCGPEDQPL

TPTGSDPQSGLGRHLGVVTGVLVAFVLLLFLLLLLFLVLRHRRQGKRWTSAQRKADFQHP

AGAVEPEPRDRGLQRRSSPAANTQEENLYAAVKDTQPEDGVELDSRSPHDEDPQAVTYAR

VKHSRPRREMASPPSPLSEEFLDTKDTQAAASEDPQDVTYAQLQSLTLRRETTEPPPSQE

REPPVESSIYATLTIH

Rhesus ILT2 extracellular domain (aa 24-460)
(SEQ ID NO: 17)

GTFPKPTLWAEPGSMISKGSPVTLRCQGSLPVQDYRLQREKKTASWVRRIQQELVKKGYF

PIASITSEHAGQYRCQYYSHSWWSEPSDPLELVVTGAYSKPTLSALPSPVVASGGNVTLQ

CDSQVAXGGFVLCKEGEDEHPQCLNSQPHTRGSSRAVFSVGPVSPSRRWSYRCYGYDSRS

PYVWSLPSDLLELLVPGVSKKPSLSVQPGPVVAPGDKLTLQCGSDAGYNRFALYKEGERD

FLQRPGRQPQAGLSQANFLLDPVRRSHGGQYRCSGAHNLSSEWSAPSDPLDILIAGQIRG

RPSLLVQPGPTVVSGENVTLLCQSSWQFHVFLLTQAGAADAHLHLRSMYKYPKYQAEFPM

SPVTSAHAGTYRCYGSHSSDSYLLSIPSDPLELVVSGPSGGPSSPTTGPTSTCGPEDQPL

TPTGSDPQSGLGRHLGV

Rhesus ILT2 Ig-like C2-type domain 1 amino acid sequence (aa 27-114)
(SEQ ID NO: 18)

PKPTLWAEPGSMISKGSPVTLRCQGSLPVQDYRLQREKKTASWVRRIQQELVKKGYFPIA

SITSEHAGQYRCQYYSHSWWSEPSDPLE

Rhesus ILT2 Ig-like C2-type domain 2 amino acid sequence n (aa 115-220)
(SEQ ID NO: 19)

LVVTGAYSKPTLSALPSPVVASGGNVTLQCDSQVAXGGFVLCKEGEDEHPQCLNSQPHTR

GSSRAVFSVGPVSPSRRWSYRCYGYDSRSPYVWSLPSDLLELLVPG

Rhesus ILT2 Ig-like C2-type domain 3 amino acid sequence n (aa 221-311)
(SEQ ID NO: 20)

VSKKPSLSVQPGPVVAPGDKLTLQCGSDAGYNRFALYKEGERDFLQRPGRQPQAGLSQAN

FLLDPVRRSHGGQYRCSGAHNLSSEWSAPSD

Rhesus ILT2 Ig-like C2-type domain 4 amino acid sequence n (aa 312-408)
(SEQ ID NO: 21)

PLDILIAGQIRGRPSLLVQPGPTVVSGENVTLLCQSSWQFHVFLLTQAGAADAHLHLRSM

YKYPKYQAEFPMSPVTSAHAGTYRCYGSHSSDSYLLS

27F9 Heavy chain variable region amino acid sequence
(SEQ ID NO: 125)

QVQLKESGPGLVAPSQSLSITCTVSGFSLTNYGVSWVRQPPGKGLEWLGIIWGDGSTNYH

SALISRLSISKDNSKSQVFLKLNSLQADDTATYYCAKPNWDTYAMDFWGQGTSVTVSS

27F9 Light chain variable region amino acid sequence
(SEQ ID NO: 126)

DIQMTQTTSSLSASLGDRVTISCRASQDISNFLNWYQQKPDGTVKLLIYCTSKLHSGVPS

RFSGSGSETDYSLTISNLEQEDIATYFCQQGNTLPPTFGGGTKLEII

-continued

47C8 Heavy chain variable region amino acid sequence
(SEQ ID NO: 127)
EVQLQQSGPDLVKPGASVKISCKASGYSFTGYYMHWVKQSHGKSLEWIGRVYPNNGDTSY

NQKFKVKAILTVDKSSSTAYMELRSLTSEDSAVYYCARGATVVESLFAYWGQGTLVTVSA

47C8 Light chain variable region amino acid sequence
(SEQ ID NO: 128)
DIVLTQSPASLAVSLGQRATISCRASESVDNYGNNFLHWYQQKPGQPPKWYRTSNLES

GIPARFSGSGSRTDFTLTINPVEADDVATYYCQQSNEDPYTFGGGTKLEIK

48A5 Heavy chain variable region amino acid sequence
(SEQ ID NO: 129)
QIQLVQSGPELKKPGETVKISCKASGYTFTNYGMNWVKQAPGKGLKWMGWINTYIGEPIY

ADDFKGRFAFSLETSASTAYLQINNLKNEDMATYFCARRSDYDGYAMDYWGQGTSVTVSS

48A5 Light chain variable region amino acid sequence
(SEQ ID NO: 130)
DIVMSQSPSSLAVSVGERVTMSCKSSQSLLYSGNQKNYLAWYQQKPGQSPKLLIYWASTR

ESGVPDRFTGSGSGTDFTLTISSVKAEDLAVYYCQQHDSYPTFGGGSRLEIK

47H6 Heavy chain variable region amino acid sequence
(SEQ ID NO: 131)
EVQLQQSGPELVKPGASVKISCKASGYTFTDYYMNWVKQSHGKSLEWIGDFNPNNGGTTY

NQKFEGKATLTVDKSSNTAYMDLRSLTSEDSAVYYCARGRFYYGSLYSFDYWGQGTTLTVSS

47H6 Light chain variable region amino acid sequence
(SEQ ID NO: 132)
DIQMTQSPASLSASVGETVTITCRASGNIHNYLAWYQQKQGKSPHLLVYNAKTLADGVPS

RFSGSGSGTQYSLKINNLQPEDFGSYYCQHFWTSITFGAGTKLDLK

Hz47H6.v2 Heavy chain variable region amino acid sequence
(SEQ ID NO: 133)
QVQLVQSGAEVKKPGASVKVSCKASGYTFTDYYMNWVRQAPGQRLEWIGDFNPNNAGTTYN

QKFEGRVTITVDKSASTAYMELSSLRSEDTAVYYCARGRFYYGSLYSFDYWGQGTLVTVSS

Hz47H6.v2 Light chain variable region amino acid sequence
(SEQ ID NO: 134)
DIQMTQSPSSLSASVGDRVTITCRASGNIHNYLAWYQQKPGKAPKWYNAKTLADGVPSR

FSGSGSGTDFTLTISSLQPEDFATYYCQHFWTSITFGPGTKVDIK

51A1 Heavy chain variable region amino acid sequence
(SEQ ID NO: 135)
EVQLVESGGGLVQPKGSLKLSCAASGFTFNTYAMHWVRQAPGKGLEWVARIRSKSSNYAT

YYADSVKDRFTISRDDSQSMLYLQMNNLKTEDTAMYYCVRDGIYYYGTMYYYAMDYWGQG

TSVIVSS

51A1 Light chain variable region amino acid sequence
(SEQ ID NO: 136)
NIVLTQSPASLAVSILGQRATISCRASESVDYYGNSFMYWYQQKPGQPPKWYFASNILES

GVPARFSGSGSRTDFTLTIDPVEAADAASYYCQQNNEDPWTFGGGTKLEIK

64A12 Heavy chain variable region amino acid sequence
(SEQ ID NO: 137)
EVQLVESGGGLVQPKGSLKLSCAASGFTFNTYAMHWVRQAPGKGLEWVARIRSKSSNYAT

YYADSVKDRFTISRDDSQSMLYLQMNNLKTEDTAMYYCVRDGIYYYDTMYYYAMDYWGQG

TSVTVSS

64A12 Light chain variable region amino acid sequence
(SEQ ID NO: 138)
NIVLTQSPASLAVSLGQRATISCRASESVDYYGNSFIYWYQQKPGQPPKWYFASNLES

GVPARFSGSGSRTDFTLTIDPVEAADAASYYCQQNNEDPWTFGGGTKLEIK

Heavy chain variable region amino acid sequence
(SEQ ID NO: 139)
EVQLVESGGGLVQPGGSLRLSCAASGFTFNTYAMHWVRQAPGKGLEWVARIRSKSSNYAT

YYADSVKDRFTISRDDAKNSLYLQMNSLRAEDTAVYYCARDGIYYYDTMYYYAMDYWGQG

TLVTVSS

Hz64A12 Light chain variable region amino acid sequence
(SEQ ID NO: 140)
NIVLTQSPDSLAVSLGERATINCRASESVDYYGNSFIYWYQQKPGQPPKWYFASNLES

GVPDRFSGSGSGTDFTLTISSLQAEDVAVYYCQQNNEDPWTFGGGTKVEIK

73C4 Heavy chain variable region amino acid sequence
(SEQ ID NO: 141)
AVQLQQSGPELVKPGASVKISCKASGYTFTDYYMNWVKQSHGKSLEWIGNVNPNNGGTSY

NQKFKGKATLTVDKSSSTAYMELRSLTSEDSAVYYCARREIYFYGTIYYYAMDYWGQGTS

VTVSS

73C4 and 73D1 Light chain variable region amino acid sequence
(SEQ ID NO: 142)
DIVLTQSPASLAVSLGQRATISCRASESVDYYGNSFMYWYQQKPGRPPNLLIYFASNLES

GVPARFSGSGSRTDFTLTIDPVEADDAATYYCQQNNEDPWTFGGGTKLEIK

73D1 Heavy chain variable region amino acid sequence
(SEQ ID NO: 143)
AVQLQQSGPELVKPGASVKISCKASGYTFTDYYINWVKQSHGKSLQWIGNVNPNDGGTTY

NQKFKGKATLTVDKSSSTAYMELRSLTSEDSAVYYCARREIYFYGTIYYYAMDYWGQGTS

VTVSS

Hz73D1.v1 Heavy chain variable region amino acid sequence
(SEQ ID NO: 144)
QVQLVQSGAEVKKPGASVKVSCKASGYTFTDYYINWVRQAPGQGLEWMGNVNPNDGGTTY

NQKFKGRVTMTTDTSTSTAYMELRSLRSDDTAVYYCARREIYFYGTIYYYAMDYWGQGTL

VTVSS

Hz73D1.v1 Light chain variable region amino acid sequence
(SEQ ID NO: 145)
DIQLTQSPSFLSASVGDRVTITCRASESVDYYGNSFMYWYQQKPGKAPKWYFASNLES

GVPSRFSGSGSGTEFTLTISSLQPEDFATYYCQQNNEDPWTFGGGTKVEIK

Hz47H6.v2 Heavy chain amino acid sequence with signal sequence underlined
(SEQ ID NO: 146)
<u>MDMRVPAQLLGLLLLWLRGARC</u>QVQLVQSGAEVKKPGASVKVSCKASGYTFTDYYMNWVR

QAPGQRLEWIGDFNPNNAGTTYNQKFEGRVTITVDKSASTAYMELSSLRSEDTAVYYCAR

GRFYYGSLYSFDYWGQGTLVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYGSTYRVVSVLTVLHQDWLNGKEYKCKVSNKALPAPIE

KTISKAKGQPREPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSLSPGK

Hz47H6.v2 Light chain amino acid sequence with signal sequence underlined
(SEQ ID NO: 147)
<u>MDMRVPAQLLGLLLLWLRGARC</u>DIQMTQSPSSLSASVGDRVTITCRASGNIHNYLAWYQQ

KPGKAPKWYNAKTLADGVPSRFSGSGSGTDFTLTISSLQPEDFATYYCQHFWTSITFG

PGTKVDIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

-continued

Hz47H6.v2 Heavy chain amino acid sequence without signal sequence
(SEQ ID NO: 148)
QVQLVQSGAEVKKPGASVKVSCKASGYTFTDYYMNWVRQAPGQRLEWIGDFNPNNAGTTY

NQKFEGRVTITVDKSASTAYMELSSLRSEDTAVYYCARGRFYYGSLYSFDYWGQGTLVTV

SSASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREEQ

YGSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDKS

RWQQGNVFSCSVMHEALHNHYTQKSLSLSPGK

Hz47H6.v2 Light chain amino acid sequence without signal sequence
(SEQ ID NO: 149)
DIQMTQSPSSLSASVGDRVTITCRASGNIHNYLAWYQQKPGKAPKWYNAKTLADGVPS

RFSGSGSGTDFTLTISSLQPEDFATYYCQHFWTSITFGPGTKVDIKRTVAAPSVFIFPPS

DEQLKSGTASVVCLLNNFYPREAKVQWKVDNALQSGNSQESVTEQDSKDSTYSLSSTLTL

SKADYEKHKVYACEVTHQGLSSPVTKSFNRGEC

Hz64A12 Heavy chain amino acid sequence with signal sequence underlined
(SEQ ID NO: 150)
<u>MDMRVPAQLLGLLLLWLRGARC</u>EVQLVESGGGLVQPGGSLRLSCAASGFTFNTYAMHWVR

QAPGKGLEWVARIRSKSSNYATYYADSVKDRFTISRDDAKNSLYLQMNSLRAEDTAVYYC

ARDGIYYYDTMYYYAMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSN

TKVDKKVEPKSCDKTHTCPPCPAPELLGGPSVFLFPPKPKDTLMISRTPEVTCVVVDVSH

EDPEVKFNWYVDGVEVHNAKTKPREEQYGSTYRVVSVLTVLHQDWLNGKEYKCKVSNKAL

PAPIEKTISKAKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQKSLSLSPGK

Hz64A12 Light chain amino acid sequence with signal sequence underlined
(SEQ ID NO: 151)
<u>MDMRVPAQLLGLLLLWLRGARC</u>NIVLTQSPDSLAVSLGERATINCRASESVDYYGNSFIY

WYQQKPGQPPKLLIYFASNLESGVPDRFSGSGSGTDFTLTISSLQAEDVAVYYCQQNNED

PWTFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Hz64A12 Heavy chain amino acid sequence without signal sequence
(SEQ ID NO: 152)
EVQLVESGGGLVQPGGSLRLSCAASGFTFNTYAMHWVRQAPGKGLEWVARIRSKSSNYAT

YYADSVKDRFTISRDDAKNSLYLQMNSLRAEDTAVYYCARDGIYYYDTMYYYAMDYWGQG

TLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAKTK

PREEQYGSTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKL

TVDKSRWQQGNVFSCSVMHEALHNHYTQKSLSLSPGK

Hz64A12 Light chain amino acid sequence without signal sequence
(SEQ ID NO: 153)
NIVLTQSPDSLAVSLGERATINCRASESVDYYGNSFIYWYQQKPGQPPKWYFASNLES

GVPDRFSGSGSGTDFTLTISSLQAEDVAVYYCQQNNEDPWTFGGGTKVEIKRTVAAPSVF

```
IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC

Hz73D1.v1 Heavy chain amino acid sequence with signal sequence underlined
                                                           (SEQ ID NO: 154)
MDMRVPAQLLGLLLLWLRGARCQVQLVQSGAEVKKPGASVKVSCKASGYTFTDYYINWVR

QAPGQGLEWMGNVNPNDGGTTYNQKFKGRVTMTTDTSTSTAYMELRSLRSDDTAVYYCAR

REIYFYGTIYYYAMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNTK

VDKKVEPKSCDKTHTCPPCPAPELLGGPSVFLFPPKPKDTLMISRTPEVTCVVVDVSHED

PEVKFNWYVDGVEVHNAKTKPREEQYGSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPGK

Hz73D1.v1 Light chain amino acid sequence with signal sequence underlined
                                                           (SEQ ID NO: 155)
MDMRVPAQLLGLLLLWLRGARCDIQLTQSPSFLSASVGDRVTITCRASESVDYYGNSFMY

WYQQKPGKAPKWYFASNLESGVPSRFSGSGSGTEFTLTISSLQPEDFATYYCQQNNED

PWTFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Hz73D1.v1 Heavy chain amino acid sequence without signal sequence
                                                           (SEQ ID NO: 156)
QVQLVQSGAEVKKPGASVKVSCKASGYTFTDYYINWVRQAPGQGLEWMGNVNPNDGGTTY

NQKFKGRVTMTTDTSTSTAYMELRSLRSDDTAVYYCARREIYFYGTIYYYAMDYWGQGTL

VTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKTKPR

EEQYGSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGK

Hz73D1.v1 Light chain amino acid sequence without signal sequence
                                                           (SEQ ID NO: 157)
DIQLTQSPSFLSASVGDRVTITCRASESVDYYGNSFMYWYQQKPGKAPKWYFASNLES

GVPSRFSGSGSGTEFTLTISSLQPEDFATYYCQQNNEDPWTFGGGTKVEIKRTVAAPSVF

IFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC

Human IgG1 constant region
                                                           (SEQ ID NO: 158)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 constant region E233A/L235A
                                                           (SEQ ID NO: 159)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPALAGG

PSVFLFPPKPKDTLMISRTPEVTCVVVDVSHEDPEVKFNWYVDGVEVHNAKTKPREEQYN
```

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 constant region L234A/L235A
(SEQ ID NO: 160)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG1 constant region L234A/L235A/P329G
(SEQ ID NO: 161)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALGAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Human IgG1 constant region N297G
(SEQ ID NO: 162)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYG

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 constant region N297G/H310A
(SEQ ID NO: 163)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYG

STYRVVSVLTVLAQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human Kappa light chain constant region
(SEQ ID NO: 164)
RTVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

Human Lambda light chain constant region
(SEQ ID NO: 165)
GQPKAAPSVTLFPPSSEELQANKATLVCLISDFYPGAVTVAWKADSSPVKAGVETTTPSK

QSNNKYAASSYLSLTPEQWKSHRSYSCQVTHEGSTVEKTVAPTECS

Cyno ILT2 amino acid sequence with predicted signal sequence underlined
(SEQ ID NO: 166)
<u>MTPILMVLICLGLSLGPRTHVQA</u>GILPKPTLWAEPGSMISEGSPVTLRCQGSLQVQEYRL

YREKKPASWVRRIQQELVKKGYFAIGFITWEHTGQYRCQYYSHSWWSEPSDPLELVVTGA

-continued

```
YSKPTLSALPSPVVASGGNVTLQCDSQVAFDSFTLCKEGEDEHPQRLNCQSHARGWSWAV

FSVGPVSPSRRWSYRCYGYISSAPNVWSLPSDLLELLVPGVSKKPSLSVQPGPVVAPGDK

LTLQCGSDAGYDRFALYKEGEGDFLQRPVRQPQAGLSQANFLLGPVSRSHGGQYRCSGAH

NLSSEWSAPSDPLDILIAGQIRGRPFLSVQPGPKVVSGENVTLLCQSSWQFHAFLLTQAG

AADAHLHLRSMYKYPKYQAEFPMSPVTSAHAGTYRCYGSRSSNPYLLSVPSDPLELVVSG

PSGGPSSPTTGPTSTCAGPEDQPLTPTGSDPQSGLGRHLGVVTGILVAFVLLLFLLLLLF

LVLRHQRQGKHWTSAQRKADFQHPAGAVEPEPRDRGLQRRSSPAADTQEENLYAAVKDTQ

PEDGVELDSRQRPHDEDPQAVTYARVKHSRPRREMASPPSPLSEEFLDTKDTQAEEDRQM

DTEAAASEDPQDVTYAQLQSLTLRRETTEPPPSQERAPPVESSIYATLTIH
```

Cyno ILT2 amino acid sequence without predicted signal sequence
(SEQ ID NO: 167)
```
GILPKPTLWAEPGSMISEGSPVTLRCQGSLQVQEYRLYREKKPASWVRRIQQELVKKGYF

AIGFITWEHTGQYRCQYYSHSWWSEPSDPLELVVTGAYSKPTLSALPSPVVASGGNVTLQ

CDSQVAFDSFTLCKEGEDEHPQRLNCQSHARGWSWAVFSVGPVSPSRRWSYRCYGYISSA

PNVWSLPSDLLELLVPGVSKKPSLSVQPGPVVAPGDKLTLQCGSDAGYDRFALYKEGEGD

FLQRPVRQPQAGLSQANFLLGPVSRSHGGQYRCSGAHNLSSEWSAPSDPLDILIAGQIRG

RPFLSVQPGPKVVSGENVTLLCQSSWQFHAFLLTQAGAADAHLHLRSMYKYPKYQAEFPM

SPVTSAHAGTYRCYGSRSSNPYLLSVPSDPLELVVSGPSGGPSSPTTGPTSTCAGPEDQP

LTPTGSDPQSGLGRHLGVVTGILVAFVLLLFLLLLLFLVLRHQRQGKHWTSAQRKADFQH

PAGAVEPEPRDRGLQRRSSPAADTQEENLYAAVKDTQPEDGVELDSRQRPHDEDPQAVTY

ARVKHSRPRREMASPPSPLSEEFLDTKDTQAEEDRQMDTEAAASEDPQDVTYAQLQSLTL

RRETTEPPPSQERAPPVESSIYATLTIH
```

Cyno ILT2 extracellular domain (aa 24-461)
(SEQ ID NO: 168)
```
GILPKPTLWAEPGSMISEGSPVTLRCQGSLQVQEYRLYREKKPASWVRRIQQELVKKGYF

AIGFITWEHTGQYRCQYYSHSWWSEPSDPLELVVTGAYSKPTLSALPSPVVASGGNVTLQ

CDSQVAFDSFTLCKEGEDEHPQRLNCQSHARGWSWAVFSVGPVSPSRRWSYRCYGYISSA

PNVWSLPSDLLELLVPGVSKKPSLSVQPGPVVAPGDKLTLQCGSDAGYDRFALYKEGEGD

FLQRPVRQPQAGLSQANFLLGPVSRSHGGQYRCSGAHNLSSEWSAPSDPLDILIAGQIRG

RPFLSVQPGPKVVSGENVTLLCQSSWQFHAFLLTQAGAADAHLHLRSMYKYPKYQAEFPM

SPVTSAHAGTYRCYGSRSSNPYLLSVPSDPLELVVSGPSGGPSSPTTGPTSTCAGPEDQP

LTPTGSDPQSGLGRHLGV
```

Cyno ILT2 Ig-like C2-type domain 1 amino acid sequence (aa 27-114)
(SEQ ID NO: 169)
```
PKPTLWAEPGSMISEGSPVTLRCQGSLQVQEYRLYREKKPASWVRRIQQELVKKGYFAIG

FITWEHTGQYRCQYYSHSWWSEPSDPLE
```

Cyno ILT2 Ig-like C2-type domain 2 amino acid sequence n (aa 115-220)
(SEQ ID NO: 170)
```
LVVTGAYSKPTLSALPSPVVASGGNVTLQCDSQVAFDSFTLCKEGEDEHPQRLNCQSHAR

GWSWAVFSVGPVSPSRRWSYRCYGYISSAPNVWSLPSDLLELLVPG
```

Cyno ILT2 Ig-like C2-type domain 3 amino acid sequence n (aa 221-311)
(SEQ ID NO: 171)
```
VSKKPSLSVQPGPVVAPGDKLTLQCGSDAGYDRFALYKEGEGDFLQRPVRQPQAGLSQAN

FLLGPVSRSHGGQYRCSGAHNLSSEWSAPSD
```

-continued

Cyno ILT2 Ig-like C2-type domain 4 amino acid sequence n (aa 312-408)
(SEQ ID NO: 172)

PLDILIAGQIRGRPFLSVQPGPKVVSGENVTLLCQSSWQFHAFLLTQAGAADAHLHLRSMY
KYPKYQAEFPMSPVTSAHAGTYRCYGSRSSNPYLLS

Hexahistidine peptide tag
(SEQ ID NO: 173)

HHHHHH

---

What is claimed is:

1. A binding agent binding specifically to both human immunoglobulin-like transcript 2 (ILT2) and human immunoglobulin-like transcript 4 (ILT4), comprising:
   (i) a heavy chain variable region (VH) comprising a VH-complementarity determining region (CDR)1, a VH-CDR2, and a VH-CDR3 from the amino acid sequence of SEQ ID NO:144;
   and a light chain variable region (VL) comprising a VL-CDR1, a VL-CDR2, and a VL-CDR3 from the amino acid sequence of SEQ ID NO:145;
   (ii) a VH comprising a VH-CDR1, a VH-CDR2, and a VH-CDR3 from the amino acid sequence of SEQ ID NO:139; and a VL comprising a VL-CDR1, a VL-CDR2, and a VL-CDR3 from the amino acid sequence of SEQ ID NO:140;
   (iii) a VH comprising a VH-CDR1, a VH-CDR2, and a VH-CDR3 from the amino acid sequence of SEQ ID NO:133; and a VL comprising a VL-CDR1, a VL-CDR2, and a VL-CDR3 from the amino acid sequence of SEQ ID NO:134;
   (iv) a VH comprising a VH-CDR1, a VH-CDR2, and a VH-CDR3 from the amino acid sequence of SEQ ID NO:143; and a VL comprising a VL-CDR1, a VL-CDR2, and a VL-CDR3 from the amino acid sequence of SEQ ID NO:142;
   (v) a VH comprising a VH-CDR1, a VH-CDR2, and a VH-CDR3 from the amino acid sequence of SEQ ID NO:131; and a VL comprising a VL-CDR1, a VL-CDR2, and a VL-CDR3 from the amino acid sequence of SEQ ID NO:132;
   (vi) a VH comprising a VH-CDR1, a VH-CDR2, and a VH-CDR3 from the amino acid sequence of SEQ ID NO:137; and a VL comprising a VL-CDR1, a VL-CDR2, and a VL-CDR3 from the amino acid sequence of SEQ ID NO:138;
   (vii) a VH comprising a VH-CDR1, a VH-CDR2, and a VH-CDR3 from the amino acid sequence of SEQ ID NO:135; and a VL comprising a VL-CDR1, a VL-CDR2, and a VL-CDR3 from the amino acid sequence of SEQ ID NO:136; or
   (viii) a VH comprising a VH-CDR1, a VH-CDR2, and a VH-CDR3 from the amino acid sequence of SEQ ID NO:141; and a VL comprising a VL-CDR1, a VL-CDR2, and a VL-CDR3 from the amino acid sequence of SEQ ID NO:142.

2. The binding agent of claim 1, wherein:
   (i) the VH comprises the VH-CDR1, the VH-CDR2, and the VH-CDR3 from the amino acid sequence of SEQ ID NO:144; and the VL comprises the VL-CDR1, the VL-CDR2, and the VL-CDR3 from the amino acid sequence of SEQ ID NO:145, and wherein
      (a) the VH-CDR1 comprises the amino acid sequence of SEQ ID NO:115, the VH-CDR2 comprises the amino acid sequence of SEQ ID NO: 112, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
      (b) the VH-CDR1 comprises the amino acid sequence of SEQ ID NO:111, the VH-CDR2 comprises the amino acid sequence of SEQ ID NO: 112, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
      (c) the VH-CDR1 comprises the amino acid sequence of SEQ ID NO:76, the VH-CDR2 comprises the amino acid sequence of SEQ ID NO:113, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
      (d) the VH-CDR1 comprises the amino acid sequence of SEQ ID NO:111, the VH-CDR2 comprises the amino acid sequence of SEQ ID NO:114, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91; or
      (e) the VH-CDR1 comprises the amino acid sequence of SEQ ID NO:116, the VH-CDR2 comprises the amino acid sequence of SEQ ID NO:124, the VH-CDR3 comprises the amino acid sequence of SEQ ID NO:110, the VL-CDR1 comprises the amino acid sequence of SEQ ID NO:99, the VL-CDR2 comprises the amino acid sequence of SEQ ID NO: 100, and the VL-CDR3 comprises the amino acid sequence of SEQ ID NO:101; or
   (ii) the VH comprises the VH-CDR1, the VH-CDR2, and the VH-CDR3 from the amino acid sequence of SEQ ID NO:139; and the VL comprises the VL-CDR1, the VL-CDR2, and the VL-CDR3 from the amino acid sequence of SEQ ID NO:140, and wherein
      (a) the VH-CDR1 comprises the amino acid sequence of SEQ ID NO:95, the VH-CDR2 comprises the amino acid sequence of SEQ ID NO:87, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
(b) the VH-CDR1 comprises the amino acid sequence of SEQ ID NO:86, the VH-CDR2 comprises the amino acid sequence of SEQ ID NO:87, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
(c) the VH-CDR1 comprises the amino acid sequence of SEQ ID NO:92, the VH-CDR2 comprises the amino acid sequence of SEQ ID NO:93, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
(d) the VH-CDR1 comprises the amino acid sequence of SEQ ID NO:86, the VH-CDR2 comprises the amino acid sequence of SEQ ID NO:94, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91; or
(e) the VH-CDR1 comprises the amino acid sequence of SEQ ID NO:96, the VH-CDR2 comprises the amino acid sequence of SEQ ID NO:97, the VH-CDR3 comprises the amino acid sequence of SEQ ID NO:123, the VL-CDR1 comprises the amino acid sequence of SEQ ID NO:105, the VL-CDR2 comprises the amino acid sequence of SEQ ID NO:100, and the VL-CDR3 comprises the amino acid sequence of SEQ ID NO:101; or
(iii) the VH comprises the VH-CDR1, the VH-CDR2, and the VH-CDR3 from the amino acid sequence of SEQ ID NO:133; and the VL comprises the VL-CDR1, the VL-CDR2, and the VL-CDR3 from the amino acid sequence of SEQ ID NO: 134, and wherein
(a) the VH-CDR1 comprises the amino acid sequence of SEQ ID NO:79, the VH-CDR2 comprises the amino acid sequence of SEQ ID NO:118, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
(b) the VH-CDR1 comprises the amino acid sequence of SEQ ID NO:70, the VH-CDR2 comprises the amino acid sequence of SEQ ID NO:118, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
(c) the VH-CDR1 comprises the amino acid sequence of SEQ ID NO:76, the VH-CDR2 comprises the amino acid sequence of SEQ ID NO:119, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
(d) the VH-CDR1 comprises the amino acid sequence of SEQ ID NO:70, the VH-CDR2 comprises the amino acid sequence of SEQ ID NO:120, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75; or
(e) the VH-CDR1 comprises the amino acid sequence of SEQ ID NO:80, the VH-CDR2 comprises the amino acid sequence of SEQ ID NO:121, the VH-CDR3 comprises the amino acid sequence of SEQ ID NO:82, the VL-CDR1 comprises the amino acid sequence of SEQ ID NO:83, the VL-CDR2 comprises the amino acid sequence of SEQ ID NO: 122, and the VL-CDR3 comprises the amino acid sequence of SEQ ID NO:85; or
(iv) the VH comprises the VH-CDR1, the VH-CDR2, and the VH-CDR3 from the amino acid sequence of SEQ ID NO:143; and the VL comprises the VL-CDR1, the VL-CDR2, and the VL-CDR3 from the amino acid sequence of SEQ ID NO:142, and wherein
(a) the VH-CDR1 comprises the amino acid sequence of SEQ ID NO:115, the VH-CDR2 comprises the amino acid sequence of SEQ ID NO:112, the VH-CDR3 comprises the amino acid sequence of SEQ ID NO: 107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(b) the VH-CDR1 comprises the amino acid sequence of SEQ ID NO:111, the VH-CDR2 comprises the amino acid sequence of SEQ ID NO:112, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(c) the VH-CDR1 comprises the amino acid sequence of SEQ ID NO:76, the VH-CDR2 comprises the amino acid sequence of SEQ ID NO:113, the VH-CDR3 comprises the amino acid sequence of SEQ ID NO: 107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(d) the VH-CDR1 comprises the amino acid sequence of SEQ ID NO:111, the VH-CDR2 comprises the amino acid sequence of SEQ ID NO:114, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91; or
(e) the VH-CDR1 comprises the amino acid sequence of SEQ ID NO:116, the VH-CDR2 comprises the amino acid sequence of SEQ ID NO:117, the VH-CDR3 comprises the amino acid sequence of SEQ ID NO:110, the VL-CDR1 comprises the amino acid sequence of SEQ ID NO:99, the VL-CDR2 comprises the amino acid sequence of SEQ ID NO: 100, and the VL-CDR3 comprises the amino acid sequence of SEQ ID NO:101; or (v) the VH comprises the VH-CDR1, the VH-CDR2, and the VH-CDR3 from the amino acid sequence of SEQ ID NO:131; and the VL comprises the VL-CDR1, the VL-CDR2, and the VL-CDR3 from the amino acid sequence of SEQ ID NO:132, and wherein
- (a) the VH-CDR1 comprises the amino acid sequence of SEQ ID NO:79, the VH-CDR2 comprises the amino acid sequence of SEQ ID NO:71, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
- (b) the VH-CDR1 comprises the amino acid sequence of SEQ ID NO:70, the VH-CDR2 comprises the amino acid sequence of SEQ ID NO:71, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
- (c) the VH-CDR1 comprises the amino acid sequence of SEQ ID NO:76, the VH-CDR2 comprises the amino acid sequence of SEQ ID NO:77, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75;
- (d) the VH-CDR1 comprises the amino acid sequence of SEQ ID NO:70, the VH-CDR2 comprises the amino acid sequence of SEQ ID NO:78, the VH-CDR3 comprises the amino acid sequence of SEQ ID NO:72, the VL-CDR1 comprises the amino acid sequence of SEQ ID NO:73, the VL-CDR2 comprises the amino acid sequence of SEQ ID NO:74, and the VL-CDR3 comprises the amino acid sequence of SEQ ID NO:75; or
- (e) the VH-CDR1 comprises the amino acid sequence of SEQ ID NO:80, the VH-CDR2 comprises the amino acid sequence of SEQ ID NO:81, the VH-CDR3 comprises the amino acid sequence of SEQ ID NO:82, the VL-CDR1 comprises the amino acid sequence of SEQ ID NO:83, the VL-CDR2 comprises the amino acid sequence of SEQ ID NO:84, and the VL-CDR3 comprises the amino acid sequence of SEQ ID NO:85; or (vi) the VH comprises the VH-CDR1, the VH-CDR2, and the VH-CDR3 from the amino acid sequence of SEQ ID NO:137; and the VL comprises the VL-CDR1, the VL-CDR2, and the VL-CDR3 from the amino acid sequence of SEQ ID NO:138, and wherein
- (a) the VH-CDR1 comprises the amino acid sequence of SEQ ID NO:95, the VH-CDR2 comprises the amino acid sequence of SEQ ID NO:87, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
- (b) the VH-CDR1 comprises the amino acid sequence of SEQ ID NO:86, the VH-CDR2 comprises the amino acid sequence of SEQ ID NO:87, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
- (c) the VH-CDR1 comprises the amino acid sequence of SEQ ID NO:92, the VH-CDR2 comprises the amino acid sequence of SEQ ID NO:93, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91;
- (d) the VH-CDR1 comprises the amino acid sequence of SEQ ID NO:86, the VH-CDR2 comprises the amino acid sequence of SEQ ID NO:94, the VH-CDR3 comprises the amino acid sequence of SEQ ID NO:102, the VL-CDR1 comprises the amino acid sequence of SEQ ID NO:103, the VL-CDR2 comprises the amino acid sequence of SEQ ID NO:90, and the VL-CDR3 comprises the amino acid sequence of SEQ ID NO:91; or
- (e) the VH-CDR1 comprises the amino acid sequence of SEQ ID NO:96, the VH-CDR2 comprises the amino acid sequence of SEQ ID NO:97, the VH-CDR3 comprises the amino acid sequence of SEQ ID NO:104, the VL-CDR1 comprises the amino acid sequence of SEQ ID NO:105, the VL-CDR2 comprises the amino acid sequence of SEQ ID NO:100, and the VL-CDR3 comprises the amino acid sequence of SEQ ID NO:101; or (vii) the VH comprises the VH-CDR1, the VH-CDR2, and the VH-CDR3 from the amino acid sequence of SEQ ID NO:135; and the VL comprises the VL-CDR1, the VL-CDR2, and the VL-CDR3 from the amino acid sequence of SEQ ID NO:136, and wherein
- (a) the VH-CDR1 comprises the amino acid sequence of SEQ ID NO:95, the VH-CDR2 comprises the amino acid sequence of SEQ ID NO:87, the VH-CDR3 comprises the amino acid sequence of SEQ ID NO:88, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
- (b) the VH-CDR1 comprises the amino acid sequence of SEQ ID NO:86, the VH-CDR2 comprises the amino acid sequence of SEQ ID NO:87, the VH-CDR3 comprises the amino acid sequence of SEQ ID NO:88, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
- (c) the VH-CDR1 comprises the amino acid sequence of SEQ ID NO:92, the VH-CDR2 comprises the amino acid sequence of SEQ ID NO:93, the VH-CDR3 comprises the amino acid sequence of SEQ ID NO:88, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(d) the VH-CDR1 comprises the amino acid sequence of SEQ ID NO:86, the VH-CDR2 comprises the amino acid sequence of SEQ ID NO:94, the VH-CDR3 comprises the amino acid sequence of SEQ ID NO:88, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91; or
(e) the VH-CDR1 comprises the amino acid sequence of SEQ ID NO:96, the VH-CDR2 comprises the amino acid sequence of SEQ ID NO:97, the VH-CDR3 comprises the amino acid sequence of SEQ ID NO:98, the VL-CDR1 comprises the amino acid sequence of SEQ ID NO:99, the VL-CDR2 comprises the amino acid sequence of SEQ ID NO:100, and the VL-CDR3 comprises the amino acid sequence of SEQ ID NO:101; or (viii) the VH comprises the VH-CDR1, the VH-CDR2, and the VH-CDR3 from the amino acid sequence of SEQ ID NO:141; and the VL comprises the VL-CDR1, the VL-CDR2, and the VL-CDR3 from the amino acid sequence of SEQ ID NO:142, and wherein
(a) the VH-CDR1 comprises the amino acid sequence of SEQ ID NO:79, the VH-CDR2 comprises the amino acid sequence of SEQ ID NO:106, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(b) the VH-CDR1 comprises the amino acid sequence of SEQ ID NO:70, the VH-CDR2 comprises the amino acid sequence of SEQ ID NO:106, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(c) the VH-CDR1 comprises the amino acid sequence of SEQ ID NO:76, the VH-CDR2 comprises the amino acid sequence of SEQ ID NO:77, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(d) the VH-CDR1 comprises the amino acid sequence of SEQ ID NO:70, the VH-CDR2 comprises the amino acid sequence of SEQ ID NO: 108, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91; or
(e) the VH-CDR1 comprises the amino acid sequence of SEQ ID NO:80, the VH-CDR2 comprises the amino acid sequence of SEQ ID NO: 109, the VH-CDR3 comprises the amino acid sequence of SEQ ID NO:110, the VL-CDR1 comprises the amino acid sequence of SEQ ID NO:99, the VL-CDR2 comprises the amino acid sequence of SEQ ID NO:100, and the VL-CDR3 comprises the amino acid sequence of SEQ ID NO:101.

3. The binding agent of claim 1, wherein:
(a) the VH comprises the amino acid sequence of SEQ ID NO: 144, and/or the VL comprises the amino acid sequence of SEQ ID NO:145,
(b) the VH comprises the amino acid sequence of SEQ ID NO: 139, and/or the VL comprises the amino acid sequence of SEQ ID NO:140,
(c) the VH comprises the amino acid sequence of SEQ ID NO: 133, and/or the VL comprises the amino acid sequence of SEQ ID NO:134,
(d) the VH comprises the amino acid sequence of SEQ ID NO:143, and/or the VL comprises the amino acid sequence of SEQ ID NO:142,
(e) the VH comprises the amino acid sequence of SEQ ID NO: 131, and/or the VL comprises the amino acid sequence of SEQ ID NO:132,
(f) the VH comprises the amino acid sequence of SEQ ID NO: 137, and/or the VL comprises the amino acid sequence of SEQ ID NO:138,
(g) the VH comprises the amino acid sequence of SEQ ID NO: 135, and/or the VL comprises the amino acid sequence of SEQ ID NO:136, or
(h) the VH comprises the amino acid sequence of SEQ ID NO: 141, and/or the VL comprises the amino acid sequence of SEQ ID NO:142.

4. The binding agent of claim 1, wherein the binding agent is
(i) a whole antibody;
(ii) an antibody fragment comprising at least one antigen-binding site; or
(iii) attached to a half-life extending moiety.

5. The binding agent of claim 1, comprising:
(a) a heavy chain comprising an amino acid sequence having at least 80% sequence identity to the amino acid sequence of SEQ ID NO:148, and/or a light chain comprising an amino acid sequence having at least 80% sequence identity to the amino acid sequence of SEQ ID NO:149;
(b) a heavy chain comprising an amino acid sequence having at least 80% sequence identity to the amino acid sequence of SEQ ID NO:152, and/or a light chain comprising an amino acid sequence having at least 80% sequence identity to the amino acid sequence of SEQ ID NO:153;
(c) a heavy chain comprising an amino acid sequence having at least 80% sequence identity to the amino acid sequence of SEQ ID NO:156, and/or a light chain comprising an amino acid sequence having at least 80% sequence identity to the amino acid sequence of SEQ ID NO: 157;
(d) a heavy chain comprising the amino acid sequence of SEQ ID NO:148, and/or a light chain comprising the amino acid sequence of SEQ ID NO:149;
(e) a heavy chain comprising the amino acid sequence of SEQ ID NO:152, and/or a light chain comprising the amino acid sequence of SEQ ID NO:153; or
(f) a heavy chain comprising the amino acid sequence of SEQ ID NO:156, and/or a light chain comprising the amino acid sequence of SEQ ID NO:157.

6. A pharmaceutical composition comprising the binding agent of claim 4 and a pharmaceutically acceptable carrier.

7. An isolated polynucleotide or polynucleotides encoding the binding agent of claim 1, wherein the binding agent is (i) a whole antibody; or
(ii) an antibody fragment comprising at least one antigen-binding site.

8. A vector or vectors comprising the polynucleotide or polynucleotides of claim 7.

9. An isolated cell comprising the polynucleotide or polynucleotides of claim 7.

10. An isolated cell comprising the vector or vectors of claim 8.

11. A method of making a binding agent that specifically binds to ILT2 and ILT4, the method comprising:
(a) culturing the cell of claim 9 under conditions that result in the expression of the binding agent, and
(b) isolating the binding agent.

12. A method of making a binding agent that specifically binds to ILT2 and ILT4, the method comprising:
(a) culturing the cell of claim 10 under conditions that result in the expression of the binding agent, and
(b) isolating the binding agent.

13. A method of disrupting, inhibiting, or blocking in a mixture of cells and/or in a subject at least one of the following:
(a) the binding of ILT2 and/or ILT4 to an MHC I molecule, and
(b) MHC I-induced ILT2 and/or ILT4 activity;
the method comprising contacting the cells with, or administering to the subject, the binding agent of claim 1.

14. A method of disrupting, inhibiting, or blocking in a mixture of cells and/or in a subject at least one of the following:
(a) the binding of ILT2 and/or ILT4 to an MHC I molecule, and
(b) MHC I-induced ILT2 and/or ILT4 activity;
the method comprising contacting the cells with, or administering to the subject, the pharmaceutical composition of claim 6.

15. A method of
(a) disrupting, inhibiting, or blocking ILT2- and ILT4-induced suppression of myeloid cells;
(b) inhibiting or decreasing myeloid-derived suppressor cell (MDSC) activity;
(c) enhancing or increasing natural killer (NK) cell activity, or
(d) enhancing or increasing cytolytic T lymphocyte (CTL) activity;
the method comprising contacting respectively the myeloid cells of (a); the MDSCs of (b); the NK cells of (c); or the CTLs of (d) with the binding agent of claim 1.

16. A method of
(a) disrupting, inhibiting, or blocking the binding of ILT2 and/or ILT4 to an MHC I molecule in a subject;
(b) disrupting, inhibiting, or blocking MHC I-induced ILT2 and/or ILT4 activity in a subject;
(c) disrupting, inhibiting, or blocking ILT2 or ILT4-induced suppression of myeloid cells in a subject;
(d) inhibiting or decreasing MDSC activity in a subject;
(e) enhancing or increasing NK cell activity in a subject;
(f) enhancing or increasing CTL activity in a subject;
(g) treating cancer in a subject;
(h) inhibiting tumor growth in a subject;
(i) increasing or enhancing an immune response to a tumor or tumor cells in a subject;
(j) inhibiting tumor relapse or tumor regrowth in a subject; or
(k) activating myeloid cells in the tumor microenvironment in a subject with a tumor;
the method comprising administering to the subject a therapeutically effective amount of the binding agent of claim 1.

17. A method of
(a) disrupting, inhibiting, or blocking the binding of ILT2 and/or ILT4 to an MHC I molecule in a subject;
(b) disrupting, inhibiting, or blocking MHC I-induced ILT2 and/or ILT4 activity in a subject;
(c) disrupting, inhibiting, or blocking ILT2 or ILT4-induced suppression of myeloid cells in a subject;
(d) inhibiting or decreasing MDSC activity in a subject;
(e) enhancing or increasing NK cell activity in a subject;
(f) enhancing or increasing CTL activity in a subject;
(g) treating cancer in a subject;
(h) inhibiting tumor growth in a subject;
(i) increasing or enhancing an immune response to a tumor or tumor cells in a subject;
(j) inhibiting tumor relapse or tumor regrowth in a subject; or
(k) activating myeloid cells in the tumor microenvironment in a subject with a tumor;
the method comprising administering to the subject a therapeutically effective amount of the pharmaceutical composition of claim 6.

18. A pharmaceutical composition, comprising:
(a) a means for inhibiting the interaction between ILT2 and/or ILT4 and MHC Class I; and
(b) a pharmaceutically acceptable carrier,
wherein the means comprises the binding agent of claim 1.

19. A combination comprising a means for inhibiting the interaction between ILT2 and/or ILT4 and MHC Class I, and an immune checkpoint inhibitor, wherein the means comprises the binding agent of claim 1.

20. The method of claim 16, wherein (i) the cancer is mesothelioma, glioblastoma, renal cell carcinoma, non-small cell lung cancer, melanoma, pancreatic ductal adenocarcinoma, gastric cancer, squamous cell carcinoma of the head and neck, biliary duct cancer, breast cancer, ovarian cancer, cervical cancer, endocervical cancer, colorectal cancer, or esophageal cancer; and/or (ii) the tumor is a pancreatic tumor, a breast tumor, a lung tumor, a non-small cell lung tumor, a head and neck tumor, a colorectal tumor, a prostate tumor, a skin tumor, a melanoma, a gastric tumor, a colorectal tumor, an ovarian tumor, a cervical tumor, a uterine tumor, an endometrial tumor, an endocervical tumor, a bladder tumor, a brain tumor, an esophageal tumor, a liver tumor, a kidney tumor, a renal tumor, mesothelioma, glioblastoma, a biliary duct tumor, or a testicular tumor.

21. The method of claim 17, wherein (i) the cancer is mesothelioma, glioblastoma, renal cell carcinoma, non-small cell lung cancer, melanoma, pancreatic ductal adenocarcinoma, gastric cancer, squamous cell carcinoma of the head and neck, biliary duct cancer, breast cancer, ovarian cancer, cervical cancer, endocervical cancer, colorectal cancer, or esophageal cancer; and/or (ii) the tumor is a pancreatic tumor, a breast tumor, a lung tumor, a non-small cell lung tumor, a head and neck tumor, a colorectal tumor, a prostate tumor, a skin tumor, a melanoma, a gastric tumor, a colorectal tumor, an ovarian tumor, a cervical tumor, a uterine tumor, an endometrial tumor, an endocervical tumor, a bladder tumor, a brain tumor, an esophageal tumor, a liver tumor, a kidney tumor, a renal tumor, mesothelioma, glioblastoma, a biliary duct tumor, or a testicular tumor.

22. The method of claim 16, wherein the binding agent is administered as part of a combination therapy comprising a PD-1 antagonist, wherein the PD-1 antagonist is an anti-PD-1 antibody.

23. The method of claim 17, wherein the binding agent is administered as part of a combination therapy comprising a PD-1 antagonist, wherein the PD-1 antagonist is an anti-PD-1 antibody.

24. The method of claim 22, wherein the PD-1 antagonist is pembrolizumab.

25. The method of claim 23, wherein the PD-1 antagonist is pembrolizumab.

26. An binding agent binding specifically to both human ILT2 and human ILT4, comprising a VH comprising a VH-CDR1, a VH-CDR2, and a VH-CDR3 from the amino acid sequence of SEQ ID NO:144; and a VL comprising a VL-CDR1, a VL-CDR2, and a VL-CDR3 from the amino acid sequence of SEQ ID NO:145.

27. The binding agent of claim 26, wherein:
(a) the VH-CDR1 comprises the amino acid sequence of SEQ ID NO:115, the VH-CDR2 comprises the amino acid sequence of SEQ ID NO:112, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(b) the VH-CDR1 comprises the amino acid sequence of SEQ ID NO:111, the VH-CDR2 comprises the amino acid sequence of SEQ ID NO:112, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(c) the VH-CDR1 comprises the amino acid sequence of SEQ ID NO:76, the VH-CDR2 comprises the amino acid sequence of SEQ ID NO:113, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91;
(d) the VH-CDR1 comprises the amino acid sequence of SEQ ID NO:111, the VH-CDR2 comprises the amino acid sequence of SEQ ID NO:114, the VH-CDR3 comprises the amino acid sequence of SEQ ID NO:107, the VL-CDR1 comprises the amino acid sequence of SEQ ID NO:89, the VL-CDR2 comprises the amino acid sequence of SEQ ID NO:90, and the VL-CDR3 comprises the amino acid sequence of SEQ ID NO:91; or
(e) the VH-CDR1 comprises the amino acid sequence of SEQ ID NO:116, the VH-CDR2 comprises the amino acid sequence of SEQ ID NO:124, the VH-CDR3 comprises the amino acid sequence of SEQ ID NO:110, the VL-CDR1 comprises the amino acid sequence of SEQ ID NO:99, the VL-CDR2 comprises the amino acid sequence of SEQ ID NO: 100, and the VL-CDR3 comprises the amino acid sequence of SEQ ID NO:101.

28. The binding agent of claim 26, wherein the VH comprises the amino acid sequence of SEQ ID NO:144, and the VL comprises the amino acid sequence of SEQ ID NO:145.

29. The binding agent of claim 26, comprising a heavy chain comprising the amino acid sequence of SEQ ID NO:156, and a light chain comprising the amino acid sequence of SEQ ID NO:157.

30. A method of treating cancer, or inhibiting tumor growth, tumor relapse, or tumor regrowth in a subject, comprising administering to the subject a therapeutically effective amount of the binding agent of claim 26.

31. The method of claim 30, wherein (i) the cancer is mesothelioma, glioblastoma, renal cell carcinoma, non-small cell lung cancer, melanoma, pancreatic ductal adenocarcinoma, gastric cancer, squamous cell carcinoma of the head and neck, biliary duct cancer, breast cancer, ovarian cancer, cervical cancer, endocervical cancer, colorectal cancer, or esophageal cancer; and/or (ii) the tumor is a pancreatic tumor, a breast tumor, a lung tumor, a non-small cell lung tumor, a head and neck tumor, a colorectal tumor, a prostate tumor, a skin tumor, a melanoma, a gastric tumor, a colorectal tumor, an ovarian tumor, a cervical tumor, a uterine tumor, an endometrial tumor, an endocervical tumor, a bladder tumor, a brain tumor, an esophageal tumor, a liver tumor, a kidney tumor, a renal tumor, mesothelioma, glioblastoma, a biliary duct tumor, or a testicular tumor.

32. The method of claim 30, wherein the binding agent is administered as part of a combination therapy comprising a PD-1 antagonist, wherein the PD-1 antagonist is an anti-PD-1 antibody.

33. The method of claim 32, wherein the PD-1 antagonist is pembrolizumab.

34. An isolated cell comprising a polynucleotide or polynucleotides encoding the binding agent of claim 26, or a vector or vector comprising a polynucleotide or polynucleotides encoding the binding agent of claim 26.

\* \* \* \* \*